(12) United States Patent
Ombrato et al.

(10) Patent No.: US 10,633,366 B2
(45) Date of Patent: Apr. 28, 2020

(54) ANTIBACTERIAL COMPOUNDS

(71) Applicant: AZIENDE CHIMICHE RIUNITE ANGELINI FRANCESCO A.C.R.A.F. S.p.A., Rome (IT)

(72) Inventors: Rosella Ombrato, Rome (IT); Gabriele Magaro, Rome (IT); Barbara Garofalo, Rome (IT); Guido Furlotti, Rome (IT); Giorgina Mangano, Rome (IT); Alessandra Capezzone De Joannon, Rome (IT)

(73) Assignee: AZIENDE CHIMICHE RIUNITE ANGELINI FRANCESCO A.C.R.A.F. S.p.A., Rome (IT)

( * ) Notice: Subject to any disclaimer, the term of this patent is extended or adjusted under 35 U.S.C. 154(b) by 0 days.

(21) Appl. No.: 16/307,410

(22) PCT Filed: Jun. 5, 2017

(86) PCT No.: PCT/EP2017/063601
§ 371 (c)(1),
(2) Date: Dec. 5, 2018

(87) PCT Pub. No.: WO2017/211760
PCT Pub. Date: Dec. 14, 2017

(65) Prior Publication Data
US 2019/0161472 A1  May 30, 2019

(30) Foreign Application Priority Data
Jun. 8, 2016 (EP) .................. 16173550

(51) Int. Cl.
*C07D 311/06* (2006.01)
*C07D 217/00* (2006.01)
(Continued)

(52) U.S. Cl.
CPC ............ *C07D 401/14* (2013.01); *A61P 31/04* (2018.01); *C07D 471/04* (2013.01);
(Continued)

(58) Field of Classification Search
CPC ............................. C07D 311/06; C07D 217/00
(Continued)

(56) References Cited
U.S. PATENT DOCUMENTS
6,921,821 B2 * 7/2005 Blackburn ........... C07D 401/14
540/364
2009/0306089 A1  12/2009 Alemparte-Gallardo et al.
(Continued)

FOREIGN PATENT DOCUMENTS
JP           3-118380 A     5/1991
WO     WO 96/10568 A1     4/1996
(Continued)

OTHER PUBLICATIONS
Patel et al., International Journal of Chemistry (Toronto, ON, Canada) (2011), 3(2), 117-123.*
(Continued)

*Primary Examiner* — Niloofar Rahmani
(74) *Attorney, Agent, or Firm* — Oblon, McClelland, Maier & Neustadt, L.L.P.

(57) ABSTRACT

The present invention relates to novel antibacterial compounds (1) as defined below, pharmaceutical compositions containing them and their use as antimicrobials. A compound of formula (1): A-L$_1$-Y-L$_2$-R—B, wherein A is a cyclic group having one of the following formulae (I), (II) and (III), and wherein B is cyclic group having one of the following formulae (IV) to (IX).

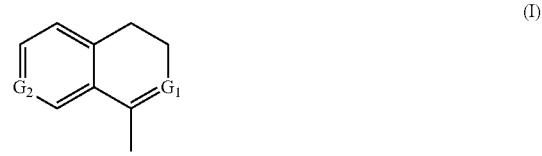

(I)

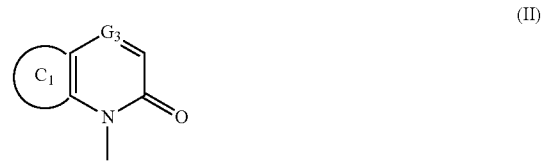

(II)

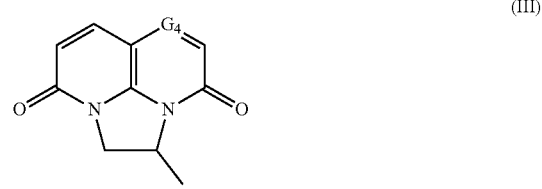

(III)

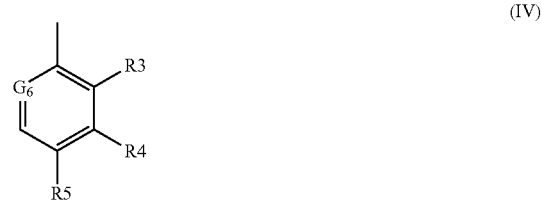

(IV)

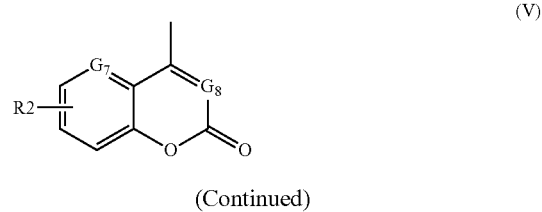

(V)

(Continued)

-continued (VI)

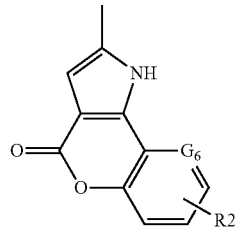

(VII)

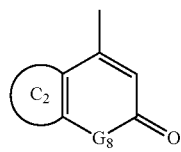

(VIII)

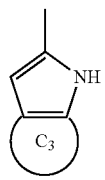

(IX)

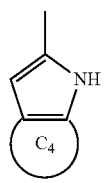

18 Claims, No Drawings

(51) Int. Cl.
*C07D 401/14* (2006.01)
*C07D 471/04* (2006.01)
*C07D 491/04* (2006.01)
*C07D 493/04* (2006.01)
*C07D 498/04* (2006.01)
*C07D 513/04* (2006.01)
*C07D 471/16* (2006.01)
*C07D 491/052* (2006.01)
*C07D 519/00* (2006.01)
*A61P 31/04* (2006.01)

(52) U.S. Cl.
CPC ......... *C07D 471/16* (2013.01); *C07D 491/04* (2013.01); *C07D 491/052* (2013.01); *C07D 493/04* (2013.01); *C07D 498/04* (2013.01); *C07D 513/04* (2013.01); *C07D 519/00* (2013.01)

(58) Field of Classification Search
USPC .......................................... 549/398; 546/139
See application file for complete search history.

(56) References Cited

U.S. PATENT DOCUMENTS

| | | |
|---|---|---|
| 2012/0040957 A1 | 2/2012 | Gaucher et al. |
| 2012/0115899 A1 | 5/2012 | Alemparte-Gallardo et al. |
| 2014/0221348 A1 | 8/2014 | Gaucher et al. |
| 2014/0243302 A1 | 8/2014 | Fukuda et al. |
| 2015/0080373 A1 | 3/2015 | Gaucher et al. |

FOREIGN PATENT DOCUMENTS

| | | |
|---|---|---|
| WO | WO 02/072572 A1 | 9/2002 |
| WO | WO 2006/021448 A1 | 3/2006 |
| WO | WO 2006/105289 A1 | 10/2006 |
| WO | WO 2006/125974 A1 | 11/2006 |
| WO | WO 2008/139288 A2 | 11/2008 |
| WO | WO 2009/141398 A1 | 11/2009 |
| WO | WO 2010/081874 A1 | 7/2010 |
| WO | WO 2010/084152 A1 | 7/2010 |
| WO | WO 2012/003418 A2 | 1/2012 |
| WO | WO 2013/068948 A1 | 5/2013 |
| WO | WO 2013/080156 A1 | 6/2013 |
| WO | WO 2016/027249 A1 | 2/2016 |
| WO | 2016096631 * | 6/2016 |
| WO | 2016096686 * | 6/2016 |
| WO | WO 2016/096631 A1 | 6/2016 |
| WO | WO 2016/096686 A1 | 6/2016 |

OTHER PUBLICATIONS

International Search Report dated Jul. 24, 2017 in PCT/EP2017/063601 Filed on Jun. 5, 2017.
Zayane, M. et al: "Design and synthesis of antimicrobial, anticoagulant, and anticholinesterase hybrid molecules from 4-methylumbelliferone", Journal of Enzyme Inhibition and Medicinal Chemistry, Informa Healthcare, vol. 31, No. 6, 2016, pp. 1566-1575, XP009192605.
Hayera, H J, et al: "Analgetic Activity of Cyclized Basic Anilides", ACTA Chemica Scandinavica, Munksgaard, Copenhage, Denmark, vol. 12, 1994, pp. 580-583, XP001029546.
Kowalski, P. et al: "Biologically Active 1-Arylpiperazines Synthesis of N-[3-(4-Aryl-1-piperazinyl)propyl] Derivatives of Benzoxazolinone", Journal of Heterocyclic Chemistry, Wiley-Blackwell Publishing, Inc., US, vol. 37, No. 1, 2000, pp. 187-189, XP001022231.
Savelon, L. et al: "Substituted pyrido[3,2-b]oxazin-3(4H)-ones: synthesis and evaluation of antinociceptive activity", Bioorganic & Medicinal Chemistry, vol. 6, No. 2, 1998, pp. 133-142, XP55388930.
Jacoby, G.A. et al: "Mechanisms of Resistance to Quinolones", Clinical Infectious Diseases, Lahey Clinic, 2005:41, Suppl. 2, pp. S120-S126.
Mitton-Fry, M.J. et al: "Novel quinolone derivatives as inhibitors of bacterial DNA gyrase and topoisomerase IV", Bioorganic & Medicinal Chemistry Letters, Pfizer Worldwide Research and Development, 2013, pp. 2955-2961.
Surivet, J.P. et al: "Design, Synthesis, and Characterization of Novel Tetrahydropyran-Based Bacterial Topoisomerase Inhibitors with Potent Anti-Gram-Positive Activity", Journal of Medicinal Chemistry, Actelion Pharmaceuticals Ltd., 2013, vol. 56, pp. 7396-7415.
Blanche, F. et al: "Differential Behaviors of *Staphylococcus aureus* and *Escherichia coli* Type II DNA Topoisomerases", Antimicrobial Agents and Chemotherapy, 1996, vol. 40, No. 12, pp. 2714-2720.

* cited by examiner

ANTIBACTERIAL COMPOUNDS

CROSS REFERENCE TO RELATED APPLICATIONS

This application is a 371 of International Patent Application No. PCT/EP2017/063601, filed on Jun. 5, 2017, and claims priority to European Patent Application No. 16173550.1, filed on Jun. 8, 2016, both of which are incorporated herein by reference in their entireties.

FIELD OF THE INVENTION

The present invention relates to novel antibacterial compounds, pharmaceutical compositions containing them and their use as antimicrobials.

BACKGROUND OF THE INVENTION

DNA topoisomerases are enzymes involved in the modification of the DNA-supercoiling during replication or transcription. These enzymes bind to single-stranded or double-stranded DNA and they cut the phosphate backbone of the DNA such that the DNA strand is untangled or unwound. At the end of the replication or transcription processes, the enzymes themselves reseal the DNA backbone.

DNA topoisomerases are classified as type I when they cut a single strand of a DNA double helix and as type II when they cut both strands of a DNA double helix.

Bacterial type II topoisomerases comprise DNA gyrase and topoisomerase IV (TopoIV), which are heterotetrameric enzymes concurrently present in almost all the prokaryotic cells. Both the enzymes are necessary for DNA replication and, hence, for bacterial cell growth and division.

Bacterial type II topoisomerases are proven antibacterial targets, in particular of compounds belonging to fluoroquinolone class.

Fluoroquinolones are broad-spectrum antibacterial drugs that play an important role in treatment of bacterial infections, especially hospital-acquired infections and infections in which resistance to other classes of antibacterial drugs is suspected. Fluoroquinolones act by inhibiting the DNA gyrase in Gram negative bacteria and the topoisomerase IV in Gram positive bacteria.

However, resistance to fluoroquinolones emerged in recent years due to mutations that altered either the active site of the drug targets DNA gyrase and topoisomerase IV or the drug accumulation. In addition, resistance to quinolones can be mediated by plasmids that produce the Qnr protein, which protects the quinolone targets from inhibition (G. A. Jacoby, CID, 2005:41, Suppl. 2, SD120-S126).

According to the World Health Organization, the antimicrobial resistance (AMR) is the resistance of a microorganism to an antimicrobial drug to which it was originally sensitive. Resistant bacteria are able to withstand attack by antibiotics and antibacterial drugs, so that standard treatments become ineffective and infections persist increasing risk of spread to others.

Mitton-Fry M. J. et al. (Bioorg. Med. Chem. Lett., 23, 2010, 2955-2961) developed novel quinolone derivatives as inhibitors of bacterial DNA gyrase and topoisomerase IV. Given the importance of stepwise target mutations in the clinical history of fluoroquinolones resistance, the authors felt strongly that providing inhibition of TopoIV alongside DNA gyrase was critically important. According to the authors, such dual-targeting activity should slow the rate of resistance emergence in the clinic, since organism which mutate DNA gyrase to avoid inhibition would still be susceptible to killing via TopoIV inhibition.

Surivet J. P. et al. (J. Med. Chem. 2013, 56, 7396-7415) reported the design of novel bacterial dual DNA gyrase and TopoIV inhibitors comprising a tetrahydropyran core and demonstrated that dual inhibition of DNA gyrase and TopoIV is required to minimize the rate of resistance development.

Zayane Marwa et al. (Journal of Enzyme Inhibition and Medicinal Chemistry 2016, 31(6):1566-1575) reported the design and synthesis of 4-methylumbelliferone derivatives with antimicrobial, anticoagulant, and anticholinesterase activity.

WO 2006/105289 relates to heterocyclic compounds, more particularly pyrazole compounds, which were tested for inhibition of both DNA gyrase and topoisomerase IV.

WO 02/072572, WO 2006/021448, WO 2008/139288, WO 2009/141398, WO 2010/081874, WO 2010/084152, WO 2013/068948, WO 2013/080156, WO 2016/027249, WO 2016/096631 and WO 2016/096686 disclose heterocyclic compounds endowed with antimicrobial activity.

WO 96/10568 and WO 2012/003418 disclose heterocyclic compounds endowed with other therapeutic activity.

SUMMARY OF THE INVENTION

The Applicant recognized that there is a strong and continuous need for antibacterial drugs that overcome the problem of resistant bacteria.

The Applicant faced the problem to develop new antibacterial compounds that allow to overcome the problem of antibacterial resistance.

More in particular, the Applicant faced the problem to develop new antibacterial compounds capable of concurrently inhibit bacterial type II topoisomerases, i.e. DNA gyrase and topoisomerase IV.

Also, the Applicant faced the problem to develop new antibacterial compounds having broad spectrum of activity, i.e. useful against Gram positive and/or Gram negative bacteria.

Thus, in a first embodiment, the present invention relates to a compound of formula (1):

$$A\text{-}L_1\text{-}Y\text{-}L_2\text{-}R\text{—}B \qquad (1)$$

wherein

A is a cyclic group having one of the following formulae (I), (II) and (III)

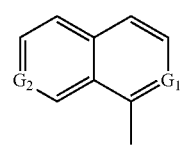

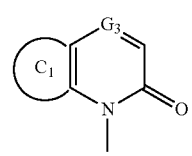

-continued

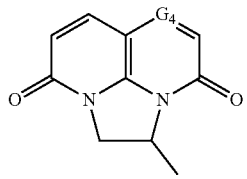
(III)

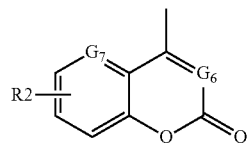
(V)

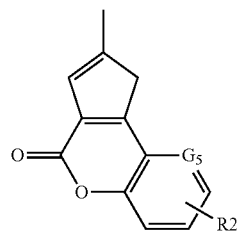
(VI)

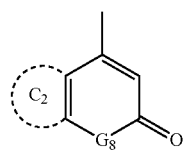
(VII)

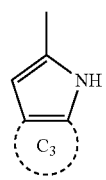
(VIII)

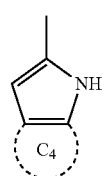
(IX)

wherein
G$_1$ is CH or N;
G$_2$ is CR$_1$ or N;
G$_3$ is CH or N when the dashed line represents a double bond, or CH$_2$, NH or O when the dashed line represents a single bond;
G$_4$ is CH or N when the dashed line represents a double bond, or CH$_2$, NH or O when the dashed line represents a single bond;
C$_1$ represents the atoms necessary to form an aliphatic or aromatic six-membered cycle optionally comprising one or more heteroatom selected from nitrogen atom and oxygen atom, said cycle being optionally substituted by one or more substituent selected from the group consisting of halogen atom, (C$_{1-3}$)alkyl group, cyano group, oxo group (=O), and (C$_{1-3}$)alkoxy group;
R$_1$ is hydrogen atom, halogen atom, cyano or (C$_{1-3}$) alkoxy group;
L$_1$ is σ bond, or (C$_{1-3}$)alkylenyl group, optionally substituted with hydroxy group;
Y is a ring selected from the group consisting of piperidinyl, piperazinyl, pyrrolidinyl, 1-3 cyclobutyl, 1-3 cyclopentyl, 1-2 cyclopropyl, azetidinyl, azabicyclo-octyl, morpholinyl and cyclohexyl ring, said ring being optionally substituted by one or more substituent selected from the group consisting of hydroxy group, (C$_{1-3}$)alkylenyl-OH group, (C$_{1-3}$)alkylenyl-O—(C$_{1-3}$)alkyl group, (C$_{1-3}$)alkylenyl-CONR'R" group, and CONR'R" group, wherein R' and R" are hydrogen atom or (C$_{1-3}$)alkyl;
L$_2$ is σ bond, —(C$_{1-3}$)alkylenyl group, NR''' group, NR'''—(C$_{1-3}$)alkylenyl group, (C$_{1-3}$)alkylenyl-NR''' group, NR'''—(C$_{1-3}$)alkylenyl-NR''' group, or (C$_{1-3}$)alkylenyl-NR'''—(C$_{1-3}$)alkylenyl group, said group being optionally substituted with a hydroxy group, wherein R''' is hydrogen, (C$_{1-3}$)alkyl, (C$_{1-3}$)alkylenyl-OH, (C$_{1-3}$)alkylenyl-O—(C$_{1-3}$) alkyl, or (C$_{1-3}$)alkylenyl-CONR'R", wherein R' and R" are hydrogen atom or (C$_{1-3}$)alkyl;
R is σ bond or heterocyclic ring, aliphatic or aromatic, having 5 members containing one or more nitrogen atoms, optionally substituted with CH$_2$OH, CH$_2$CN, CN or CONR'R", wherein R' and R" are hydrogen atom or (C$_{1-3}$) alkyl; and
B is a cyclic group having one of the following formula (IV) to (IX)

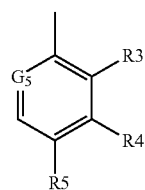
(IV)

wherein
G$_5$ is CH or N;
G$_6$ is CH or N;
G$_7$ is CH or N;
G$_8$ is O or NR$_6$;
R$_2$ is hydrogen atom or halogen atom;
R$_3$ is hydrogen atom or cyano group;
R$_4$ and R$_5$ are hydrogen atoms, or together form a six-membered aliphatic ring containing one oxygen atom;
R$_6$ is a hydrogen atom or a (C$_{1-3}$)alkyl group;
C$_2$ represents the atoms necessary to form a six-membered aliphatic or aromatic heterocycle comprising an oxygen atom or a nitrogen atom;
C$_3$ represents the atoms necessary to form a six-membered aliphatic heterocycle comprising one oxygen atom and optionally one nitrogen atom, said heterocycle being optionally substituted by one or more substituent selected from the group consisting of (C$_{1-3}$)haloalkyl group, amido group (—CONH$_2$), and oxo group (=O); and
C$_4$ represents the atoms necessary to form a ten-membered fused bicycle comprising at least one nitrogen atom and at least one other heteroatom selected from oxygen atom and sulfur atom, said bicycle being optionally substituted by one or more substituent selected from the group consisting of halogen atom, (C$_{1-3}$)alkyl group, cyano group, and oxo group (=O);

with the proviso that when Y is piperidinyl ring or piperazinyl ring, if A is represented by formula (I) and B is represented by formula (V) or (VI), then $G_2$ is only N, and addition salts with pharmaceutically acceptable organic or inorganic acids or basis, enantiomers, N-oxides and quaternary ammonium salts of said compound of formula (1).

In a second embodiment, the present invention relates to a pharmaceutical composition comprising at least one compound of formula (1).

In a third embodiment, the present invention relates to the compounds of formula (1) for use in medicine.

In a fourth embodiment, the present invention relates to the compounds of formula (1) for use in the treatment of bacterial infections.

In a fifth embodiment, the present invention relates to a method for treating a bacterial infection, comprising the administration of a compound of formula (1) to a patient in need thereof.

According to a preferred aspect of the present invention, $G_1$ is N.

According to a preferred aspect of the present invention $G_2$ is CR1.

According to a preferred aspect of the present invention $G_3$ is CH or N when the dashed line represents a double bond, or O when the dashed line represents a single bond.

According to a preferred aspect of the present invention $G_4$ is N when the dashed line represents a double bond, or O when the dashed line represents a single bond.

Preferably, $R_1$ is a halogen atom, a cyano group, or an alkoxy group having from 1 to 2 carbon atoms.

Advantageously, $R_1$ is selected from the group consisting of a fluorine atom, a chlorine atom, a cyano group and a methoxy group.

Preferably, $R_2$ is a hydrogen atom, a fluorine atom, a chlorine atom, and a bromine atom.

Advantageously, $R_2$ is selected from the group consisting of a hydrogen atom and a fluorine atom.

According to a preferred embodiment, $R_3$ is hydrogen atom or cyano group, provided that, when $R_3$ is cyano group, A is different from formula (III).

Preferably, $R_4$ and $R_5$ are hydrogen atoms.

Preferably, $C_1$ is optionally substituted by one or more substituent selected from the group consisting of fluorine or chlorine atom, methyl or ethyl group, methoxy or propoxy group, and oxo group (═O).

Advantageously, $L_1$ is a σ bond or a methylene group (—$CH_2$—).

Preferably, $L_2$ is a σ bond, a ($C_{1-3}$)alkylenyl group, NR''' group, —NR'''—($C_{1-3}$)alkylenyl group, ($C_{1-3}$)alkylenyl-NR'''— group, —NR'''—($C_{1-3}$)alkylenyl-NR'''— group, or ($C_{1-3}$)alkylenyl-NR'''—($C_{1-3}$)alkylenyl group, said group being optionally substituted with one or more hydroxy group.

More preferably, $L_2$ is a σ bond, a ($C_{1-2}$)alkylenyl group, NR''' group, —NR'''—($C_{1-2}$)alkylenyl group, ($C_{1-2}$)alkylenyl-NR'''— group, —NR'''—($C_{1-2}$)alkylenyl-NR'''— group, or ($C_{1-2}$)alkylenyl-NR'''—($C_{1-2}$)alkylenyl group, said group being optionally substituted with one hydroxy group.

Preferably, R''' is hydrogen, ($C_{1-2}$)alkyl, ($C_{1-2}$)alkylenyl-OH, ($C_{1-2}$)alkylenyl-O—($C_{1-2}$)alkyl, or ($C_{1-2}$)alkylenyl-CONR'R'', wherein R' and R'' are hydrogen atom or ($C_{1-2}$) alkyl.

Preferably, R''' is hydrogen, methyl, $CH_2$—OH, or $CH_2CONR'R''$, wherein R' and R'' are hydrogen atom or methyl.

Preferably, R is a σ bond or an aromatic heterocyclic ring having 5 members containing one or more nitrogen atoms, optionally substituted with $CH_2CN$ or CN.

Advantageously, R is a σ bond, a 1H-imidazol-4-yl group, or a 1H-pyrrol-2-yl group, optionally substituted with $CH_2CN$ or CN.

Preferably, $C_3$ is optionally substituted by one or more substituent selected from the group consisting of ($C_{1-3}$) fluoroalkyl group, amido group (—$CONH_2$), or oxo group (═O). More preferably, said ($C_{1-3}$)fluoroalkyl group is a trifluoromethyl group.

Preferably, $C_4$ is optionally substituted by one or more substituent selected from the group consisting of fluoride atom, methyl group, cyano group, or oxo group (═O).

According to a preferred aspect of the present invention, A is a cyclic group having one of the following formulas

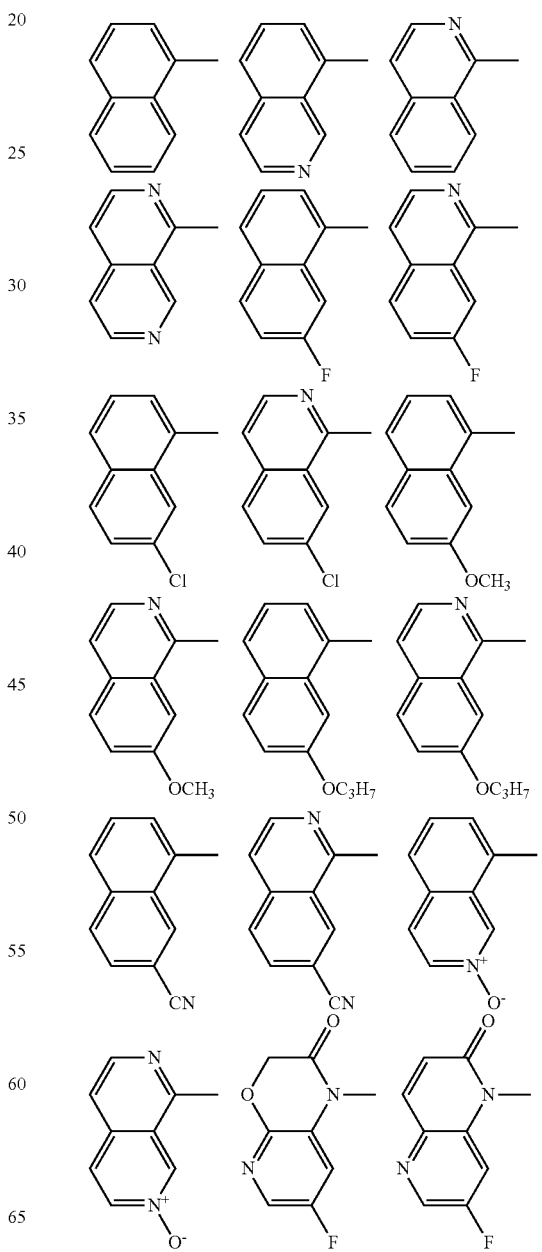

According to a preferred aspect of the present invention, Y is a ring having one of the following formulae:
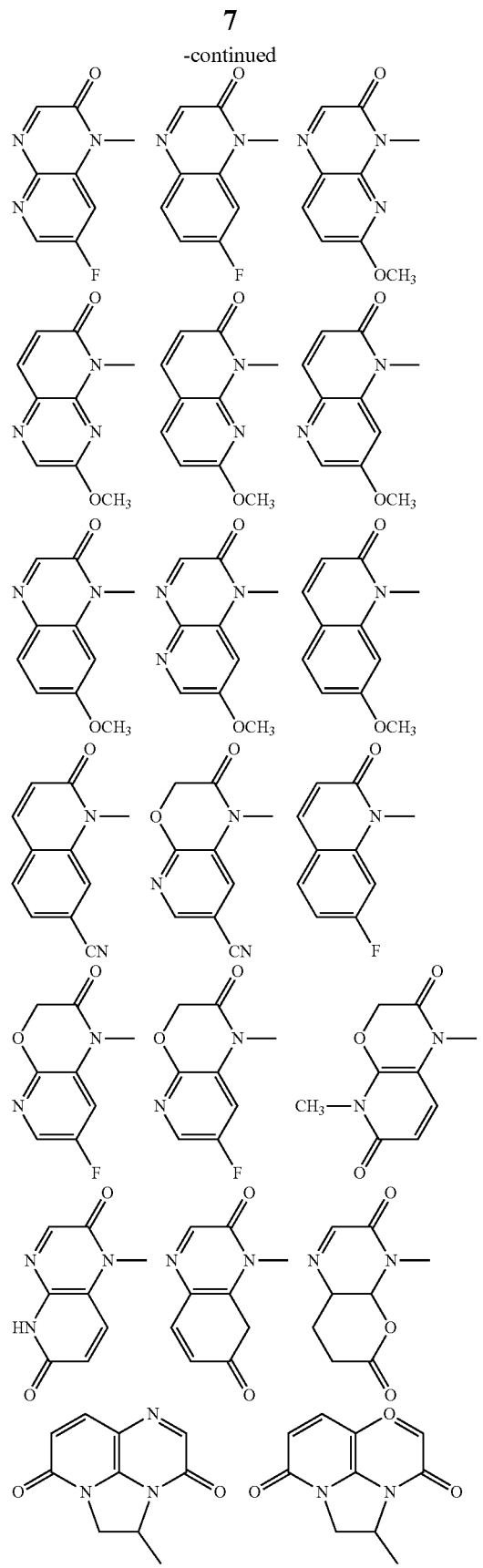
According to a preferred aspect of the present invention, B is a cyclic group having one of the following formulae:
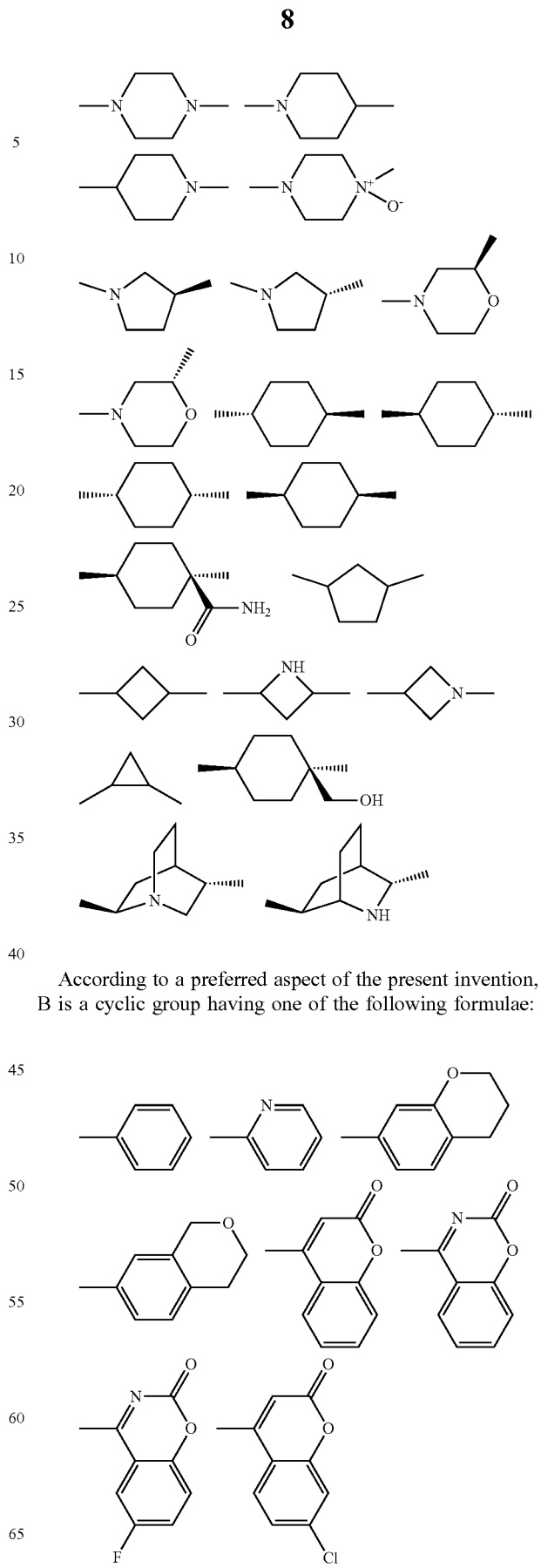

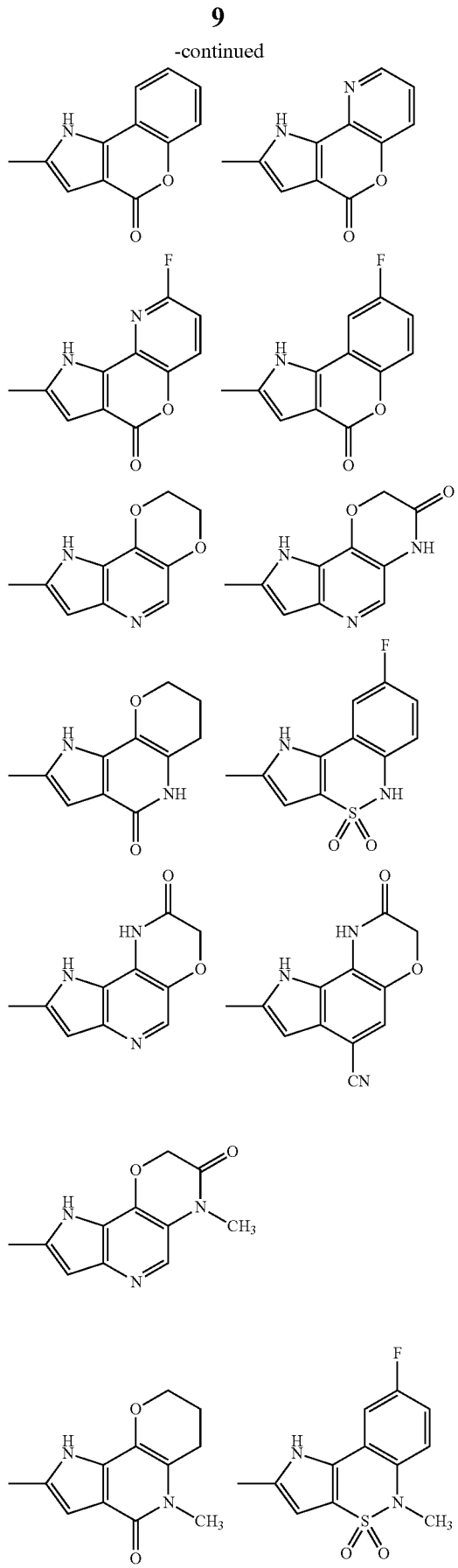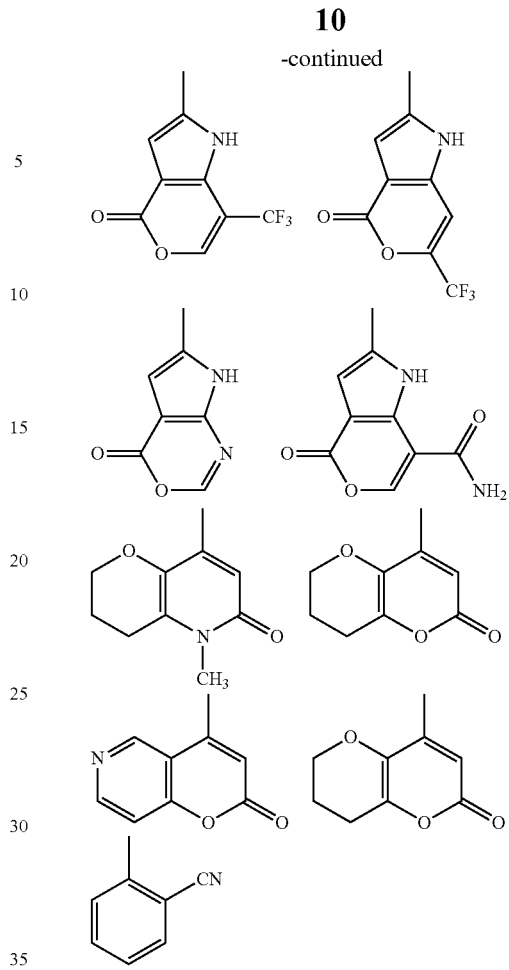

In the present description and in the following claims, the term "(C$_{1-6}$)alkyl" means a linear or branched alkyl chain comprising from 1 to 6 carbon atoms, such as for example methyl, ethyl, propyl, isopropyl, n-butyl, isobutyl, sec-butyl, tert-butyl, pentyl, isopentyl, sec-pentyl, tert-pentyl, neopentyl, 3-pentyl, hexyl, isohexyl.

In the present description and in the following claims, the term "(C$_{1-3}$)alkyl" means a linear or branched alkyl chain comprising from 1 to 3 carbon atoms, such as for example methyl, ethyl, propyl, isopropyl.

In the present description and in the following claims, the term "(C$_{1-6}$)alkylenyl" means a divalent linear or branched alkyl chain comprising from 1 to 6 carbon atoms, such as for example methylenyl (—CH$_2$—), ethylenyl (—CH$_2$CH$_2$—), propylenyl (—CH$_2$CH$_2$CH$_2$—) or butylenyl (—CH$_2$CH$_2$CH$_2$CH$_2$—).

In the present description and in the following claims, the term "(C$_{4-5}$)cycloalkylenyl" means a divalent cycloalkyl group comprising 4 or 5 carbon atoms, such as cyclobutylenyl and cyclopentylenyl.

In the present description and in the following claims, the term "(C$_{1-3}$)alkoxy" means a linear or branched alkoxy chain comprising from 1 to 3 carbon atoms, such as for example methoxy, ethoxy, propoxy, isopropoxy.

In the present description and in the following claims, the term "(C$_{1-3}$)haloalkyl" means a linear or branched haloalkyl chain comprising from 1 to 3 carbon atoms wherein one or more hydrogen atoms are substituted by a halide atom, such as for example, fluoromethyl, chloromethyl, trifluoromethyl, trichloromethyl, fluoroethyl, chloroethyl pentafluoroethyl, pentachloroethyl, fluoropropyl, chloropropyl, esafluoropropyl, and esachloroisopropyl.

Certain compounds of this invention may exist in tautomeric forms, and this invention includes all such tautomeric forms of those compounds unless otherwise specified.

Unless otherwise stated, structures depicted herein are also meant to include all stereochemical forms of the structure; i.e., the R and S configurations for each asymmetric center. Thus, single stereochemical isomers as well as enantiomeric and diastereomeric mixtures of the present compounds are within the scope of the invention. Thus, this invention encompasses each diastereomer or enantiomer substantially free of other isomers (>90%, and preferably >95%, free from other stereoisomers on a molar basis) as well as a mixture of such isomers.

Particular optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereomers by crystallization followed by liberation of the optically active bases from these salts. A different process for separation of optical isomers involves the use of a chiral chromatography column optimally chosen to maximize the separation of the enantiomers. Still another method involves synthesis of covalent diastereomers by reacting compounds of the invention with an optically pure acid in an activated form or an optically pure isocyanate. The synthesized diastereomers can be separated by conventional means such as chromatography, distillation, crystallization or sublimation, and then hydrolyzed to deliver the enantiomerically pure compound.

Optically active compounds of the invention can be obtained by using active starting materials. These isomers may be in the form of a free acid, a free base, an ester or a salt.

The compounds of this invention can exist in radiolabeled form, i.e., said compounds may contain one or more atoms containing an atomic mass or mass number different from the atomic mass or mass number ordinarily found in nature. Radioisotopes of hydrogen, carbon, phosphorous, fluorine and chlorine include $^3H$, $^{14}C$, $^{32}P$, $^{35}S$, $^{18}F$ and $^{36}Cl$, respectively. Compounds of this invention which contain those radioisotopes and/or other radioisotopes of other atoms are within the scope of this invention. Tritiated, i.e., $^3H$, and carbon-14, i.e., $^{14}C$, radioisotopes are particularly preferred for their ease of preparation and detectability.

Radiolabeled compounds of this invention can generally be prepared by methods well known to those skilled in the art. Conveniently, such radiolabeled compounds can be prepared by carrying out the procedures disclosed herein except substituting a readily available radiolabeled reagent for a non-radiolabelled reagent.

In a second embodiment, the present invention relates to a pharmaceutical composition comprising at least one compound of formula (1) as described above, a salt thereof with a pharmaceutically acceptable organic or inorganic acid or base, or an enantiomer thereof, or a N-oxide thereof, or a quaternary ammonium salt thereof, and at least one pharmaceutically acceptable excipient.

Preferably, the pharmaceutical composition of the present invention is prepared in suitable dosage forms.

Examples of suitable dosage forms are tablets, capsules, coated tablets, granules, solutions and syrups for oral administration; solutions, pomade and ointment for topical administration; medicated patches for transdermal administration; suppositories for rectal administration and injectable sterile solutions. Other suitable dosage forms are those with sustained release and those based on liposomes for oral, injectable or transdermal administration. The pharmaceutical compositions of this invention may also be administered by nasal aerosol or inhalation or delivered by implantation (e.g., surgically), such as with an implantable or indwelling device like a stent.

Other suitable dosage forms are those with sustained release and those based on liposomes for oral, injectable or transdermal administration.

The dosage forms of the pharmaceutical composition of the present invention can be prepared by techniques that are familiar to a pharmaceutical chemist, and comprise mixing, granulation, compression, dissolution, sterilization and the like.

Typically, the amount of compound of formula (1) or of the pharmaceutically acceptable quaternary ammonium salt, N-oxide and salt thereof in the pharmaceutical composition of the present invention will be between 0.01 mg to 1,500 mg, preferably between 0.1 mg and 500 mg and more preferably between 1 mg and 200 mg.

Typically, the amount of compound of formula (1) in the pharmaceutical composition of the present invention will be such to ensure a level of administration from 0.001 to 20 mg/kg/day. Preferably, the level of administration is from 0.01 to 7.5 mg/kg/day, more preferably from 0.1 to 5 mg/kg/day, and most preferably from 0.5 to 2.5 mg/kg/day.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

The pharmaceutical compositions of this invention may be administered orally, parenterally, by inhalation spray, topically, rectally, nasally, buccally, vaginally or via an implanted reservoir. The term parenteral as used herein includes subcutaneous, intracutaneous, intravenous, intramuscular, intra-articular, intrasynovial, intrasternal, intrathecal, intralesional and intracranial injection or infusion techniques.

As mentioned above, depending on the nature of the substituents, the compound of formula (1) may form addition salts with a pharmaceutically acceptable organic or inorganic acid or base.

Typical examples of suitable physiologically acceptable inorganic acids are hydrochloric acid, hydrobromic acid, sulfuric acid, phosphoric acid and nitric acid.

Typical examples of suitable physiologically acceptable organic acids are acetic acid, ascorbic acid, benzoic acid, citric acid, fumaric acid, lactic acid, maleic acid, methanesulfonic acid, oxalic acid, para-toluenesulfonic acid, benzenesulfonic acid, succinic acid, tannic acid and tartaric acid.

Typical examples of suitable physiologically acceptable inorganic bases are hydroxides, carbonates and hydrogen carbonates of ammonium, calcium, magnesium, sodium and potassium, for instance ammonium hydroxide, calcium hydroxide, magnesium carbonate, sodium hydrogen carbonate and potassium hydrogen carbonate.

Typical examples of suitable physiologically acceptable organic bases are: arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, N-methylglucamine, glucamine, glucosamine, histidine, N-(2-hydroxyethyl)-piperidine, N-(2-hydroxyethyl)pyrrolidine, isopropylamine, lysine, methylglucamine, morpholine, piperazine, piperidine, theobromine, triethylamine, trimethylamine, tripropylamine and tromethamine.

As described herein, the pharmaceutical composition of the present invention comprises a compound of the invention together with a pharmaceutically acceptable excipient, which, as used herein, includes any and all solvents, diluents, or other vehicle, dispersion or suspension aids, surface active agents, isotonic agents, thickening or emulsifying agents, preservatives, solid binders, lubricants and the like, as suited to the particular dosage form desired.

Some examples of materials which can serve as pharmaceutically acceptable excipient include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, other non-toxic compatible lubricants such as sodium lauryl sulfate and magnesium stearate, coloring agents, releasing agents, coating agents, sweetening, flavoring and perfuming agents, preservatives and antioxidants.

The terms "pharmaceutically acceptable" and "physiologically acceptable" are intended to define, without any particular limitation, any material suitable for preparing a pharmaceutical composition to be administered to a living being.

In a third embodiment, the present invention relates to the compounds of formula (1) for use in medicine.

In a fourth embodiment, the present invention relates to the compounds of formula (1) for use in the treatment of bacterial infections.

In a fifth embodiment, the present invention relates to a method for treating a bacterial infection, comprising the administration of a compound of formula (1) to a patient in need thereof.

Preferably, said bacterial infection is a skin infection, a mucosal infection, a gynaecological infection, a respiratory tract infection (RTI), a CNS infection, a gastro-intestinal infection, a bone infection, a cardiovascular infection, a sexually transmitted infection, or a urinary tract infection.

More in particular, said bacterial infection is a acute exacerbation of chronic bronchitis (ACEB), an acute otitis media, an acute sinusitis, an infection caused by drug resistant bacteria, a catheter-related sepsis, a chancroid, a chlamydia, a community-acquired pneumonia (CAP), a complicated skin and skin structure infection, an uncomplicated skin and skin structure infection, an endocarditis, a febrile neutropenia, a gonococcal cervicitis, a gonococcal urethritis, a hospital-acquired pneumonia (HAP), a osteomyelitis, a sepsis, a syphilis, a ventilator-associated pneumonia, an intraabdominal infections, a gonorrhoeae, a meningitis, a tetanus, or a tuberculosis.

Even more, said bacterial infection can be an atherosclerosis or cardiovascular disease related to infection by *Helicobacter pylori* or *Chlamydia* pneumonia; a blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, aminoglycosides, quinolones, chloramphenicol, tetracyclines and macrolides; bronchitis; catheter-related sepsis; chancroid; *chlamydia*; community-acquired pneumonia; disseminated *Mycobacterium avium* complex (MAC) disease related to infection by *Mycobacterium avium*, or *Mycobacterium intracellulare*; endocarditis; febrile neutropenia; gas gangrene related to infection by *Clostridium perfringens* or *Bacteroides* spp; gastroenteritis infection; glomerulonephritis related to infection by *Streptococcus pyogenes*, Groups C and G streptococci, *Corynebacterium diphtheriae*, or *Actinobacillus haemolyticum*; gonococcal cervicitis; gonococcal urethritis; gynaecological infection; hospital-acquired pneumonia (HAP); infection caused by drug resistant bacteria; infections caused by *Mycobacterium tuberculosis, M. leprae, M. paratuberculosis, M. kansasii*, or *M. chelonei*; intestinal protozoa related to infection by *Cryptosporidium* spp; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. injluenzae*, or *Listeria* spp.; mastoiditis related to infection by *Streptococcus pneumoniae, Haemophilus injluenzae, Moraxella catarrhalis Staphylococcus aureus, Enterococcus faecalis, E. faecium, E. casseliflavus, S. epidermidis, S. haemolyticus*, or *Peptostreptococcus* spp; odontogenic infection related to infection by *viridans* streptococci; osteomyelitis; otitis media; persistent cough related to infection by *Bordetella pertussis*; pharyngitis; puerperal fever related to infection by *Staphylococcus aureus*, coagulase-negative staphylococci *Streptococcus pyogenes, Streptococcus agalactiae*, Streptococcal groups C-F (minute colony streptococci), *viridans* streptococci *Corynebacterium minutissimum, Clostridium* spp., or *Bartonella henselae*; respiratory tract infections related to infection by *Mycoplasma pneumoniae, Legionella pneumophila, Streptococcus pneumoniae, Haemophilus injluenzae*, or *Chlamydia pneumoniae*; rheumatic fever; sepsis; sexually transmitted diseases related to infection by *Chlamydia trachomatis, Haemophilus ducreyi, Treponema pallidum, Ureaplasma urealyticum*, or *Neiseria gonorrhoeae*; sinusitis; syphilis; systemic febrile syndromes related to infection by *Borrelia recurrentis*; tonsillitis; toxin diseases related to infection by *S. aureus* (food poisoning and toxic shock syndrome), or Groups A, B, and C streptococci; ulcers related to infection by *Helicobacter pylori*; uncomplicated acute urinary tract infections related to infection by *Staphylococcus aureus* coagulase-negative staphylococcal species, or *Enterococcus* spp; uncomplicated skin and soft tissue infections and abscesses; urethritis and cervicitis; urinary tract infection; central nervous system infections; device related infections caused by staphylococci; muscoleskeletal infection caused by staphylococci; Shiga toxin-producing *E. coli; Haemophilus influenzae* (invasive disease); legionellosis; psittacosis/ornithosis *chlamydia psittaci; salmonellosis* caused by *salmonella* spp; shigellosis by *shigella* spp; streptococcal toxic shock syndrome; staphylococcal toxic shock syndrome; and typhoid fever caused by *Salmonella typhi*.

The bacterial infection can be an infection caused by *Acinetobacter* spp, *Bacteroides* spp, *Burkholderia* spp, *Campylobacter* spp, *Chlamydia* spp, *Chlamydophila* spp, *Clostridium* spp, *Enterobacter* spp, *Enterococcus* spp, *Escherichia* spp, *Gardnerella* spp, *Haemophilus* spp, *Helicobacter* spp, *Klebsiella* spp, *Legionella* spp, *Moraxella* spp, *Morganella* spp, *Mycoplasma* spp, *Neisseria* spp, *Peptostreptococcus* spp, *Proteus* spp, *Pseudomonas* spp, *Salmonella* spp, *Serratia* spp, *Staphylococcus* spp, *Streptococcus* spp, *Stenotrophomonas* spp, *Ureaplasma* spp, aerobes, obligate anaerobes, facultative anaerobes, gram-positive bacteria, gram-negative bacteria, gram-variable bacteria, and atypical respiratory pathogens.

More in particular, the bacterial infection can be an infection caused by *Acinetobacter baumanii, Acinetobacter haemolyticus, Acinetobacter junii, Acinetobacter johnsonii, Acinetobacter lwoffi, Bacteroides bivius, Bacteroides fragilis, Burkholderia cepacia, Campylobacter jejuni, Chlamydia pneumoniae, Chlamydia urealyticus, Chlamydophila pneumoniae, Clostridium difficile, Enterobacter aerogenes, Enterobacter cloacae, Enterococcus faecalis, Enterococcus faecium, Escherichia coli, Gardnerella vaginalis, Haemophilus parainfluenzae, Haemophilus influenzae, Helicobacter pylori, Klebsiella pneumoniae, Legionella pneumophila*, Methicillin-resistant *Staphylococcus aureus*, Methicillin-susceptible *Staphylococcus aureus, Moraxella catarrhalis, Morganella morganii, Mycoplasma pneumoniae, Neisseria gonorrhoeae*, Penicillin-resistant *Streptococcus pneumoniae*, Penicillin-susceptible *Streptococcus pneumoniae, Peptostreptococcus magnus, Peptostreptococcus micros, Peptostreptococcus anaerobius, Peptostreptococcus asaccharolyticus, Peptostreptococcus prevotii, Peptostreptococcus tetradius, Peptostreptococcus vaginalis, Proteus mirabilis, Pseudomonas aeruginosa*, Quinolone-Resistant *Staphylococcus aureus*, Quinolone-Resistant *Staphylococcus epidermis, Salmonella typhi, Salmonella paratyphi, Salmonella enteritidis, Salmonella typhimurium, Serratia marcescens, Staphylococcus aureus, Staphylococcus epidermidis, Staphylococcus saprophyticus, Streptococcus agalactiae, Streptococcus pneumoniae, Streptococcus pyogenes, Stenotrophomonas maltophilia, Ureaplasma urealyticum*, Vancomycin-Resistant *Enterococcus faecium*, Vancomycin-Resistant *Enterococcus faecalis*, Vancomycin-Resistant *Staphylococcus aureus*, and Vancomycin-Resistant *Staphylococcus epidermis*.

Examples of compounds according to the present invention are provided in the following Table 1.

TABLE 1

| No. | A | L₁ | Y | L₂ | R | B |
|---|---|---|---|---|---|---|
| 157 | isoquinoline (N at 1,6-positions) | σ bond | piperazine | CH₂CH(OH)CH₂-NH- | σ bond | 6-fluoro-4-methyl-2H-benzo[d][1,3]oxazin-2-one |
| 160 | 7-fluoroisoquinoline | σ bond | piperidine | —NH—CH₂— | 2,4-dimethylimidazole | 2-pyridyl |
| 164 | isoquinoline N-oxide | σ bond | piperazine | (S)-CH₂CH(OH)CH₂-NH- | σ bond | 6-fluoro-4-methyl-2H-benzo[d][1,3]oxazin-2-one |
| 165 | isoquinoline | σ bond | N-methylpiperazine N-oxide | CH₂CH(OH)CH₂-NH- | σ bond | 6-fluoro-4-methyl-2H-benzo[d][1,3]oxazin-2-one |

TABLE 1-continued

| No. | A | L₁ | Y | L₂ | R | B |
|---|---|---|---|---|---|---|
| 180 | 6-fluoroisoquinolin-1-yl | σ bond | (S)-1,3-dimethylpyrrolidin-3-yl | —CH₂—NH—CH₂— | σ bond | 2-methyl-4-oxo-1,4-dihydrochromeno[4,3-b]pyrrole |
| 181 | 6-fluoroisoquinolin-1-yl | σ bond | (R)-1,3-dimethylpyrrolidin-3-yl | —CH₂—NH—CH₂— | σ bond | 2-methyl-4-oxo-1,4-dihydrochromeno[4,3-b]pyrrole |
| 182 | 6-fluoroisoquinolin-1-yl | σ bond | (S)-2,4-dimethylmorpholin-2-yl | —CH₂—NH—CH₂— | σ bond | 2-methyl-4-oxo-1,4-dihydrochromeno[4,3-b]pyrrole |
| 183 | 6-fluoroisoquinolin-1-yl | σ bond | (R)-2,4-dimethylmorpholin-2-yl | —CH₂—NH—CH₂— | σ bond | 2-methyl-4-oxo-1,4-dihydrochromeno[4,3-b]pyrrole |
| 193 | 6-fluoro-4-methyl-2H-pyrido[3,2-b][1,4]oxazin-3(4H)-one | σ bond | trans-1,4-cyclohexylene | —NH—CH₂— | σ bond | 8-fluoro-2-methyl-4-oxo-1,4-dihydrochromeno[4,3-b]pyrrole |
| 194 | 6-fluoro-4-methyl-2H-pyrido[3,2-b][1,4]oxazin-3(4H)-one | σ bond | 1-methylpiperidin-4-yl | —CH₂—CH₂— | σ bond | 8-fluoro-2-methyl-4-oxo-1,4-dihydrochromeno[4,3-b]pyrrole |

TABLE 1-continued
| No. | A | L₁ | Y | L₂ | R | B |
|---|---|---|---|---|---|---|
| 197 | 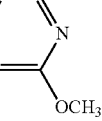 | σ bond |  | —CH₂—CH₂— | σ bond | 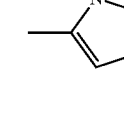 |
| 200 | 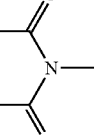 | σ bond | 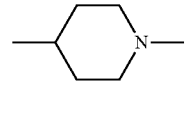 | —CH₂—CH₂— | σ bond | 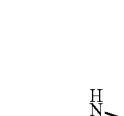 |
| 201 | 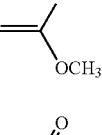 | σ bond | 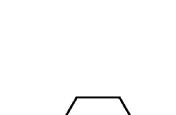 | —NH—CH₂— | σ bond |  |
| 202 | 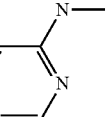 | σ bond |  | —CH₂—CH₂— | σ bond | 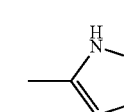 |
| 204 | 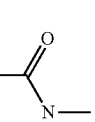 | σ bond | 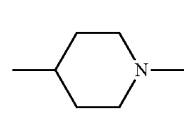 | —NH—CH₂— | σ bond |  |
| 205 | 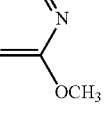 | σ bond |  | —NH—CH₂— | σ bond | 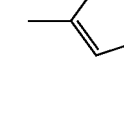 |

TABLE 1-continued
| No. | A | L₁ | Y | L₂ | R | B |
|---|---|---|---|---|---|---|
| 206 | 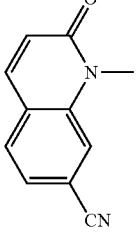 | σ bond |  | —NH—CH₂— | σ bond | 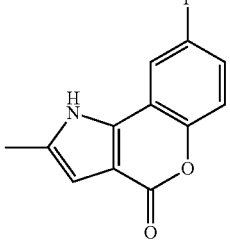 |
| 207 | 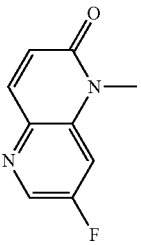 | σ bond | 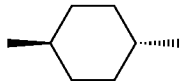 | —NH—CH₂— | σ bond | 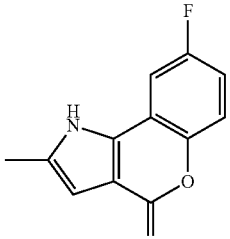 |
| 208 | 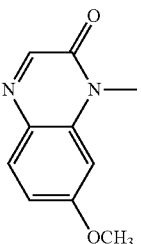 | σ bond |  | —NH—CH₂— | σ bond | 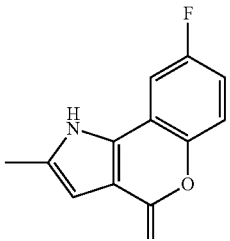 |
| 209 | 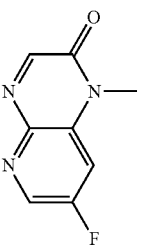 | σ bond |  | —NH—CH₂— | σ bond | 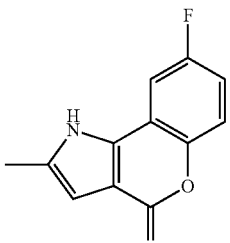 |
| 210 | 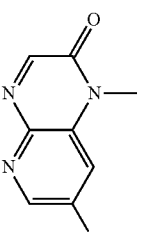 | σ bond |  | —NH—CH₂— | σ bond | 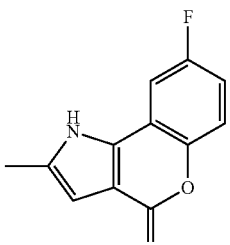 |
| 211 | 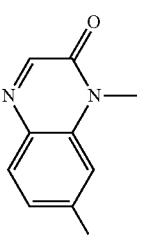 | σ bond |  | —NH—CH₂— | σ bond | 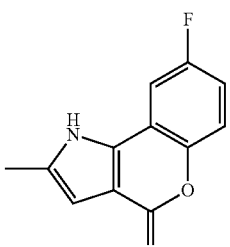 |

TABLE 1-continued

| No. | A | L₁ | Y | L₂ | R | B |
|---|---|---|---|---|---|---|
| 212 | pyrido-pyrazinone with OCH₃ | σ bond | trans-cyclohexyl | —NH—CH₂— | σ bond | fluoro pyrrolo-chromenone |
| 213 | pyrido-pyrazinone with OCH₃ | σ bond | cis-cyclohexyl | —NH—CH₂— | σ bond | fluoro pyrrolo-chromenone |
| 214 | pyrido-oxazinone with CN | σ bond | trans-cyclohexyl | —NH—CH₂— | σ bond | fluoro pyrrolo-chromenone |
| 215 | pyrido-oxazinone with CN | σ bond | trans-cyclohexyl | —NH—CH₂— | σ bond | fluoro pyrrolo-chromenone |
| 216 | quinolinone with F | σ bond | trans-cyclohexyl | —NH—CH₂— | σ bond | fluoro pyrrolo-chromenone |
| 217 | pyrido-oxazinone with F | σ bond | cyclohexyl with CONH₂ | —NH—CH₂— | σ bond | fluoro pyrrolo-chromenone |

TABLE 1-continued
| No. | A | L₁ | Y | L₂ | R | B |
|---|---|---|---|---|---|---|
| 219 | 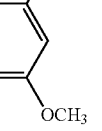 | σ bond |  | —NH—CH₂— | σ bond | 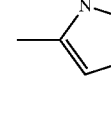 |
| 220 | 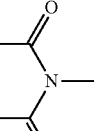 | σ bond | 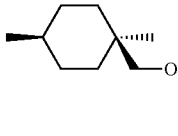 | —NH—CH₂— | σ bond |  |
| 221 | 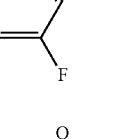 | σ bond |  | 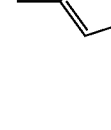 | σ bond | 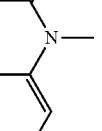 |
| 301 | 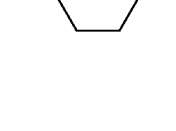 | σ bond | 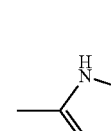 | —NH—CH₂— | σ bond | 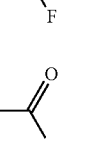 |
| 302 | 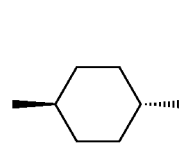 | σ bond |  | —NH—CH₂— | σ bond | 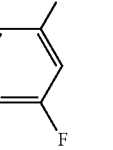 |
| 303 |  | σ bond |  |  | σ bond |  |

TABLE 1-continued
| No. | A | L₁ | Y | L₂ | R | B |
|---|---|---|---|---|---|---|
| 304 | 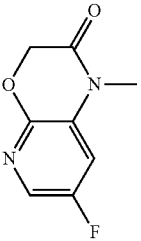 | σ bond | 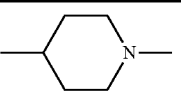 | 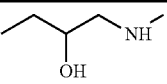 | σ bond | 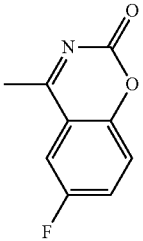 |
| 305 | 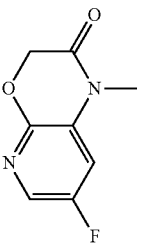 | σ bond | 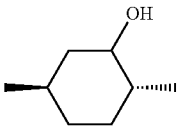 | —NH—CH₂— | σ bond | 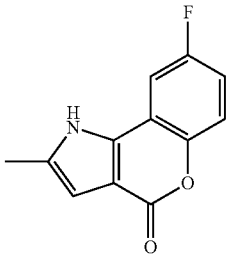 |
| 306 | 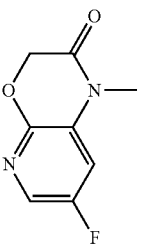 | σ bond | 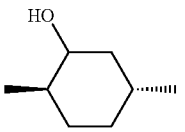 | —NH—CH₂— | σ bond | 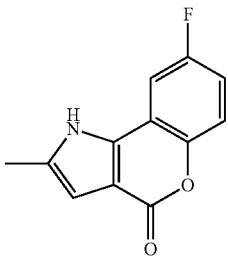 |
| 307 | 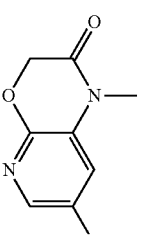 | σ bond | 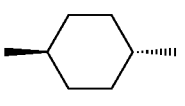 | 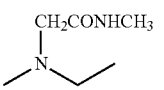 | σ bond | 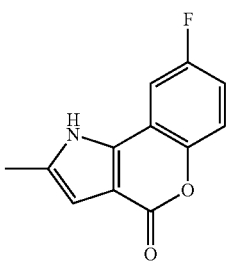 |
| 308 | 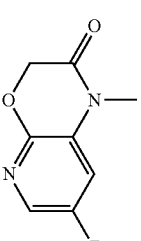 | σ bond | 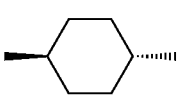 | 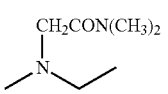 | σ bond | 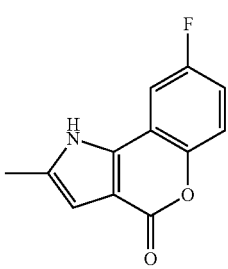 |
| 309 | 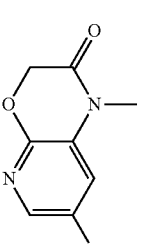 | σ bond | 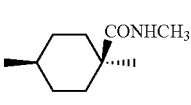 | —NH—CH₂— | σ bond | 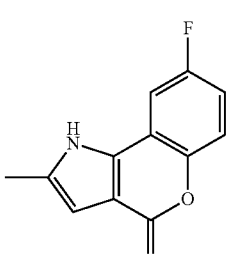 |

TABLE 1-continued

| No. | A | L₁ | Y | L₂ | R | B |
|---|---|---|---|---|---|---|
| 310 | (pyrido-oxazinone with F) | σ bond | cyclohexyl-CON(CH₃)₂ | —NH—CH₂— | σ bond | (fluoro pyrrolo-chromenone) |
| 311 | (pyrido-oxazinone with F) | σ bond | cyclobutyl | —CH₂—NH—CH₂— | σ bond | (fluoro pyrrolo-chromenone) |
| 312 | (pyrido-pyrazinone with F) | σ bond | piperidinyl | CH₂CH(OH)CH₂NHCH₃ (butyl with OH and NH) | σ bond | (fluoro methylcoumarin) |
| 313 | (pyrido-oxazinone with F) | σ bond | cyclopropyl | —CH₂—NH—CH₂— | σ bond | (fluoro pyrrolo-chromenone) |
| 314 | (pyrido-oxazinone with F) | σ bond | cyclohexyl | —NH—CH₂— | σ bond | (pyrrolo-dioxino-pyridine) |
| 315 | (pyrido-oxazinone with F) | σ bond | cyclohexyl | —NH—CH₂— | σ bond | (pyrrolo-pyrido-oxazinone) |

TABLE 1-continued
| No. | A | L₁ | Y | L₂ | R | B |
|---|---|---|---|---|---|---|
| 316 | 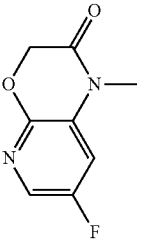 | σ bond |  | —NH—CH₂— |  | 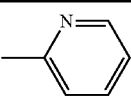 |
| 317 | 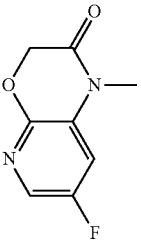 | —CH₂— | 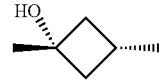 | —NH—CH₂— | σ bond | 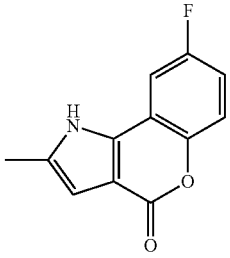 |
| 318 | 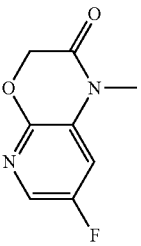 | 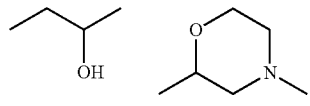 | 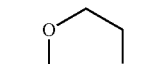 | —CH₂— | σ bond | 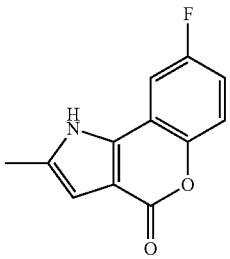 |
| 319 | 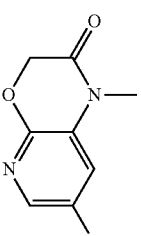 | σ bond | 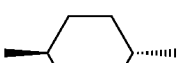 | —NH—CH₂— | σ bond | 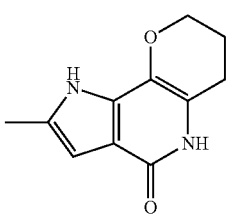 |
| 320 | 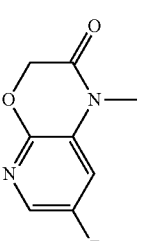 | σ bond | 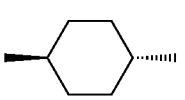 | —NH—CH₂— | σ bond | 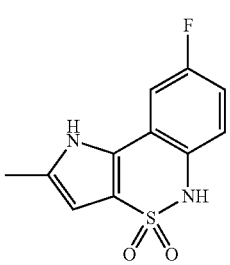 |
| 321 | 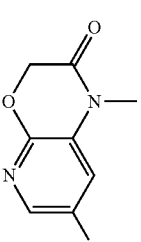 | —CH₂— |  | —CH₂— | σ bond | 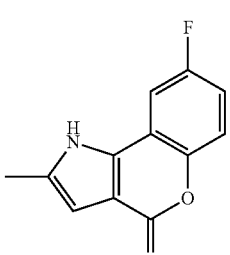 |

TABLE 1-continued
| No. | A | L₁ | Y | L₂ | R | B |
|---|---|---|---|---|---|---|
| 322 | 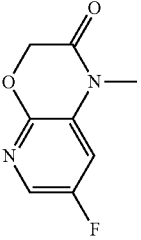 | σ bond |  | —NH—(CH₂)₂—NH— | σ bond | 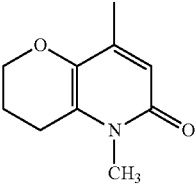 |
| 323 | 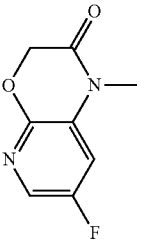 | σ bond |  | 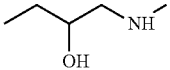 | σ bond | 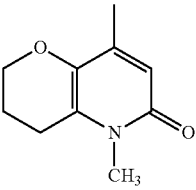 |
| 324 | 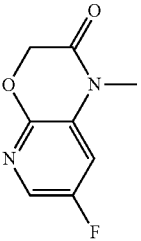 | σ bond |  | —NH—CH₂— | σ bond | 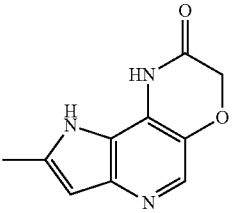 |
| 325 | 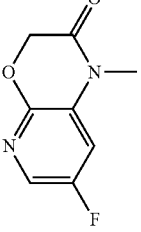 | σ bond |  | —NH—CH₂— | σ bond | 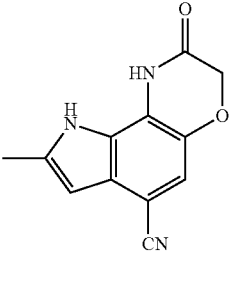 |
| 326 | 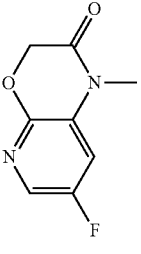 | σ bond | 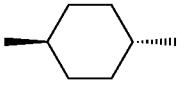 | —NH—CH₂— |  | 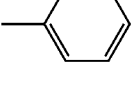 |
| 327 | 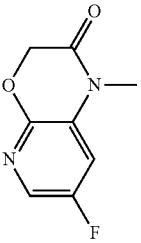 | 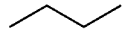 | 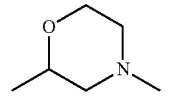 | —CH₂— | σ bond | 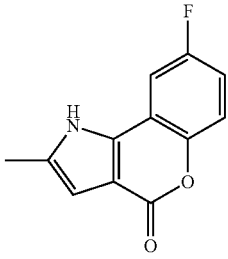 |

TABLE 1-continued

| No. | A | L₁ | Y | L₂ | R | B |
|-----|---|----|----|----|----|---|
| 328 | pyrido-oxazinone with F | butyl chain | 2,5-dimethylmorpholine (NH) | σ bond | σ bond | fluoro pyrrolo-chromenone |
| 329 | pyrido-oxazinone with F | butyl chain | 2,5-dimethylmorpholine (O) | σ bond | σ bond | fluoro pyrrolo-chromenone |
| 330 | pyrido-oxazinone with F | σ bond | trans-cyclohexyl | —NH—CH₂— | σ bond | pyrrolo-pyrido-oxazinone N-CH₃ |
| 331 | pyrido-oxazinone with F | σ bond | trans-cyclohexyl | —NH—CH₂— | σ bond | pyrrolo-pyrano-pyridinone N-CH₃ |
| 332 | pyrido-oxazinone with F | σ bond | trans-cyclohexyl | —NH—CH₂— | σ bond | fluoro pyrrolo-benzothiazine dioxide N-CH₃ |
| 333 | pyrido-oxazinone with F | σ bond | 4-methylpiperidine | —CH₂—CH₂— | σ bond | pyrrolo-pyranone CF₃ |

TABLE 1-continued

| No. | A | L₁ | Y | L₂ | R | B |
|---|---|---|---|---|---|---|
| 334 | [fluoro-pyrido-oxazinone] | σ bond | [piperidine] | —CH₂—CH₂— | σ bond | [methyl-pyrrolo-pyranone with CF₃] |
| 335 | [fluoro-pyrido-oxazinone] | σ bond | [piperidine] | —CH₂—CH₂— | σ bond | [methyl-pyrrolo-oxazinone] |
| 336 | [fluoro-pyrido-oxazinone] | σ bond | [piperidine] | —CH₂—CH₂— | σ bond | [methyl-pyrrolo-pyranone carboxamide] |
| 337 | [fluoro-pyrido-oxazinone] | σ bond | [piperidine] | —CH₂—CH₂— | [dimethyl-triazole] | [o-tolunitrile] |
| 338 | [fluoro-pyrido-oxazinone] | σ bond | [piperidine] | —CH₂—CH₂— | [dimethyl-triazole] | [methyl-pyridine] |
| 339 | [N-methyl pyrido-oxazine-dione] | σ bond | [cyclohexane] | —NH—CH₂— | σ bond | [fluoro-methyl-pyrrolo-chromenone] |

TABLE 1-continued

| No. | A | L₁ | Y | L₂ | R | B |
|---|---|---|---|---|---|---|
| 340 | (structure) | —CH₂— | piperazine | —CH₂— | σ bond | (fluoro-pyrrolo-chromenone) |
| 341 | (structure) | —CH₂— | morpholine (with NH) | —CH₂— | σ bond | (fluoro-pyrrolo-chromenone) |
| 342 | (structure) | —CH₂— | piperidine | —NH— | σ bond | (fluoro-pyrrolo-chromenone) |
| 343 | (structure) | —CH₂— | piperidine | (OH, NH) | σ bond | (fluoro-methylchromenone) |
| 344 | (structure) | —CH₂— | piperidine | (OH, NH) | σ bond | (fluoro-methyl-benzoxazinone) |
| 345 | (structure) | —CH₂— | azetidine | (OH, NH) | σ bond | (fluoro-methylchromenone) |

TABLE 1-continued
| No. | A | L$_1$ | Y | L$_2$ | R | B |
|---|---|---|---|---|---|---|
| 347 |  | —CH$_2$— |  |  | σ bond | 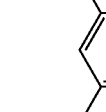 |
| 348 | 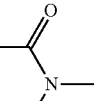 | σ bond | 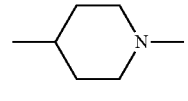 | 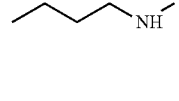 | σ bond | 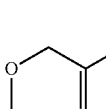 |
| 349 | 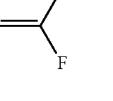 | σ bond |  |  | σ bond |  |
| 350 | 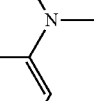 | σ bond | 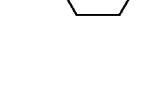 |  | σ bond | 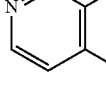 |
| 351 | 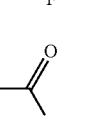 | σ bond | 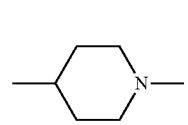 | 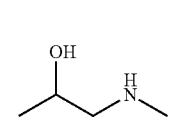 | σ bond |  |
| 352 | 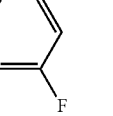 | σ bond |  |  | σ bond |  |

TABLE 1-continued

| No. | A | L₁ | Y | L₂ | R | B |
|---|---|---|---|---|---|---|
| 354 | (structure) | σ bond | (cyclohexyl) | NH-CH₂CH₂-NH | σ bond | (structure) |

The above compounds can be prepared as explained in the synthetic examples below.

The man skilled in the art has a well-established literature of heterocyclic and other relevant chemical transformations, recovery and purification technologies to draw upon, in combination with the information contained in the examples which follow, for guidance on synthetic strategies, protecting groups, and other materials and methods useful for the synthesis, recovery and characterization of the compounds of this invention, including compounds containing the various choices for A, L₁, Y, L₂, R and B.

Various synthetic approaches may be used to produce the compounds described herein, including those approaches depicted schematically below. The man skilled in the art will appreciate that protecting groups may be used in these approaches. "Protecting groups", are moieties that are used to temporarily block chemical reaction at a potentially reactive site (e.g., an amine, hydroxy, thiol, aldehyde, etc.) so that a reaction can be carried out selectively at another site in a multifunctional compound. In preferred embodiments, a protecting group reacts selectively in good yield to give a protected substrate that is suitable for the planned reactions; the protecting group should be selectively removable in good yield by readily available, preferably nontoxic reagents that do not unduly attack the other functional groups present; the protecting group preferably forms an readily separable derivative (more preferably without the generation of new stereogenic centers); and the protecting group preferably has a minimum of additional functionality to avoid the complication of further sites of reaction. A wide variety of protecting groups and strategies, reagents and conditions for deploying and removing them are known in the art.

Also, one may chose reagents enriched for a desired isotope, e.g. tritium in place of hydrogen, to create compounds of this invention containing such isotope(s). Compounds containing tritium in place of hydrogen in one or more locations, or containing various isotopes of C, N, P and O, are encompassed by this invention and may be used, for instance, for studying metabolism and/or tissue distribution of the compounds or to alter the rate or path of metabolism or other aspects of biological functioning.

The compounds of the this invention can be synthesized using the methods described below, together with synthetic methods known in the art of synthetic organic chemistry, or by a variation thereon as appreciated by those skilled in the art. Preferred methods include, but are not limited to those described below. The reactions are performed in a solvent appropriate to the reagents and materials employed and suitable for the transformation being effected. It will be understood by those skilled in the art of organic synthesis that the functionality present on the molecule should be consistent the transformations proposed. This will sometimes required some judgment to modify the order of the synthetic steps or to select one particular process scheme over another in order to obtain a desired compound of the invention.

A compound of the present invention could be prepared as outlined in the synthetic pathways described hereinafter and via standard methods known to those skilled in the art.

EXAMPLES

List of the abbreviations used in the synthetic pathways described hereinafter:
Boc: tert-butyl carbamate
cHex cyclohexane
CV column volume
DBU: 1,5-diazabiciclo[5.4.0]undec-5-ene
DCM: dichloromethane
DIPEA N,N-diisopropylethylamine
DME: 1,2-dimethoxyethane
DMF: N,N-dimethylformamide
Et₂O: diethyl ether
EtOAc: ethylacetate
MS: mass spectroscopy
TEA: triethylamine
TFA: trifluoroacetic acid
THF: tetrahydrofuran
Pd/C: palladium on activated charcoal
Pd(OH)₂/C: palladium hydroxide on activated charcoal
r.t.: room temperature
UPLC: Ultra High Performance Liquid Chromatography
Preparation of Compound 157
Compound 157 was prepared as described herein below.

Step 1—Synthesis of methyl 5-fluoro-2-hydroxybenzoate

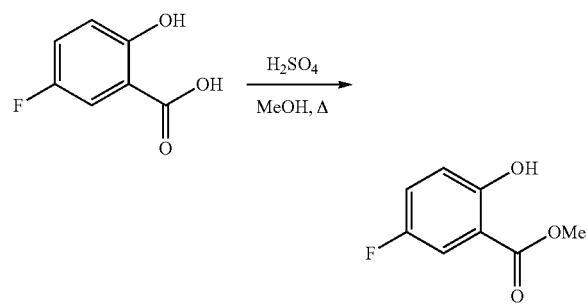

To a stirred solution of 5-fluoro salicylic acid (25 g, 160 mmol) in MeOH (250 mL), conc. sulfuric acid (20 mL) was added slowly at 0° C. The resulting reaction mixture was refluxed for 48 h then was concentrated under reduced pressure and the resulting crude was basified to pH 8.0 with sat. NaHCO₃. The mixture was neutralized by 1.5 N HCl solution and extracted with EtOAc. The organic layer was dried over anhydrous Na₂SO₄ and concentrated to afford methyl 5-fluoro-2-hydroxybenzoate as a light brown liquid (22.8 g, 83% yield). GC-MS (AcqMethod HP-1MS.M): 170.1 (M). ¹H NMR (400 MHz, DMSO-d6): δ ppm 10.29 (s, 1H), 7.51-7.49 (m, 1H), 7.42-7.41 (m, 1H), 7.03-7.01 (m, 1H), 3.89 (s, 3H).

Step 2—Synthesis of 5-fluoro-2-hydroxybenzamide

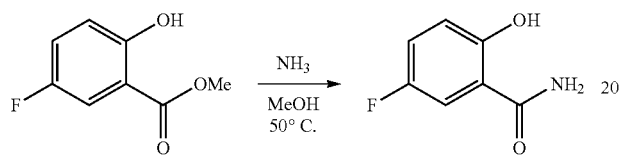

A mixture of methyl 5-fluoro-2-hydroxybenzoate (22 g, 129 mmol) and methanolic ammonia (250 mL) was heated at 50° C. in an autoclave for 10 h. The reaction mixture was concentrated under reduced pressure, the resulting crude was codistilled with toluene and dried to give 5-fluoro-2-hydroxybenzamide as a brown solid (18.5 g, 92% yield). LC-MS m/z: 154.0 (M−H⁺). ¹H NMR (400 MHz, DMSO-d6): δ ppm 12.74 (s, 1H), 8.40 (s, 1H), 8.03 (s, 1H), 7.73-7.71 (m, 1H), 7.31-7.29 (m, 1H), 6.91-6.90 (m, 1H).

Step 3—Synthesis of 6-fluoro-2H-1,3-benzoxazine-2,4(3H)-dione

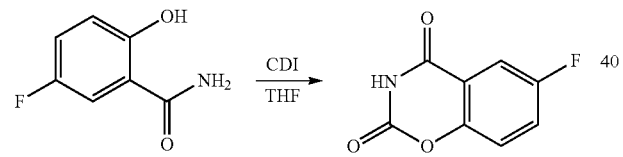

To a stirred solution of 5-fluoro-2-hydroxybenzamide (8.0 g, 51.6 mmol) in dry THF (80 mL), 1,1'-carbonyldiimidazole (10.9 g, 67.09 mmol) was added at 0° C. The mixture was stirred at room temperature for 14 h then was concentrated under reduced pressure. The resulting crude was treated with MeOH and washed with diethyl ether. The resulting white solid was dried and used in the next step without further purification (5.1 g, 55% yield, white solid). LC-MS m/z: 180.0 (M−H⁺). ¹H NMR (400 MHz, DMSO-d6): δ ppm 12.19 (s, 1H), 7.68-7.67 (m, 2H), 7.50-7.48 (m, 1H).

Step 4—Synthesis of 4-chloro-6-fluoro-2H-1,3-benzoxazin-2-one

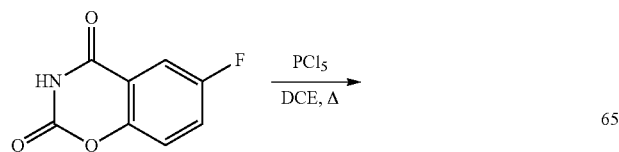

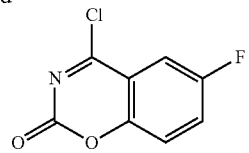

To a stirred solution of 6-fluoro-2H-1,3-benzoxazine-2,4 (3H)-dione (0.5 g, 2.76 mmol) in dry 1,2-dichloroethane (2.5 mL), phosphorous pentachloride (0.69 g, 3.31 mmol) was added at 0° C. The resulting mixture was refluxed for 6 h then was concentrated under reduced pressure. DCM (15 mL) was added to the resulting crude, washed with water (2 mL) and dried over anhydrous Na₂SO₄. The solvent was concentrated under reduced pressure to afford 4-chloro-6-fluoro-2H-1,3-benzoxazin-2-one as an off-white solid (0.46 g, 84% yield). ¹H NMR (400 MHz, DMSO-d6): δ ppm 7.69-7.67 (m, 2H), 7.50-7.49 (m, 1H).

Step 5—Synthesis of tert-butyl 4-(3-chloro-2-hydroxypropyl)piperazine-1-carboxylate

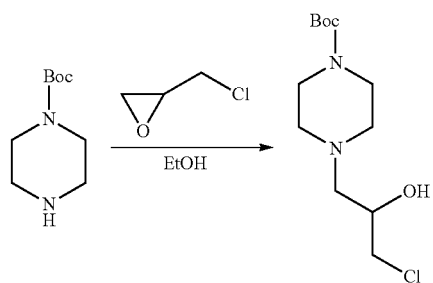

To a solution of tert-butyl piperazine-1-carboxylate (6.0 g, 32.2 mmol) in ethanol (100 mL), epichlorohydrine (14.8 g, 161.0 mmol) was added and the solution was stirred for 15 h at room temperature. After completion of the reaction, the mixture was concentrated under reduced pressure and the resulting crude product (colorless thick liquid, 8.9 g, 99% yield) was used as such in the following step. LC-MS m/z: 279.2 (M+1). ¹HNMR (400 MHz, DMSO-d6): δ 1.40 (s, 9H), 2.27-2.42 (m, 6H), 3.21-3.32 (m, 4H), 3.52-3.56 (m, 1H), 3.62-3.67 (m, 1H), 3.79-3.89 (m, 1H), 5.04 (d, J=4.9 Hz, 1H).

Step 6—Synthesis of tert-butyl 4-(3-azido-2-hydroxypropyl)piperazine-1-carboxylate

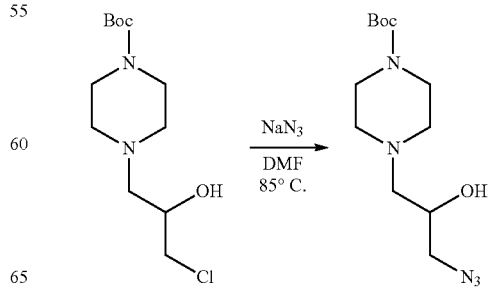

To a solution of tert-butyl 4-(3-chloro-2-hydroxypropyl) piperazine-1-carboxylate (8.9 g, 32 mmol) in DMF (80 mL) sodium azide (3.12 g, 48 mmol) was added. The mixture was stirred at 85° C. for 5 h then was diluted with ethyl acetate (300 mL) and washed with water. The organic layer was dried over sodium sulfate and concentrated under reduced pressure. The resulting crude was purified on silica gel (60-120 mesh) column chromatography (0-10% methanol in dichloromethane) to obtain tert-butyl 4-(3-azido-2-hydroxypropyl)piperazine-1-carboxylate (8.2 g, 89% yield) as a pale yellow thick liquid. LC-MS: 286.2 (M+1). $^1$HNMR (400 MHz, DMSO-d6): δ 1.40 (s, 9H), 2.29-2.42 (m, 6H), 3.15-3.20 (m, 1H), 3.24-3.32 (m, 5H), 3.79-3.82 (m, 1H), 5.04 (d, J=4.9 Hz, 1H).

Step 7—Synthesis of tert-butyl 4-(3-amino-2-hydroxypropyl) piperazine-1-carboxylate

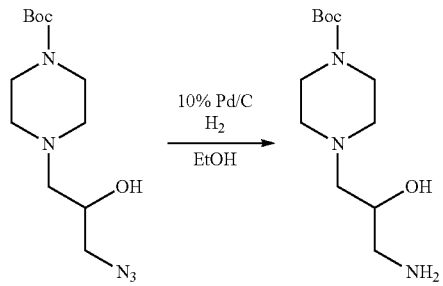 [SMILES: "EtOH" ; CC(C)(C)OC(=O)N1CCN(CC(O)CN=[N+]=[N-])CC1 ; "10% Pd/CH2" ; CC(C)(C)OC(=O)N1CCN(CC(O)CN)CC1]

To a solution of tert-butyl 4-(3-azido-2-hydroxypropyl) piperazine-1-carboxylate (1.5 g, 5.2 mmol) in ethanol (40 mL), 10% palladium on carbon (0.15 g) was added and the mixture was stirred under hydrogen atmosphere at room temperature for 3 h. The reaction mixture was filtered through a celite bed and the filtrate was concentrated under reduced pressure to obtain tert-butyl 4-(3-amino-2-hydroxypropyl) piperazine-1-carboxylate (1.25 g, 85% yield) as a pale yellow color solid. LC-MS m/z: 260.6 (M+1). $^1$HNMR (300 MHz, DMSO-d6): δ 1.39 (s, 9H), 2.22-2.43 (m, 8H), 2.58-2.66 (m, 2H), 3.48-3.52 (m, 4H), 3.88-3.90 (m, 1H).

Step 8—Synthesis of tert-butyl 4-(3-((6-fluoro-2-oxo-2H-benzo[e][1,3]oxazin-4-yl)amino)-2-hydroxypropyl)piperazine-1-carboxylate

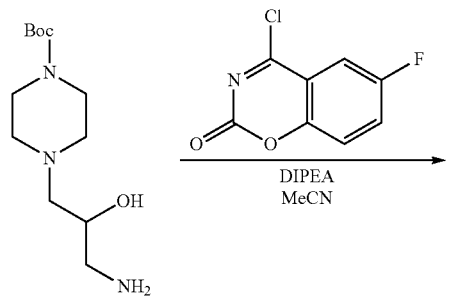

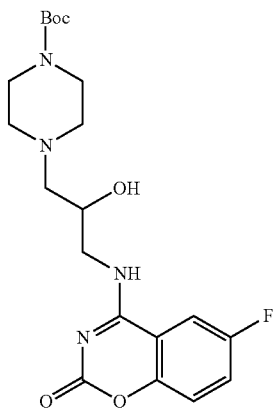

To a stirred solution of 4-chloro-6-fluoro-2H-benzo[e][1,3]oxazin-2-one (0.89 g, 4.5 mmol) and DIPEA (2.9 g, 22.5 mmol) in acetonitrile (50 mL), tert-butyl 4-(3-amino-2-hydroxypropyl)piperazine-1-carboxylate (1.39 g, 5.4 mmol) was added at room temperature. The mixture was stirred at the same temperature overnight. The solid was filtered, washed with water and dried. The crude product was purified on silica gel column chromatography (0-20% methanol in dichloromethane) to obtain the title compound (0.4 g, 21% yield) as an off-white solid. LC-MS m/z: 423.2 (M+1). $^1$HNMR (300 MHz, DMSO-d6): δ 1.38 (s, 9H), 2.27-2.50 (m, 6H), 3.28-3.39 (m, 4H), 3.66-3.71 (m, 1H), 3.98 (br. S, 1H), 4.97 (br s, 1H), 7.35-7.40 (m, 1H), 7.59-7.65 (m, 1H) 8.07-8.10 (d, J=6.3 Hz, 1H), 9.10-9.11 (m, 1H).

Step 9—Synthesis of 6-fluoro-4-((2-hydroxy-3-(piperazin-1-yl)propyl)amino)-2Hbenzo[e][1,3]oxazin-2-one Hydrochloride

-continued

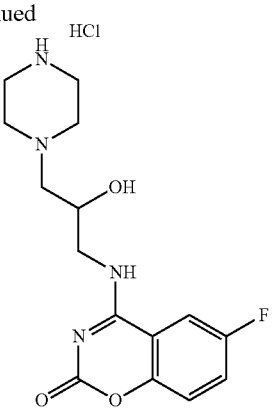

A solution of tert-butyl 4-(3-((6-fluoro-2-oxo-2H-benzo[e][1,3]oxazin-4yl) amino-2-hydroxypropyl)piperazine-1-carboxylate (100 mg, 0.023 mmol) in HCl.dioxane (4.5 N solution, 5 mL) was stirred for 4 h at room temperature. The reaction mixture was concentrated under reduced pressure and the resulting product (off-white solid, 100 mg, quant. yield) was used as such in the next step.

Step 10—Synthesis of 6-fluoro-4-({2-hydroxy-3-[4-(2,7-naphthyridin-1-yl)piperazin-1-yl]propyl}amino)-2H-1,3-benzoxazin-2-one (Compound 157)

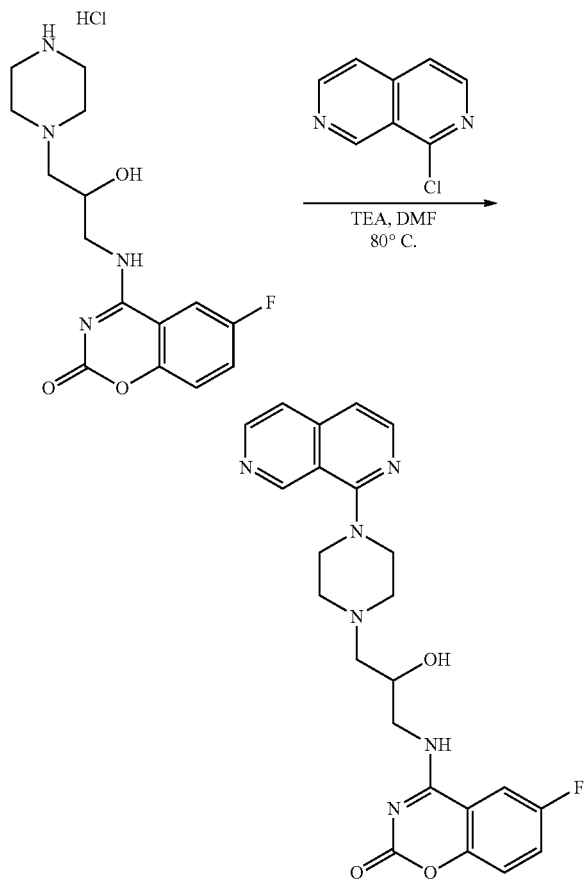

To a solution of 6-fluoro-4-((2-hydroxy-3-(piperazin-1-yl)propyl)amino)-2Hbenzo[e][1,3]oxazin-2-one hydrochloride (200 mg, 0.56 mmol) and TEA (0.18 mL, 0.85 mmol) in DMF (2 mL), 1-chloro-2,7-naphthyridine (60 mg, 0.37 mmol) was added. The reaction mixture was stirred for 8 h at 80° C. then was cooled and concentrated under reduced pressure. The resulting crude was purified by flash column chromatography (5 to 15% MeOH in DCM) to give the title compound as a light brown solid (35 mg, 14% yield). LC-MS m/z: 451.2 (M+1). $^1$HNMR (DMSO d6): 2.49-2.78 (m, 4H), 3.07-3.31 (m, 6H), 3.02-3.04 (m, 2H), 4.37-4.38 (m, 1H), 6.08 (s, 1H) 7.32-7.49 (m, 2H), 7.48-7.49 (m, 1H), 7.65-7.71 (m, 1H), 8.12-8.18 (m, 1H), 8.31-8.32 (m, 1H), 8.64-8.66 (m, 1H), 9.32-9.43 (m, 1H), 9.93-9.94 (m, 1H).

Preparation of Compound 160

Compound 160 was prepared as described herein below.

Step 1—Synthesis of tert-butyl [1-(7-fluoroisoquinolin-1-yl)piperidin-4-yl]carbamate

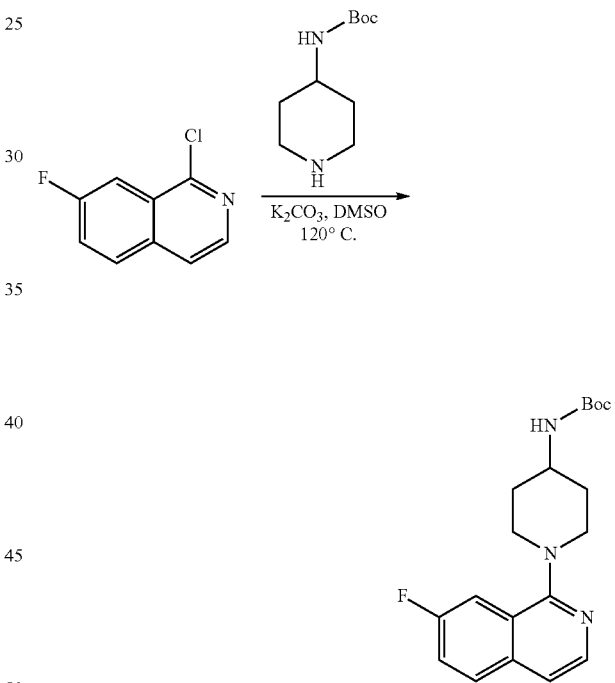

Potassium carbonate (2.9 g, 21 mmol) was added to a stirred solution of 1-chloro-7-fluoroisoquinoline (2.6, 14 mmol) and tert-butyl piperidin-4-ylcarbamate (5.2 g, 28 mmol) in DMSO (20 mL) at room temperature. The resulting mixture was stirred at 120° C. overnight then was allowed to cool to room temperature and partitioned between EtOAc (300 mL) and water (300 mL). The organic layer was separated, washed with 1M citric acid solution (100 mL) and brine (70 mL) and dried over sodium sulfate. The solvents were evaporated under reduced pressure and the resulting residue was purified by flash chromatography on silica gel (SNAP 100, from Cy to Cy/Ethyl acetate 8:2) to obtain tert-butyl [1-(7-fluoroisoquinolin-1-yl)piperidin-4-yl]carbamate (4.3 g, 12.4 mmol, 88% yield). LC-MS (M−H$^+$)=346.5

Step 2—Synthesis of 1-(7-fluoroisoquinolin-1-yl)piperidin-4-amine

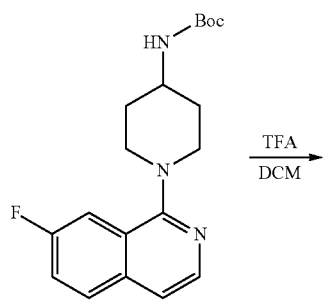

Step 4—Synthesis of 1-(7-fluoroisoquinolin-1-yl)-N-{[2-(pyridin-2-yl)-1H-imidazol-4-yl]methyl}piperidin-4-amine (Formate Salt, Compound 160)

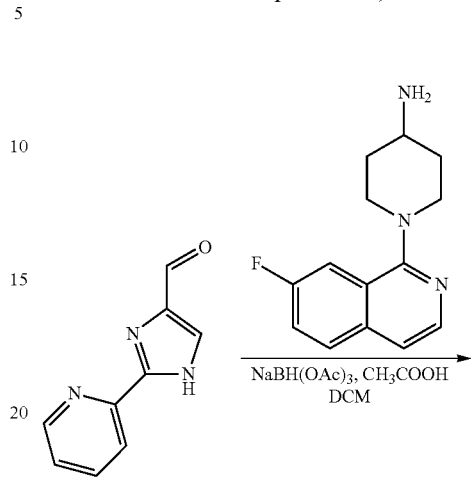

TFA (10 mL) was added to a solution of tert-butyl 4-(7-fluoroisoquinolin-1-yl)piperazine-1-carboxylate (4.3 g, 12.4 mmol) in dichloromethane (30 mL) and the resulting mixture was stirred overnight at room temperature. The volatiles were evaporated under reduced pressure, the residue was dissolved in dichloromethane (20 mL) and evaporated under reduced pressure. The resulting residue was dissolved in MeOH and loaded onto a preconditioned SCX cartridge (50 g). The SCX was eluted with MeOH and a 2M solution of ammonia in methanol. The basic fraction was evaporated under reduced pressure to give 3.1 g (Y=quant.) of 1-(7-fluoroisoquinolin-1-yl)piperidin-4-amine. LC-MS (M–H$^+$)=246.3

Step 3—Synthesis of 2-(pyridin-2-yl)-1H-imidazole-4-carbaldehyde

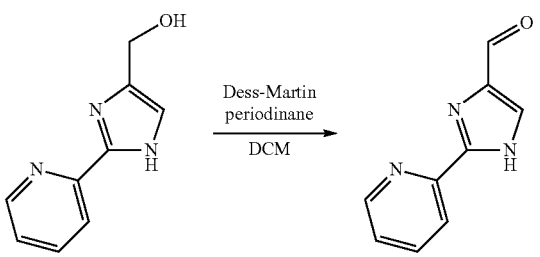

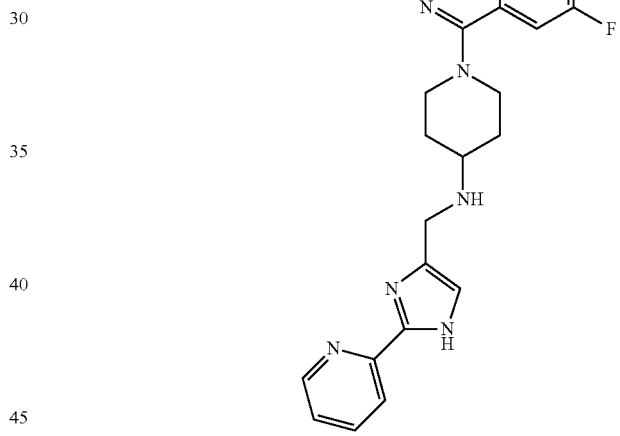

To a suspension of [2-(pyridin-2-yl)-1H-imidazol-4-yl]methanol (1 g, 5.7 mmol) in dry DCM (30 mL) Dess-Martin Periodinane (3.1 g, 1.3 eq) was added portionwise. The cloudy mixture was stirred 1.5 h at room temperature then was treated with sat. NaHCO$_3$ and 10% Na$_2$S$_2$O$_3$ solution. After stirring for 30 min. the organic phase was separated, dried over Na$_2$SO$_4$, filtered and evaporated to recover 730 mg of crude 2-(pyridin-2-yl)-1H-imidazole-4-carbaldehyde, that was progressed without further purification and characterization.

2-(pyridin-2-yl)-1H-imidazole-4-carbaldehyde (100 mg, 0.57 mmol) was dissolved in dry DCM (20 mL) and treated with 1-(7-fluoroisoquinolin-1-yl)piperidin-4-amine (140 mg, 0.57 mmol) and 2 drops of acetic acid. After stirring for 30 min. NaBH(OAc)$_3$ (180 mg, 0.86 mmol) was added in one portion and the reaction mixture was stirred overnight. The reaction was partitioned between DCM and sat. NaHCO$_3$. The organic phase was evaporated and purified by reversed phase chromatography (H2O/MeCN+0.1% HCOOH from 100/0 to 85/15) to afford 1-(7-fluoroisoquinolin-1-yl)-N-{[2-(pyridin-2-yl)-1H-imidazol-4-yl]methyl}piperidin-4-amine as formate salt (56 mg, 0.125 mmol, 21.9% yield). LC-MS (M–H$^+$)=403.4. $^1$H NMR (500 MHz, METHANOL-d$_4$) δ ppm 1.95-2.08 (m, 2H), 2.35 (dd, J=11.74, 1.47 Hz, 2H), 3.06 (t, J=12.00 Hz, 2H), 3.40-3.50 (m, 1H), 3.86 (d, J=12.00 Hz, 2H), 4.34 (s, 2H), 7.37-7.41 (m, 1H), 7.41-7.47 (m, 2H), 7.55 (td, J=8.80, 2.45 Hz, 1H), 7.75 (dd, J=10.27, 2.45 Hz, 1H), 7.86-7.99 (m, 2H), 8.06-8.11 (m, 2H), 8.44 (s, 1H), 8.63 (d, J=4.40 Hz, 1H).

Preparation of Compound 164

Compound 164 was prepared as described herein below.

Step 1—Synthesis of 8-chloro-2,7-naphthyridine 2-oxide

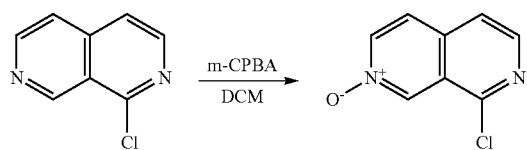

To a solution of 1-chloro-2,7-naphthyridine (0.15 g, 0.9 mmol) in DCM, m-CPBA (55%, 472 mg, 1.4 mmol) was added. The mixture was stirred 3 h at room temperature then the organic layer was washed with saturated potassium carbonate solution, water, brine solution and dried over sodium sulfate. The solvent was removed under reduced pressure to give 8-chloro-2,7-naphthyridine 2-oxide (120 mg, 73%) as a pale yellow solid. LC-MS m/z: 181.0 (M+1). $^1$HNMR (400 MHz, DMSO d6): δ 7.94 (d, J=5.6 Hz, 1H), 8.11 (d, J=7.12 Hz, 1H), 8.43-8.39 (m, 1H), 8.49-8.46 (m, 1H), 8.95 (s, 1H).

Step 2—Synthesis of 8-(4-(3-((6-fluoro-2-oxo-2H-benzo[e][1,3]oxazin-4-yl)amino)-2-hydroxypropyl) piperazin-1-yl)-2,7-naphthyridine 2-oxide (Compound 164)

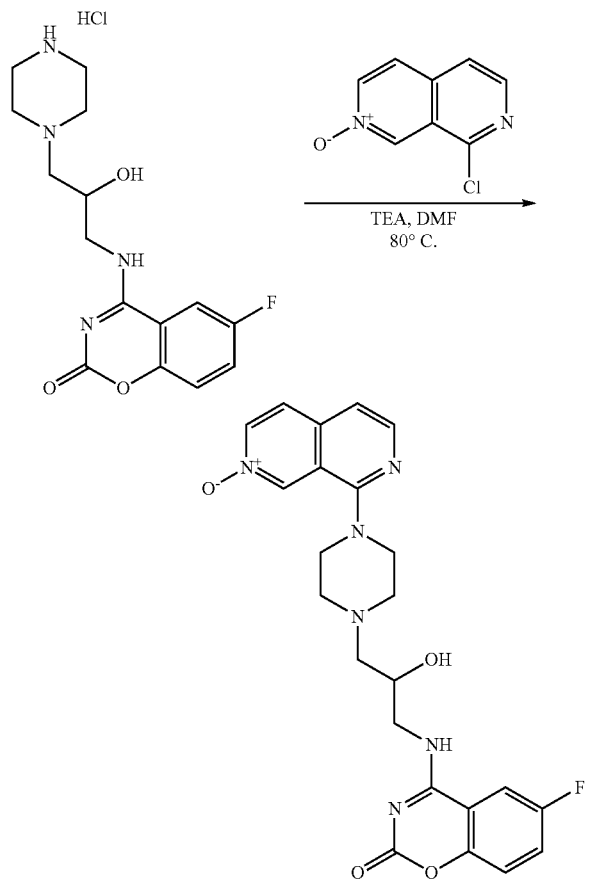

The synthesis was performed according to the procedure described for compound 157 (step 10) using 8-chloro-2,7-naphthyridine 2-oxide (23% yield). LC-MS m/z: 467.0 (M+1). $^1$HNMR (400 MHz, DMSO-d6): δ 2.74-2.60 (m, 5H), 3.16-3.09 (m, 1H), 3.42-3.21 (m, 5H), 3.72-3.70 (m, 1H), 4.06-4.05 (m, 1H), 5.01 (d, J=4.4 Hz, 1H), 7.39-7.36 (m, 2H), 7.65-7.60 (m, 1H), 7.91 (d, J=6.8 Hz, 1H), 8.13-8.10 (m, 1H), 8.18 (d, J=5.6 Hz, 1H), 8.31 (d, J=7.2 Hz, 1H), 8.64 (s, 1H), 9.14-9.12 (m, 1H).

Preparation of compound 165

Compound 165 was prepared as described herein below.

Step 1—Synthesis of 4-(3-((6-fluoro-2-oxo-2H-benzo[e][1,3]oxazin-4-yl)amino)-2-hydroxypropyl)-1-(2,7-naphthyridin-1-yl)piperazine 1-oxide (Compound 165)

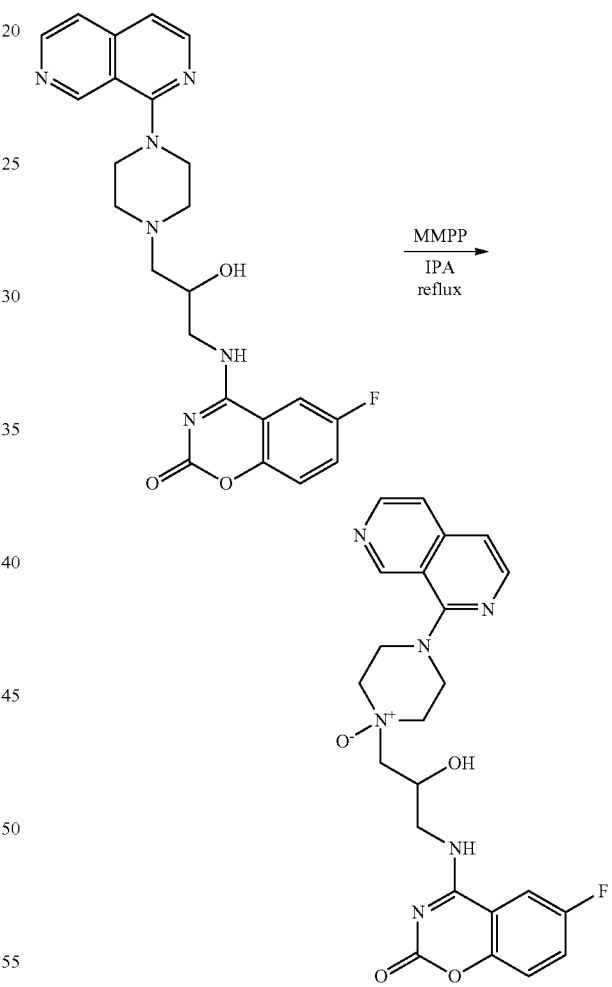

To a solution of compound 157 (30 mg, 0.06 mmol) in IPA (3 mL), magnesium monoperoxyphthalate hexahydrate (32 mg, 0.06 mmol) was added at room temperature. The reaction mixture was refluxed for 6 h then was cooled and concentrated under reduced pressure. The resulting crude was purified by flash column chromatography (8 to 10% MeOH/NH$_3$ in DCM) to give the title compound (3.5 mg, 11.2% yield). LC-MS m/z: 465.2 (M−1). $^1$HNMR (CDCl$_3$+ MeOH-d4): δ 1.28 (t, J=6.8 Hz, 3H), 3.35-3.29 (m, 2H), 3.71-3.56 (m, 5H), 3.86-3.78 (m, 2H), 4.03-3.98 (m, 2H), 4.61-4.59 (m, 1H), 7.22-7.20 (m, 2H), 7.35-7.30 (m, 1H), 7.58-7.56 (m, 1H), 7.70 (d, J=6 Hz, 1H), 8.22 (d, J=5.6 Hz, 1H), 8.53 (d, J=4.8 Hz, 1H), 9.31 (s, 1H).

Preparation of Compounds 180 and 181

Compounds 180 and 181 were prepared as described herein below.

Synthesis of 4-oxo-1,4-dihydro[1]benzopyrano[4,3-b]pyrrole-2-carbaldehyde

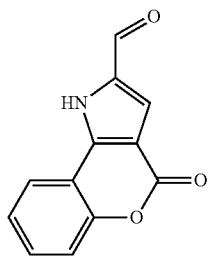 [SMILES: O=Cc1cc2c(=O)oc3ccccc3c2[nH]1]

The title intermediate was prepared according to the procedure described for the synthesis of 8-fluoro-4-oxo-1,4-dihydro[1]benzopyrano[4,3-b]pyrrole-2-carbaldehyde (compound 193, steps 1-4) starting from 4-hydroxy-2H-1-benzopyran-2-one. LC-MS m/z: 212.0 (M–H⁻). ¹HNMR (DMSO d6): δ 12.61 (s, 1H), 9.76 (s, 1H), 8.38-8.36 (m, 1H), 7.70 (d, J=2.0 Hz, 1H), 7.61 (d, J=1.6 Hz, 1H), 7.43-7.41 (m, 2H).

Step 1—Synthesis of tert-butyl 3-hydroxypyrrolidine-1-carboxylate

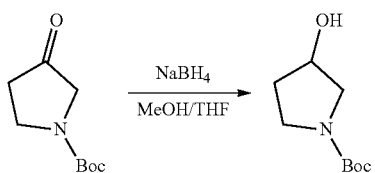 [SMILES: CC(C)(C)OC(=O)N1CCC(=O)C1 ; "MeOH/THF" ; "NaBH4" ; CC(C)(C)OC(=O)N1CCC(O)C1]

To a stirred solution of tert-butyl 3-oxopyrrolidine-1-carboxylate (5.2 g, 26.9 mmol) in MeOH/THF 1:1 (50 mL), sodium borohydride (2.05 g, 53.9 mmol) was added portionwise at 0° C. The reaction mixture was stirred for 40 min at room temperature then was quenched with ice. The solvent was concentrated under reduced pressure, the resulting residue was diluted with EtOAc (100 mL) and washed with water (50 mL) and brine (50 mL). The organic layer was dried over sodium sulfate and concentrated to afford the title compound (5.1 g, 98% yield) as a mixture of isomers. ¹HNMR (CDCl₃): δ 4.86 (d, J=4.8 Hz, 1H), 4.20 (s, 1H), 2.25-2.23 (m, 3H), 3.11-3.01 (m, 1H), 1.83-1.81 (m, 2H), 1.39 (s, 9H).

Step 2—Synthesis of tert-butyl 3-[(methanesulfonyl)oxy]pyrrolidine-1-carboxylate

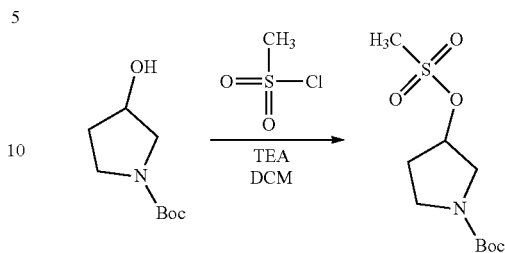

To a stirred solution of tert-butyl 3-hydroxypyrrolidine-1-carboxylate (mixture of isomers, 5.1 g, 27.2 mmol) in DCM (75 mL), TEA (5.9 mL, 42.7 mmol) was added at room temperature. The mixture was cooled to 0° C. then methane sulfonyl chloride (2.62 mL, 32.7 mmol) was added dropwise. The resulting solution was stirred at room temperature for 1 h then was diluted with DCM (100 mL) and washed with water (50 mL) and brine (50 mL). The organic layer was dried over sodium sulfate and concentrated to afford the title compound (7.15 g, 99% yield) as a mixture of isomers, that was progressed without any further purification. ¹HNMR (CDCl₃): δ 5.30-5.27 (m, 1H), 3.60-3.58 (m, 4H), 3.05 (s, 3H), 2.19-2.16 (m, 1H), 2.13-2.12 (m, 1H), 1.39 (s, 9H).

Step 3—Synthesis of tert-butyl 3-cyanopyrrolidine-1-carboxylate

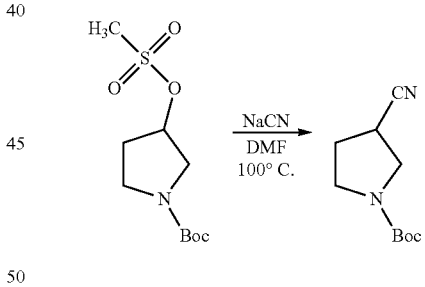

To a stirred solution of tert-butyl 3-[(methanesulfonyl)oxy]pyrrolidine-1-carboxylate (mixture of isomers, 6.1 g, 23.0 mmol) in DMF (40 mL) NaCN (3.38 g, 69.0 mmol) was added. The reaction mixture was stirred at 100° C. for 16 h then was cooled to room temperature and diluted with EtOAc (75 mL). The organic layer was washed with water (2×40 mL), dried over sodium sulfate and concentrated. The resulting crude was purified by column chromatography (silica gel: 230-400, 25% EtOAc in pet. ether) to afford the title compound (3.1 g, 15.8 mmol, 69% yield, colorless liquid) as a mixture of isomers. ¹HNMR (CDCl₃): δ 3.69-3.59 (m, 4H), 3.12-3.09 (m, 1H), 2.27-2.25 (m, 2H), 1.48 (s, 9H).

Step 4—Synthesis of tert-butyl 3-(aminomethyl)pyrrolidine-1-carboxylate

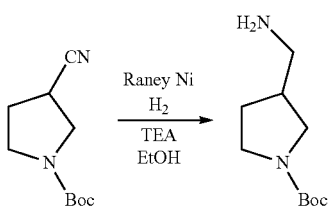 [SMILES: CC(C)(C)OC(=O)N1CCC(C#N)C1 ; "Raney NiH2" ; CC(C)(C)OC(=O)N1CCC(CN)C1]

To a stirred solution of tert-butyl 3-cyanopyrrolidine-1-carboxylate (mixture of isomers, 3.1 g, 15.8 mmol) and TEA (1.3 mL, 9.4 mmol) in EtOH (90 mL) Raney nickel (2.04 g, 23.7 mmol) was added under nitrogen. The reaction mixture was stirred at room temperature for 16 h under 30 psi hydrogen pressure then was filtered through celite washing with ethanol (50 mL). The solution was concentrated under reduced pressure to afford the title compound (2.6 g, 82% yield, yellow liquid) as a mixture of isomers. LC-MS (ELSD) m/z: 201.2 (M+H+). $^1$HNMR (CDCl$_3$): δ 3.49-3.41 (m, 4H), 3.00-2.99 (m, 1H), 2.73 (m, 2H), 2.23-2.22 (m, 1H), 2.00 (m, 1H), 1.46 (s, 9H).

Step 5—Synthesis of tert-butyl 3-({[(benzyloxy)carbonyl]amino}methyl)pyrrolidine-1-carboxylate

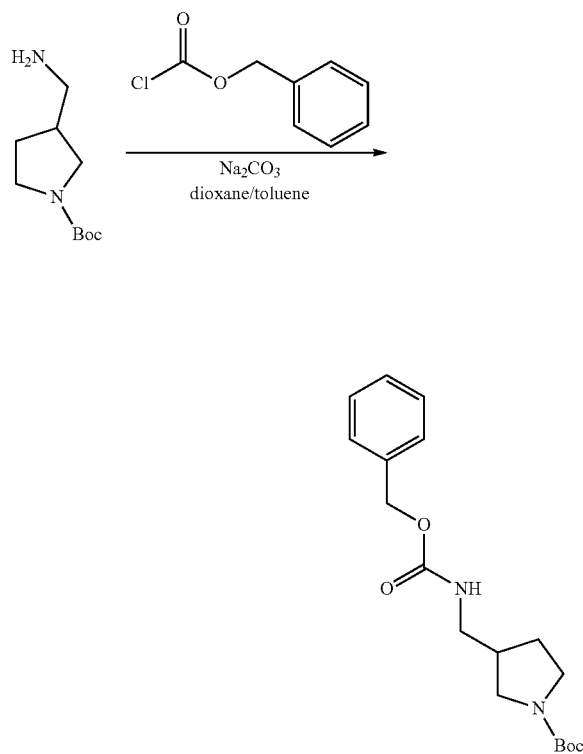

To a stirred solution of tert-butyl 3-(aminomethyl)pyrrolidine-1-carboxylate (mixture of isomers, 2.5 g, 12.4 mmol) in 1,4 dioxane (50 mL) a saturated sodium carbonate solution (14 mL) was added at room temperature. The reaction mixture was cooled to 0-5° C. then benzyl chloroformate (50% in toluene, 5.5 mL, 16 mmol) was slowly added. After stirring for 5 h at room temperature the reaction mixture was diluted with water (50 mL) and extracted with EtOAc (3×60 mL). The combined organic layers were washed with brine (50 mL), dried over sodium sulfate and evaporated under vacuum. The crude was purified by column chromatography (Silica gel: 200-400, 12-15% EtOAc in pet. ether) to afford the title compound (2.4 g, 57.5% yield, colorless liquid) as a mixture of isomers. LC-MS m/z: 235.1 (M+H+-Boc). $^1$HNMR (CDCl$_3$): δ 7.36-7.27 (m, 5H), 5.11 (s, 2H), 4.87-4.85 (m, 1H), 3.50-3.05 (m, 6H), 3.00-2.97 (m, 1H), 2.35-2.20 (m, 1H), 2.05-1.97 (m, 1H), 1.46 (s, 9H).

Step 6—Synthesis of benzyl [(pyrrolidin-3-yl)methyl]carbamate Hydrochloride

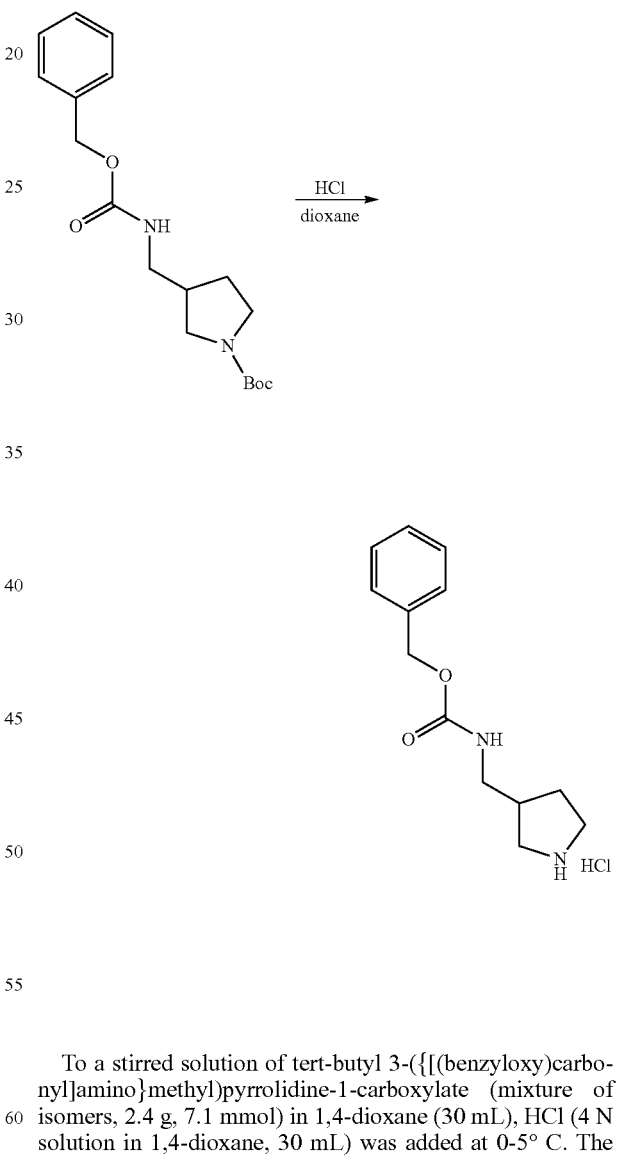

To a stirred solution of tert-butyl 3-({[(benzyloxy)carbonyl]amino}methyl)pyrrolidine-1-carboxylate (mixture of isomers, 2.4 g, 7.1 mmol) in 1,4-dioxane (30 mL), HCl (4 N solution in 1,4-dioxane, 30 mL) was added at 0-5° C. The reaction mixture was stirred for 2 h at room temperature then was concentrated under reduced pressure. The resulting crude was treated with petroleum ether, filtered and dried under reduced pressure to afford the title compound (1.7 g, crude) as a mixture of isomers, that was progressed without any further purification. LC-MS m/z: 235.2 (M−H+).

Step 7—Synthesis of benzyl {[1-(7-fluoroisoquinolin-1-yl)pyrrolidin-3-yl]methyl}carbamate

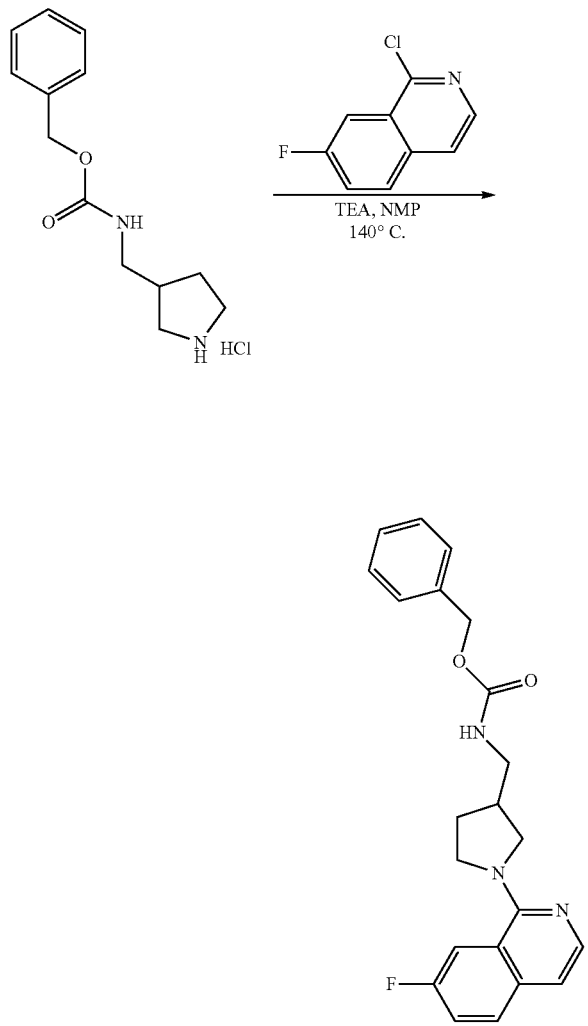

To a stirred solution of benzyl [(pyrrolidin-3-yl)methyl]carbamate hydrochloride (mixture of isomers, 957 mg, 3.5 mmol) in NMP (15 mL) TEA (1.1 g, 11.0 mmol) was added. After stirring for 15 min at room temperature, 1-chloro-7-fluoroisoquinoline (400 mg, 2.2 mmol) was added. The reaction mixture was stirred at 140° C. for 24 h then was cooled, concentrated under reduced pressure and diluted with EtOAc (50 mL). The organic phase was washed with water (2×25 mL) and brine (20 mL), dried over sodium sulfate and evaporated under vacuum. The resulting crude was purified by column chromatography (silica gel: 200-400 mesh, 30-40% EtOAc in pet. ether) to afford the title compound (500 mg, 60% yield) as a mixture of isomers. LC-MS m/z: 380.2 (M+H).

Step 8—Synthesis of 1-[1-(7-fluoroisoquinolin-1-yl)pyrrolidin-3-yl]methanamine

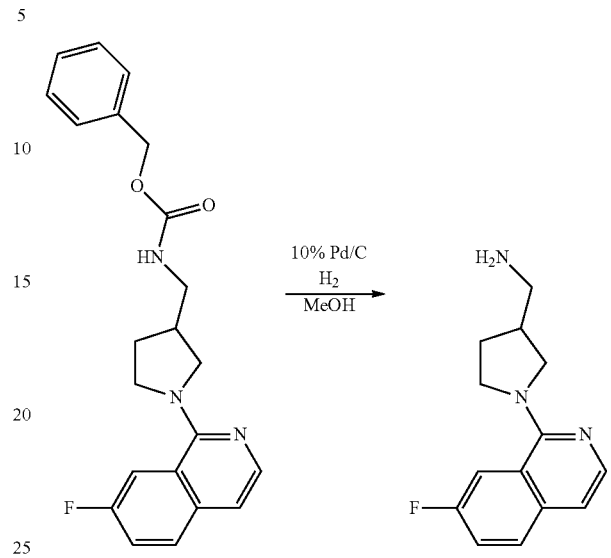

To a stirred solution of benzyl {[1-(7-fluoroisoquinolin-1-yl)pyrrolidin-3-yl]methyl}carbamate (mixture of isomers, 500 mg, 1.3 mmol) in methanol (50 mL), 10% Pd/C (100 mg, 50% wet) was added. The reaction mixture was stirred under hydrogen atmosphere for 3 h then was filtered onto a celite bed washing with methanol (50 mL). The filtrate was concentrated under reduced pressure to afford the title compound (310 mg, 1.3 mmol, 97% yield) as a mixture of isomers. LC-MS m/z: 246.1 (M+H).

Step 9—Synthesis of the enantiomers of 2-[({[1-(7-fluoroisoquinolin-1-yl)pyrrolidin-3-yl]methyl}amino)methyl][1]benzopyrano[4,3-b]pyrrol-4(1H)-one (Compounds 180 and 181)

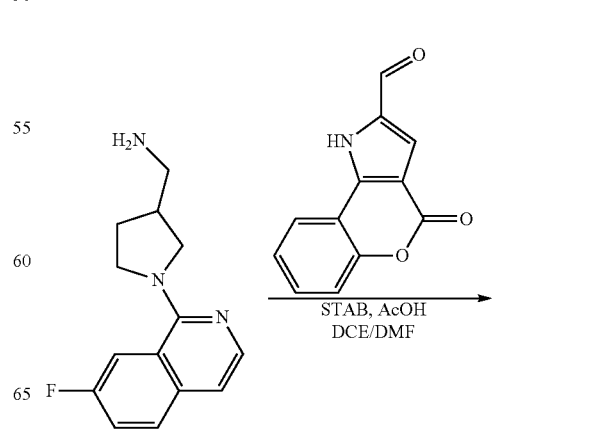

-continued

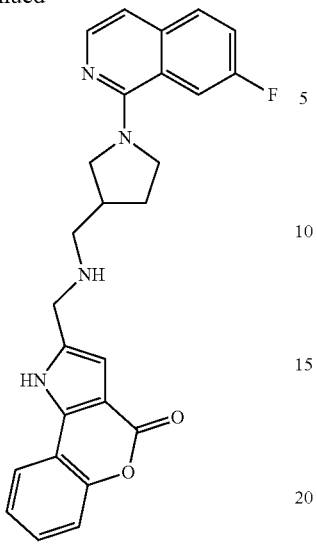

To a stirred solution of 1-[1-(7-fluoroisoquinolin-1-yl)pyrrolidin-3-yl]methanamine (mixture of isomers, 320 mg, 1.3 mmol) and 4-oxo-1, 4-dihydrochromeno [4, 3-b] pyrrole-2-carbaldehyde (330 mg, 1.56 mmol) in DCE (5 mL) and DMF (2 mL), AcOH (0.1 mL) was added at room temperature. After stirring for 20 h at 50° C. the mixture was cooled to room temperature and sodium triacetoxy borohydride (553 mg, 2.6 mmol) was added. The reaction mixture was stirred for 3 h at room temperature then was diluted with water (30 mL) and extracted with DCM (3×30 mL). The combined organic layers were washed with water (2×20 mL) and brine (20 mL), dried over sodium sulfate and concentrated under reduced pressure. The resulting crude was purified by flash chromatography (silica gel: 200-400, 3-5% MeOH in DCM) to afford the isomeric mixture of 2-[({[1-(7-fluoroisoquinolin-1-yl)pyrrolidin-3-yl]methyl}amino)methyl][1]benzopyrano[4,3-b]pyrrol-4(1H)-one. The mixture was purified by chiral HPLC to afford the 2 enantiomers.

Compound 180 (stereochemistry not assigned): 29.2 mg, 5% yield. LC-MS m/z: 443.1 (M+H). $^1$H NMR (400 MHz, DMSO-d6): δ 12.56 (brs, 1H), 8.06 (d, J=7.56 Hz, 1H), 7.93-7.80 (m, 3H), 7.55-7.50 (m, 1H), 7.45-7.36 (m, 2H), 7.34-7.32 (m, 1H), 7.05 (d, J=5.6 Hz, 1H), 6.55 (s, 1H), 3.85-3.69 (m, 5H), 3.58 (t, J=9.6 Hz, 1H), 2.66-2.50 (m, 2H), 2.43-2.41 (m, 2H), 2.09-2.06 (m, 1H), 1.70-1.68 (m, 1H).

Compound 181 (stereochemistry not assigned): 21.4 mg, 3.7% yield. LC-MS m/z: 443.1 (M+H+). $^1$H NMR (400 MHz, DMSO-d6): δ 12.46 (brs, 1H), 8.05 (d, J=7.76 Hz, 1H), 7.93-7.82 (m, 3H), 7.53 (t, J=8.5 Hz, 1H), 7.46-7.33 (m, 3H), 7.05 (d, J=5.2 Hz, 1H), 6.54 (s, 1H), 3.82-3.71 (m, 5H), 3.59 (t, J=9.08 Hz, 1H), 3.01-3.00 (m, 2H), 2.66-2.61 (m, 1H), 2.43-2.32 (m, 1H), 2.07-2.05 (m, 1H), 1.70-1.68 (m, 1H).

Preparation of Compounds 182 and 183

Compounds 182 and 183 were prepared as described herein below.

Step 1—Synthesis of Tert-butyl 2-{[(methanesulfonyl)oxy]methyl}morpholine-4-carboxylate

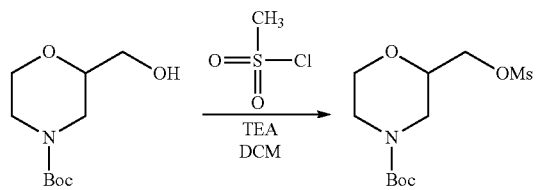

The title intermediate was prepared as a mixture of isomers according to the procedure described for the synthesis of tert-butyl 3-[(methanesulfonyl)oxy]pyrrolidine-1-carboxylate (see compounds 180-181, step 2) using tert-butyl 2-(hydroxymethyl)morpholine-4-carboxylate (92% yield). LC-MS (ELSD) m/z: 196.0 (M+H$^+$-Boc). $^1$HNMR (CDCl$_3$): δ 4.25 (d, J=4.8 Hz, 2H), 3.93-3.73 (m, 3H), 3.69-3.67 (m, 1H), 3.58-3.55 (m, 1H), 3.10 (s, 3H), 2.98-2.85 (m, 1H), 2.80-2.75 (m, 1H), 1.43 (s, 9H).

Step 2—Synthesis of Tert-butyl 2-(azidomethyl)morpholine-4-carboxylate

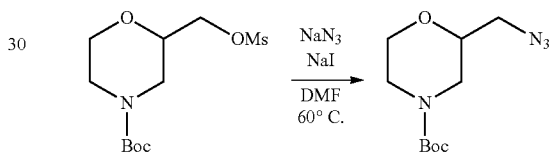

To a stirred solution of tert-butyl 2-{[(methanesulfonyl)oxy]methyl}morpholine-4-carboxylate (mixture of isomers, 2.5 g, 8.46 mmol) in DMF (25 mL), sodium azide (4.64 g, 42.3 mmol) and sodium iodide (253 mg, 1.6 mmol) were added at room temperature. The reaction mixture was stirred at 60° C. for 20 h then was diluted with water (20 mL) and extracted with EtOAc (2×50 mL). The organic layer was washed with brine (50 mL), dried over sodium sulfate and concentrated under vacuum. The resulting crude was purified by column chromatography (silica gel: 200-400, 20% EtOAc in pet. ether) to afford the title compound (1.8 g, 87% yield) as a mixture of isomers. LC-MS (ELSD) m/z: 143.2 (M+H-Boc). $^1$HNMR (CDCl$_3$): δ 4.05-3.85 (m, 3H), 3.65-3.45 (m, 2H), 3.35-3.00 (m, 2H), 3.00-2.90 (m, 1H), 2.89-2.79 (m, 1H), 1.45 (s, 9H).

Step 3—Synthesis of Tert-butyl 2-(aminomethyl)morpholine-4-carboxylate

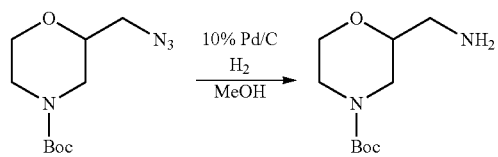 [SMILES: "MeOH" ; CC(C)(C)OC(=O)N1CCOC(CN=[N+]=[N-])C1 ; "10% Pd/CH2" ; CC(C)(C)OC(=O)N1CCOC(CN)C1]

The title intermediate was prepared as a mixture of isomers according to the procedure described for the synthesis of 1-[1-(7-fluoroisoquinolin-1-yl)pyrrolidin-3-yl]methanamine (see compounds 180-181, step 8) using tert-butyl 2-(azidomethyl)morpholine-4-carboxylate (93% yield). LC-MS (ELSD): m/z 217.3 (M+H).

Step 4—Synthesis of Tert-butyl 2-({[(benzyloxy)carbonyl]amino}methyl)morpholine-4-carboxylate

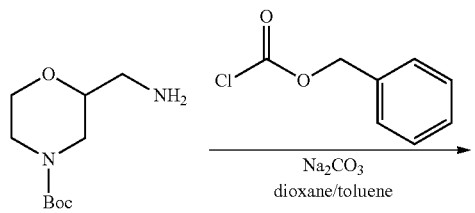

The title intermediate was prepared as a mixture of isomers according to the procedure described for the synthesis of tert-butyl 3-({[(benzyloxy)carbonyl]amino}methyl)pyrrolidine-1-carboxylate (see compounds 180-181, step 5) using tert-butyl 2-(aminomethyl)morpholine-4-carboxylate (54% yield). LC-MS m/z: 251.3 (M+H$^+$-Boc); $^1$HNMR (CDCl$_3$): δ 7.39-7.33 (m, 5H), 5.13 (s, 2H), 3.88-3.86 (m, 3H), 3.73-3.71 (m, 1H), 3.55-3.47 (m, 3H), 3.18-2.88 (m, 1H), 2.68-2.65 (m, 1H), 1.48 (s, 9H).

Step 5—Synthesis of Benzyl [(morpholin-2-yl)methyl]carbamate Hydrochloride

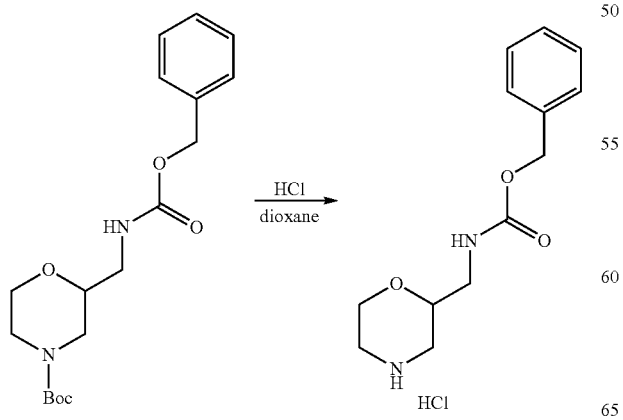

The title intermediate was prepared as a mixture of isomers according to the procedure described for the synthesis of benzyl [(pyrrolidin-3-yl)methyl]carbamate hydrochloride (see compounds 180-181, step 6) using tert-butyl 2-({[(benzyloxy)carbonyl]amino}methyl)morpholine-4-carboxylate (99% yield). LC-MS m/z: 251.1 (M+H$^+$).

Step 6—Synthesis of Benzyl {[4-(7-fluoroisoquinolin-1-yl)morpholin-2-yl]methyl}carbamate

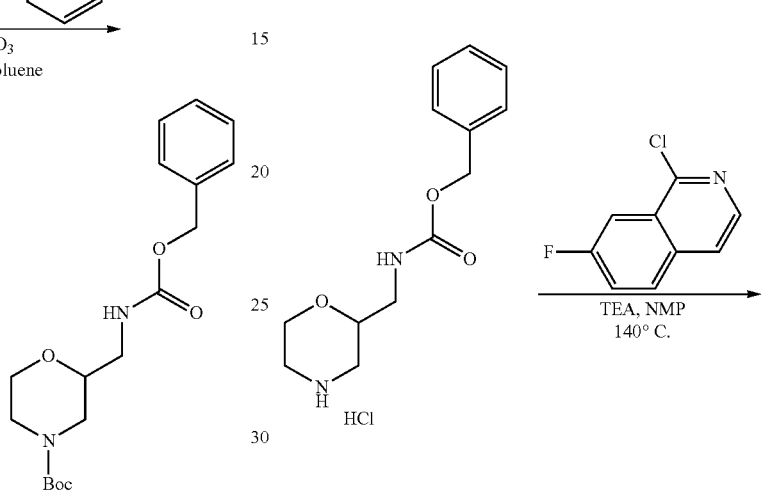

The title intermediate was prepared as a mixture of isomers according to the procedure described for the synthesis of benzyl {[1-(7-fluoroisoquinolin-1-yl)pyrrolidin-3-yl]methyl}carbamate (see compounds 180-181, step 7) using benzyl [(morpholin-2-yl)methyl]carbamate hydrochloride (37% yield). LC-MS m/z: 396.2 (M+H$^+$).

Step 7—Synthesis of 1-[4-(7-fluoroisoquinolin-1-yl) morpholin-2-yl]methanamine

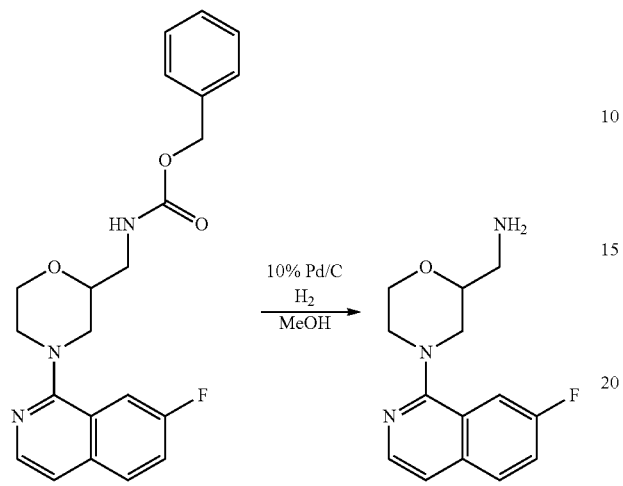

The title intermediate was prepared as a mixture of isomers according to the procedure described for the synthesis of 1-[1-(7-fluoroisoquinolin-1-yl)pyrrolidin-3-yl]methanamine (see compounds 180-181, step 8) using benzyl {[4-(7-fluoroisoquinolin-1-yl)morpholin-2-yl]methyl}carbamate (84% yield). LC-MS m/z: 262.1 (M+H$^+$).

Step 8—Synthesis of the Enantiomers of 2-[({[4-(7-fluoroisoquinolin-1-yl)morpholin-2-yl]methyl}amino)methyl][1]benzopyrano[4,3-b]pyrrol-4(1H)-one (Compounds 182 and 183)

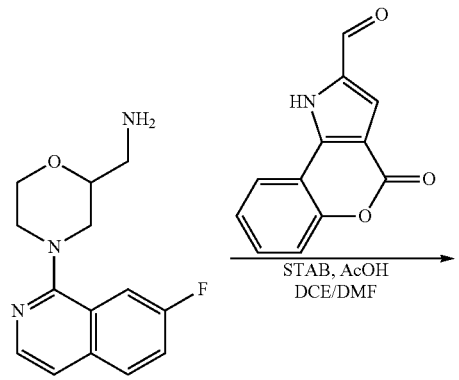

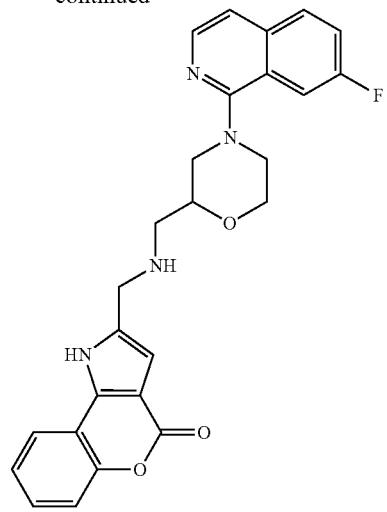

Compounds 182 and 183 were prepared according to the procedure described for compounds 180 and 181 (step 9) using the isomeric mixture of 1-[4-(7-fluoroisoquinolin-1-yl)morpholin-2-yl]methanamine.

Compound 182 (stereochemistry not assigned): 9.9 mg, 2.6% yield. LC-MS m/z: 459.2 (M+H$^+$). $^1$H NMR (400 MHz, DMSO-d6): δ 12.35 (brs, 1H), 8.11 (d, J=5.6 Hz, 1H), 8.04-7.99 (m, 2H), 7.76 (d, J=10.2 Hz, 1H), 7.66-7.62 (m, 1H), 7.47-7.32 (m, 4H), 6.53 (s, 1H), 3.96-3.83 (m, 5H), 3.64-3.48 (m, 2H), 3.01 (t, J=10.2 Hz, 1H), 2.82-2.76 (m, 1H), 2.70-2.67 (m, 2H).

Compound 183 (stereochemistry not assigned): 12.9 mg, 3.3% yield. LC-MS m/z: 459.2 (M+H$^+$). $^1$H NMR (400 MHz, DMSO-d6): δ 12.50 (brs, 1H), 8.12 (d, J=5.6 Hz, 1H), 8.05-8.00 (m, 2H), 7.79-7.76 (m, 1H), 7.68-7.63 (m, 1H), 7.48-7.34 (m, 4H), 6.57 (s, 1H), 3.97-3.86 (m, 5H), 3.64-3.61 (m, 1H), 3.52-3.49 (m, 1H), 3.03-3.00 (m, 1H), 2.83-2.51 (m, 3H).

Preparation of Compound 193

Compound 193 was prepared as described herein below.

Step 1—Synthesis of 4-chloro-6-fluoro-2-oxo-2H-1-benzopyran-3-carbaldehyde

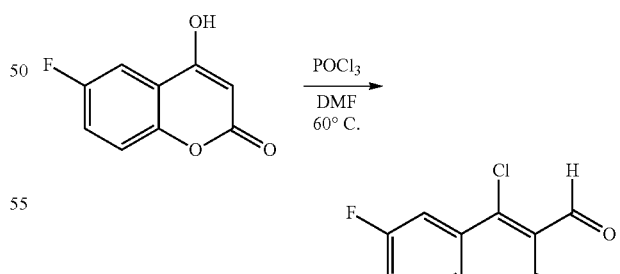

POCl$_3$ (25.8 mL) was added to DMF (40 mL) in one portion at 0° C. The resulting mixture was heated at 50° C. for 0.5 h then a solution of 6-fluoro-4-hydroxycoumarin (10 g, 55.5 mmol) in DMF (30 mL) was added at 50° C. The reaction mixture was further heated at 60° C. overnight. The mixture was concentrated in vacuo, treated with toluene (2×50 mL) and evaporated. DCM (400 mL) was added, the resulting mixture was poured onto ice and stirred for 10 min keeping the temperature around 0° C. The organic phase was separated, dried and evaporated in vacuo to obtain 12.5 g of the crude product. The title intermediate was progressed into the next step without further purification and characterization.

Step 2—Synthesis of Ethyl 8-fluoro-4-oxo-1,4-dihydro[1]benzopyrano[4,3-b]pyrrole-2-carboxylate

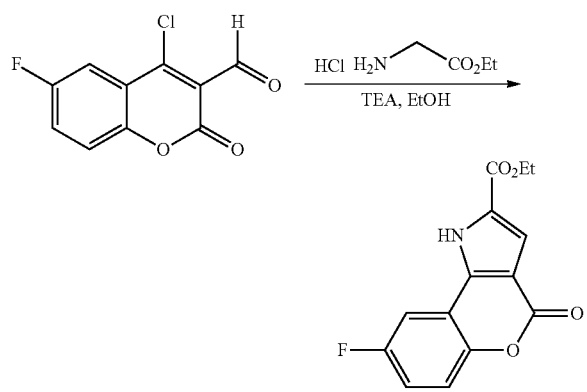

4-chloro-6-fluoro-2-oxo-2H-chromene-3-carbaldehyde (12.5 g, crude material) and glycine ethyl ester hydrochloride (8.1 g, 58.3 mmol) were suspended in absolute ethanol (120 mL). TEA (3 eq.) was added at 0° C. then the resulting mixture was stirred at the same temperature for 1 hour and at 80° C. for 24 hours. The mixture was concentrated in vacuo, dissolved in DCM (400 mL) and washed with sat. NaHCO$_3$ (200 mL). The organic phase was dried over Na$_2$SO$_4$ and evaporated in vacuo. The crude material was treated with EtOH (10 mL) to obtain the title compound (7.9 g, 28.7 mmol, 51% yield over two steps). LC-MS (M–H$^+$)=276.0

Step 3—Synthesis of 8-fluoro-2-(hydroxymethyl)[1]benzopyrano[4,3-b]pyrrol-4(1H)-one

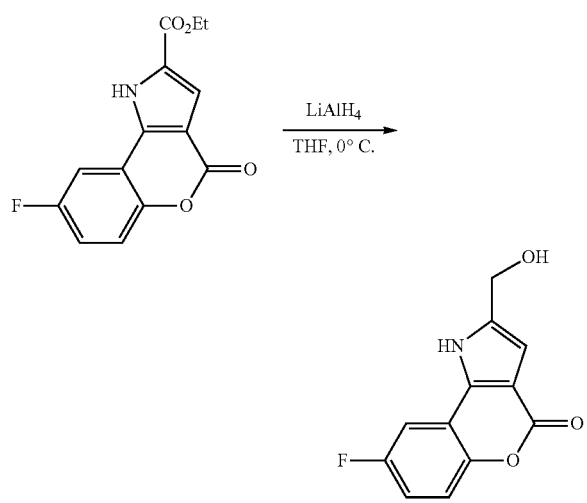

8-fluoro-4-oxo-1,4-dihydro[1]benzopyrano[4,3-b]pyrrole-2-carboxylate (7.9 g, 28.7 mmol) was dissolved in dry THF (240 mL). The solution was chilled to −10° C. then LiAlH$_4$ (1 M solution in THF, 38.2 mL) was slowly added. The reaction mixture was stirred at 0° C. for 4 hours then was quenched by adding Na$_2$SO$_4$.10H$_2$O. The inorganic salts were filtered off and the solvents were evaporated to recover the title product (3.2 g, 13.7 mmol, 48% yield), that was progressed without any further purification. LC-MS (M–H$^+$)=234.1

Step 4—Synthesis of 8-fluoro-4-oxo-1,4-dihydro[1]benzopyrano[4,3-b]pyrrole-2-carbaldehyde

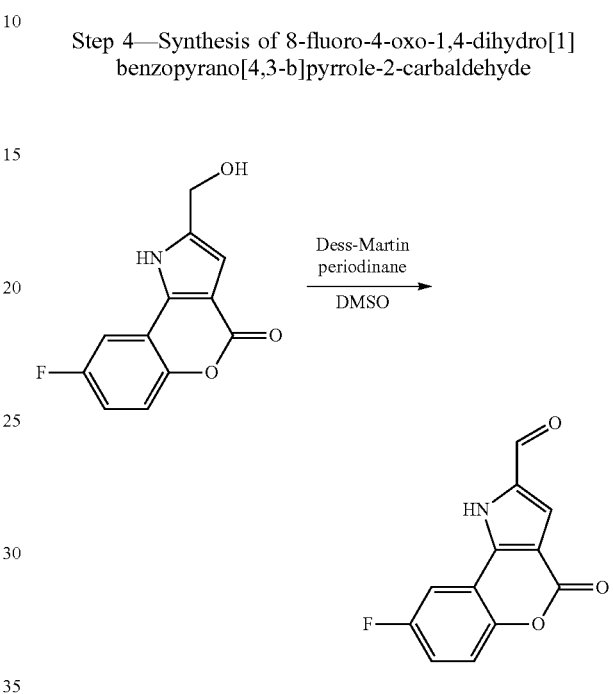

To a solution of 8-fluoro-2-(hydroxymethyl)[1]benzopyrano[4,3-b]pyrrol-4(1H)-one (1.2 g, 5.15 mmol) in DMSO (12 mL), Dess-Martin periodinane (2.4 g, 5.66 mmol) was added. The mixture was stirred at rt for 30 min then an aqueous solution of sat. NaHCO$_3$/10% Na$_2$S$_2$O$_3$ 1:1 was added. The precipitate was filtered, washed with water and treated with MeCN (4 mL) and diethyl ether (10 mL) to obtain the title intermediate (1.1 g, 4.76 mmol, 92% yield). LC-MS (M–H$^+$)=232.1

Step 5—Synthesis of 3-amino-5-fluoropyridin-2(1H)-one

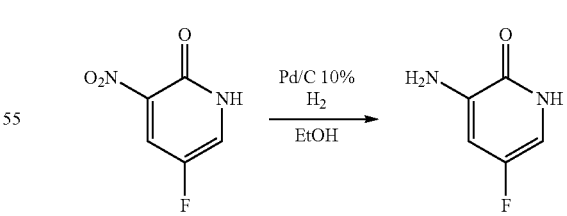

5-Fluoro-3-nitropyridin-2-ol (10 g, 63.3 mmol) was dissolved in ethanol (300 mL), 10% Pd/C (1.8 g) was added and the mixture was stirred at room temperature under atmospheric pressure of hydrogen for 2 h. Pd/C was removed by filtration and the solvent was evaporated in vacuum to obtain the title compound as an off-white solid (7.5 g, 58.5 mmol, Y=92%). LC-MS (M–H$^+$)=129.0

Step 6—Synthesis of Tert-butyl {4-[(5-fluoro-2-hydroxypyridin-3-yl)amino]cyclohexyl}carbamate

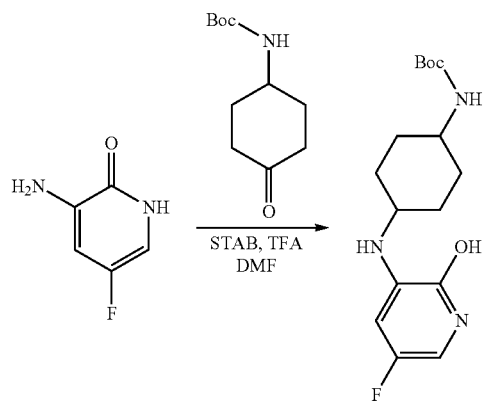

3-amino-5-fluoropyridin-2(1H)-one (3.7 g, 28.9 mmol) and tert-butyl (4-oxocyclohexyl)carbamate (8 g, 37.6 mmol) were dissolved in DMF (213 mL). TFA (18.4 mL, 240 mmol) was added dropwise followed by sodium triacetoxyborohydride (9.19 g, 43.4 mmol). The mixture was stirred at room temperature for 1.5 h then the reaction was quenched with sat. NaHCO$_3$. The mixture was extracted with ethyl acetate, dried over Na$_2$SO$_4$ and evaporated under reduced pressure. The residue was purified by flash chromatography (SNAP C-18 400 g, from 100% water+0.1% formic acid to 50:50 water+0.1% formic acid/acetonitrile+0.1% formic acid) to give the title compound as a formate salt. This material was dissolved in ethyl acetate, washed with sat. NaHCO$_3$ sat. sol., dried over Na$_2$SO$_4$ and evaporated under reduced pressure to give the free base of target compound as mixture of isomers (5.8 g, 17.8 mmol, 60% yield). LC-MS (M−H$^+$)=326.3

Step 7—Synthesis of Tert-butyl [4-(7-fluoro-2-oxo-2,3-dihydro-1H-pyrido[2,3-b][1,4]oxazin-1-yl)cyclohexyl]carbamate

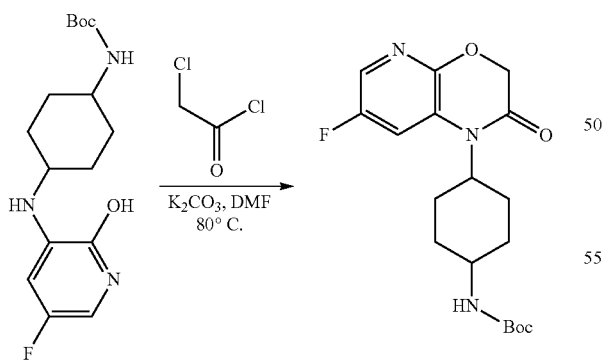

To a suspension of tert-butyl {4-[(5-fluoro-2-hydroxypyridin-3-yl)amino]cyclohexyl}carbamate (5.8 g, 17.8 mmol) and potassium carbonate (9.9 g, 71.3 mmol) in DMF (110 mL) chloroacetyl chloride (3.1 mL, 39.2 mmol) was added. The mixture was stirred at room temperature for 30 minutes then was heated to 80° C. for 5 h. The mixture was cooled to 0° C. then sat. NaHCO$_3$ was added (50 mL) followed by ethyl acetate (200 mL). The organic phase was separated, dried over Na$_2$SO$_4$ and evaporated in vacuo. The crude product was purified by Silica gel column (from 100% of cy to cy/ethyl acetate 50:50) to obtain the title compound (3.79 g, 10.4 mmol, 58% yield) as a mixture of isomers. LC-MS (M−H$^+$)=366.4

Step 8—Synthesis of 1-(trans-4-aminocyclohexyl)-7-fluoro-1H-pyrido[2,3-b][1,4]oxazin-2(3H)-one

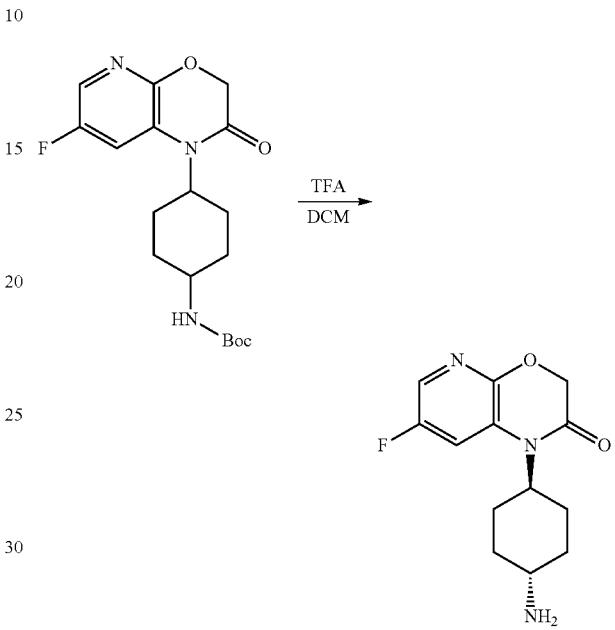

tert-butyl [4-(7-fluoro-2-oxo-2,3-dihydro-1H-pyrido[2,3-b][1,4]oxazin-1-yl)cyclohexyl]carbamate (3.79 g, 10.4 mmol) was dissolved in DCM (70 mL), TFA (10 mL) was added at 0° C. then the mixture was stirred at rt for 2 h. The solvent was evaporated in vacuo and the residue was purified by SCX column and then by preparative HPLC purification under basic conditions (0.1% v/v ammonia aqueous solution/acetonitrile) to afford the trans diastereoisomer (1.15 g, 4.3 mmol, 41% yield). LC-MS (M−H$^+$)=266.0

Step 9—Synthesis of 8-fluoro-2-({[trans-4-(7-fluoro-2-oxo-2,3-dihydro-1H-pyrido[2,3-b][1,4]oxazin-1-yl)cyclohexyl]amino}methyl)[1]benzopyrano[4,3-b]pyrrol-4(1H)-one (Hydrochloride, Compound 193)

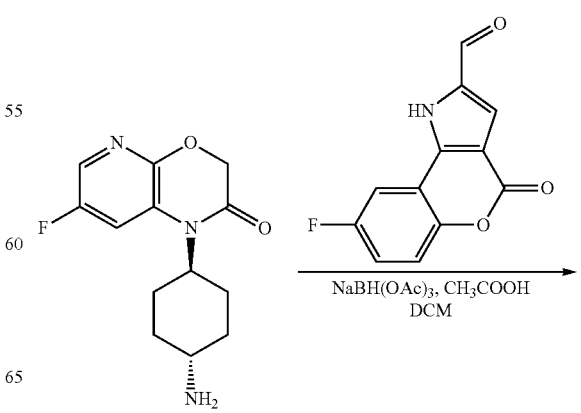

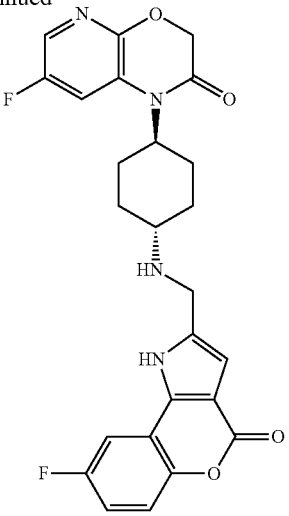

8-fluoro-4-oxo-1,4-dihydro[1]benzopyrano[4,3-b]pyrrole-2-carbaldehyde (158 mg, 0.41 mmol) and 1-(trans-4-aminocyclohexyl)-7-fluoro-1H-pyrido[2,3-b][1,4]oxazin-2(3H)-one (100 mg, 0.37 mmol) were suspended in dry dichloromethane (20 mL). 2 drops of acetic acid were added. The mixture was stirred for 2 hours at 50° C. then NaBH(OAc)₃ (195 mg, 0.925 mmol) was added in one portion. The mixture was stirred at room temperature for 3 h then was partitioned between DCM (50 mL) and a sat. NaHCO₃ (20 mL). The organic phase was dried over Na₂SO₄, filtered and evaporated in vacuo. The crude product was purified by SCX column, the resulting free base was dissolved in DCM/MeOH (20:1, 12 mL), the mixture was cooled to 0° C. and HCl (1 M solution in diethyl ether) was added. After stirring at room temperature for 10 min the solvent was evaporated in vacuo and the solid was treated with diethyl ether and dried to afford 170 mg (0.29 mmol, 78% yield) of the title product. LC-MS (M–H⁺)=481.3. ¹H NMR (400 MHz, DMSO-d₆) δ ppm 1.55-1.73 (m, 2H), 1.86 (d, J=10.74 Hz, 2H), 2.26 (d, J=11.51 Hz, 2H), 2.34-2.47 (m, 2H), 3.24 (br. s., 1H), 4.03-4.17 (m, 1H), 4.37 (br. s., 2H), 4.72 (s, 2H), 6.95 (s, 1H), 7.37 (td, J=8.77, 2.96 Hz, 1H), 7.53 (dd, J=9.10, 4.60 Hz, 1H), 7.82-7.90 (m, 2H), 7.97 (dd, J=9.92, 2.47 Hz, 1H), 9.33 (br. s., 2H), 13.40 (br. s., 1H).

Preparation of Compound 194

Compound 194 was prepared as described herein below.

Step 1—Synthesis of 8-fluoro-4-oxo-1-{[2-(trimethylsilyl)ethoxy]methyl}-1,4-dihydro[1]benzopyrano[4,3-b]pyrrole-2-carbaldehyde

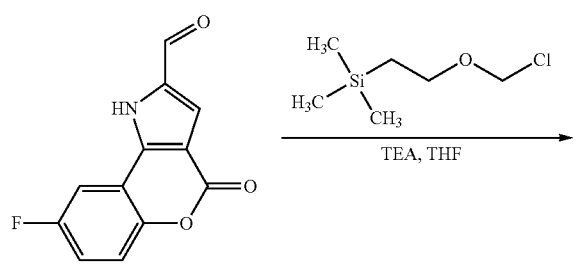

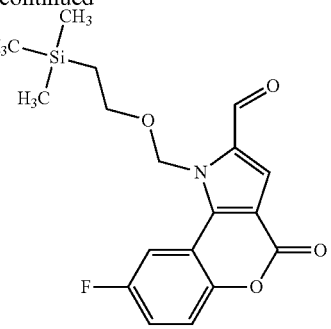

8-fluoro-4-oxo-1,4-dihydro[1]benzopyrano[4,3-b]pyrrole-2-carbaldehyde (see compound 193, 3.5 g, 15.2 mmol) was dissolved in dry THF (120 mL) and cooled to 0° C. TEA (4.2 mL, 30.3 mmol) and SEM-Cl (3.2 mL, 18.2 mmol) were added. After stirring 45 min at the same temperature, a saturated solution of NaHCO₃ was added at 0° C. followed by ethyl acetate. The organic phase was separated, washed with sat. NH₄Cl and brine, dried over Na₂SO₄ and evaporated in vacuo. The crude material was purified by Si-column SNAP 100 eluting with cyclohexane/ethyl acetate from 95:5 to 7:3. The resulting residue was treated with diethyl ether and filtered to give the title compound (860 mg, 2.4 mmol, 16% yield). LC-MS (M–H⁺)=362.3

Step 2—Synthesis of 8-fluoro-2-[(E)-2-methoxyethenyl]-1-{[2-(trimethylsilyl)ethoxy]methyl}[1]benzopyrano[4,3-b]pyrrol-4(1H)-one

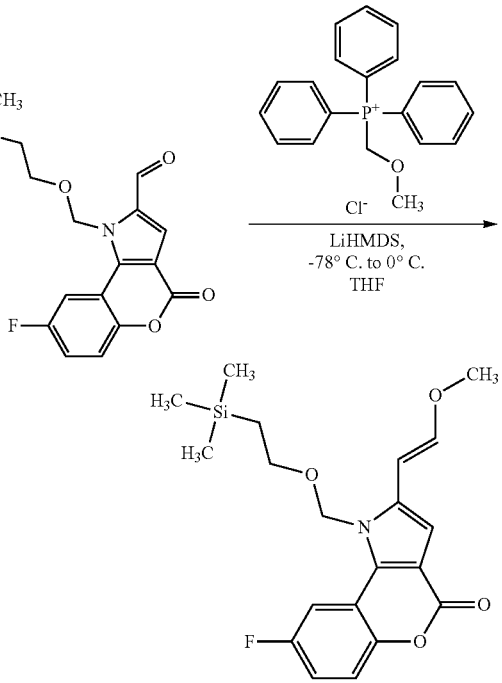

A solution of (methoxymethyl)triphenylphosphonium chloride (1.2 g, 3.6 mmol) in THF (20 mL) was cooled to −78° C. LiHMDS (1 M solution in THF, 3.6 mL) was added and the mixture was allowed to warm to 0° C. The mixture was cooled again to −78° C. and a solution of 8-fluoro-4- oxo-1-{[2-(trimethylsilyl)ethoxy]methyl}-1,4-dihydro[1]benzopyrano[4,3-b]pyrrole-2-carbaldehyde (645 mg, 1.8 mmol) in THF (10 mL) was added dropwise. After stirring for 2 hours at −78° C. sat. NH₄Cl was added, the resulting mixture was diluted with ethyl acetate and the organic phase was separated, dried and evaporated in vacuo. The crude material was purified by Si-column eluting with cy to cy/ethyl acetate 7:3 to obtain the title intermediate (600 mg, 1.5 mmol, 83% yield) as a mixture of cis/trans isomers. LC-MS (M−H⁺)=390.4

Step 3—Synthesis of (8-fluoro-4-oxo-1,4-dihydro[1]benzopyrano[4,3-b]pyrrol-2-yl)acetaldehyde

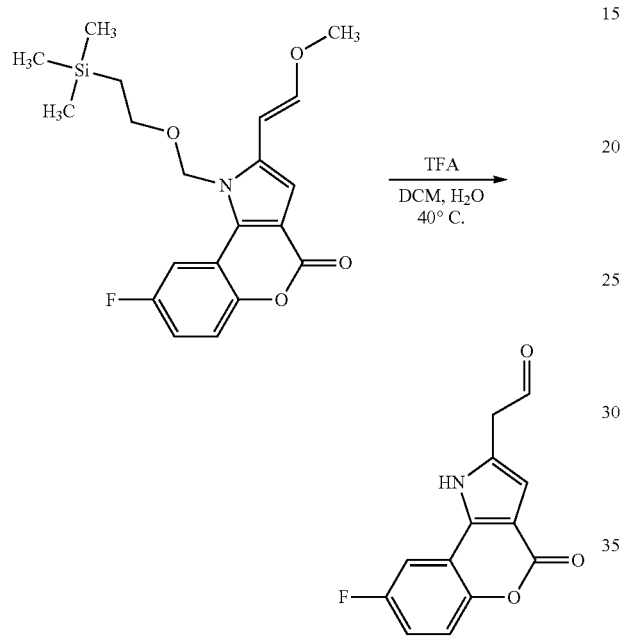

TFA (1.5 mL) was added to a solution of 8-fluoro-2-[(E)-2-methoxyethenyl]-1-{[2-(trimethylsilyl)ethoxy]methyl}[1]benzopyrano[4,3-b]pyrrol-4(1H)-one (100 mg, 0.26 mmol) in DCM (6 mL). The resulting mixture was stirred at 40° C. for 3 hours then was diluted with toluene (60 mL) and evaporated under vacuo to afford the title intermediate, that was progressed without further purification. LC-MS (M−H⁺)=246.3

Step 4—Synthesis of Tert-butyl 4-[(5-fluoro-2-hydroxypyridin-3-yl)amino]piperidine-1-carboxylate

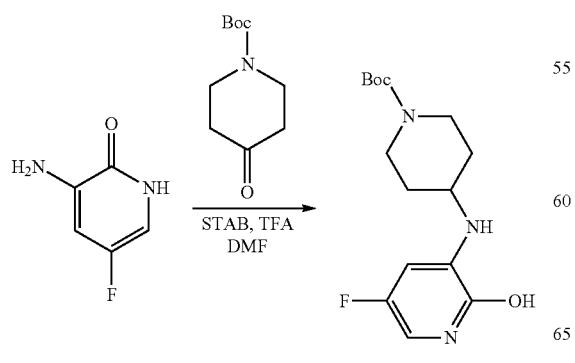

The synthesis was performed according to the procedure described for the preparation of intermediate tert-butyl {4-[(5-fluoro-2-hydroxypyridin-3-yl)amino]cyclohexyl}carbamate (see compound 193, step 6) using tert-butyl 4-oxopiperidine-1-carboxylate (51% yield). LC-MS (M−H⁺)=312.3

Step 5—Synthesis of tert-butyl 4-(7-fluoro-2-oxo-2,3-dihydro-1H-pyrido[2,3-b][1,4]oxazin-1-yl)piperidine-1-carboxylate

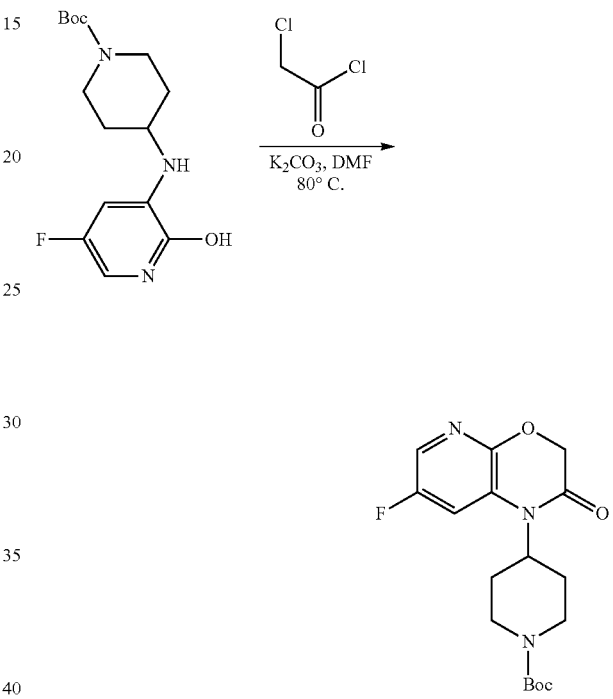

The synthesis was performed according to the procedure described for the preparation of intermediate tert-butyl [4-(7-fluoro-2-oxo-2,3-dihydro-1H-pyrido[2,3-b][1,4]oxazin-1-yl)cyclohexyl]carbamate (see compound 193, step 7) using tert-butyl 4-[(5-fluoro-2-hydroxypyridin-3-yl)amino]piperidine-1-carboxylate (46% yield). LC-MS (M−H⁺)=352.3

Step 6—Synthesis of 7-fluoro-1-(piperidin-4-yl)-1H-pyrido[2,3-b][1,4]oxazin-2(3H)-one

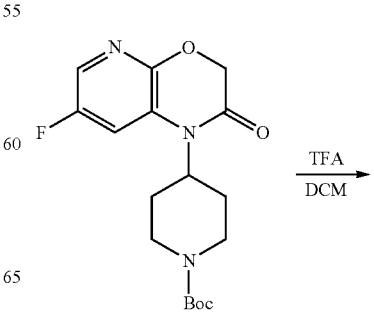

-continued

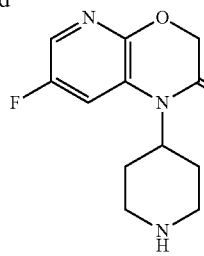

The synthesis was performed according to the procedure described for the preparation of intermediate 1-(trans-4-aminocyclohexyl)-7-fluoro-1H-pyrido[2,3-b][1,4]oxazin-2(3H)-one (see compound 193, step 8) using tert-butyl 4-(7-fluoro-2-oxo-2,3-dihydro-1H-pyrido[2,3-b][1,4]oxazin-1-yl)piperidine-1-carboxylate (87% yield). LC-MS (M–H$^+$)=252.3

Step 7—Synthesis of 8-fluoro-2-{2-[4-(7-fluoro-2-oxo-2,3-dihydro-1H-pyrido[2,3-b][1,4]oxazin-1-yl)piperidin-1-yl]ethyl}[1]benzopyrano[4,3-b]pyrrol-4(1H)-one (Compound 194)

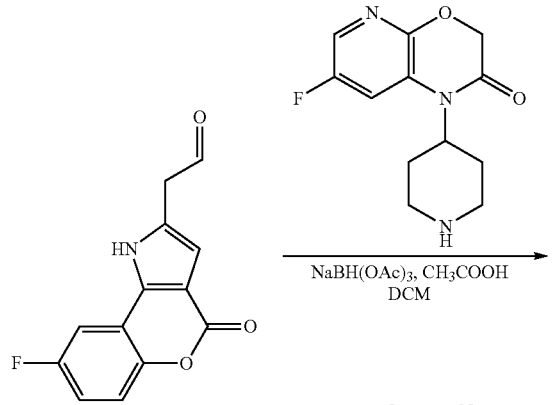

The title compound was prepared according to the procedure described for the synthesis of 8-fluoro-2-({[trans-4-(7-fluoro-2-oxo-2,3-dihydro-1H-pyrido[2,3-b][1,4]oxazin-1-yl)cyclohexyl]amino}methyl)[1]benzopyrano[4,3-b]pyrrol-4(1H)-one (compound 193, step 9) using (8-fluoro-4-oxo-1,4-dihydro[1]benzopyrano[4,3-b]pyrrol-2-yl)acetaldehyde and 7-fluoro-1-(piperidin-4-yl)-1H-pyrido[2,3-b][1,4]oxazin-2(3H)-one (39% yield). LC-MS (M–H$^+$)=481.3. $^1$H NMR (500 MHz, DMSO-d$_6$) δ ppm 1.70 (d, J=9.74 Hz, 2H), 2.18 (t, J=11.40 Hz, 2H), 2.44-2.61 (m, 2H), 2.65-2.73 (m, 2H), 2.90 (t, J=7.48 Hz, 2H), 3.02 (d, J=11.39 Hz, 2H), 3.95-4.08 (m, 1H), 4.71 (s, 2H), 6.50 (s, 1H), 7.29 (td, J=8.71, 3.02 Hz, 1H), 7.47 (dd, J=8.70, 4.53 Hz, 1H), 7.75-7.93 (m, 3H), 12.39 (br. s., 1H).

Preparation of Compound 197

Compound 197 was prepared as described herein below.

Step 1—Synthesis of Tert-butyl 4-[(6-methoxy-3-nitropyridin-2-yl)amino]piperidine-1-carboxylate

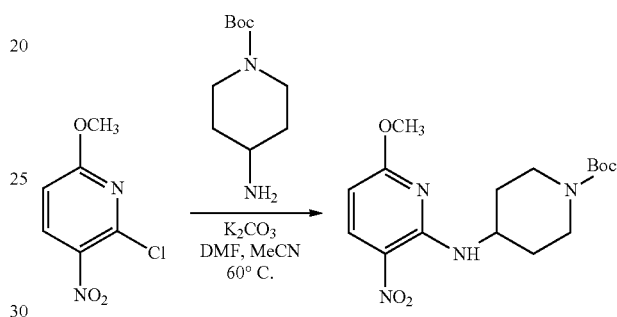

A mixture of tert-butyl 4-aminopiperidine-1-carboxylate (2.34 g, 11.7 mmol), 2-chloro-6-methoxy-3-nitropyridine (3 g, 10.6 mmol) and K$_2$CO$_3$ (1.47 g, 10.6 mmol) in MeCN (60 mL) and DMF (15 mL) was heated at 60° C. for 3 h. The mixture was filtered and concentrated in vacuo. The residue was suspended in diethyl ether/water 1:1, the organic phase was dried over MgSO$_4$ and concentrated. The residue was purified by flash chromatography (silica-gel) to afford the title compound (2.3 g, 6.5 mmol, 61% yield). LC-MS (M–H$^+$)=353.3

Step 2—Synthesis of Tert-butyl 4-[(3-amino-6-methoxypyridin-2-yl)amino]piperidine-1-carboxylate

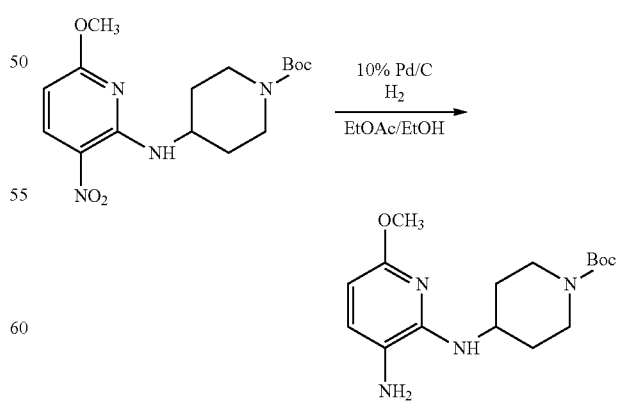

tert-Butyl 4-[(6-methoxy-3-nitropyridin-2-yl)amino]piperidine-1-carboxylate (2.3 g, 6.5 mmol) was dissolved in ethyl acetate/ethanol 1:1 (60 mL), Pd/C (10% wt, 0.2 g) was added and the mixture was stirred at room temperature under atmospheric pressure of hydrogen for 24 h. Pd/C was removed by filtration and the solvent was evaporated in vacuo. The resulting residue was purified by Si-column eluting with cy to cy/ethyl acetate 1:1 to obtain the title product (1.2 g, 3.7 mmol, 57% yield). LC-MS (M–H$^+$)=323.4

Step 3—Synthesis of Tert-butyl 4-({3-[(2-ethoxy-2-oxoethyl)amino]-6-methoxypyridin-2-yl}amino)piperidine-1-carboxylate

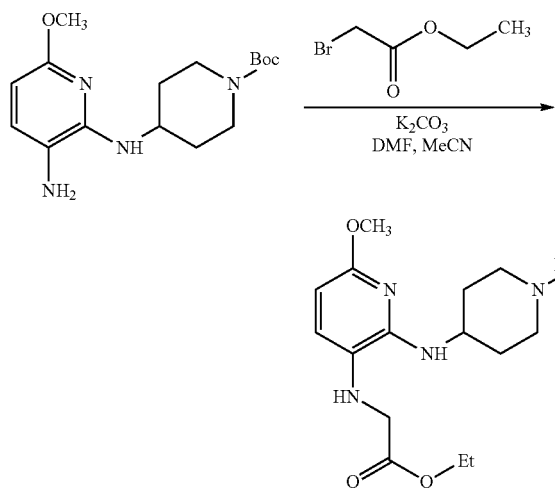

tert-Butyl 4-[(3-amino-6-methoxypyridin-2-yl)amino]piperidine-1-carboxylate (1.2 g, 3.7 mmol) was dissolved in DMF/MeCN 1:2 (30 mL), potassium carbonate (513 mg, 3.7 mmol) was added followed by ethyl bromoacetate (0.43 mL, 3.8 mmol). The mixture was stirred at room temperature overnight then ethyl acetate was added followed by water. The organic phase was separated, washed with brine, dried and evaporated in vacuo. The crude material was purified by Si-column eluting with cy to cy/ethyl acetate 7:3 to obtain the title intermediate (1.4 g, 3.4 mmol, 92% yield). LC-MS (M–H$^+$)=409.5

Step 4—Synthesis of Tert-butyl 4-(6-methoxy-3-oxo-2,3-dihydropyrido[2,3-b]pyrazin-4(1H)-yl)piperidine-1-carboxylate

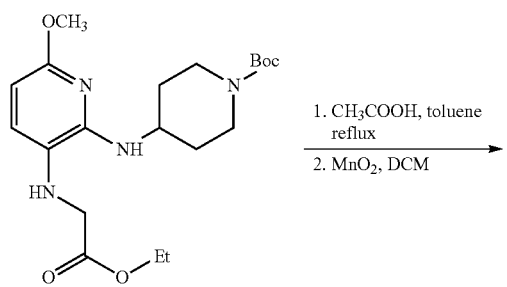

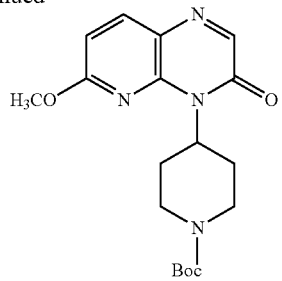

A solution of tert-butyl 4-({3-[(2-ethoxy-2-oxoethyl)amino]-6-methoxypyridin-2-yl}amino)piperidine-1-carboxylate (500 mg, 1.2 mmol) and cat. acetic acid (0.1 mL) in toluene (25 mL) was refluxed overnight. The reaction mixture was concentrated, the residue was dissolved in DCM (20 mL) and treated with MnO$_2$ (2 g) at room temperature for 2 hours. The solid was filtered and the solvent was evaporated in vacuo. The crude material was purified by Si-column eluting with cy to cy/ethyl acetate 8:2 to obtain the title compound (137 mg, 0.38 mmol, 32% yield). LC-MS (M–Na$^+$)=383.3

Step 5—Synthesis of 6-methoxy-4-(piperidin-4-yl)pyrido[2,3-b]pyrazin-3(4H)-one

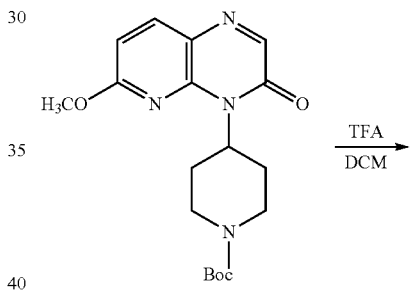

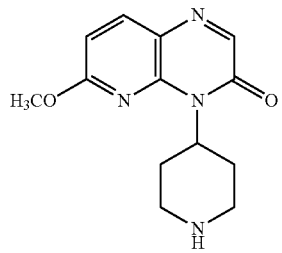

The synthesis was performed according to the procedure described for the preparation of intermediate 1-(trans-4-aminocyclohexyl)-7-fluoro-1H-pyrido[2,3-b][1,4]oxazin-2(3H)-one (see compound 193, step 8) using tert-butyl 4-(6-methoxy-3-oxo-2,3-dihydropyrido[2,3-b]pyrazin-4(1H)-yl)piperidine-1-carboxylate (98% yield). LC-MS (M–H$^+$)=261.3

Step 6—Synthesis of 8-fluoro-2-{2-[4-(6-methoxy-3-oxopyrido[2,3-b]pyrazin-4(3H)-yl)piperidin-1-yl]ethyl}[1]benzopyrano[4,3-b]pyrrol-4(1H)-one

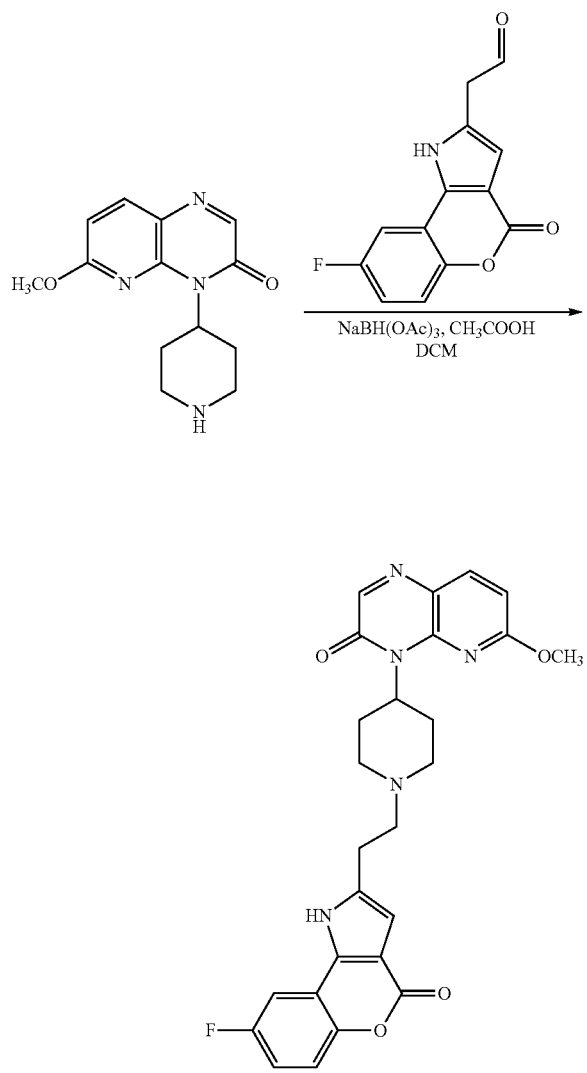

The title compound was prepared according to the procedure described for the synthesis of 8-fluoro-2-({[trans-4-(7-fluoro-2-oxo-2,3-dihydro-1H-pyrido[2,3-b][1,4]oxazin-1-yl)cyclohexyl]amino}methyl)[1]benzopyrano[4,3-b]pyrrol-4(1H)-one (compound 193, step 9) using (8-fluoro-4-oxo-1,4-dihydro[1]benzopyrano[4,3-b]pyrrol-2-yl)acetaldehyde and 6-methoxy-4-(piperidin-4-yl)pyrido[2,3-b]pyrazin-3(4H)-one (11% yield). LC-MS (M–H⁺)=490.5. ¹H NMR (500 MHz, DMSO-d₆) δ ppm 1.62 (d, J=10.43 Hz, 2H), 2.13 (t, J=11.05 Hz, 2H), 2.66-2.77 (m, 2H), 2.85-3.01 (m, 4H), 3.12 (d, J=11.39 Hz, 2H), 3.92 (s, 3H), 5.25 (br. s., 1H), 6.52 (s, 1H), 6.84 (d, J=8.64 Hz, 1H), 7.29 (td, J=8.71, 3.02 Hz, 1H), 7.48 (dd, J=9.06, 4.53 Hz, 1H), 7.81 (dd, J=8.92, 3.02 Hz, 1H), 8.07 (s, 1H), 8.12 (d, J=8.64 Hz, 1H), 12.40 (br. s., 1H).

Preparation of Compound 200

Compound 200 was prepared as described herein below.

Step 1—Synthesis of 3-chloro-6-methoxypyrazin-2-amine

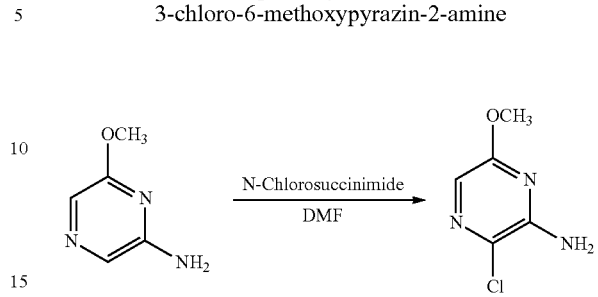

To a solution of 6-methoxypyrazin-2-amine (3 g, 24 mmol) in dry DMF (35 mL), N-chlorosuccinimide (3.2 g, 24 mmol) was added. The reaction mixture was stirred at room temperature for 16 h then was poured into ice and brine (130 mL). The aqueous solution was extracted with ethyl acetate (3×120 mL), the organic phase was washed with 5% solution of LiCl, dried over Na₂SO₄ and evaporated under reduced pressure. The crude was purified by SNAP-340-NH (cyclohexane/ethyl acetate from 95:5 up to 8:2) and by SNAP100-Si—OH (eluting with DCM) to afford the title intermediate (1.98 g, 12.5 mmol, 52% yield). LC-MS (M–H⁺)=160.1

Step 2—Synthesis of Tert-butyl 4-[(3-chloro-6-methoxypyrazin-2-yl)amino]piperidine-1-carboxylate

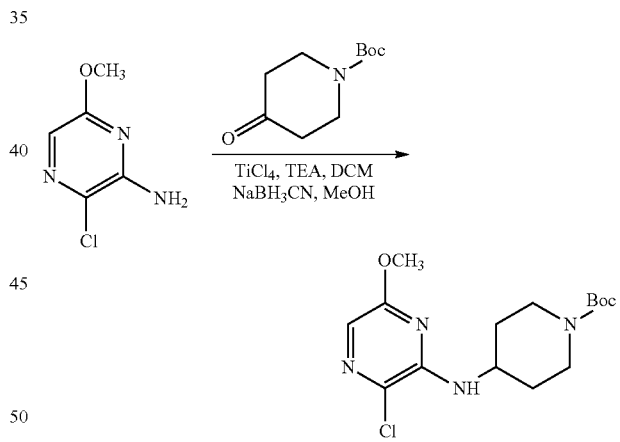

A solution of titanium (IV) chloride (1 M in dichloromethane, 5.8 mL) was added dropwise at 0° C. to a stirred solution of 3-chloro-6-methoxypyrazin-2-amine (1.85 g, 11.6 mmol), tert-butyl 4-oxopiperidine-1-carboxylate (2.55 g, 12.8 mmol) and triethylamine (4.85 mL, 34.8 mmol) in dry dichloromethane (58 mL). The reaction mixture was slowly allowed to warm to room temperature and stirred overnight. To the resulting mixture a solution of sodium cyanoborohydride (2.18 g, 34.8 mmol) in MeOH (23 mL) was then added at room temperature. After 4 hours the reaction mixture was quenched with a 3 M NaOH solution (180 mL). EtOAc (600 mL) was then added and the mixture was filtered onto a Celite pad (10 cm diameter, 3 cm height). The phases were separated and the organic layer was washed with aqueous sodium bicarbonate solution and brine, dried over sodium sulfate and evaporated under reduced pressure. The crude was purified by flash chromatography (Biotage KP-Sil 100 g SNAP cartridge, eluent from 100% DCM to DCM/MeOH 95:5) to give the title compound (1 g, 2.9 mmol, 25% yield). LC-MS (M–H⁺)=343.4

Step 3—Synthesis of Tert-butyl 4-({3-[(1E)-3-ethoxy-3-oxoprop-1-en-1-yl]-6-methoxypyrazin-2-yl}amino)piperidine-1-carboxylate

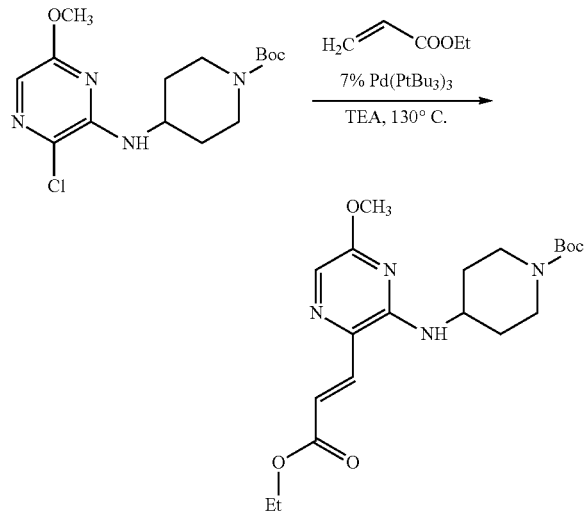

tert-Butyl 4-[(3-chloro-6-methoxypyrazin-2-yl)amino]piperidine-1-carboxylate (0.764 g, 2.23 mmol), Pd(PtBu₃)₃ (0.08 g, 0.156 mmol, 7% mol) and ethyl acrylate (0.29 mL, 2.67 mmol) were suspended in triethylamine (5.0 mL). The resulting mixture was stirred for 90 min at 130° C. then was cooled and partitioned between water and EtOAc. The aqueous layer was extracted twice with EtOAc, the combined organic layers were washed with brine, dried over Na₂SO₄ and concentrated under vacuum. The resulting crude was purified by column chromatography on SiO₂ (cyclohexane/EtOAc from 9:1 to 1:1) to afford the title compound (448 mg, 1.1 mmol, 49% yield). LC-MS (M–H⁺)=407.5

Step 4—Synthesis of Tert-butyl 4-(3-methoxy-6-oxopyrido[2,3-b]pyrazin-5(6H)-yl)piperidine-1-carboxylate

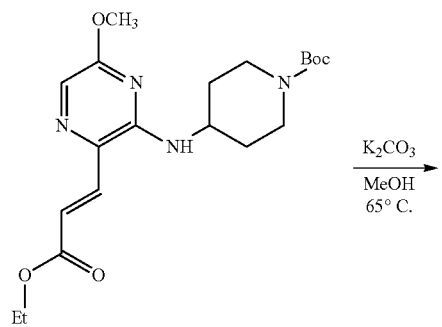

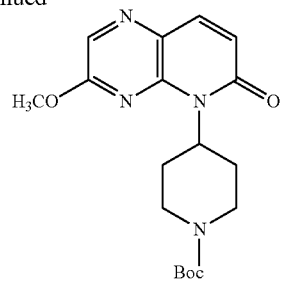

Intermediate tert-butyl 4-({3-[(1E)-3-ethoxy-3-oxoprop-1-en-1-yl]-6-methoxypyrazin-2-yl}amino)piperidine-1-carboxylate (0.34 g, 0.85 mmol) was dissolved in MeOH (17 mL), potassium carbonate (234 mg, 1.69 mmol) was added and the mixture was stirred at 65° C. for 24 h. The volatiles were removed under vacuum, the residue was partitioned between EtOAc and H₂O and the aqueous layer was extracted with EtOAc. The combined organic layers were washed with brine and dried over Na₂SO₄. The solvent was removed under vacuum to afford a crude which was purified by column chromatography (from cyclohexane/EtOAc 7:3 to EtOAc) to give the title compound (177 mg, 0.49 mmol, 58% yield). LC-MS (M–H⁺)=361.4

Step 5—Synthesis of 3-methoxy-5-(piperidin-4-yl)pyrido[2,3-b]pyrazin-6(5H)-one

The synthesis was performed according to the procedure described for the preparation of intermediate 1-(trans-4-aminocyclohexyl)-7-fluoro-1H-pyrido[2,3-b][1,4]oxazin-2(3H)-one (see compound 193, step 8) using tert-butyl 4-(3-methoxy-6-oxopyrido[2,3-b]pyrazin-5(6H)-yl)piperidine-1-carboxylate (92% yield). LC-MS (M–H⁺)=261.3

Step 6—Synthesis of 8-fluoro-2-{2-[4-(6-methoxy-3-oxopyrido[2,3-b]pyrazin-4(3H)-yl)piperidin-1-yl]ethyl}[1]benzopyrano[4,3-b]pyrrol-4(1H)-one (Hydrochloride, Compound 200)

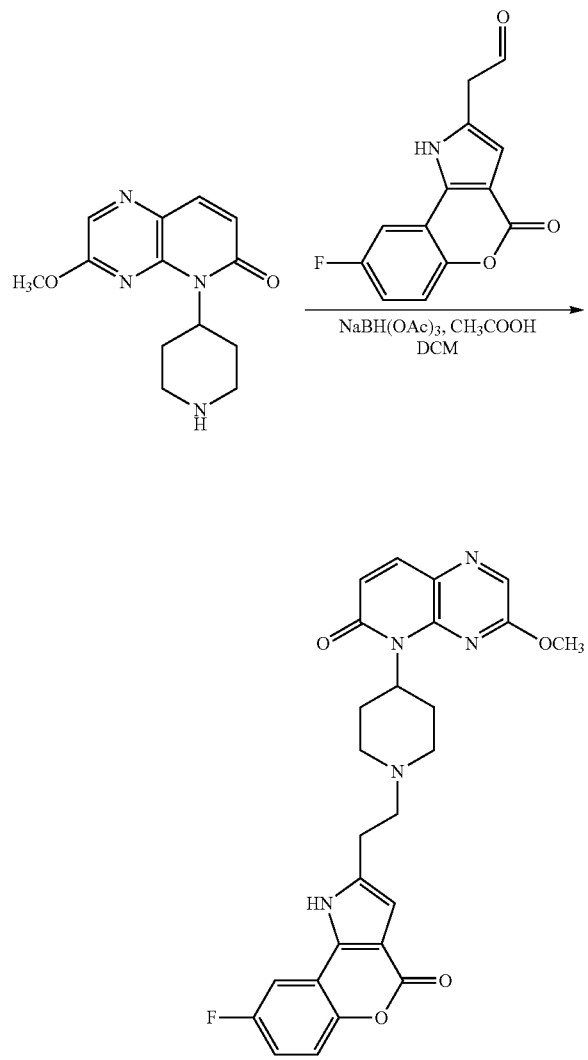

The title compound was prepared according to the procedure described for the synthesis of 8-fluoro-2-({[trans-4-(7-fluoro-2-oxo-2,3-dihydro-1H-pyrido[2,3-b][1,4]oxazin-1-yl)cyclohexyl]amino}methyl)[1]benzopyrano[4,3-b]pyrrol-4(1H)-one (compound 193, step 9) using (8-fluoro-4-oxo-1,4-dihydro[1]benzopyrano[4,3-b]pyrrol-2-yl)acetaldehyde and 3-methoxy-5-(piperidin-4-yl)pyrido[2,3-b]pyrazin-6(5H)-one (12% yield). LC-MS (M–H$^+$)=490.4. $^1$H NMR (500 MHz, METHANOL-d$_4$) δ ppm 2.08 (d, J=13.69 Hz, 2H), 3.32-3.43 (m, 6H), 3.55-3.66 (m, 2H), 3.87 (d, J=10.76 Hz, 2H), 4.18 (s, 3H), 5.87 (br. s., 1H), 6.64-6.78 (m, 2H), 7.24 (td, J=8.56, 2.93 Hz, 1H), 7.45 (dd, J=9.29, 4.40 Hz, 1H), 7.64 (dd, J=8.31, 2.93 Hz, 1H), 7.96 (d, J=9.29 Hz, 1H), 8.21 (s, 1H).

Preparation of Compound 201

Compound 201 was prepared as described herein below.

Step 1—Synthesis of Tert-butyl {trans-4-[(6-methoxy-3-nitropyridin-2-yl)amino]cyclohexyl}carbamate

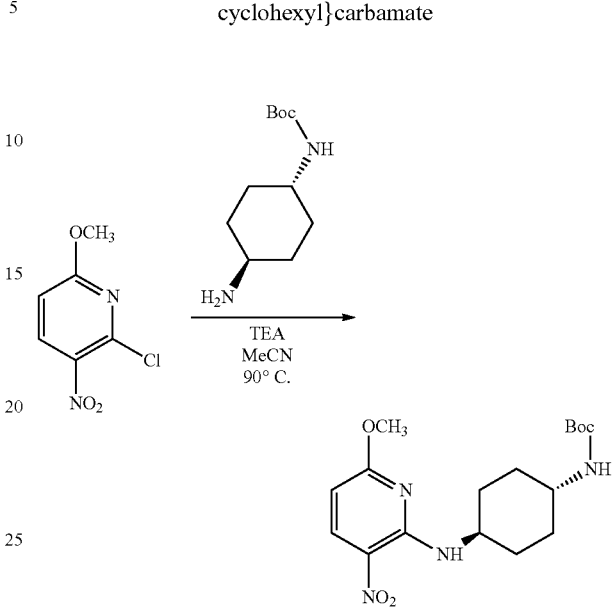

To a solution of tert-butyl (trans-4-aminocyclohexyl)carbamate (1.7 g, 8 mmol) and TEA (1.1 mL, 8 mmol) in acetonitrile (53 mL) 2-chloro-6-methoxy-3-nitropyridine (1.5 g, 7.95 mmol) was added. The reaction mixture was heated at 90° C. overnight then was cooled, filtered, and the filtrate was concentrated. The residue was treated with 50 mL of hot ethyl acetate, filtered and concentrated. The residue was dissolved in DCM and washed with sat. NH$_4$Cl. The organic phase was dried over Na$_2$SO$_4$ and concentrated to afford the title compound (1.5 g, 6.7 mmol, 84% yield). LC-MS (M–H$^+$)=367.4

Step 2—Synthesis of Tert-butyl {trans-4-[(3-amino-6-methoxypyridin-2-yl)amino]cyclohexyl}carbamate

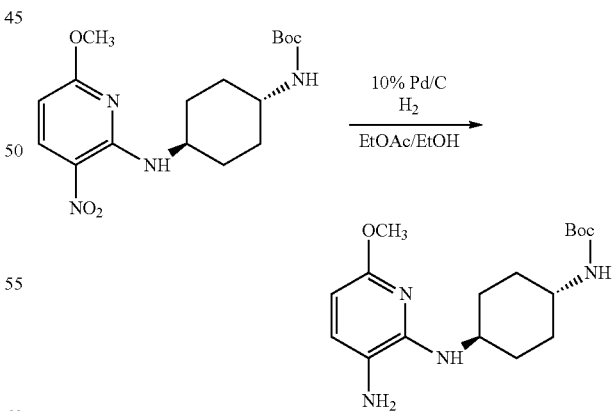

The title compound was prepared according to the procedure described for the synthesis of tert-butyl 4-[(3-amino-6-methoxypyridin-2-yl)amino]piperidine-1-carboxylate (see compound 197, step 2) using tert-butyl {trans-4-[(6-methoxy-3-nitropyridin-2-yl)amino]cyclohexyl}carbamate (94% yield). LC-MS (M–H$^+$)=337.4

Step 3—Synthesis of Ethyl N-[2-({trans-4-[(tert-butoxycarbonyl)amino]cyclohexyl}amino)-6-methoxypyridin-3-yl]glycinate

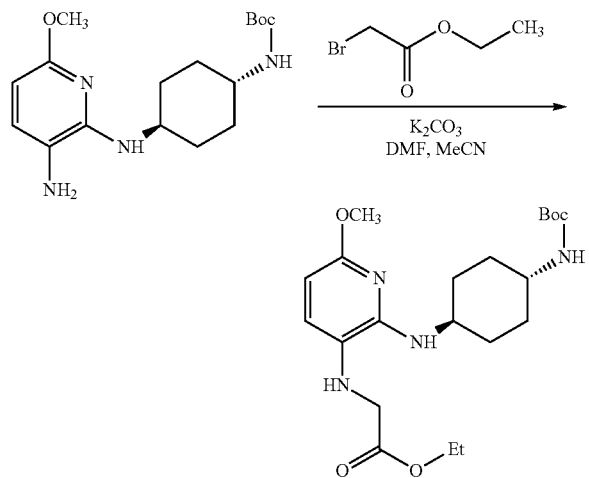

The title compound was prepared according to the procedure described for the synthesis of tert-butyl 4-({3-[(2-ethoxy-2-oxoethyl)amino]-6-methoxypyridin-2-yl}amino)piperidine-1-carboxylate (see compound 197, step 3) using tert-butyl {trans-4-[(3-amino-6-methoxypyridin-2-yl)amino]cyclohexyl}carbamate (62% yield). LC-MS (M−H+)=423.5

Step 4—Synthesis of Tert-butyl [trans-4-(6-methoxy-3-oxopyrido[2,3-b]pyrazin-4(3H)-yl)cyclohexyl]carbamate

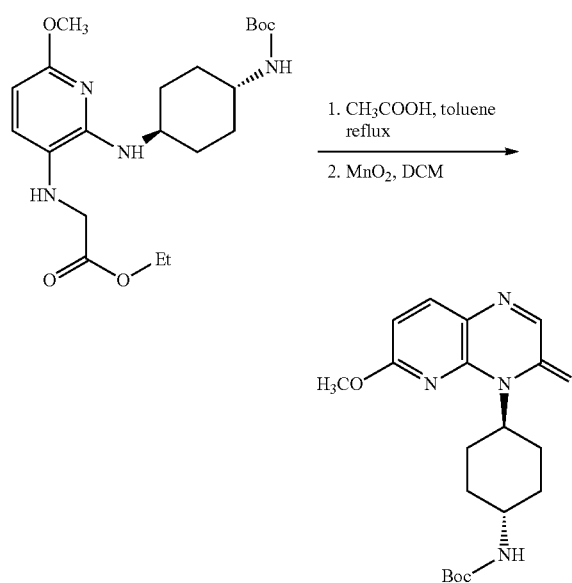

The title compound was prepared according to the procedure described for the synthesis of tert-butyl 4-(6-methoxy-3-oxo-2,3-dihydropyrido[2,3-b]pyrazin-4(1H)-yl)piperidine-1-carboxylate (see compound 197, step 4) using ethyl N-[2-({trans-4-[(tert-butoxycarbonyl)amino]cyclohexyl}amino)-6-methoxypyridin-3-yl]glycinate (51% yield). LC-MS (M-Na+)=397.5

Step 5—Synthesis of 4-(trans-4-aminocyclohexyl)-6-methoxypyrido[2,3-b]pyrazin-3(4H)-one

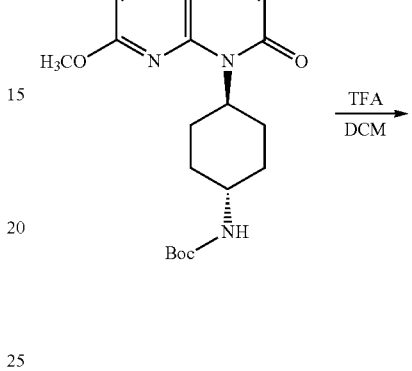

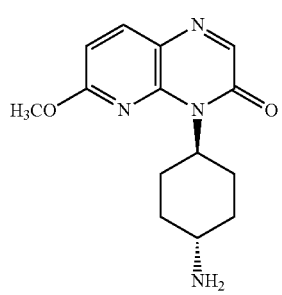

The title compound was prepared according to the procedure described for the synthesis of 1-(trans-4-aminocyclohexyl)-7-fluoro-1H-pyrido[2,3-b][1,4]oxazin-2(3H)-one (see compound 193, step 8) using tert-butyl [trans-4-(6-methoxy-3-oxopyrido[2,3-b]pyrazin-4(3H)-yl)cyclohexyl]carbamate (87% yield). LC-MS (M-Na+)=275.3

Step 6—Synthesis of 8-fluoro-2-({[trans-4-(6-methoxy-3-oxopyrido[2,3-b]pyrazin-4(3H)-yl)cyclohexyl]amino}methyl)[1]benzopyrano[4,3-b]pyrrol-4(1H)-one (Formate Salt, Compound 201)

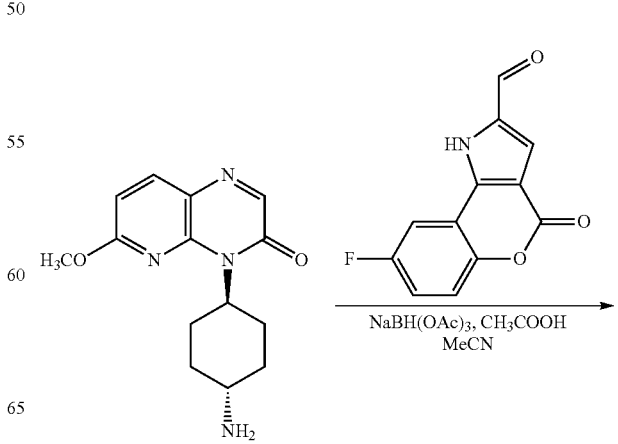

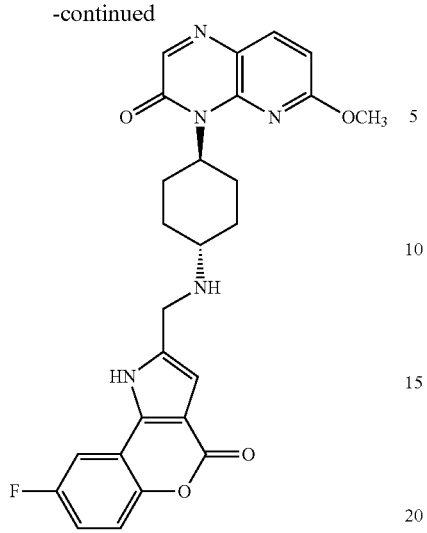

The title compound was prepared according to the procedure described for the synthesis of 8-fluoro-2-({[trans-4-(7-fluoro-2-oxo-2,3-dihydro-1H-pyrido[2,3-b][1,4]oxazin-1-yl)cyclohexyl]amino}methyl)[1]benzopyrano[4,3-b]pyrrol-4(1H)-one (compound 193, step 9) using 4-(trans-4-aminocyclohexyl)-6-methoxypyrido[2,3-b]pyrazin-3(4H)-one (17% yield). LC-MS (M–H⁺)=490.3. ¹H NMR (500 MHz, DMSO-d₆) δ ppm 1.21-1.32 (m, 2H), 1.67 (d, J=10.27 Hz, 2H), 2.10 (d, J=11.98 Hz, 2H), 2.41-2.56 (m, 1H), 2.72 (br. s., 2H), 3.83-3.96 (m, 5H), 4.96-5.49 (m, 1H), 6.58 (s, 1H), 6.83 (d, J=8.56 Hz, 1H), 7.29 (td, J=8.80, 2.93 Hz, 1H), 7.48 (dd, J=9.05, 4.65 Hz, 1H), 7.95 (dd, J=9.05, 2.93 Hz, 1H), 8.00-8.07 (m, 1H), 8.10 (d, J=8.56 Hz, 1H), 8.22 (s, 1H), 12.61 (br. s, 2H).

Preparation of Compound 202

Compound 202 was prepared as described herein below.

Step 1—Synthesis of N-(6-chloropyridin-2-yl)-2,2-dimethylpropanamide

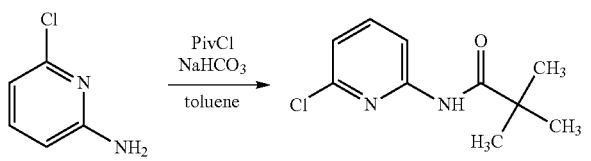

To a solution of 2-amino-6-chloropyridine (10.7 g, 83.5 mmol) in toluene (103 mL) NaHCO₃ (14 g, 167 mmol) and pivaloyl chloride (15.4 mL, 125.2 mmol) were added at 0° C. The resulting mixture was stirred at room temperature for 5 hours then the suspension was filtered and the solid was washed with DCM. The filtrates were concentrated under vacuum then heptane (22 mL) was added and the resulting mixture was filtered, washed with heptane (15 mL) and dried under vacuum to afford the title intermediate (15.4 g, 72.4 mmol, 87% yield). LC-MS (M–H⁺)=213.2

Step 2—Synthesis of N-(6-chloro-3-formylpyridin-2-yl)-2,2-dimethylpropanamide

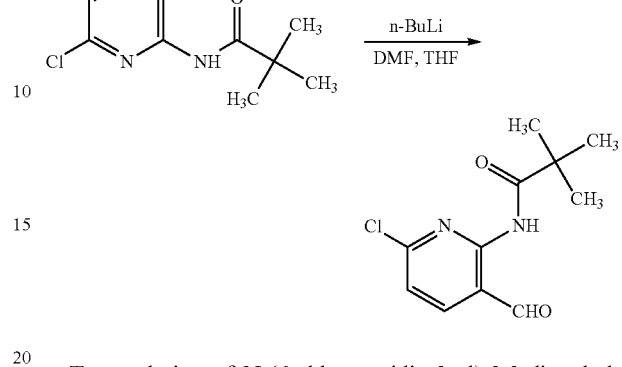

To a solution of N-(6-chloropyridin-2-yl)-2,2-dimethylpropanamide (10.6 g, 50 mmol) in THF (100 mL) n-butyllithium (2.5 M solution in hexane, 50 mL, 125 mmol) was added. The resulting mixture was stirred at –20° C. for 3 h. After the addiction of DMF (4 mL) the reaction mixture was allowed to warm to room temperature and then was quenched with 0.5 M HCl. Ethyl acetate was added, the organic phase was washed with water, sat. K₂CO₃ and with brine. The crude material was purified by Si-column eluting with cy to cy/ethyl acetate 7:3 to obtain the title product (6.7 g, 27.8 mmol, 56% yield). LC-MS (M–H⁺)=241.3

Step 3—Synthesis of Tert-butyl 3-[6-chloro-2-(2,2-dimethylpropanamido)pyridin-3-yl]-3-hydroxypropanoate

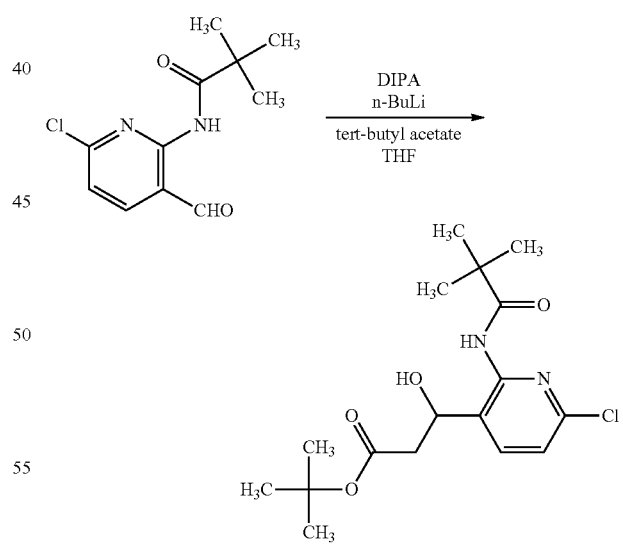

An oven-dried flask was charged with THF (80 mL) and diisopropylamine (8.2 mL, 58.4 mmol). The solution was cooled to –78° C. then n-butyllithium (2.5 M solution in hexane, 23.3 mL, 58.3 mmol) was added. The mixture was stirred for 15 min then a solution of tert-butyl acetate (7.8 mL, 58.3 mmol) in THF (2 mL) was added. After stirring at –78° C. for 20 min a solution of N-(6-chloro-3-formylpyridin-2-yl)-2,2-dimethylpropanamide (6.7 g, 27.8 mmol) in THF (5 mL) was added. The mixture was allowed to warm to room temperature then was poured into sat. NH₄Cl. The resulting mixture was extracted with ethyl acetate and the organic phase was dried and evaporated in vacuo to obtain the title compound (9.4 g, 26.4 mmol, 95% yield). LC-MS (M–H⁺)=357.3

Step 4—Synthesis of 7-chloro-1,8-naphthyridin-2(1H)-one

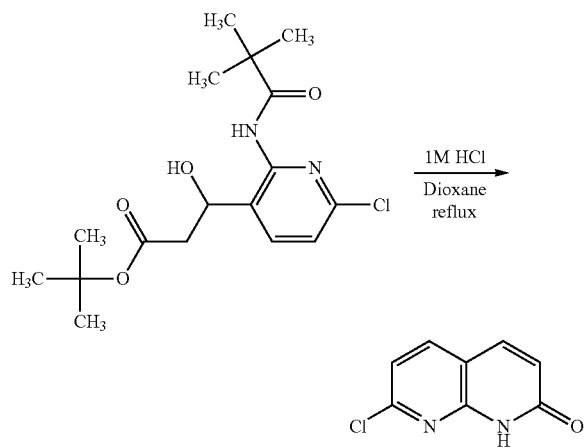

Intermediate tert-butyl 3-[6-chloro-2-(2,2-dimethylpropanamido)pyridin-3-yl]-3-hydroxypropanoate (4 g, 11 mmol) was dissolved in 1 M HCl/dioxane 1:1 (50 mL) and refluxed overnight. Ice was added to the mixture and the resulting solid was filtered and dried to afford the title product (1.7 g, 9.4 mmol, 86% yield), that was used without any further purification. LC-MS (M–H⁺)=181.1

Step 5—Synthesis of 7-methoxy-1,8-naphthyridin-2(1H)-one

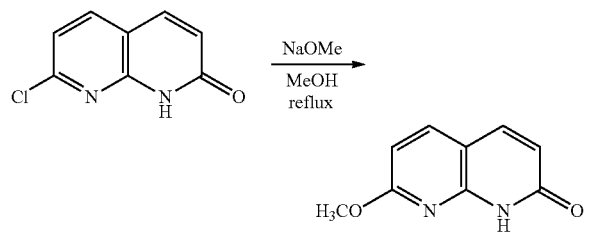

To a suspension of 7-chloro-1,8-naphthyridin-2(1H)-one (700 mg, 3.9 mmol) in MeOH (15 mL), NaOMe (25% solution in MeOH, 20 mL) was added. The resulting solution was stirred at reflux for 15 h then the solvent was removed in vacuo. Water (100 mL) and EtOAc (80 mL) were added, the phases were separated and the aqueous layer was extracted with EtOAc (8×80 mL). The combined organic layers were washed with brine (50 mL), dried over MgSO₄, filtered and concentrated under reduced pressure to give the title compound (630 mg, 3.6 mmol, 92% yield). LC-MS (M–H⁺)=177.2

Step 6—Synthesis of Tert-butyl 4-(7-methoxy-2-oxo-1,8-naphthyridin-1(2H)-yl)piperidine-1-carboxylate

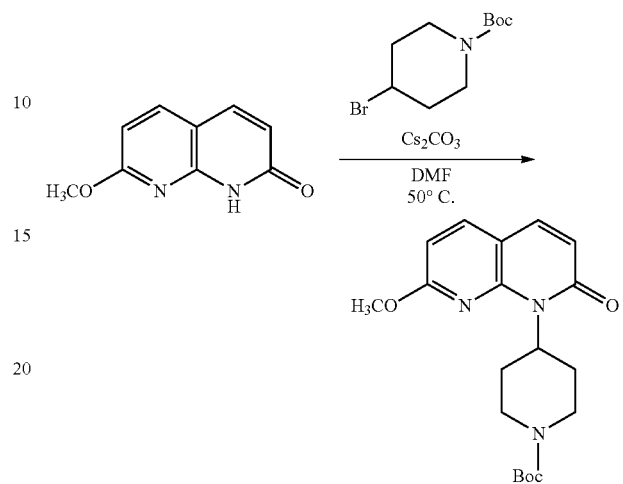

Cs₂CO₃ (828 mg, 2.6 mmol) and tert-butyl 4-bromopiperidine-1-carboxylate (1.35 g, 5.1 mmol) were sequentially added to a solution of 7-methoxy-1,8-naphthyridin-2(1H)-one (150 mg, 0.85 mmol) in DMF (15 mL). The reaction mixture was stirred at 50° C. overnight then was partitioned between EtOAc and water. The organic phases were dried over Na₂SO₄, filtered and evaporated in vacuo. The crude material was purified by silica-gel chromatography (cyclohexane/EtOAc from 100:0 to 50:50) to afford the title product (70 mg, 0.2 mmol, 22% yield). LC-MS (M–H⁺)=360.4

Step 7—Synthesis of 7-methoxy-1-(piperidin-4-yl)-1,8-naphthyridin-2(1H)-one

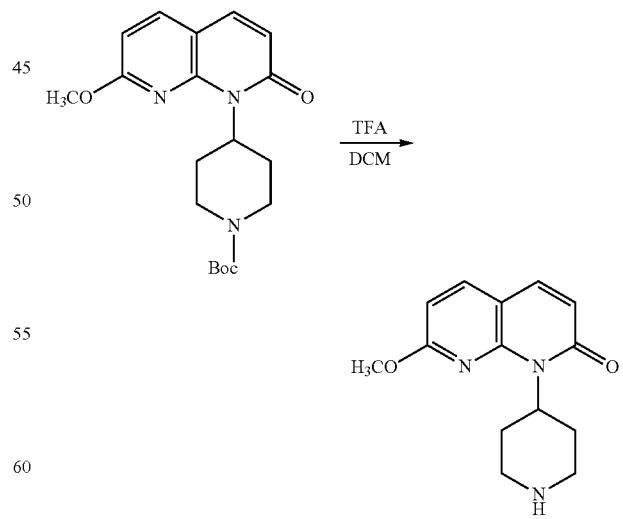

The title intermediate was prepared according to the procedure described for the synthesis of 1-(trans-4-aminocyclohexyl)-7-fluoro-1H-pyrido[2,3-b][1,4]oxazin-2(3H)-one (see compound 193, step 8) using tert-butyl 4-(7- methoxy-2-oxo-1,8-naphthyridin-1(2H)-yl)piperidine-1-carboxylate (72% yield). LC-MS (M−H⁺)=260.3

Step 8—Synthesis of 8-fluoro-2-{2-[4-(7-methoxy-2-oxo-1,8-naphthyridin-1(2H)-yl)piperidin-1-yl]ethyl}[1]benzopyrano[4,3-b]pyrrol-4(1H)-one (Hydrochloride, Compound 202)

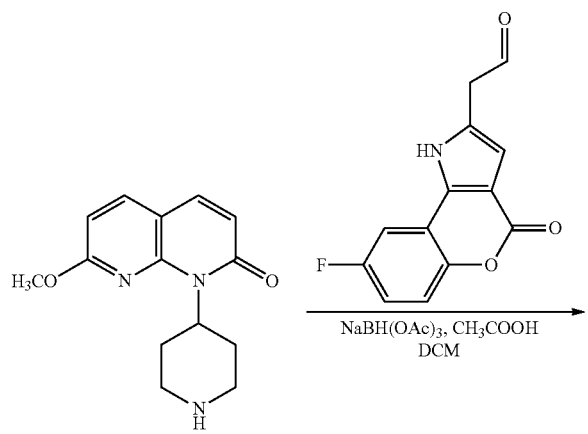

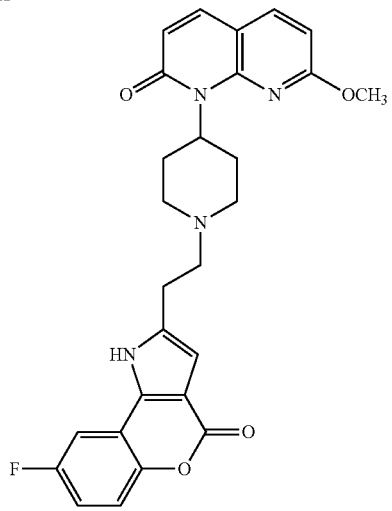

The title compound was prepared according to the procedure described for the synthesis of 8-fluoro-2-({[trans-4-(7-fluoro-2-oxo-2,3-dihydro-1H-pyrido[2,3-b][1,4]oxazin-1-yl)cyclohexyl]amino}methyl)[1]benzopyrano[4,3-b]pyrrol-4(1H)-one (compound 193, step 9) using (8-fluoro-4-oxo-1,4-dihydro[1]benzopyrano[4,3-b]pyrrol-2-yl)acetaldehyde and 7-methoxy-1-(piperidin-4-yl)-1,8-naphthyridin-2(1H)-one (11% yield). LC-MS (M−H⁺)=489.3. ¹H NMR (500 MHz, METHANOL-d₄) δ ppm 1.95-2.11 (m, 2H), 3.30-3.40 (m, 6H), 3.55-3.63 (m, 2H), 3.81-3.88 (m, 2H), 4.08 (s, 3H), 6.03 (br. s., 1H), 6.50 (d, J=9.39 Hz, 1H), 6.69 (s, 1H), 6.75 (d, J=8.41 Hz, 1H), 7.22 (td, J=8.71, 2.93 Hz, 1H), 7.43 (dd, J=9.10, 4.40 Hz, 1H), 7.62 (dd, J=8.61, 2.93 Hz, 1H), 7.83 (d, J=9.39 Hz, 1H), 7.98 (d, J=8.61 Hz, 1H).

Preparation of Compounds 204 and 205

Compounds 204 and 205 were prepared as described herein below.

Step 1—Synthesis of Tert-butyl {4-[(2-bromo-5-fluoropyridin-3-yl)amino]cyclohexyl}carbamate

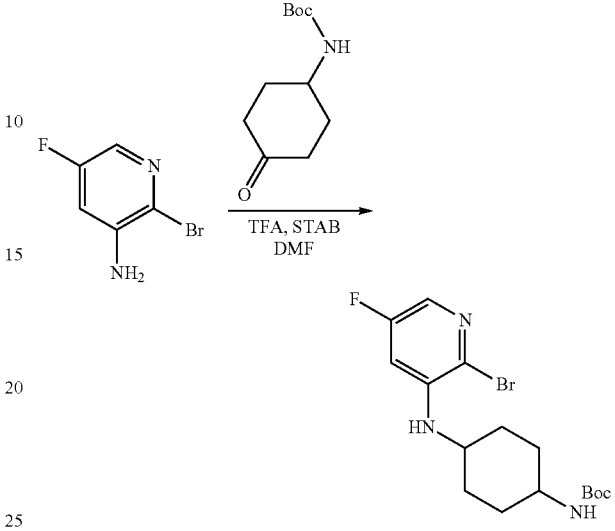

The title compound was obtained as a mixture of isomers following the procedure described for the preparation of intermediate tert-butyl {4-[(5-fluoro-2-hydroxypyridin-3-yl)amino]cyclohexyl}carbamate (see compound 193, step 6) using 2-bromo-5-fluoropyridin-3-amine (98% yield). LC-MS (M−H⁺)=388.2

Step 2—Synthesis of Ethyl (2E)-3-[3-({4-[(tert-butoxycarbonyl)amino]cyclohexyl}amino)-5-fluoropyridin-2-yl]prop-2-enoate

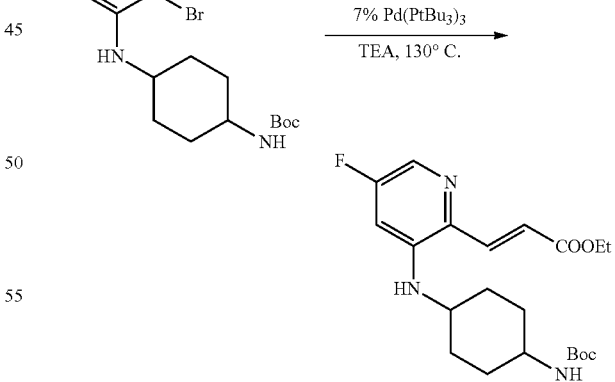

The title compound was obtained as a mixture of isomers following the procedure described for the preparation of intermediate tert-butyl 4-({3-[(1E)-3-ethoxy-3-oxoprop-1-en-1-yl]-6-methoxypyrazin-2-yl}amino)piperidine-1-carboxylate (see compound 200, step 3) using tert-butyl {4-[(2-bromo-5-fluoropyridin-3-yl)amino]cyclohexyl}carbamate (66% yield). LC-MS (M−H⁺)=408.5

Step 3—Synthesis of Tert-butyl 4-({3-[(1E)-3-ethoxy-3-oxoprop-1-en-1-yl]-6-methoxypyrazin-2-yl}amino)piperidine-1-carboxylate

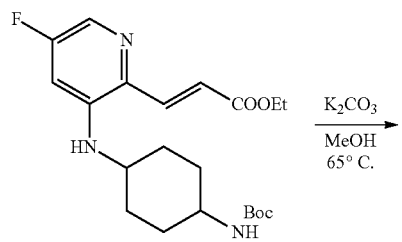

The title compound was obtained as a mixture of isomers following the procedure described for the preparation of intermediate tert-butyl 4-(3-methoxy-6-oxopyrido[2,3-b]pyrazin-5(6H)-yl)piperidine-1-carboxylate (see compound 200, step 4) using ethyl (2E)-3-[3-({4-[(tert-butoxycarbonyl)amino]cyclohexyl}amino)-5-fluoropyridin-2-yl]prop-2-enoate (17% yield). LC-MS (M–H+)=374.3

Step 4—Synthesis of 1-(4-aminocyclohexyl)-7-methoxy-1,5-naphthyridin-2(1H)-one

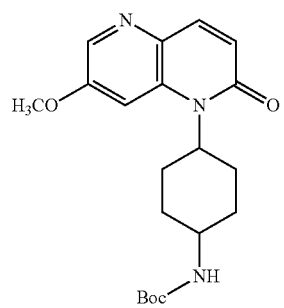

The title compound was obtained as a mixture of isomers following the procedure described for the preparation of intermediate 1-(trans-4-aminocyclohexyl)-7-fluoro-1H-pyrido[2,3-b][1,4]oxazin-2(3H)-one (see compound 193, step 8) using tert-butyl 4-({3-[(1E)-3-ethoxy-3-oxoprop-1-en-1-yl]-6-methoxypyrazin-2-yl}amino)piperidine-1-carboxylate (73% yield). LC-MS (M–H+)=274.1

Step 5—Synthesis of 8-fluoro-2-({[trans-4-(7-methoxy-2-oxo-1,5-naphthyridin-1(2H)-yl)cyclohexyl]amino}methyl)[1]benzopyrano[4,3-b]pyrrol-4(1H)-one (Hydrochloride, Compound 204) and 8-fluoro-2-({[cis-4-(7-methoxy-2-oxo-1,5-naphthyridin-1(2H)-yl)cyclohexyl]amino}methyl)[1]benzopyrano[4,3-b]pyrrol-4(1H)-one (Hydrochloride, Compound 205)

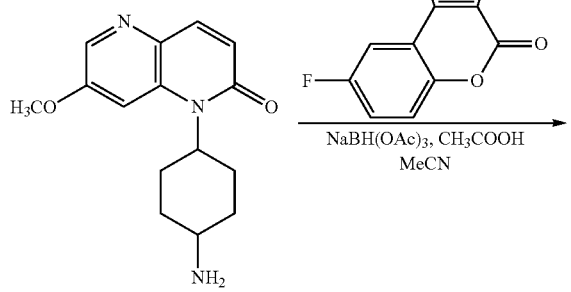

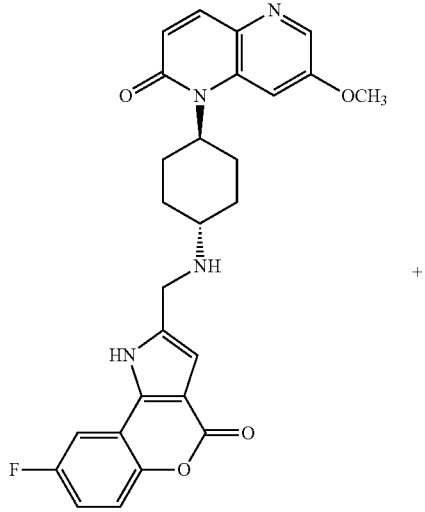

95

-continued

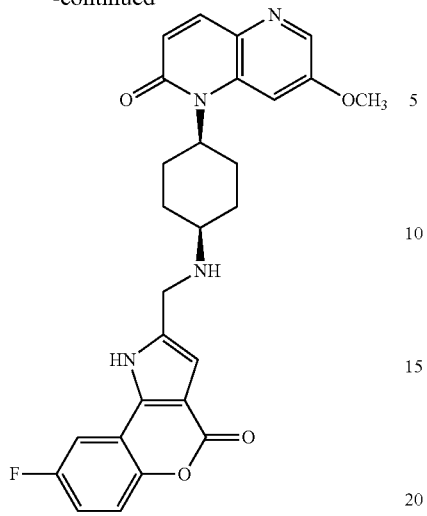

The title compounds were prepared according to the procedure described for the synthesis of 8-fluoro-2-({[trans-4-(7-fluoro-2-oxo-2,3-dihydro-1H-pyrido[2,3-b][1,4]oxazin-1-yl)cyclohexyl]amino}methyl)[1]benzopyrano[4,3-b]pyrrol-4(1H)-one (compound 193, step 9) using 1-(4-aminocyclohexyl)-7-methoxy-1,5-naphthyridin-2(1H)-one as a mixture of isomers.

A purification by preparative HPLC (A=0.1% ammonia aqueous solution, B=acetonitrile, form 98:2 A:B to 100% B) followed by treatment with HCl under the previously described conditions afforded the trans (20% yield) and cis (15% yield) diastereoisomers.

Compound 204: LC-MS (M–H$^+$)=489.2; $^1$H NMR (400 MHz, DMSO-d$_6$) δ ppm 1.62-1.91 (m, 4H), 2.20-2.40 (m, 2H), 2.67 (br. s., 2H), 3.28 (br. s., 1H), 4.01 (s, 3H), 4.34-4.86 (m, 3H), 6.60 (d, J=9.59 Hz, 1H), 6.95 (d, J=1.57 Hz, 1H), 7.38 (td, J=8.75, 3.03 Hz, 1H), 7.53 (dd, J=9.10, 4.50 Hz, 1H), 7.63 (br. s., 1H), 7.78-7.92 (m, 2H), 8.32 (d, J=2.15 Hz, 1H), 9.33 (br. s., 2H), 13.41 (br. s., 1H).

Compound 205: LC-MS (M–H$^+$)=489.2; $^1$H NMR (400 MHz, DMSO-d$_6$) δ ppm 1.65 (d, J=11.74 Hz, 2H), 2.00 (m, J=13.89 Hz, 2H), 2.17 (d, J=14.28 Hz, 2H), 2.76 (m, J=12.13 Hz, 2H), 3.40-3.56 (m, 1H), 4.01 (s, 3H), 4.39-4.51 (m, 2H), 4.59-4.92 (m, 1H), 6.62 (d, J=9.59 Hz, 1H), 6.99 (d, J=1.76 Hz, 1H), 7.38 (td, J=8.75, 3.03 Hz, 1H), 7.53 (dd, J=9.10, 4.60 Hz, 1H), 7.67 (s, 1H), 7.78-7.92 (m, 2H), 8.33 (d, J=2.15 Hz, 1H), 9.23 (br. s., 2H), 13.49 (s, 1H).

Preparation of Compound 206

Compound 206 was prepared as described herein below.

Step 1—Synthesis of Tert-butyl [4-(5-cyano-2-iodoanilino)cyclohexyl]carbamate

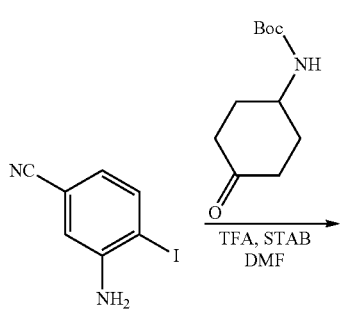

96

-continued

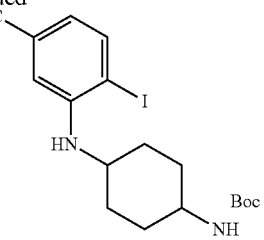

The title compound was obtained as a mixture of isomers following the procedure described for the preparation of intermediate tert-butyl {4-[(5-fluoro-2-hydroxypyridin-3-yl)amino]cyclohexyl}carbamate (see compound 193, step 6) using 3-amino-4-iodobenzonitrile (24% yield). LC-MS (M–H$^+$)=442.2

Step 2—Synthesis of Ethyl (2E)-3-[2-({4-[(tert-butoxycarbonyl)amino]cyclohexyl}amino)-4-cyanophenyl]prop-2-enoate

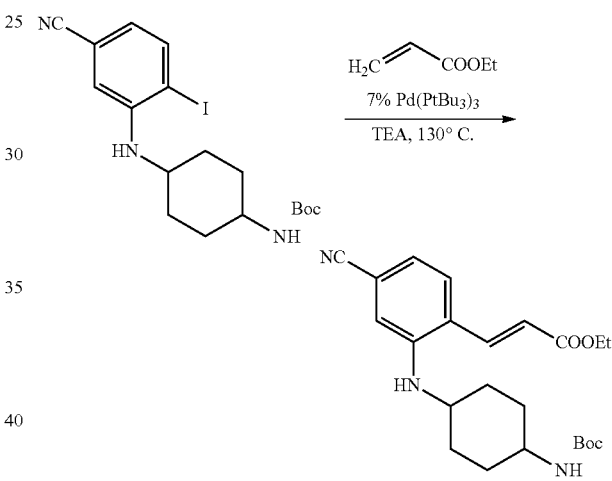

The title compound was obtained as a mixture of isomers following the procedure described for the preparation of intermediate tert-butyl 4-({3-[(1E)-3-ethoxy-3-oxoprop-1-en-1-yl]-6-methoxypyrazin-2-yl}amino)piperidine-1-carboxylate (see compound 200, step 3) using tert-butyl [4-(5-cyano-2-iodoanilino)cyclohexyl]carbamate (88% yield). LC-MS (M–H$^+$)=414.4

Step 3—Synthesis of Ethyl 3-[2-({4-[(tert-butoxycarbonyl)amino]cyclohexyl}amino)-4-cyanophenyl]propanoate

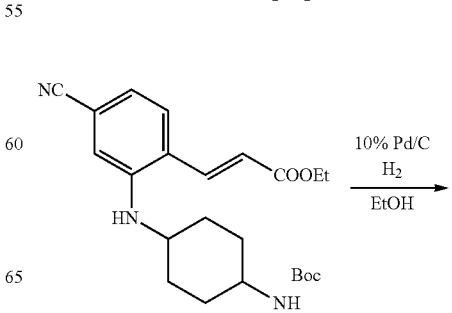

-continued

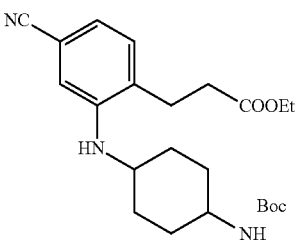

Ethyl (2E)-3-{2-[(4-{[(tert-butoxy)carbonyl]amino}cyclohexyl)amino]-4-cyanophenyl}prop-2-enoate (37.9 g, 91.7 mmol) was dissolved in ethyl acetate (379 mL), 10% Pd/C (7.6 g) was added and the mixture was stirred under hydrogen atmosphere (1 atm) overnight. The catalyst was removed by filtration and the solvent was evaporated in vacuo to obtain the title intermediate as a mixture of isomers (35.7 g, 85.9 mmol, Y=94%, LC-MS (M−H$^+$)=416.4

Step 4—Synthesis of 3-[2-({4-[(tert-butoxycarbonyl)amino]cyclohexyl}amino)-4-cyanophenyl]propanoic Acid

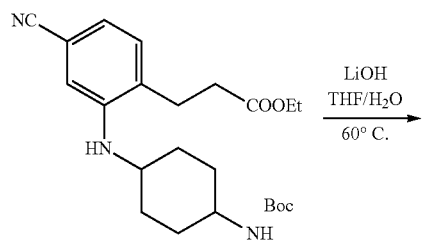

Ethyl 3-{2-[(4-{[(tert-butoxy)carbonyl]amino}cyclohexyl)amino]-4-cyanophenyl}propanoate (43.5 g, 0.11 mol) was dissolved in THF/H$_2$O (455/136 mL), LiOH.H$_2$O (8.8 g, 0.21 mol) was added and the mixture was stirred at room temperature overnight. The solvent was evaporated in vacuo, the residue was treated with acetonitrile, filtered and concentrated in vacuo. The crude title product (mixture of isomers) was progressed without any further purification.

Step 5—Synthesis of Tert-butyl [trans-4-(7-cyano-2-oxo-3,4-dihydroquinolin-1(2H)-yl)cyclohexyl]carbamate

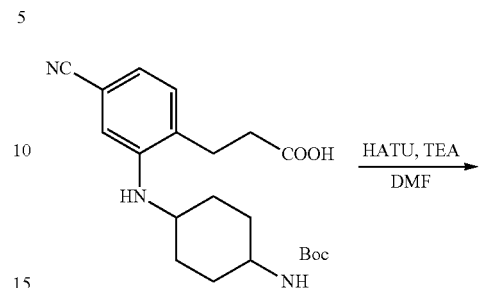

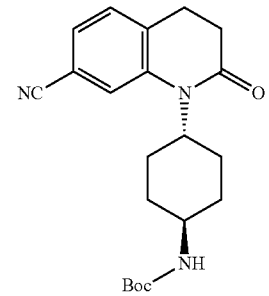

3-[2-({4-[(tert-butoxycarbonyl)amino]cyclohexyl}amino)-4-cyanophenyl]propanoic acid (0.11 mol from previous step) was dissolved in DMF (910 mL), TEA (30.5 mL, 0.22 mol) was added and the mixture was cooled to 0° C. HATU (41.6 g, 0.11 mol) was added at the same temperature and the mixture was allowed to slowly reach room temperature. After stirring overnight the mixture was partitioned between water (1 L) and EtOAc (500 mL). The organic phase was washed with brine and dried over Na$_2$SO$_4$. The volatiles were removed under vacuum and the crude residue was purified by Si-column (cyclohexane/ethyl acetate from 8:2 to 1:1) to obtain the title trans diastereoisomer (14.4 g, 39 mmol, 35% yield over two steps). LC-MS (M−H$^+$)=370.2

Step 6—Synthesis of Tert-butyl [trans-4-(7-cyano-2-oxoquinolin-1(2H)-yl)cyclohexyl]carbamate

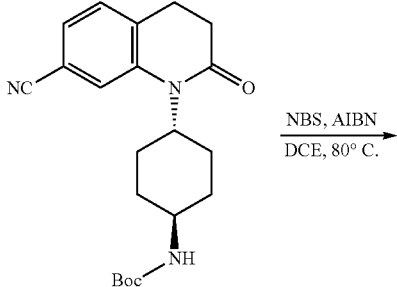

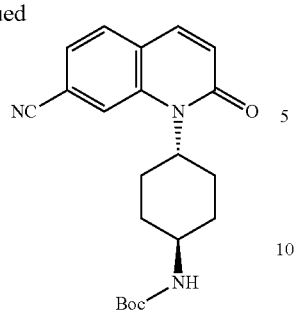

tert-Butyl [trans-4-(7-cyano-2-oxo-3,4-dihydroquinolin-1(2H)-yl)cyclohexyl]carbamate (13.7 g 37.2 mmol) was dissolved in DCE (274 mL), N-bromosuccinimide (8.6 g, 48.4 mmol) and 2,2'-azobis(2-methylpropionitrile) (917 mg, 5.6 mmol) were added and the mixture was stirred at 80° C. for 4 h. Water (100 mL) was added, the organic phase was separated, washed with brine (80 mL) and evaporated in vacuo to obtain the crude title product that was progressed without any further purification. LC-MS (M−H$^+$)=368.3

Step 7—Synthesis of 1-(trans-4-aminocyclohexyl)-2-oxo-1,2-dihydroquinoline-7-carbonitrile The title intermediate was prepared according to the procedure described for the synthesis of 1-(trans-4-aminocyclohexyl)-7-fluoro-1H-pyrido[2,3-b][1,4]oxazin-2(3H)-one (see compound 193, step 8) using tert-butyl [trans-4-(7-cyano-2-oxoquinolin-1(2H)-yl)cyclohexyl]carbamate (quant. yield). LC-MS (M−H$^+$)=268.2

Step 8—Synthesis of 1-(trans-4-{[(8-fluoro-4-oxo-1,4-dihydro[1]benzopyrano[4,3-b]pyrrol-2-yl)methyl]amino}cyclohexyl)-2-oxo-1,2-dihydroquinoline-7-carbonitrile (Hydrochloride, Compound 206)

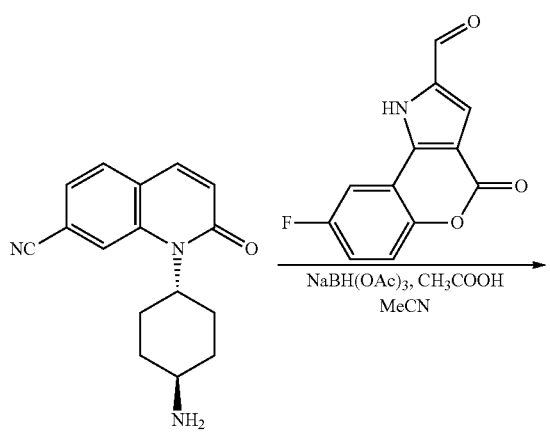

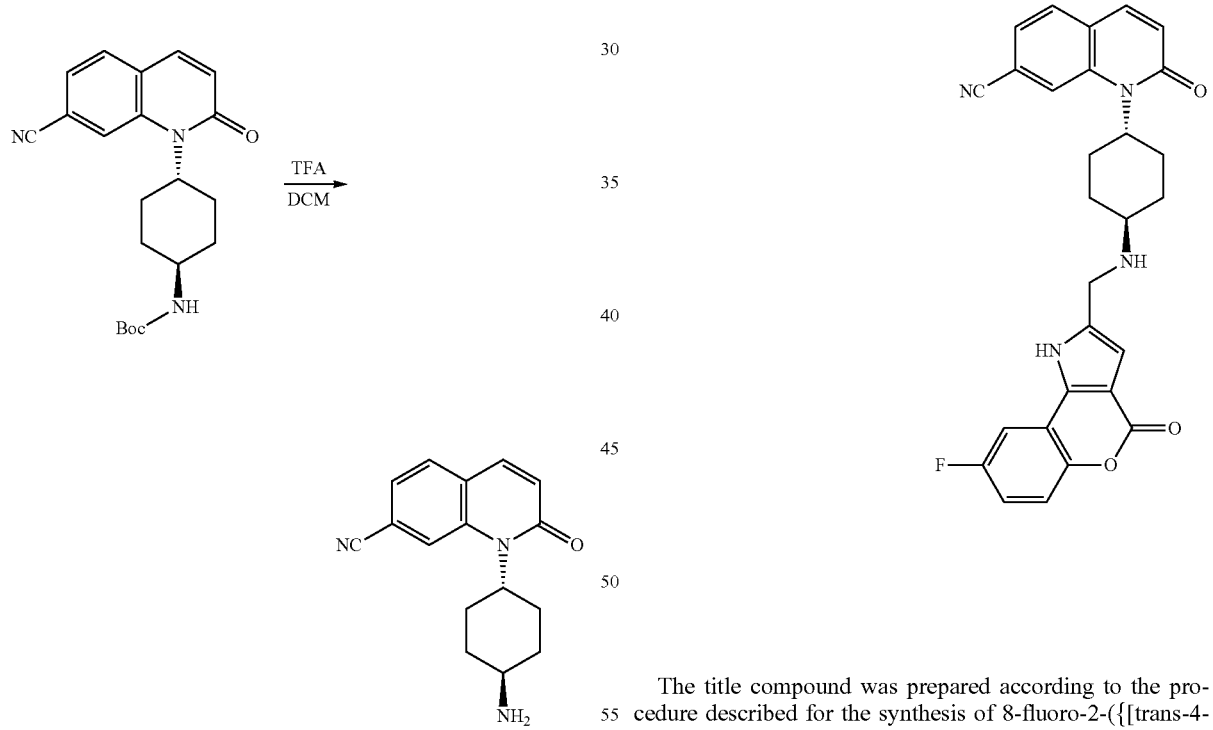

The title compound was prepared according to the procedure described for the synthesis of 8-fluoro-2-({[trans-4-(7-fluoro-2-oxo-2,3-dihydro-1H-pyrido[2,3-b][1,4]oxazin-1-yl)cyclohexyl]amino}methyl)[1]benzopyrano[4,3-b]pyrrol-4(1H)-one (compound 193, step 9) using 1-(trans-4-aminocyclohexyl)-2-oxo-1,2-dihydroquinoline-7-carbonitrile (12% yield). LC-MS (M−H$^+$)=483.3. $^1$H NMR (500 MHz, DMSO-d$_6$) δ ppm 1.66-1.90 (m, 4H), 2.19-2.40 (m, 2H), 2.61-2.82 (m, 2H), 3.08-3.42 (m, 1H), 4.40 (br. s., 2H), 4.64 (br. s., 1H), 6.70 (d, J=8.51 Hz, 1H), 6.96 (br. s., 1H), 7.37 (td, J=8.71, 2.88 Hz, 1H), 7.53 (dd, J=9.13, 4.60 Hz, 1H), 7.66 (d, J=8.10 Hz, 1H), 7.85-7.93 (m, 2H), 7.96 (d, J=9.61 Hz, 1H), 8.40 (br. s., 1H), 9.44 (br. s., 1H), 13.53 (br. s., 1H).

Preparation of Compound 207
Compound 207 was prepared as described herein below.

Step 1—Synthesis of Tert-butyl {4-[(2-bromo-5-fluoropyridin-3-yl)amino]cyclohexyl}carbamate

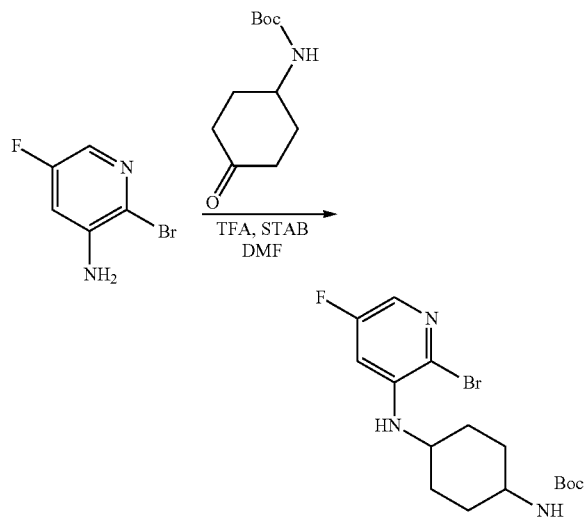

The title compound was obtained as a mixture of isomers following the procedure described for the preparation of intermediate tert-butyl {4-[(5-fluoro-2-hydroxypyridin-3-yl)amino]cyclohexyl}carbamate (see compound 193, step 6) using 2-bromo-5-fluoropyridin-3-amine (98% yield). LC-MS (M–H$^+$)=388.2

Step 2—Synthesis of ethyl (2E)-3-[3-({4-[(tert-butoxycarbonyl)amino]cyclohexyl}amino)-5-fluoropyridin-2-yl]prop-2-enoate

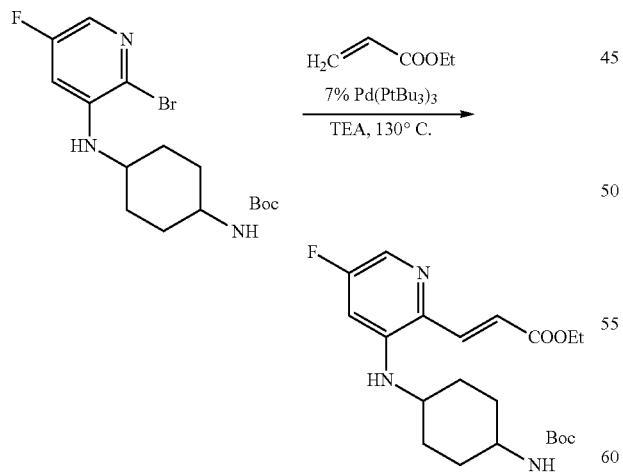

The title compound was obtained as a mixture of isomers following the procedure described for the preparation of intermediate tert-butyl 4-({3-[(1E)-3-ethoxy-3-oxoprop-1-en-1-yl]-6-methoxypyrazin-2-yl}amino)piperidine-1-carboxylate (see compound 200, step 3) using tert-butyl {4-[(2-bromo-5-fluoropyridin-3-yl)amino]cyclohexyl}carbamate (66% yield). LC-MS (M–H$^+$)=408.5

Step 3—Synthesis of Ethyl 3-[3-({4-[(tert-butoxycarbonyl)amino]cyclohexyl}amino)-5-fluoropyridin-2-yl]propanoate

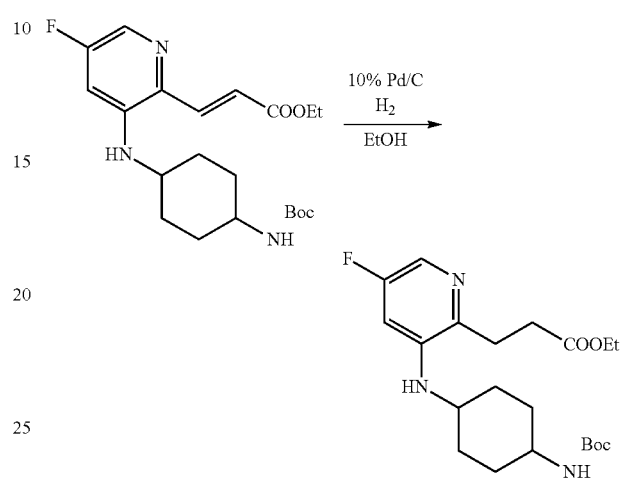

The title compound was obtained as a mixture of isomers following the procedure described for the preparation of intermediate ethyl 3-[2-({4-[(tert-butoxycarbonyl)amino]cyclohexyl}amino)-4-cyanophenyl]propanoate (see compound 206, step 3) using ethyl (2E)-3-[3-({4-[(tert-butoxycarbonyl)amino]cyclohexyl}amino)-5-fluoropyridin-2-yl]prop-2-enoate (97% yield). LC-MS (M–H$^+$)=410.5

Step 4—Synthesis of Tert-butyl [trans-4-(7-fluoro-2-oxo-3,4-dihydro-1,5-naphthyridin-1(2H)-yl)cyclohexyl]carbamate

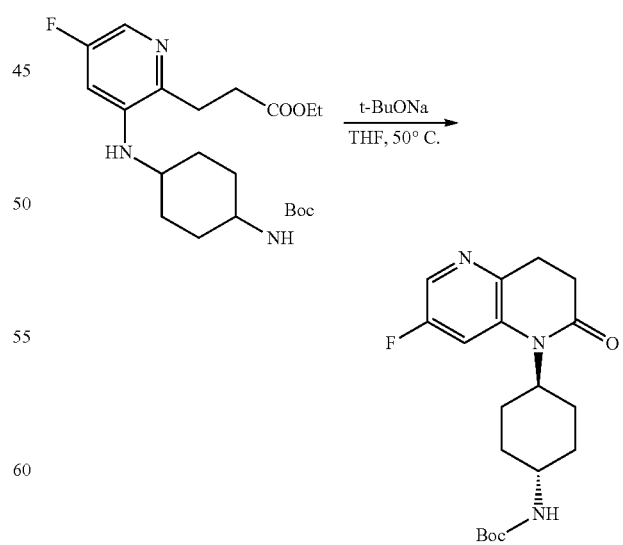

3-[3-({4-[(tert-butoxycarbonyl)amino]cyclohexyl}amino)-5-fluoropyridin-2-yl]propanoate (1.8 g, 4.5 mmol) was dissolved in THF (20 mL), t-BuONa (0.87 g, 9 mmol) was added and the mixture was stirred at 50° C. for 4 h. Ethyl acetate was added followed by water. The organic phase was separated, dried over Na$_2$SO$_4$ and evaporated in vacuo. The crude was purified by Si-column (cy to cy/ethyl acetate 1:1) to obtain 180 mg of the title trans diastereoisomer (0.18 g, 0.5 mmol, 11% yield). LC-MS (M−H$^+$)=364.4

Step 5—Synthesis of Tert-butyl [trans-4-(7-fluoro-2-oxo-1,5-naphthyridin-1(2H)-yl)cyclohexyl]carbamate

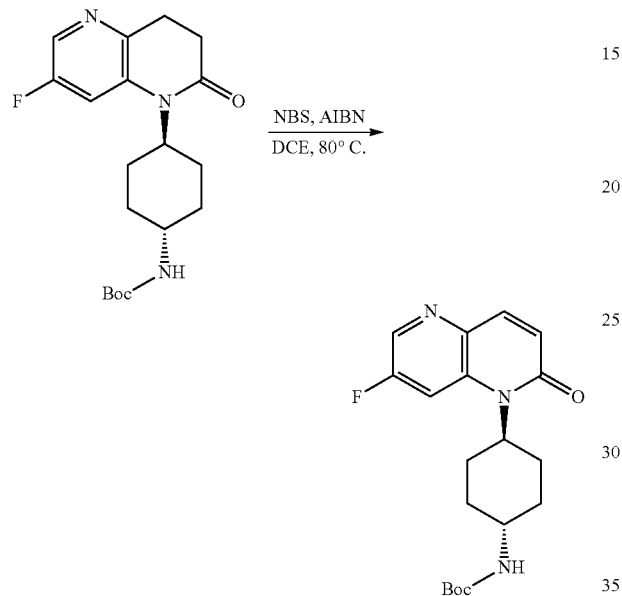

The title compound was prepared following the procedure described for the synthesis of intermediate tert-butyl [trans-4-(7-cyano-2-oxoquinolin-1(2H)-yl)cyclohexyl]carbamate (see compound 206, step 6) using tert-butyl [trans-4-(7-fluoro-2-oxo-3,4-dihydro-1,5-naphthyridin-1(2H)-yl)cyclohexyl]carbamate (96% yield). LC-MS (M−H$^+$)=362.2

Step 6—Synthesis of 1-(trans-4-aminocyclohexyl)-7-fluoro-1,5-naphthyridin-2(1H)-one

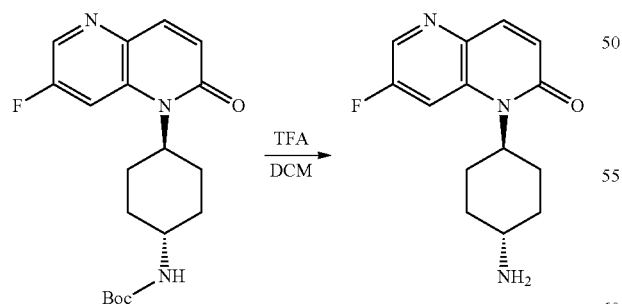

The title compound was obtained following the procedure described for the preparation of intermediate 1-(trans-4-aminocyclohexyl)-7-fluoro-1H-pyrido[2,3-b][1,4]oxazin-2(3H)-one (see compound 193, step 8) using tert-butyl [trans-4-(7-fluoro-2-oxo-1,5-naphthyridin-1(2H)-yl)cyclohexyl]carbamate (98% yield). LC-MS (M−H$^+$)=262.2

Step 7—Synthesis of 8-fluoro-2-({[trans-4-(7-fluoro-2-oxo-1,5-naphthyridin-1(2H)-yl)cyclohexyl]amino}methyl)[1]benzopyrano[4,3-b]pyrrol-4(1H)-one (Formate Salt, Compound 207)

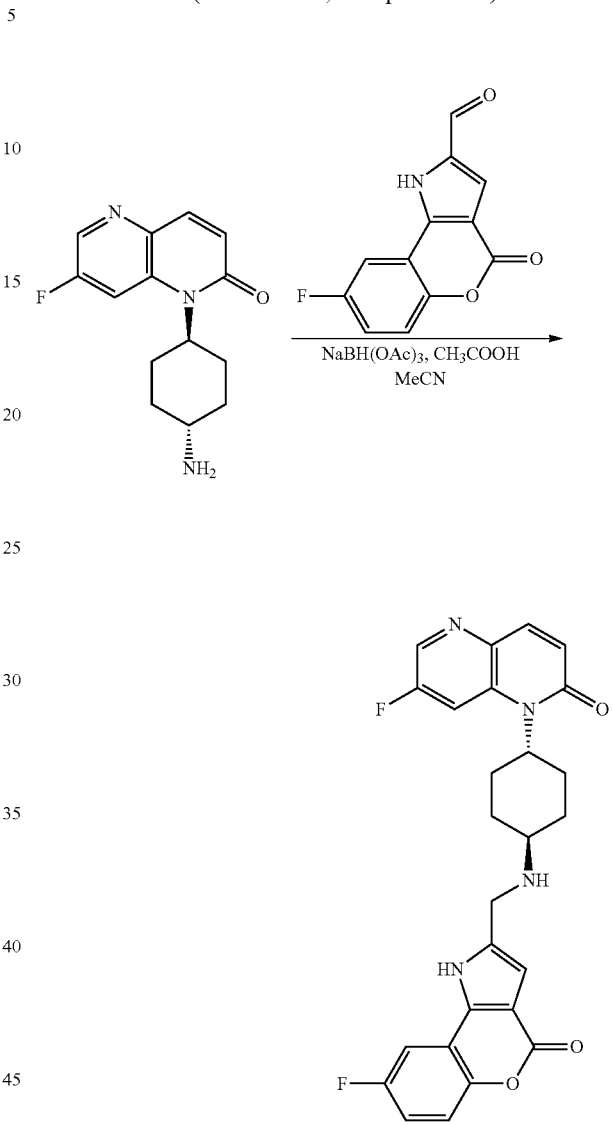

The title compound was prepared according to the procedure described for the synthesis of 8-fluoro-2-({[trans-4-(7-fluoro-2-oxo-2,3-dihydro-1H-pyrido[2,3-b][1,4]oxazin-1-yl)cyclohexyl]amino}methyl)[1]benzopyrano[4,3-b]pyrrol-4(1H)-one (compound 193, step 9) using 1-(trans-4-aminocyclohexyl)-7-fluoro-1,5-naphthyridin-2(1H)-one (18% yield). LC-MS (M−H$^+$)=477.2; $^1$H NMR (400 MHz, DMSO-d$_6$) δ ppm 1.28-1.46 (m, 2H), 1.56-1.70 (m, 2H), 1.93-2.12 (m, 2H), 2.57 (br. s., 2H), 3.90 (s, 2H), 4.45 (br. s., 1H), 6.59 (s, 1H), 6.72 (d, J=9.29 Hz, 1H), 7.28 (td, J=8.80, 2.93 Hz, 1H), 7.46 (dd, J=9.05, 4.65 Hz, 1H), 7.86 (d, J=9.29 Hz, 1H), 7.94 (dd, J=8.80, 2.93 Hz, 1H), 8.18 (s, 1H), 8.28 (d, J=9.78 Hz, 1H), 8.52 (d, J=1.96 Hz, 1H), 12.62 (br. s., 1H).

Preparation of Compound 208

Compound 208 was prepared as described herein below.

Step 1—Synthesis of Tert-butyl [trans-4-(5-methoxy-2-nitroanilino)cyclohexyl]carbamate

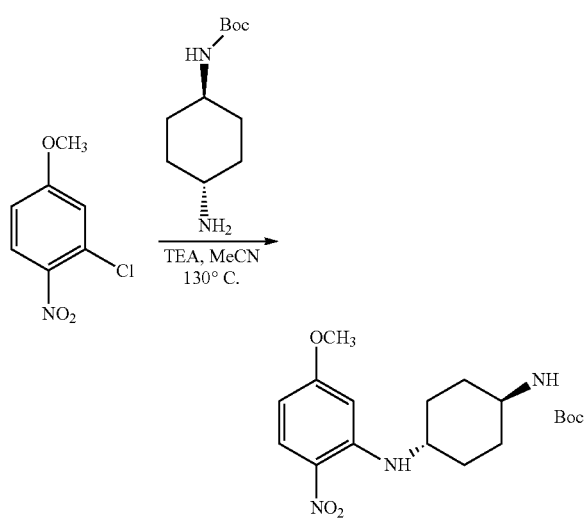

A suspension of 2-chloro-4-methoxy-1-nitrobenzene (2.0 g, 10.7 mmol), N-Boc-trans-1,4-cyclohexanediamine (2.3 g, 10.7 mmol) and triethylamine (1.8 mL, 12.8 mmol) in acetonitrile (80 mL) was heated at 130° C. in a sealed tube for 3 days. The mixture was cooled to room temperature, the volatiles were removed under vacuum and the crude was purified by column chromatography (from cyclohexane/EtOAc 85:15 to cyclohexane/EtOAc/MeOH 6:3:1) to afford the title compound (1.2 g, 3.3 mmol, 31% yield). LC-MS (M−H⁺)=366.4

Step 2—Synthesis of Tert-butyl [trans-4-(2-amino-5-methoxyanilino)cyclohexyl]carbamate

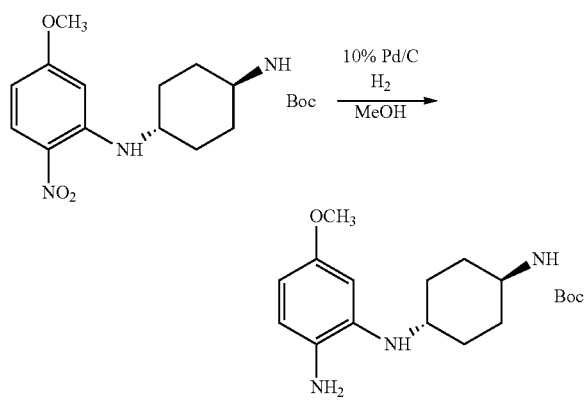

The title compound was prepared according to the procedure described for the synthesis of tert-butyl 4-[(3-amino-6-methoxypyridin-2-yl)amino]piperidine-1-carboxylate (see compound 197, step 2) using tert-butyl [trans-4-(5-methoxy-2-nitroanilino)cyclohexyl]carbamate and MeOH as solvent (94% yield). LC-MS (M−H⁺)=336.4

Step 3—Synthesis of Ethyl N-[2-({trans-4-[(tert-butoxycarbonyl)amino]cyclohexyl}amino)-4-methoxyphenyl]glycinate

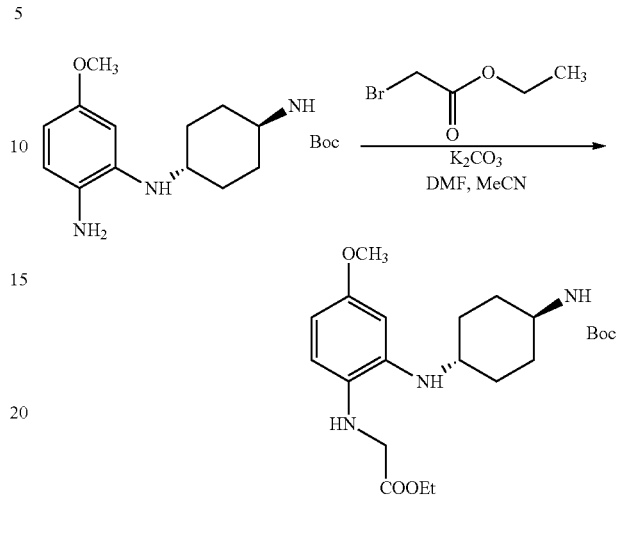

The title compound was prepared according to the procedure described for the synthesis of tert-butyl 4-({3-[(2-ethoxy-2-oxoethyl)amino]-6-methoxypyridin-2-yl}amino)piperidine-1-carboxylate (see compound 197, step 3) using tert-butyl [trans-4-(2-amino-5-methoxyanilino)cyclohexyl]carbamate (63% yield). LC-MS (M−H⁺)=422.5

Step 4—Synthesis of Tert-butyl [trans-4-(7-methoxy-2-oxoquinoxalin-1(2H)-yl)cyclohexyl]carbamate

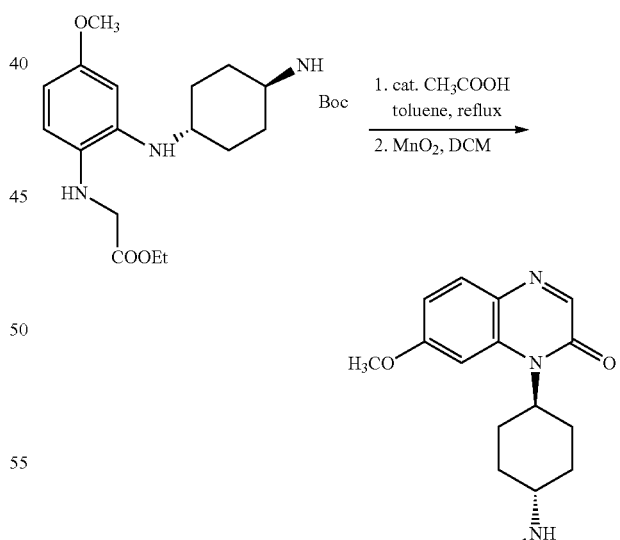

The title compound was prepared according to the procedure described for the synthesis of tert-butyl 4-(6-methoxy-3-oxo-2,3-dihydropyrido[2,3-b]pyrazin-4(1H)-yl)piperidine-1-carboxylate (see compound 197, step 4) using ethyl N-[2-({trans-4-[(tert-butoxycarbonyl)amino]cyclohexyl}amino)-4-methoxyphenyl]glycinate (59% yield). LC-MS (M−H⁺)=374.4

Step 5—Synthesis of 1-(trans-4-aminocyclohexyl)-7-methoxyquinoxalin-2(1H)-one

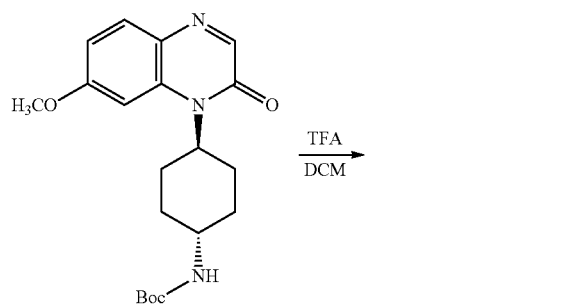

The title compound was prepared according to the procedure described for the synthesis of 1-(trans-4-aminocyclohexyl)-7-fluoro-1H-pyrido[2,3-b][1,4]oxazin-2(3H)-one (see compound 193, step 8) using tert-butyl [trans-4-(7-methoxy-2-oxoquinoxalin-1(2H)-yl)cyclohexyl]carbamate (96% yield). LC-MS (M–H$^+$)=274.3

Step 6—Synthesis of 8-fluoro-2-({[trans-4-(7-methoxy-2-oxoquinoxalin-1(2H)-yl)cyclohexyl]amino}methyl)[1]benzopyrano[4,3-b]pyrrol-4(1H)-one (Formate Salt, Compound 208)

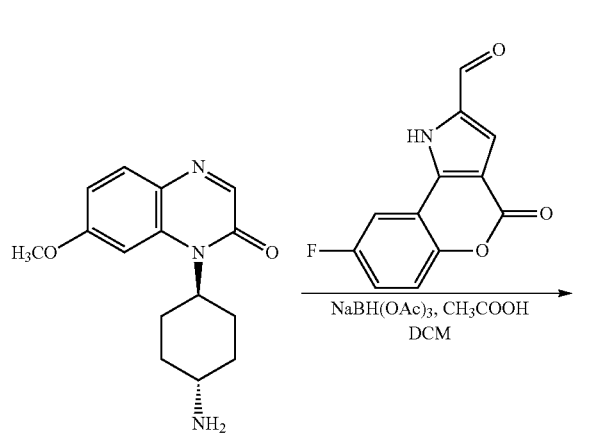

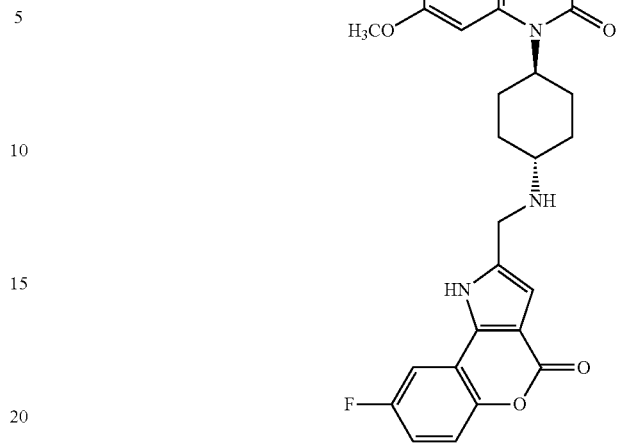

The title compound was prepared according to the procedure described for the synthesis of 8-fluoro-2-({[trans-4-(7-fluoro-2-oxo-2,3-dihydro-1H-pyrido[2,3-b][1,4]oxazin-1-yl)cyclohexyl]amino}methyl)[1]benzopyrano[4,3-b]pyrrol-4(1H)-one (compound 193, step 9) using 1-(trans-4-aminocyclohexyl)-7-methoxyquinoxalin-2(1H)-one (20% yield). LC-MS (M–H$^+$)=489.2. $^1$H NMR (400 MHz, DMSO-d$_6$) δ ppm 1.31-1.50 (m, 2H), 1.69 (d, J=10.63 Hz, 2H), 2.07 (d, J=10.85 Hz, 2H), 2.52-2.70 (m, 3H), 3.91 (s, 3H), 3.94 (s, 2H), 4.58 (br. s., 1H), 6.62 (s, 1H), 7.01 (dd, J=8.82, 2.36 Hz, 1H), 7.20 (br. s., 1H), 7.30 (td, J=8.74, 3.01 Hz, 1H), 7.47 (dd, J=9.10, 4.60 Hz, 1H), 7.74 (d, J=8.88 Hz, 1H), 7.88-8.00 (m, 2H), 8.18 (s, 1H), 12.72 (br. s., 1H).

Preparation of Compounds 209 and 210

Compounds 209 and 210 were prepared as described herein below.

Step 1—Synthesis of Ethyl N-(5-fluoro-3-nitropyridin-2-yl)glycinate

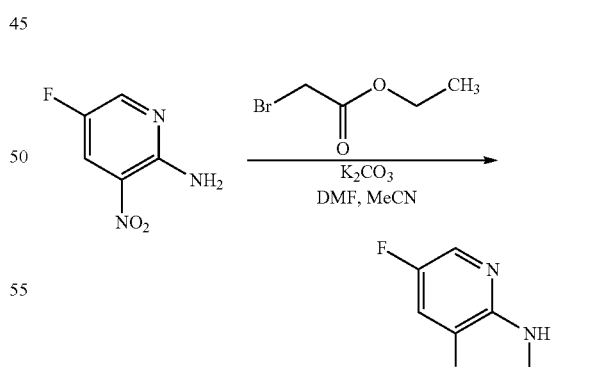

The synthesis was performed according to the procedure described for the preparation of intermediate tert-butyl 4-({3-[(2-ethoxy-2-oxoethyl)amino]-6-methoxypyridin-2-yl}amino)piperidine-1-carboxylate (see compound 197, step 3) using N-(5-fluoro-3-nitropyridin-2-yl)glycinate (95% yield). LC-MS (M–H$^+$)=244.2

Step 2—Synthesis of Tert-butyl 4-[(3-amino-6-methoxypyridin-2-yl)amino]piperidine-1-carboxylate

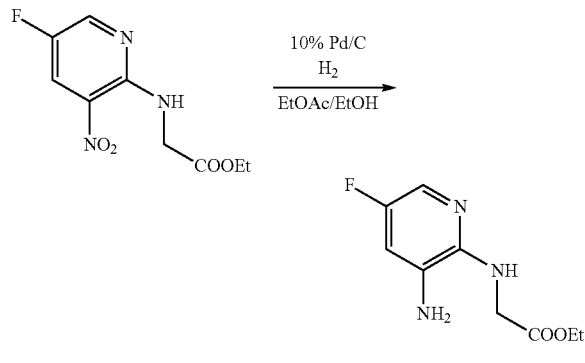

The synthesis was performed according to the procedure described for the preparation of intermediate tert-butyl 4-[(3-amino-6-methoxypyridin-2-yl)amino]piperidine-1-carboxylate (see compound 197, step 2) using 5-fluoro-3-nitropyridin-2-amine (47% yield). LC-MS (M–H$^+$)=214.0

Step 3—Synthesis of Ethyl N-[3-({4-[(tert-butoxycarbonyl)amino]cyclohexyl}amino)-5-fluoropyridin-2-yl]glycinate

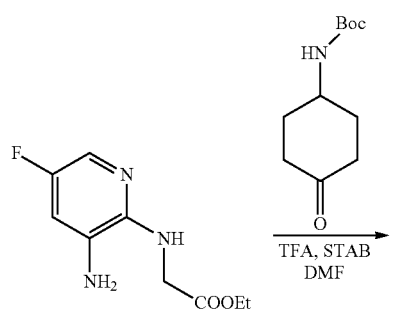

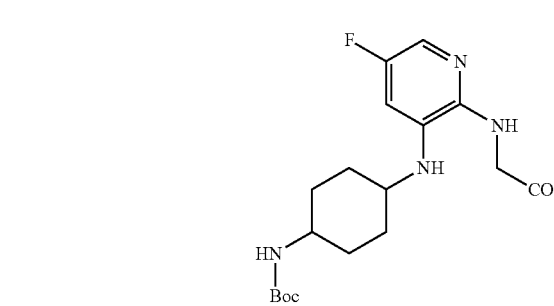

The title compound was obtained as a mixture of isomers following the procedure described for the preparation of intermediate tert-butyl {4-[(5-fluoro-2-hydroxypyridin-3-yl)amino]cyclohexyl}carbamate (see compound 193, step 6) using tert-butyl 4-[(3-amino-6-methoxypyridin-2-yl)amino]piperidine-1-carboxylate (69% yield). LC-MS (M–H$^+$)=411.4

Step 4—Synthesis of Tert-butyl [4-(7-fluoro-2-oxopyrido[2,3-b]pyrazin-1(2H)-yl)cyclohexyl]carbamate

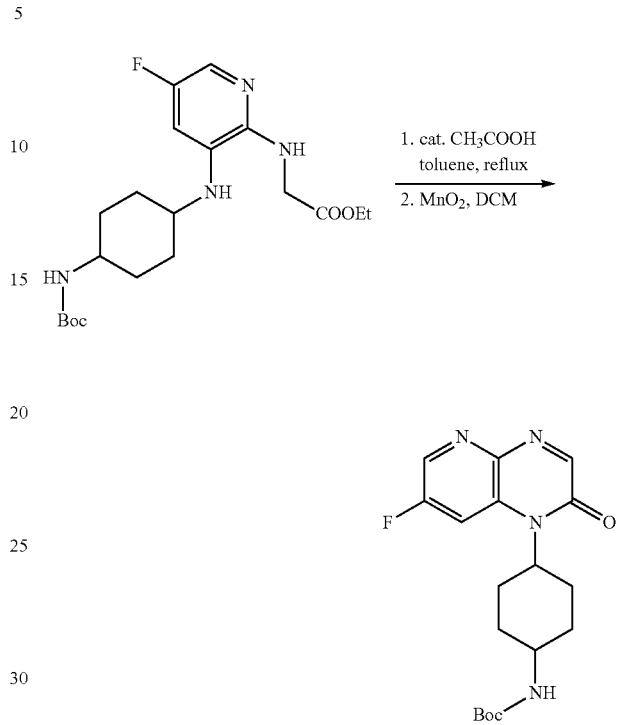

The title compound was obtained as a mixture of isomers following the procedure described for the preparation of intermediate tert-butyl 4-(6-methoxy-3-oxo-2,3-dihydropyrido[2,3-b]pyrazin-4(1H)-yl)piperidine-1-carboxylate (see compound 197, step 4) using ethyl N-[3-({4-[(tert-butoxycarbonyl)amino]cyclohexyl}amino)-5-fluoropyridin-2-yl]glycinate (43% yield). LC-MS (M–H$^+$)=363.4

Step 5—Synthesis of 1-(4-aminocyclohexyl)-7-fluoropyrido[2,3-b]pyrazin-2(1H)-one

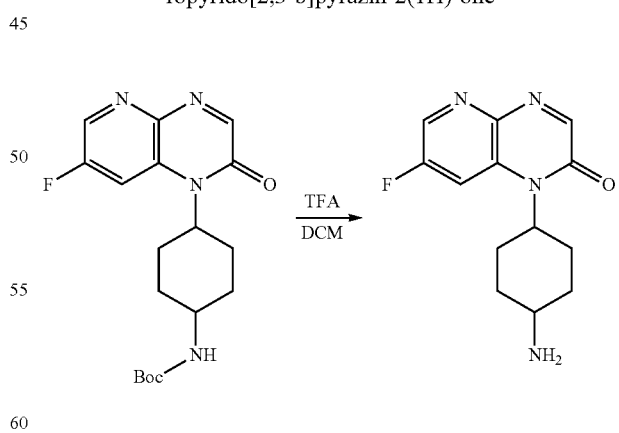

The title compound was obtained as a mixture of isomers following the procedure described for the preparation of intermediate 1-(trans-4-aminocyclohexyl)-7-fluoro-1H-pyrido[2,3-b][1,4]oxazin-2(3H)-one (see compound 193, step 8) using tert-butyl [4-(7-fluoro-2-oxopyrido[2,3-b]pyrazin-1(2H)-yl)cyclohexyl]carbamate (94% yield). LC-MS (M–H$^+$)=263.1

Step 6—Synthesis of 8-fluoro-2-({[trans-4-(7-fluoro-2-oxopyrido[2,3-b]pyrazin-1(2H)-yl)cyclohexyl]amino}methyl)[1]benzopyrano[4,3-b]pyrrol-4(1H)-one (Formate Salt, Compound 209) and 8-fluoro-2-({[cis-4-(7-fluoro-2-oxopyrido[2,3-b]pyrazin-1(2H)-yl)cyclohexyl]amino}methyl)[1]benzopyrano[4,3-b]pyrrol-4(1H)-one (Formate Salt, Compound 210)

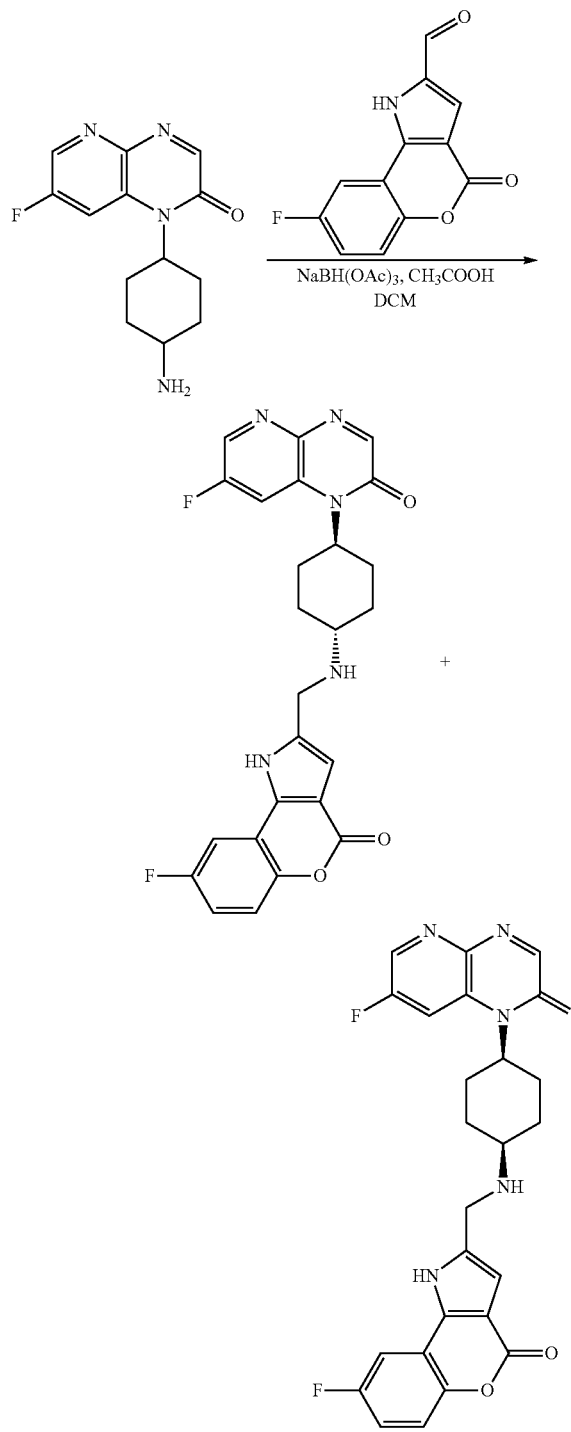

The title compounds were prepared according to the procedure described for the synthesis of 8-fluoro-2-({[trans-4-(7-fluoro-2-oxo-2,3-dihydro-1H-pyrido[2,3-b][1,4]oxazin-1-yl)cyclohexyl]amino}methyl)[1]benzopyrano[4,3-b]pyrrol-4(1H)-one (compound 193, step 9) using 1-(4-aminocyclohexyl)-7-fluoropyrido[2,3-b]pyrazin-2(1H)-one as a mixture of isomers.

A purification by preparative HPLC (A=0.1% ammonia aqueous solution, B=acetonitrile, form 98:2 A:B to 100% B) afforded the trans (10% yield) and cis (6% yield) diastereoisomers.

Compound 209: LC-MS (M–H$^+$)=478.4. $^1$H NMR (400 MHz, DMSO-d$_6$) δ ppm 1.41 (m, J=11.80 Hz, 2H), 1.70 (d, J=11.29 Hz, 2H), 2.06 (d, J=10.29 Hz, 2H), 2.51-2.58 (m, 2H), 2.67 (br. s., 1H), 3.96 (s, 2H), 4.47-4.79 (m, 1H), 6.63 (s, 1H), 7.30 (td, J=8.78, 3.01 Hz, 1H), 7.48 (dd, J=9.03, 4.52 Hz, 1H), 7.95 (dd, J=9.03, 3.01 Hz, 1H), 8.21 (s, 1H), 8.29 (s, 1H), 8.45 (d, J=11.04 Hz, 1H), 8.58 (d, J=2.26 Hz, 1H).

Compound 210: LC-MS (M–H$^+$)=478.4. $^1$H NMR (400 MHz, DMSO-d$_6$) δ ppm 1.50 (d, J=9.39 Hz, 2H), 1.67 (t, J=12.91 Hz, 2H), 1.95 (d, J=14.09 Hz, 2H), 2.69-2.80 (m, 2H), 2.92 (br. s., 1H), 3.90 (s, 2H), 4.92 (br. s., 1H), 6.65 (s, 1H), 7.21-7.31 (m, 1H), 7.45 (dd, J=9.00, 4.70 Hz, 1H), 7.87 (dd, J=9.00, 3.13 Hz, 1H), 8.19 (s, 1H), 8.33 (s, 1H), 8.47 (d, J=10.56 Hz, 1H), 8.54 (d, J=2.35 Hz, 1H).

Preparation of Compound 211

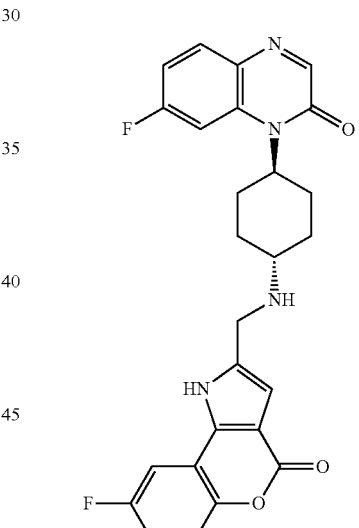

Compound 8-fluoro-2-({[trans-4-(7-fluoro-2-oxoquinoxalin-1(2H)-yl)cyclohexyl]amino}methyl)[1]benzopyrano[4,3-b]pyrrol-4(1H)-one (Formate Salt, Compound 211) was prepared according to the procedure described for the synthesis of compound 208, starting from 2,4-difluoro-1-nitrobenzene.

LC-MS (M–H$^+$)=477.4. $^1$H NMR (400 MHz, DMSO-d$_6$) δ ppm 1.32-1.50 (m, 2H), 1.68 (d, J=10.56 Hz, 2H), 2.05 (d, J=11.35 Hz, 2H), 2.37-2.64 (m, 3H), 3.93 (s, 2H), 4.56 (br. s., 1H), 6.62 (s, 1H), 7.24 (td, J=8.41, 2.35 Hz, 1H), 7.29 (td, J=8.71, 2.93 Hz, 1H), 7.47 (dd, J=9.00, 4.70 Hz, 1H), 7.86 (dd, J=8.80, 6.46 Hz, 2H), 7.95 (dd, J=9.19, 2.93 Hz, 1H), 8.06 (s, 1H), 8.23 (s, 1H), 10.48-13.49 (m, 2H).

Preparation of Compounds 212 and 213

Compounds 212 and 213 were prepared as described herein below.

113

Step 1—Synthesis of Tert-butyl [4-(7-methoxy-2-oxopyrido[2,3-b]pyrazin-1(2H)-yl)cyclohexyl]carbamate

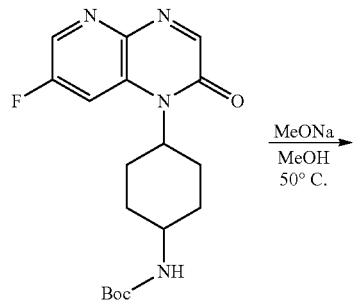

200 mg (0.55 mmol) of tert-butyl [4-(7-fluoro-2-oxopyrido[2,3-b]pyrazin-1(2H)-yl)cyclohexyl]carbamate, prepared as previously described (step 4 in the synthesis of compounds 209 and 210, mixture of isomers), was dissolved in MeOH (10 mL). NaOMe (25% wt solution in MeOH, 25 mL) was added and the mixture was stirred at 50° C. for 3 h. The solvent was evaporated in vacuo, DCM was added and the solution was washed with sat. NaHCO$_3$. The organic phase was separated, dried over Na$_2$SO$_4$ and concentrated in vacuo to obtain 210 mg (0.55 mmol, quant. yield) of the title product, that was progressed without any further purification. LC-MS (M–H$^+$)=375.4

Step 2—Synthesis of 1-(4-aminocyclohexyl)-7-methoxypyrido[2,3-b]pyrazin-2(1H)-one

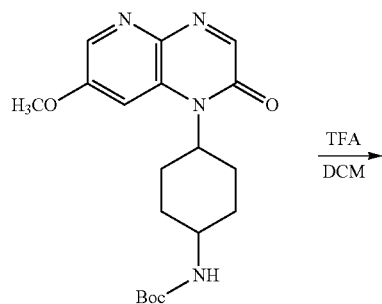

114

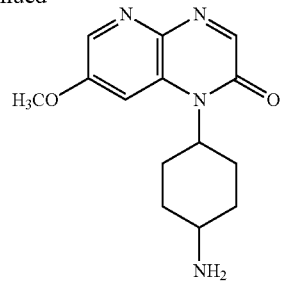

The title compound was obtained as a mixture of isomers following the procedure described for the preparation of intermediate 1-(trans-4-aminocyclohexyl)-7-fluoro-1H-pyrido[2,3-b][1,4]oxazin-2(3H)-one (see compound 193, step 8) using tert-butyl [4-(7-methoxy-2-oxopyrido[2,3-b]pyrazin-1(2H)-yl)cyclohexyl]carbamate (82% yield). LC-MS (M–H$^+$)=275.2

Step 3—Synthesis of 8-fluoro-2-({[trans-4-(7-methoxy-2-oxopyrido[2,3-b]pyrazin-1(2H)-yl)cyclohexyl]amino}methyl)[1]benzopyrano[4,3-b]pyrrol-4(1H)-one (Hydrochloride, Compound 212) and 8-fluoro-2-({[cis-4-(7-methoxy-2-oxopyrido[2,3-b]pyrazin-1(2H)-yl)cyclohexyl]amino}methyl)[1]benzopyrano[4,3-b]pyrrol-4(1H)-one (Hydrochloride, Compound 213)

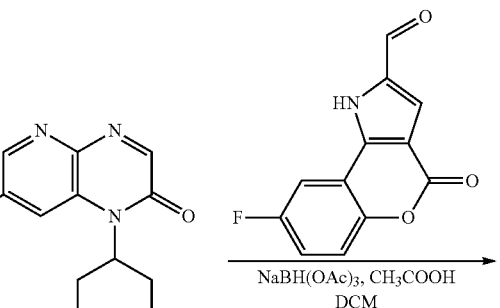

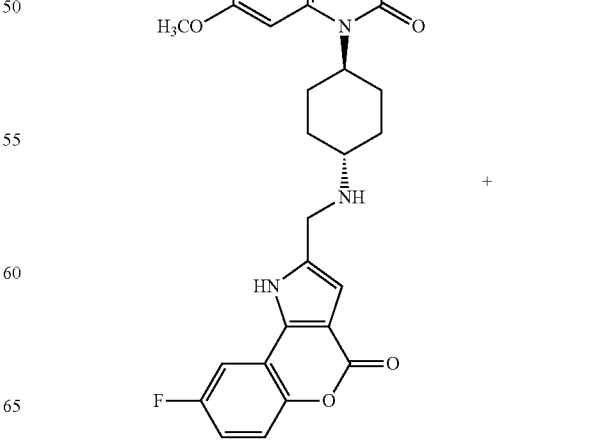

-continued

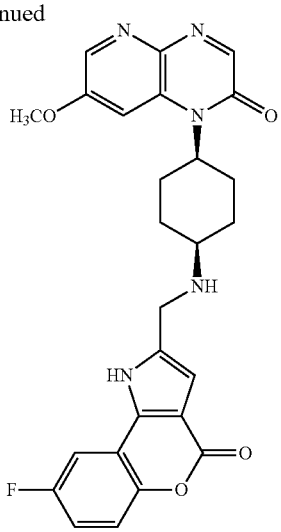

The title compounds were prepared according to the procedure described for the synthesis of 8-fluoro-2-({[trans-4-(7-fluoro-2-oxo-2,3-dihydro-1H-pyrido[2,3-b][1,4]oxazin-1-yl)cyclohexyl]amino}methyl)[1]benzopyrano[4,3-b]pyrrol-4(1H)-one (compound 193, step 9) using 1-(4-aminocyclohexyl)-7-methoxypyrido[2,3-b]pyrazin-2(1H)-one as a mixture of the isomers.

A purification by preparative HPLC (A=0.1% ammonia aqueous solution, B=acetonitrile, form 98:2 A:B to 100% B) followed by the formation of the hydrochloride salt under standard conditions afforded the trans (43% yield) and cis (10% yield) diastereoisomers.

Compound 212: LC-MS (M–H$^+$)=490.1. $^1$H NMR (400 MHz, DMSO-d$_6$) δ ppm 1.69-1.79 (m, 2H), 1.84 (d, J=10.98 Hz, 2H), 2.25-2.34 (m, 2H), 2.56-2.71 (m, 2H), 3.17-3.35 (m, 1H), 4.03 (s, 3H), 4.37-4.45 (m, 2H), 4.67 (br. s., 1H), 6.96 (d, J=1.65 Hz, 1H), 7.38 (td, J=8.78, 3.02 Hz, 1H), 7.53 (dd, J=9.19, 4.53 Hz, 1H), 7.69-7.81 (m, 1H), 7.88 (dd, J=8.65, 2.88 Hz, 1H), 8.16 (s, 1H), 8.35 (d, J=2.47 Hz, 1H), 9.42 (br. s., 2H), 13.54 (br. s., 1H).

Compound 213: LC-MS (M–H$^+$)=490.1. $^1$H NMR (400 MHz, DMSO-d$_6$) δ ppm 1.69 (d, J=10.96 Hz, 2H), 2.01 (m, J=13.59 Hz, 2H), 2.18 (d, J=14.03 Hz, 2H), 2.66-2.80 (m, 2H), 3.49 (br. s., 1H), 4.03 (s, 3H), 4.40-4.45 (m, 2H), 4.62-4.78 (m, 1H), 6.99 (d, J=1.75 Hz, 1H), 7.38 (td, J=8.77, 3.07 Hz, 1H), 7.53 (dd, J=9.21, 4.38 Hz, 1H), 7.76 (d, J=2.19 Hz, 1H), 7.87 (dd, J=8.33, 3.07 Hz, 1H), 8.18 (s, 1H), 8.36 (d, J=2.19 Hz, 1H), 9.25 (br. s., 2H), 13.49 (s, 1H).

Preparation of Compounds 214 and 215

Compounds 214 and 215 were prepared as described herein below.

Step 1—Synthesis of (aminooxy)(6-hydroxy-5-nitropyridin-3-yl)methanone

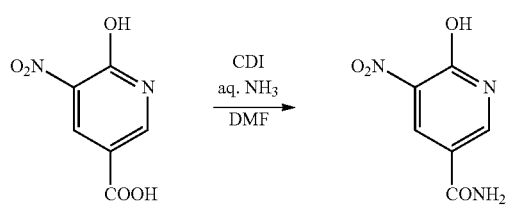

6-hydroxy-5-nitropyridine-3-carboxylic acid (3.3 g, 17.9 mmol) was dissolved in DMF (16 mL). CDI (3.2 g, 19.7 mmol) was added portionwise at room temperature. The resulting mixture was stirred for 2 hours at 60° C. then was cooled to room temperature. 30% aqueous ammonia (23 mL) was added and the resulting mixture was stirred for 20 min. The precipitate was filtered, washed with water (5 mL) and dried to give the title product (2.85 g, 15.5 mmol, 86% yield), that was progressed without any further purification. LC-MS (M–H$^+$)=184.1

Step 2—Synthesis of 6-hydroxy-5-nitropyridine-3-carbonitrile

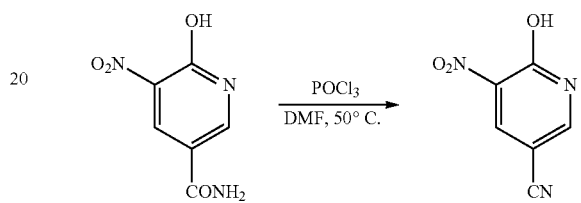

Phosphorus(V) oxychloride (0.66 mL, 7.1 mmol) was added to DMF (11 mL) at 0° C. and the resulting mixture was stirred at the same temperature for 15 min. Intermediate (aminooxy)(6-hydroxy-5-nitropyridin-3-yl)methanone (1.1 g, 6.0 mmol) was added portionwise. The reaction mixture was heated at 50° C. for 1 hour then was cooled to 0° C. Water (12 mL) was added, the precipitate was collected by filtration and washed with additional water (6 mL). Acetonitrile was added to the solid and evaporated under vacuum several times to remove residual water. The obtained title compound (0.74 g, 4.5 mmol, 75% yield) was progressed without any further purification. LC-MS (M–H$^+$)=166.1

Step 3—Synthesis of 5-amino-6-hydroxypyridine-3-carbonitrile

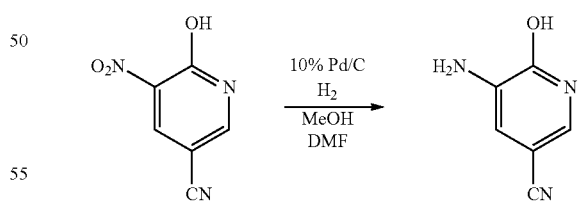

The title compound was prepared according to the procedure described for the synthesis of tert-butyl 4-[(3-amino-6-methoxypyridin-2-yl)amino]piperidine-1-carboxylate (see compound 197, step 2) using 6-hydroxy-5-nitropyridine-3-carbonitrile and MeOH/DMF as solvents (96% yield). LC-MS (M–H$^+$)=136.1

Step 4—Synthesis of Tert-butyl {4-[(5-cyano-2-hydroxypyridin-3-yl)amino]cyclohexyl}carbamate

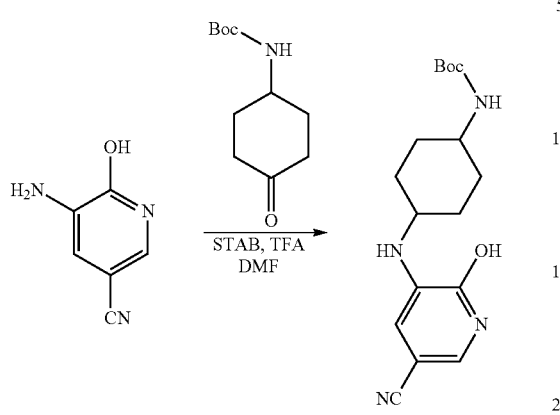

The title compound was obtained as a mixture of isomers following the procedure described for the preparation of intermediate tert-butyl {4-[(5-fluoro-2-hydroxypyridin-3-yl)amino]cyclohexyl}carbamate (see compound 193, step 6) using 5-amino-6-hydroxypyridine-3-carbonitrile (15% yield). LC-MS (M–H$^+$)=333.3

Step 5—Synthesis of Tert-butyl [4-(7-cyano-2-oxo-2,3-dihydro-1H-pyrido[2,3-b][1,4]oxazin-1-yl)cyclohexyl]carbamate

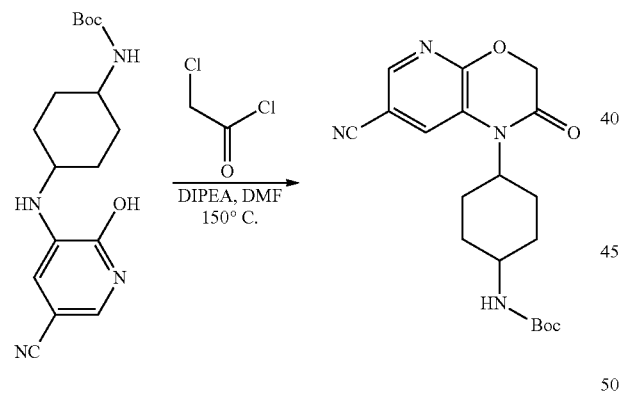

DIPEA (4.0 mL, 23.4 mmol) and chloroacetyl chloride (934 µL, 11.7 mmol) were added to a stirred solution of tert-butyl {4-[(5-cyano-2-hydroxypyridin-3-yl)amino]cyclohexyl}carbamate (390 mg, 1.17 mmol) in DMF (24 mL). The reaction mixture was heated at 150° C. in a sealed flask for 1 hour then was cooled and partitioned between EtOAc and a 1/1 mixture of brine and sat. NaHCO$_3$. The aqueous layer was extracted three times with EtOAc and the combined organic layers were washed with brine. The volatiles were removed under vacuum and the residue was purified by column chromatography on silica gel (from cyclohexane/EtOAc 85:15 to cyclohexane/EtOAc/MeOH 6:3:1). A further purification through column chromatography on NH—SiO$_2$ (cyclohexane/EtOAc from 6:4 to 0:100) afforded the title product as a mixture of isomers (208 mg, 1 mmol, 48% yield). LC-MS (M–H$^+$)=373.3

Step 6—Synthesis of 1-(4-aminocyclohexyl)-2-oxo-2,3-dihydro-1H-pyrido[2,3-b][1,4]oxazine-7-carbonitrile

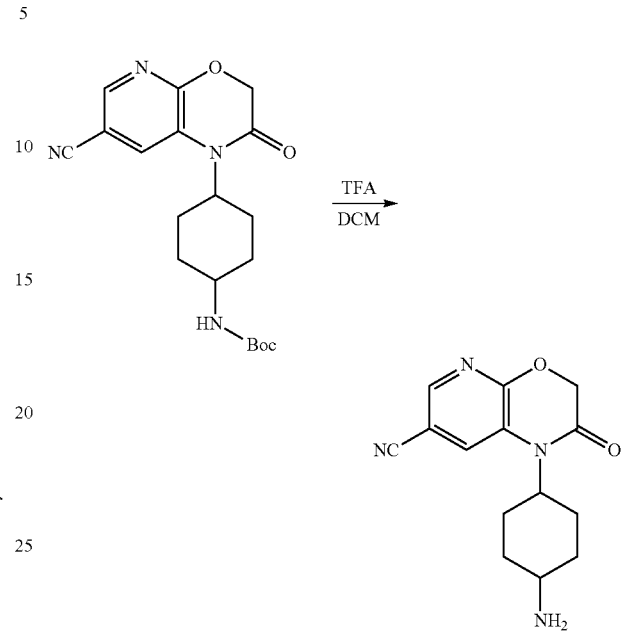

The title intermediate was prepared as a mixture of isomers according to the procedure described for the synthesis of 1-(trans-4-aminocyclohexyl)-7-fluoro-1H-pyrido[2,3-b][1,4]oxazin-2(3H)-one (see compound 193, step 8) using tert-butyl [4-(7-cyano-2-oxo-2,3-dihydro-1H-pyrido[2,3-b][1,4]oxazin-1-yl)cyclohexyl]carbamate (98% yield). LC-MS (M–H$^+$)=273.3

Step 7—Synthesis of 1-(trans-4-{[(8-fluoro-4-oxo-1,4-dihydro[1]benzopyrano[4,3-b]pyrrol-2-yl)methyl]amino}cyclohexyl)-2-oxo-2,3-dihydro-1H-pyrido[2,3-b][1,4]oxazine-7-carbonitrile (formate salt, compound 214) and 1-(cis-4-{[(8-fluoro-4-oxo-1,4-dihydro[1]benzopyrano[4,3-b]pyrrol-2-yl)methyl]amino}cyclohexyl)-2-oxo-2,3-dihydro-1H-pyrido[2,3-b][1,4]oxazine-7-carbonitrile (Formate Salt, Compound 215)

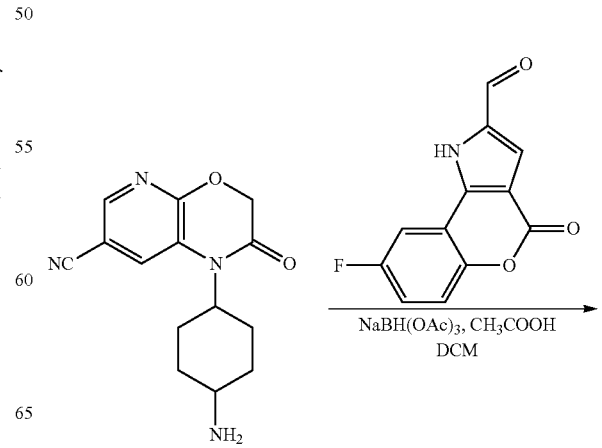

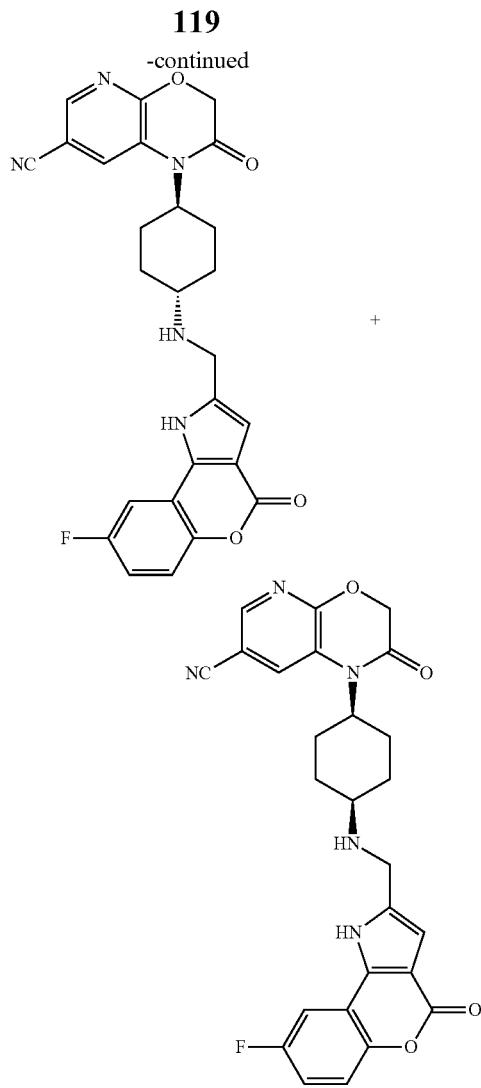

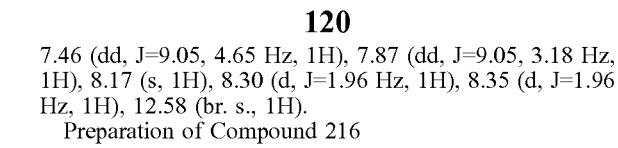

7.46 (dd, J=9.05, 4.65 Hz, 1H), 7.87 (dd, J=9.05, 3.18 Hz, 1H), 8.17 (s, 1H), 8.30 (d, J=1.96 Hz, 1H), 8.35 (d, J=1.96 Hz, 1H), 12.58 (br. s., 1H).

Preparation of Compound 216

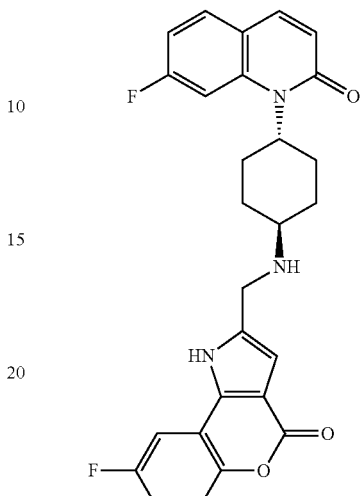

Compound 8-fluoro-2-({[trans-4-(7-fluoro-2-oxoquinolin-1(2H)-yl)cyclohexyl]amino}methyl)[1]benzopyrano[4,3-b]pyrrol-4(1H)-one (Hydrochloride, Compound 216) was prepared according to the procedure described for the synthesis of compound 206, starting from 5-fluoro-2-iodoaniline.

LC-MS (M–H⁺)=476.1. ¹H NMR (400 MHz, DMSO-d₆) δ ppm 1.43-1.79 (m, 4H), 2.18 (br. s., 2H), 2.57-2.77 (m, 2H), 2.80-3.13 (m, 1H), 4.19 (br. s., 2H), 4.32-5.63 (m, 1H), 6.47 (d, J=5.87 Hz, 1H), 6.81 (br. s., 1H), 7.13 (td, J=8.44, 2.20 Hz, 1H), 7.34 (td, J=8.56, 2.93 Hz, 1H), 7.51 (dd, J=9.05, 4.65 Hz, 1H), 7.66-7.81 (m, 2H), 7.86 (d, J=9.29 Hz, 1H), 7.91 (dd, J=8.80, 2.93 Hz, 1H), 8.32-10.31 (m, 1H), 13.13 (br. s., 1H).

Preparation of Compound 217

Compound 217 was prepared as described herein below.

Step 1—Synthesis of Diethyl 1-[(diphenylmethylidene)amino]-4-oxocyclohexane-1,3-dicarboxylate

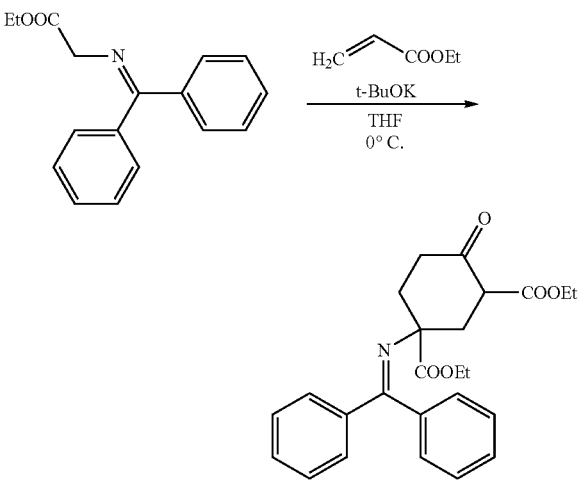

The title compounds were prepared according to the procedure described for the synthesis of 8-fluoro-2-({[trans-4-(7-fluoro-2-oxo-2,3-dihydro-1H-pyrido[2,3-b][1,4]oxazin-1-yl)cyclohexyl]amino}methyl)[1]benzopyrano[4,3-b]pyrrol-4(1H)-one (compound 193, step 9) using 1-(4-aminocyclohexyl)-2-oxo-2,3-dihydro-1H-pyrido[2,3-b][1,4]oxazine-7-carbonitrile as mixture of isomers.

A purification by preparative HPLC (A=0.1% ammonia aqueous solution, B=acetonitrile, form 98:2 A:B to 100% B) followed by the formation of the formate salts under standard conditions afforded the trans (21% yield) and cis (15% yield) diastereoisomers.

Compound 214: LC-MS (M–H⁺)=488.2. ¹H NMR (400 MHz, DMSO-d₆) δ ppm 1.35 (q, J=11.74 Hz, 2H), 1.75 (d, J=10.96 Hz, 2H), 2.06 (d, J=11.35 Hz, 2H), 2.25-2.40 (m, 2H), 2.61-2.71 (m, 1H), 3.99 (s, 2H), 4.04-4.14 (m, 1H), 4.83 (s, 2H), 6.65 (s, 1H), 7.30 (td, J=8.71, 2.93 Hz, 1H), 7.47 (dd, J=9.00, 4.70 Hz, 1H), 7.95 (dd, J=9.00, 3.13 Hz, 1H), 8.21 (s, 1H), 8.31 (d, J=1.56 Hz, 1H), 8.35 (d, J=1.96 Hz, 1H), 12.35-13.58 (m, 1H).

Compound 215: LC-MS (M–H⁺)=488.2. ¹H NMR (400 MHz, DMSO-d₆) δ ppm 1.46 (d, J=10.27 Hz, 2H), 1.57 (t, J=13.69 Hz, 2H), 1.86 (d, J=13.69 Hz, 2H), 2.51-2.61 (m, 2H), 2.81 (br. s., 1H), 3.86 (s, 2H), 4.29 (t, J=11.98 Hz, 1H), 4.87 (s, 2H), 6.61 (s, 1H), 7.28 (td, J=8.80, 2.93 Hz, 1H), Ethyl N-(diphenylmethylidene)glycinate (10 g, 37 mmol) was dissolved in THF (100 mL) and the solution was cooled at 0° C. under a $N_2$ atmosphere. t-BuOK (20.9 g, 187 mmol) was added and the mixture was stirred at 0° C. for 20 min. Then ethyl acrylate (20.3 mL, 187 mmol) was added dropwise and the reaction mixture was stirred at 0° C. for 3 h. A saturated solution of $NH_4Cl$ was added, the organic phase was separated, dried over $Na_2SO_4$ and concentrated in vacuo. The residue containing the title intermediate was progressed into the next step without further purification and characterization.

Step 2—Synthesis of Diethyl 1-[(tert-butoxycarbonyl)amino]-4-oxocyclohexane-1,3-dicarboxylate

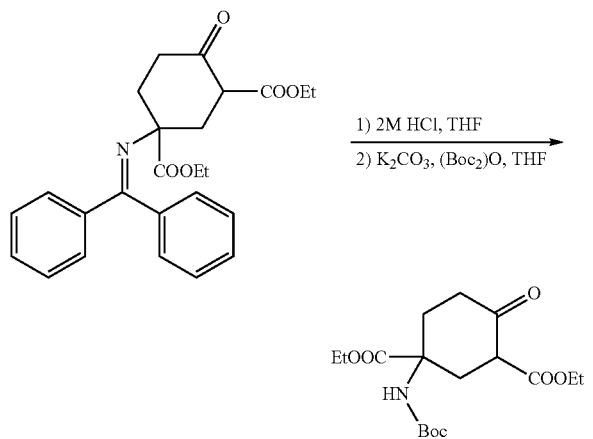

The residue from step 1 was dissolved in THF (80 mL) and treated with HCl (2 M solution, 50 mL). Ethyl acetate was added, the organic layer was discarded and the aqueous phase was basified with $K_2CO_3$ (pH 8). THF was added followed by di-tert-butyl dicarbonate (1 eq.) and the resulting mixture was stirred at room temperature overnight. Ethyl acetate was added, the organic phase was separated, dried over $Na_2SO_4$ and evaporated in vacuo. The crude material was purified by Si-column (cy to cy/EtOAc 1:1) to obtain 2.8 g (7.8 mmol, 21% yield over two steps) of the title product. LC-MS (M–H$^+$)=358.4

Step 3—Synthesis of Ethyl 1-[(tert-butoxycarbonyl)amino]-4-oxocyclohexane-1-carboxylate

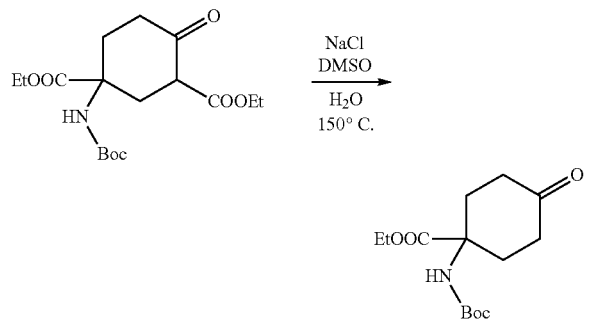

Diethyl 1-[(tert-butoxycarbonyl)amino]-4-oxocyclohexane-1,3-dicarboxylate (300 mg, 0.84 mmol) was dissolved in DMSO (1 mL), sodium chloride (200 mg, 3.4 mmol) and water (0.05 mL) were added and the reaction mixture was stirred at 150° C. for 4 h. The mixture was cooled and diluted with ethyl acetate. The organic layer was washed with water, dried over $MgSO_4$ and concentrated under reduced pressure. The residue was purified by Si-column (cy to cy/EtOAc 7:3) to obtain 185 mg (0.64 mmol, 76% yield) of the title product. LC-MS (M–H$^+$)=286.3

Step 4—Synthesis of Ethyl Trans-1-[(tert-butoxycarbonyl)amino]-4-[(5-fluoro-2-hydroxypyridin-3-yl)amino]cyclohexane-1-carboxylate

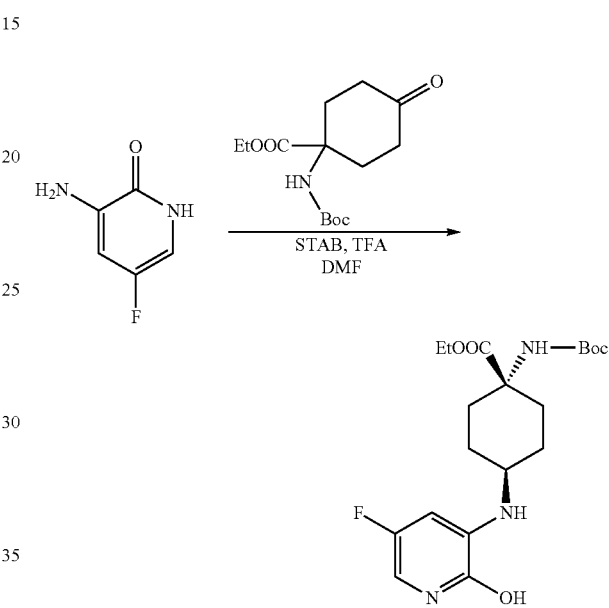

The synthesis was performed according to the procedure described for the preparation of intermediate tert-butyl {4-[(5-fluoro-2-hydroxypyridin-3-yl)amino]cyclohexyl}carbamate (see compound 193, step 6) using ethyl 1-[(tert-butoxycarbonyl)amino]-4-oxocyclohexane-1-carboxylate. A purification by C-18 chromatography (from water+0.1% formic acid to water+0.1% formic acid/acetonitrile+0.1% formic acid 8:2) provided the title compound (25% yield). LC-MS (M–H$^+$)=398.4

Step 5—Synthesis of Trans-1-[(tert-butoxycarbonyl)amino]-4-[(5-fluoro-2-hydroxypyridin-3-yl)amino]cyclohexane-1-carboxylic Acid

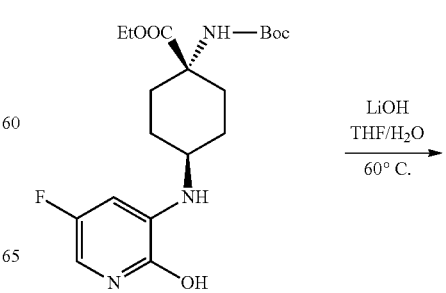

-continued

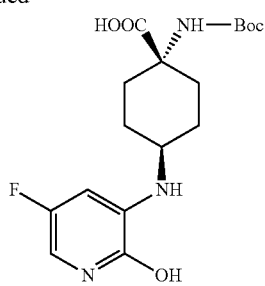

The synthesis was performed according to the procedure described for the preparation of intermediate 3-[2-({4-[(tert-butoxycarbonyl)amino]cyclohexyl}amino)-4-cyanophenyl] propanoic acid (see compound 206, step 4) using ethyl trans-1-[(tert-butoxycarbonyl)amino]-4-[(5-fluoro-2-hydroxypyridin-3-yl)amino]cyclohexane-1-carboxylate (98% yield). LC-MS (M−H⁻)=368.4

Step 6—Synthesis of Tert-butyl {trans-1-carbamoyl-4-[(5-fluoro-2-hydroxypyridin-3-yl)amino]cyclohexyl}carbamate

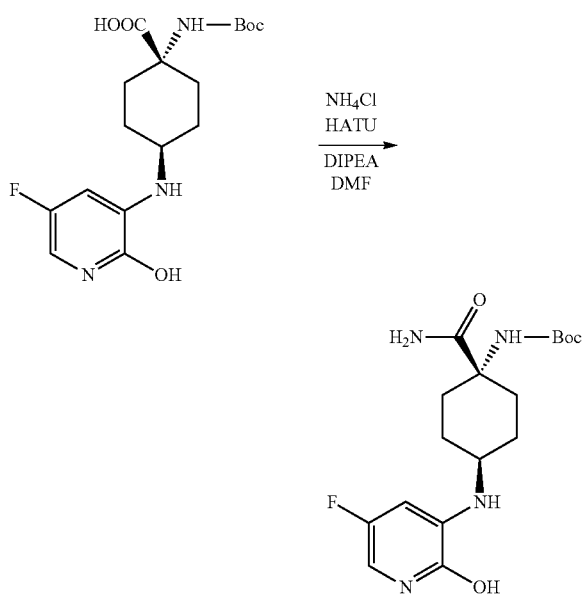

Intermediate trans-1-[(tert-butoxycarbonyl)amino]-4-[(5-fluoro-2-hydroxypyridin-3-yl)amino]cyclohexane-1-carboxylic acid (340 mg, 0.9 mmol) was dissolved in DMF (20 mL). DIPEA (0.8 mL, 4.6 mmol) and ammonium chloride (199 mg, 3.7 mmol) were added and the mixture was cooled to 0° C. HATU (426 mg, 1.1 mmol) was added at the same temperature and the mixture was allowed to slowly reach room temperature. After 6 hours water was added, the mixture was extracted with ethyl acetate, the organic phase was separated, dried over Na₂SO₄ and concentrated in vacuo. The resulting crude material was purified by Si-column (from DCM to DCM/MeOH 8:2) to obtain the title compound (233 mg, 0.63 mmol, 68% yield). LC-MS (M−H⁻)=369.3

Step 7—Synthesis of Tert-butyl [trans-1-carbamoyl-4-(7-fluoro-2-oxo-2,3-dihydro-1H-pyrido[2,3-b][1,4]oxazin-1-yl)cyclohexyl]carbamate

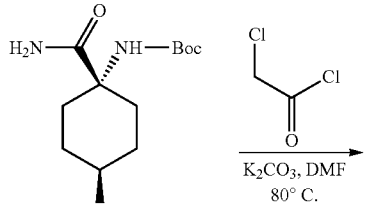

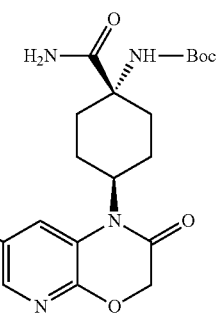

The synthesis was performed according to the procedure described for the preparation of intermediate tert-butyl [4-(7-fluoro-2-oxo-2,3-dihydro-1H-pyrido[2,3-b][1,4]oxazin-1-yl)cyclohexyl]carbamate (see compound 193, step 7) using tert-butyl {trans-1-carbamoyl-4-[(5-fluoro-2-hydroxypyridin-3-yl)amino]cyclohexyl}carbamate (47% yield). LC-MS (M−H⁺)=409.2

Step 8—Synthesis of Trans-1-amino-4-(7-fluoro-2-oxo-2,3-dihydro-1H-pyrido[2,3-b][1,4]oxazin-1-yl)cyclohexane-1-carboxamide

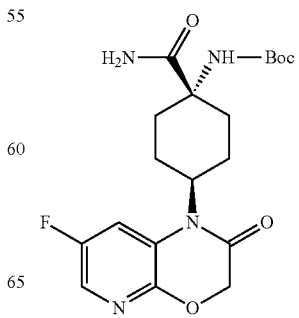

-continued

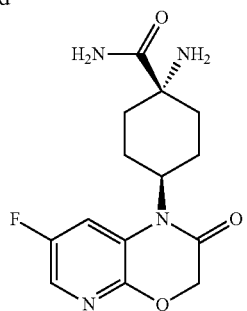

The synthesis was performed according to the procedure described for the preparation of intermediate 1-(trans-4-aminocyclohexyl)-7-fluoro-1H-pyrido[2,3-b][1,4]oxazin-2(3H)-one (see compound 193, step 8) using tert-butyl [trans-1-carbamoyl-4-(7-fluoro-2-oxo-2,3-dihydro-1H-pyrido[2,3-b][1,4]oxazin-1-yl)cyclohexyl]carbamate (62% yield). LC-MS (M–H$^+$)=309.2

Step 9—Synthesis of Trans-1-{[(8-fluoro-4-oxo-1,4-dihydro[1]benzopyrano[4,3-b]pyrrol-2-yl)methyl]amino}-4-(7-fluoro-2-oxo-2,3-dihydro-1H-pyrido[2,3-b][1,4]oxazin-1-yl)cyclohexane-1-carboxamide (Formate Salt, Compound 217)

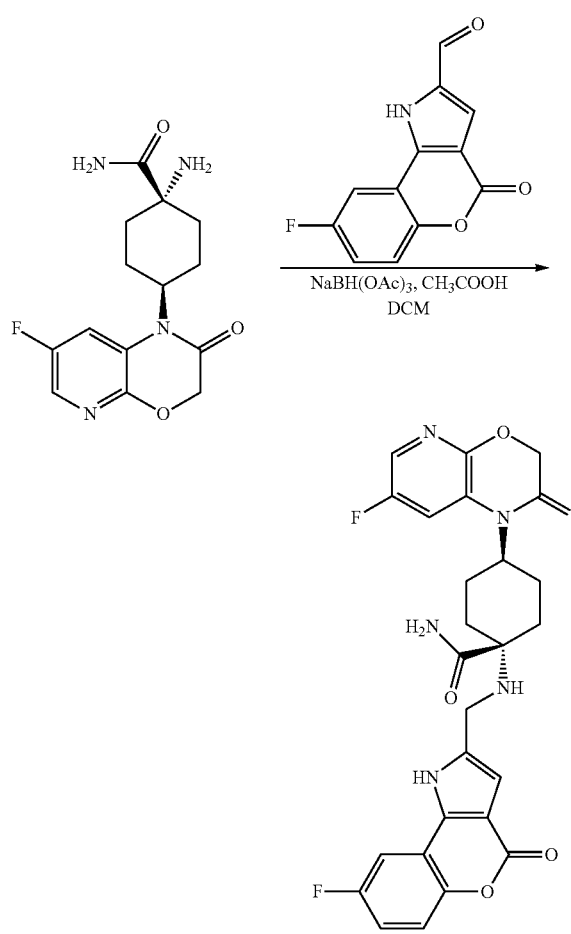

The title compound was prepared according to the procedure described for the synthesis of 8-fluoro-2-({[trans-4-(7-fluoro-2-oxo-2,3-dihydro-1H-pyrido[2,3-b][1,4]oxazin-1-yl)cyclohexyl]amino}methyl)[1]benzopyrano[4,3-b]pyrrol-4(1H)-one (compound 193, step 9) using trans-1-amino-4-(7-fluoro-2-oxo-2,3-dihydro-1H-pyrido[2,3-b][1,4]oxazin-1-yl)cyclohexane-1-carboxamide (10% yield). LC-MS (M–H$^+$)=524.3. $^1$H NMR (500 MHz, DMSO-d$_6$) δ ppm 1.53 (td, J=13.21, 3.91 Hz, 2H), 1.57-1.66 (m, 2H), 2.24 (d, J=12.23 Hz, 2H), 2.41-2.56 (m, 2H), 3.72 (s, 2H), 4.27-4.54 (m, 1H), 4.74 (s, 2H), 6.58 (s, 1H), 7.27-7.33 (m, 2H), 7.48 (dd, J=9.05, 4.65 Hz, 1H), 7.53 (s, 1H), 7.82 (dd, J=10.03, 2.69 Hz, 1H), 7.86 (d, J=2.45 Hz, 1H), 7.94 (dd, J=9.05, 3.18 Hz, 1H), 8.18 (s, 1H), 12.40 (br. s., 1H).

Preparation of Compound 219

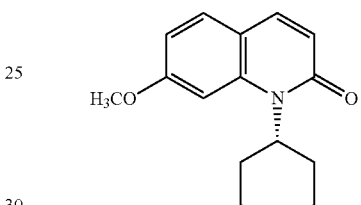

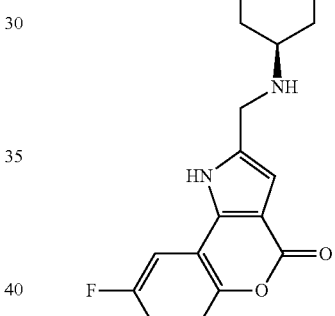

Compound 8-fluoro-2-({[trans-4-(7-methoxy-2-oxoquinolin-1(2H)-yl)cyclohexyl]amino}methyl)[1]benzopyrano[4,3-b]pyrrol-4(1H)-one (Formate Salt, Compound 219) was prepared according to the procedure described for the synthesis of compound 206, starting from 2-bromo-5-methoxyaniline.

LC-MS (M–H$^+$)=488.3. $^1$H NMR (400 MHz, DMSO-d$_6$) δ ppm 1.32-1.48 (m, 2H), 1.64 (d, J=10.74 Hz, 2H), 2.09 (d, J=8.11 Hz, 2H), 2.53-2.76 (m, 3H), 3.87 (s, 3H), 3.95 (s, 2H), 4.38 (br. s., 1H), 6.32 (d, J=7.78 Hz, 1H), 6.62 (s, 1H), 6.90 (dd, J=8.61, 2.03 Hz, 1H), 7.11 (d, J=1.75 Hz, 1H), 7.30 (td, J=8.74, 3.01 Hz, 1H), 7.48 (dd, J=9.10, 4.71 Hz, 1H), 7.62 (d, J=8.66 Hz, 1H), 7.74 (d, J=9.32 Hz, 1H), 7.96 (dd, J=9.10, 2.96 Hz, 1H), 8.18 (s, 1H), 12.83 (br. s., 1H).

Preparation of Compound 220

Compound 220 was prepared as described herein below.

Step 1—Synthesis of Tert-butyl {trans-4-[(5-fluoro-2-hydroxypyridin-3-yl)amino]-1-(hydroxymethyl)cyclohexyl}carbamate

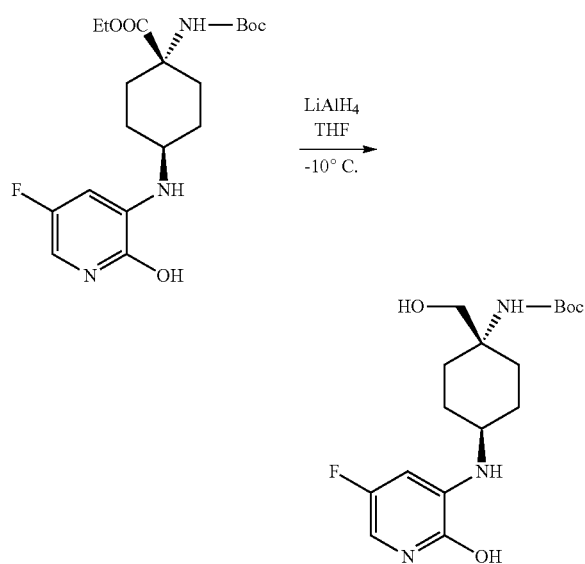

1.0 g (2.5 mmol) of intermediate ethyl trans-1-[(tert-butoxycarbonyl)amino]-4-[(5-fluoro-2-hydroxypyridin-3-yl)amino]cyclohexane-1-carboxylate, prepared as described in step 4 of the synthesis of compound 217, was dissolved in THF (20 mL). The solution was cooled to −10° C. then LiAlH$_4$ (1 M in THF, 2.5 mL, 2.5 mmol) was added dropwise. After stirring for 2 h the reaction was quenched by adding Na$_2$SO$_4$.10H$_2$O. The mixture was filtered and concentrated in vacuo. The crude material was dissolved in ethyl acetate and washed with sat. NH$_4$Cl. The organic phase was separated, dried over Na$_2$SO$_4$ and concentrated in vacuo to obtain the title product (614 mg, 1.8 mmol, 69% yield). LC-MS (M−H$^+$)=356.2

Step 2—Synthesis of Tert-butyl {trans-1-({[tert-butyl(dimethyl)silyl]oxy}methyl)-4-[(5-fluoro-2-hydroxypyridin-3-yl)amino]cyclohexyl}carbamate

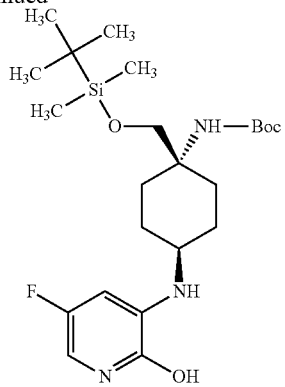

To a solution of tert-butyl {trans-4-[(5-fluoro-2-hydroxypyridin-3-yl)amino]-1-(hydroxymethyl)cyclohexyl}carbamate (344 mg, 0.96 mmol) in DMF (5 mL), imidazole (165 mg, 2.14 mmol) was added followed by TBDMSCl (581 mg, 3.87 mmol). The mixture was stirred at room temperature overnight then ethyl acetate was added followed by water. The organic phase was separated, dried over Na$_2$SO$_4$ and concentrated in vacuo. The crude material was purified by Si-column (from cy to cy/ethyl acetate 1:1) to obtain the title compound (300 mg, 0.64 mmol, 67% yield). LC-MS (M−H$^+$)=470.4

Step 3—Synthesis of Tert-butyl [trans-1-({[tert-butyl(dimethyl)silyl]oxy}methyl)-4-(7-fluoro-2-oxo-2,3-dihydro-1H-pyrido[2,3-b][1,4]oxazin-1-yl)cyclohexyl]carbamate

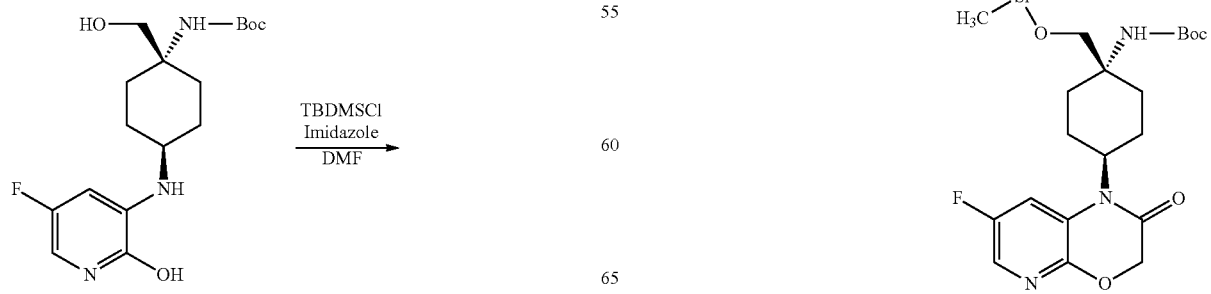

To a suspension of tert-butyl {trans-1-({[tert-butyl(dimethyl)silyl]oxy}methyl)-4-[(5-fluoro-2-hydroxypyridin-3-yl)amino]cyclohexyl}carbamate (253 mg, 0.54 mmol) and potassium carbonate (224 mg, 1.62 mmol) in DMF (5.2 mL) chloroacetyl chloride (52 μL, 0.65 mmol) was added. The mixture was stirred at 80° C. for 6 h then was cooled to 0° C. Sat. NaHCO₃ was added followed by ethyl acetate. The organic phase was separated, dried over Na₂SO₄ and the solvents were evaporated in vacuo to afford the title intermediate (220 mg, 0.43 mmol, 80% yield), that was progressed without any further purification. LC-MS (M−H⁺)=510.4

Step 4—Synthesis of 1-[trans-4-amino-4-(hydroxymethyl)cyclohexyl]-7-fluoro-1H-pyrido[2,3-b][1,4]oxazin-2(3H)-one

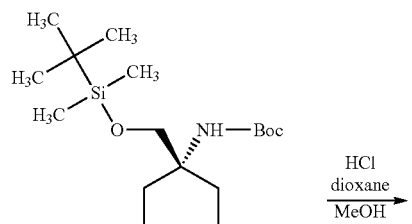

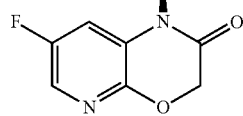

To a stirred solution of tert-butyl [trans-1-({[tert-butyl(dimethyl)silyl]oxy}methyl)-4-(7-fluoro-2-oxo-2,3-dihydro-1H-pyrido[2,3-b][1,4]oxazin-1-yl)cyclohexyl]carbamate (220 mg, 0.43 mmol) in MeOH (1.7 mL) HCl (4 M in dioxane, 2.74 mL) was added. The mixture was stirred at room temperature for 4 h then was concentrated under reduced pressure. The residue was purified by SCX column to give the title compound (98 mg, 0.33 mmol, 77% yield). LC-MS (M−H⁺)=296.1

Step 5—Synthesis of 8-fluoro-2-({[trans-4-(7-fluoro-2-oxo-2,3-dihydro-1H-pyrido[2,3-b][1,4]oxazin-1-yl)-1-(hydroxymethyl)cyclohexyl]amino}methyl)[1]benzopyrano[4,3-b]pyrrol-4(1H)-one (Hydrochloride, Compound 220)

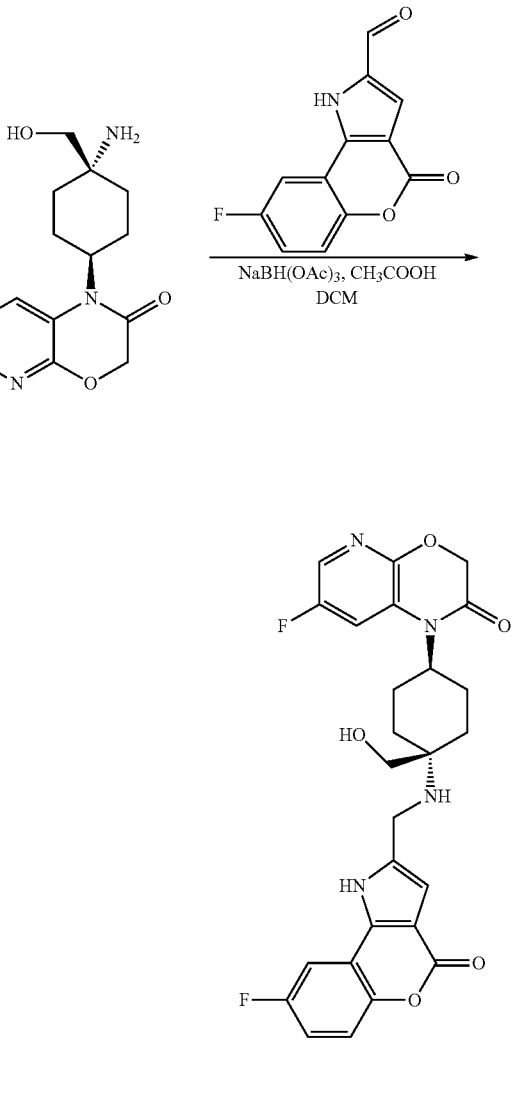

The title compound was prepared according to the procedure described for the synthesis of 8-fluoro-2-({[trans-4-(7-fluoro-2-oxo-2,3-dihydro-1H-pyrido[2,3-b][1,4]oxazin-1-yl)cyclohexyl]amino}methyl)[1]benzopyrano[4,3-b]pyrrol-4(1H)-one (compound 193, step 9) using 1-[trans-4-amino-4-(hydroxymethyl)cyclohexyl]-7-fluoro-1H-pyrido[2,3-b][1,4]oxazin-2(3H)-one (30% yield). LC-MS (M−H⁺)=511.2. ¹H NMR (400 MHz, DMSO-d₆) δ ppm 1.66-1.96 (m, 4H), 2.02-2.19 (m, 2H), 2.46 (br. s., 2H), 3.93 (s, 2H), 4.00 (br. s., 1H), 4.36 (br. s., 2H), 4.73 (s, 2H), 6.92 (d, J=1.97 Hz, 1H), 7.37 (td, J=8.77, 3.07 Hz, 1H), 7.52 (dd, J=9.21, 4.60 Hz, 1H), 7.77-8.03 (m, 3H), 9.04 (br. s., 2H), 13.49 (br. s., 1H).

Preparation of Compound 221

Compound 221 was prepared as described herein below.

Step 1—Synthesis of 8-fluoro-2-({[trans-4-(7-fluoro-2-oxo-2,3-dihydro-1H-pyrido[2,3-b][1,4]oxazin-1-yl)cyclohexyl]amino}methyl)-1-{[2-(trimethylsilyl)ethoxy]methyl}[1]benzopyrano[4,3-b]pyrrol-4(1H)-one

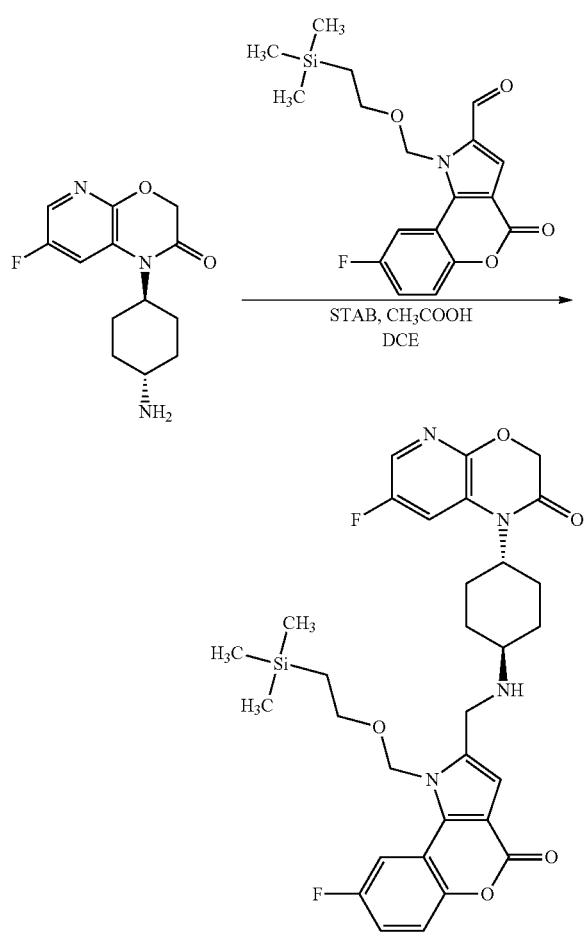

1-(4-aminocyclohexyl)-7-fluoro-1H,2H,3H-pyrido[2,3-b][1,4]oxazin-2-one (133 mg, 0.5 mmol, see step 8 in the synthesis of compound 193) was suspended in dry dichloroethane (20 mL). 8-fluoro-4-oxo-1-{[2-(trimethylsilyl)ethoxy]methyl}-1H,4H-chromeno[4,3-b]pyrrole-2-carbaldehyde (200 mg, 0.55 mmol, see step 1 in the synthesis of compound 194) was added at room temperature followed by glacial acetic acid (catalytic, 2 drops). The reaction mixture was stirred at 50° C. for 4 hours then was cooled down to room temperature. Sodium triacetoxyborohydride (264 mg, 1.25 mmol) was added and the resulting suspension was stirred overnight at room temperature. The reaction mixture was partitioned between dichloromethane and a saturated aqueous NaHCO$_3$ solution. The two layers were separated and the organic phase was dried over Na$_2$SO$_4$, filtered and concentrated in vacuo. The residue was purified by flash chromatography (Silica N—H, 28 g cartridge, cyclohexane/ethyl acetate from 70:30 to 50:50) to afford the title compound (127 mg, 0.2 mmol, 41% yield) as an off-white solid. LC-MS (M–H$^+$)=611.3

Step 2—Synthesis of 2-({(2-{[tert-butyl(dimethyl)silyl]oxy}ethyl)[trans-4-(7-fluoro-2-oxo-2,3-dihydro-1H-pyrido[2,3-b][1,4]oxazin-1-yl)cyclohexyl]amino}methyl)-8-fluoro-1-{[2-(trimethylsilyl)ethoxy]methyl}[1]benzopyrano[4,3-b]pyrrol-4(1H)-one To a solution of 8-fluoro-2-({[trans-4-(7-fluoro-2-oxo-2,3-dihydro-1H-pyrido[2,3-b][1,4]oxazin-1-yl)cyclohexyl]amino}methyl)-1-{[2-(trimethylsilyl)ethoxy]methyl}[1]benzopyrano[4,3-b]pyrrol-4(1H)-one (56 mg, 0.09 mmol) in dry dichloroethane (2 mL) 2-[(tert-butyldimethylsilyl)oxy]acetaldehyde (0.034 mL, 0.18 mmol) and glacial acetic acid (1 drop) were added. The reaction mixture was heated at 40° C. for 1 h then NaBH(OAc)$_3$ (38 mg, 0.18 mmol) was added and the resulting mixture was stirred overnight. The mixture was partitioned between dichloromethane and a saturated aq. solution of NaHCO$_3$. The two layers were separated and the organic phase was dried over Na$_2$SO$_4$, filtered and concentrated in vacuo. The crude material was eluted through a 1 g SCX cartridge with methanol and a 2 N solution of NH$_3$ in methanol. Evaporation of the solvents afforded the title intermediate (50 mg, 0.065 mmol, 72% yield), which was progressed into the next step without any further purification. LC-MS (M–H$^+$)=769.6

Step 3—Synthesis of 8-fluoro-2-({[trans-4-(7-fluoro-2-oxo-2,3-dihydro-1H-pyrido[2,3-b][1,4]oxazin-1-yl)cyclohexyl](2-hydroxyethyl)amino}methyl)[1]benzopyrano[4,3-b]pyrrol-4(1H)-one (Formate Salt, Compound 221)

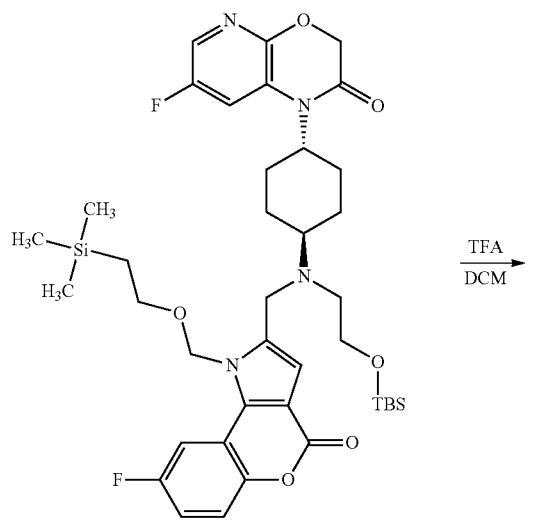

The synthesis was performed according to the procedure described for the preparation of intermediate 1-(trans-4-aminocyclohexyl)-7-fluoro-1H-pyrido[2,3-b][1,4]oxazin-2(3H)-one (see compound 193, step 8) using 2-({(2-{[tert-butyl(dimethyl)silyl]oxy}ethyl)[trans-4-(7-fluoro-2-oxo-2,3-dihydro-1H-pyrido[2,3-b][1,4]oxazin-1-yl)cyclohexyl]amino}methyl)-8-fluoro-1-{[2-(trimethylsilyl)ethoxy]methyl}[1]benzopyrano[4,3-b]pyrrol-4(1H)-one (77% yield). LC-MS (M−H⁺)=525.3. $^1$H NMR (400 MHz, DMSO-d$_6$) δ ppm 1.58-2.45 (m, 8H), 2.83-2.91 (m, 2H), 3.52 (br. s., 2H), 3.88-4.17 (m, 4H), 4.64-4.72 (m, 2H), 6.68 (br. s., 1H), 7.26 (td, J=8.71, 2.93 Hz, 1H), 7.44 (dd, J=9.00, 4.70 Hz, 1H), 7.74 (dd, J=9.98, 2.54 Hz, 1H), 7.80 (d, J=2.74 Hz, 1H), 7.92 (dd, J=9.00, 3.13 Hz, 1H), 8.12 (s, 1H).

Preparation of Compound 301

Compound 301 was prepared as described herein below.

Step 1—Synthesis of Ethyl 3-(3-hydroxypyridin-2-yl)-3-oxopropanoate

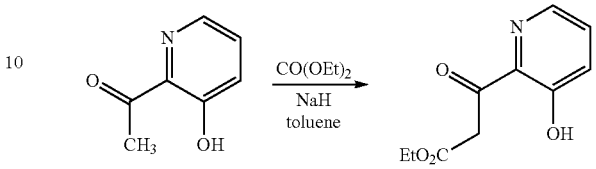

1-(3-Hydroxypyridin-2-yl)ethan-1-one (2.50 g, 18.2 mmol) in a mixture of diethyl carbonate (20 mL) and toluene (20 mL) was treated portionwise with NaH (60%, 3.3 g, 82 mmol) and stirred at RT for 1 h. A further portion of toluene (10 mL) was added and stirring continued for a further 5 h. The reaction mixture was added to a mixture of sat. aq. NH$_4$Cl and EtOAc. The aqueous phase was extracted with EtOAc and the combined organic fractions were washed with brine, dried over Na$_2$SO$_4$ and evaporated. The residue was purified by FCC (0-10% EtOAc in DCM) to afford the title compound (3.27 g, 86% yield) as a pale yellow oil. LC-MS (M−H⁺)=210. $^1$H NMR (400 MHz, CDCl$_3$): δ 11.28 (s, 1H), 8.22 (dd, J=1.4, 4.2 Hz, 1H), 7.43 (dd, J=4.2, 8.5 Hz, 1H), 7.35 (dd, J=1.4, 8.5 Hz, 1H), 4.22 (s, 2H), 4.21 (q, J=7.1 Hz, 2H), 1.26 (t, J=7.1 Hz, 3H).

Step 2—Synthesis of 4-hydroxy-2H-pyrano[3,2-b]pyridin-2-one

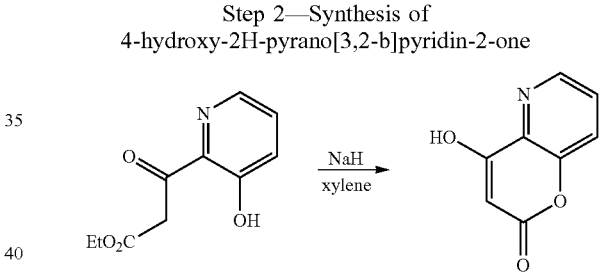

Ethyl 3-(3-hydroxypyridin-2-yl)-3-oxopropanoate (3.27 g, 15.6 mmol) in xylene (100 mL) was treated with NaH (60%, 63 mg, 1.6 mmol). The reaction mixture was heated to reflux and some solvent (15 mL) was distilled off. Heating under reflux was continued for 7 h. After cooling to RT the solid was collected by filtration, washed with toluene and dried under vacuum to afford the title compound (2.16 g, 85% yield) as a brown solid. LC-MS (M−H⁺)=164. $^1$H NMR (400 MHz, DMSO-d6): δ 8.55 (dd, J=1.2, 4.4 Hz, 1H), 7.80 (dd, J=1.2, 8.4 Hz, 1H), 7.64 (dd, J=4.4, 8.4 Hz, 1H), 5.58 (s, 1H).

Step 3—Synthesis of 4-chloro-2-oxo-2H-pyrano[3,2-b]pyridine-3-carbaldehyde

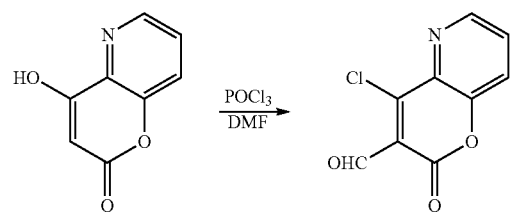

Phosphorus oxychloride (1.7 mL, 18 mmol) was added to an ice-cooled mixture of 4-hydroxy-2H-pyrano[3,2-b]pyridin-2-one (1.00 g, 6.13 mmol) and DMF (5 mL). The mixture was stirred at RT for 10 min then heated at 60° C. for 1.5 h. The reaction was cooled to RT, poured onto ice and extracted with DCM (×3). The combined organic extracts were washed with water, then dried (Na$_2$SO$_4$) and evaporated to afford the title compound (1.69 g, quantitative yield) as a brown solid. LC-MS (M-Cl+H$_2$O$^+$)=192. $^1$H NMR (400 MHz, CDCl$_3$): δ 10.42 (s, 1H), 8.81 (dd, J=1.4, 4.3 Hz, 1H), 7.76 (dd, J=1.4, 8.5 Hz, 1H), 7.69 (dd, J=4.3, 8.5 Hz, 1H).

Step 4—Synthesis of 4-oxo-1,4-dihydropyrrolo[2′,3′:4,5]pyrano[3,2-b]pyridine-2-carbaldehyde

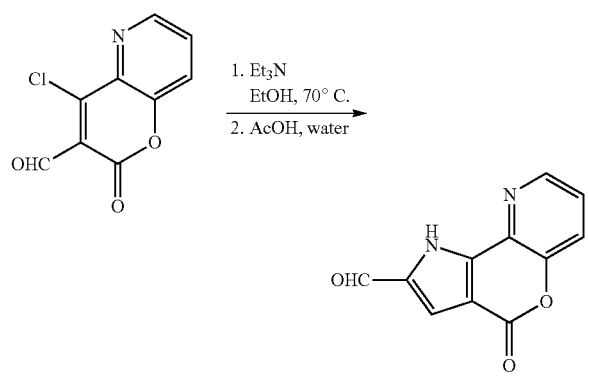

4-Chloro-2-oxo-2H-pyrano[3,2-b]pyridine-3-carbaldehyde (76%, 0.513 g, 1.86 mmol) was dissolved in ethanol (10 mL) and treated with aminoacetaldehyde dimethylacetal (0.215 g, 2.05 mmol) followed by Et$_3$N (0.54 mL, 3.9 mmol). The reaction was stirred at 70° C. for 50 min. The reaction mixture was allowed to cool, toluene was added and then evaporated. The residue was partitioned between EtOAc and water. The aqueous phase was extracted with ethyl acetate. The combined organic extracts were washed with brine, dried (Na$_2$SO$_4$) and evaporated. The resulting solid was dissolved in AcOH (20 mL). Water (0.8 mL) was added and the reaction was stirred at 110° C. for 50 min. The reaction mixture was allowed to cool, toluene was added and evaporated (×2). The residue was purified by FCC (EtOAc, then 10% MeOH in DCM) to afford the title compound (0.248 g, 62% yield) as a yellow solid. LC-MS (M-H$^+$)=215.

Step 5—Synthesis of 2-(trans-4-(7-fluoro-2-oxo-2,3-dihydro-1H-pyrido[2,3-b][1,4]oxazin-1-yl)cyclohexyl]amino}methyl)pyrrolo[2′,3′:4,5]pyrano[3,2-b]pyridin-4(1H)-one (Compound 301)

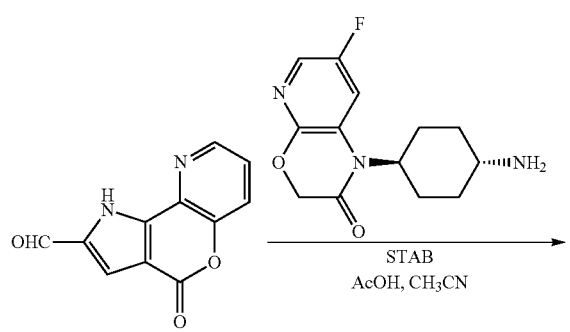

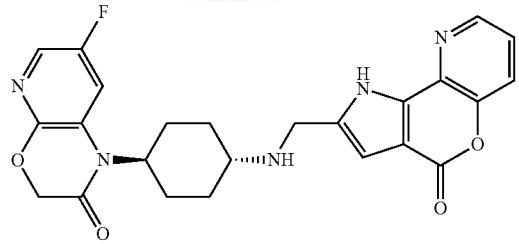

The title compound was prepared according to the procedure described for the synthesis of 8-fluoro-2-({[trans-4-(7-fluoro-2-oxo-2,3-dihydro-1H-pyrido[2,3-b][1,4]oxazin-1-yl)cyclohexyl]amino}methyl)[1]benzopyrano[4,3-b]pyrrol-4(1H)-one (compound 193, step 9) using 4-oxo-1,4-dihydropyrrolo[2′,3′:4,5]pyrano[3,2-b]pyridine-2-carbaldehyde (75% yield). LC-MS (M-H$^+$)=464.3. $^1$H NMR (400 MHz, DMSO-d6): δ 8.54 (dd, J=1.3, 4.6 Hz, 1H), 7.88-7.83 (m, 3H), 7.50 (dd, J=4.6, 8.4 Hz, 1H), 6.63 (s, 1H), 4.68 (s, 2H), 4.06-3.99 (m, 1H), 3.85 (s, 2H), 2.48-2.41 (m, 1H), 2.34-2.24 (m, 2H), 1.99-1.93 (m, 2H), 1.72-1.67 (m, 2H), 1.30-1.20 (m, 2H).

Preparation of Compound 302

Compound 302 was prepared as described herein below.

Step 1—Synthesis of 2-chloro-5-methoxypyridin-3-ol

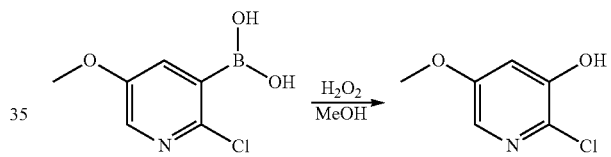

2-Chloro-5-methoxypyridin-3-yl boronic acid (1.0 g, 5.35 mmol) was suspended in methanol (20 mL) and cooled to 0° C. To the resulting suspension was added dropwise 50% aq. hydrogen peroxide (2.5 mL) and the reaction mixture was stirred for 5 hours at room temperature. The reaction was cooled to 0° C. and treated with saturated aqueous sodium thiosulphate (5 mL), followed by water (50 mL) and extracted with dichloromethane. The combined organic extracts were evaporated to dryness. The resulting residue was purified by flash column chromatography, eluting with 0 to 100% ethyl acetate/iso-hexane, to afford the title compound (506 mg, 60% yield). $^1$H NMR (400 MHz, DMSO): δ 10.75 (s, 1H), 7.67 (d, J=2.8 Hz, 1H), 6.97 (d, J=2.8 Hz, 1H), 3.84 (s, 3H).

Step 2—Synthesis of Tert-butyl [trans-4-(2-chloroacetamido)cyclohexyl]carbamate

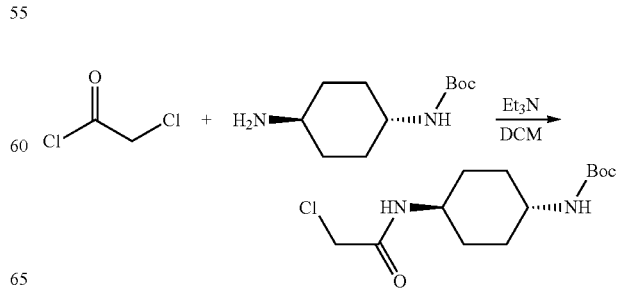

tert-Butyl (trans-4-aminocyclohexyl)carbamate (10.7 g, 50 mmol) was dissolved in DCM (200 mL), cooled to 0° C. and treated with triethylamine (6.1 g, 60.4 mmol). Chloroacetyl chloride (5.65 g, 50 mmol) was then added dropwise over 10-15 minutes and the reaction was left to stir overnight at room temperature. The reaction was quenched with water (100 mL), the phases separated and the combined DCM fractions dried over MgSO$_4$, filtered and evaporated. The resulting residue was washed with iso-hexane, filtered and dried in vacuum to give the title compound (11.12 g, 76% yield). $^1$H NMR (400 MHz, CDCl$_3$): δ 6.37 (d, J=7.3 Hz, 1H), 4.40-4.39 (m, 1H), 4.02 (s, 2H), 3.79-3.69 (m, 1H), 3.50-3.43 (m, 1H), 2.08-1.98 (m, 4H), 1.45 (s, 9H), 1.42-1.20 (m, 4H).

Step 3—Synthesis of Tert-butyl [trans-4-(7-methoxy-2-oxo-2,3-dihydro-1H-pyrido[2,3-b][1,4]oxazin-1-yl)cyclohexyl]carbamate

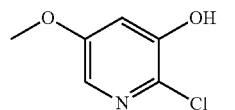

+

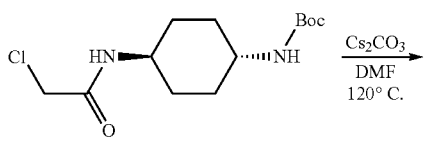

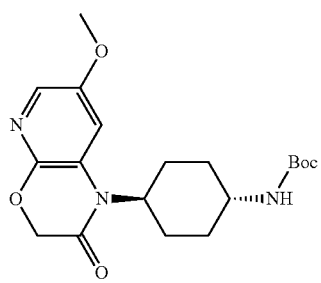

2-Chloro-5-methoxypyridin-3-ol (506 mg, 3.18 mmol) was dissolved in DMF (20 mL) and tert-butyl [trans-4-(2-chloroacetamido)cyclohexyl]carbamate (926 mg, 1 eq) and Cs$_2$CO$_3$ (2.5 g, 2.4 eq) added. The reaction mixture was heated at 120° C. for 18 h. After cooling to room temperature, the mixture was filtered and evaporated to dryness. The residue was purified by flash column chromatography eluting with 0 to 100% ethyl acetate/iso-hexane to afford the title compound (756 mg, 63% yield). LC-MS (M–H$^+$)=378. $^1$H NMR (400 MHz, DMSO): δ 7.63 (d, J=2.5 Hz, 1H), 7.39 (d, J=2.5 Hz, 1H), 6.85 (d, J=7.1 Hz, 1H), 4.68 (s, 2H), 4.16-4.06 (m, 1H), 3.90 (s, 3H), 2.47-2.34 (m, 2H), 1.90 (d, J=11.1 Hz, 2H), 1.77 (d, J=10.1 Hz, 2H), 1.44 (s, 11H).

Step 4—Synthesis of 1-[trans-4-aminocyclohexyl]-7-methoxy-1H-pyrido[2,3-b][1,4]oxazin-2(3H)-one (Hydrochloride Salt)

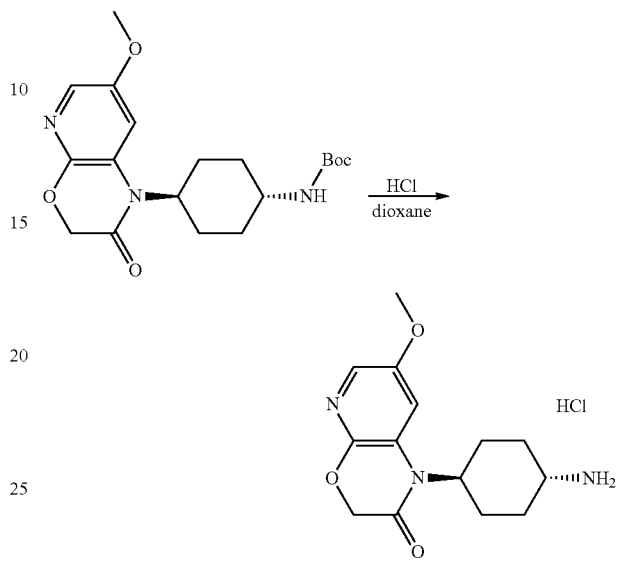

tert-butyl [trans-4-(7-methoxy-2-oxo-2,3-dihydro-1H-pyrido[2,3-b][1,4]oxazin-1-yl)cyclohexyl]carbamate (756 mg, 2.01 mmol) was dissolved in 1,4 dioxane (15 mL). A 4 N solution of HCl in dioxane (15 mL) was added and the reaction mixture stirred for 1 h at room temperature followed by addition of another 15 mL of a 4 N solution of HCl in dioxane. The reaction mixture was stirred for 1 h at room temperature, diluted with diethyl ether and filtered to yield a white solid. The precipitate was washed with ether and dried in vacuum to give the title compound (675 mg, 96% yield) as HCl salt. $^1$H NMR (400 MHz, DMSO): δ 8.16 (d, J=1.6 Hz, 3H), 7.60 (d, J=2.5 Hz, 1H), 7.41 (d, J=2.5 Hz, 1H), 4.64 (s, 2H), 4.13-4.05 (m, 1H), 3.85 (s, 3H), 3.11 (d, J=4.4 Hz, 1H), 2.42-2.32 (m, 2H), 2.05 (d, J=11.4 Hz, 2H), 1.78 (d, J=10.5 Hz, 2H), 1.61-1.50 (m, 2H).

Step 5—Synthesis of 8-fluoro-2-({[trans-4-(7-methoxy-2-oxo-2,3-dihydro-1H-pyrido[2,3-b][1,4]oxazin-1-yl)cyclohexyl]amino}methyl)[1]benzopyrano[4,3-b]pyrrol-4(1H)-one (Compound 302)

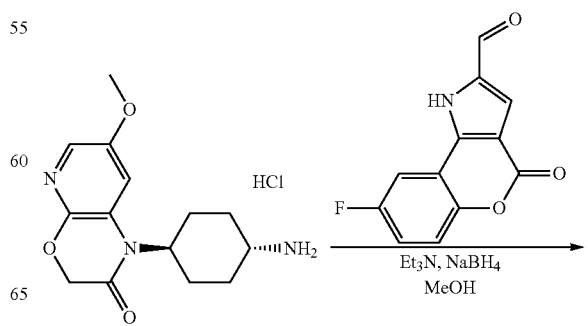

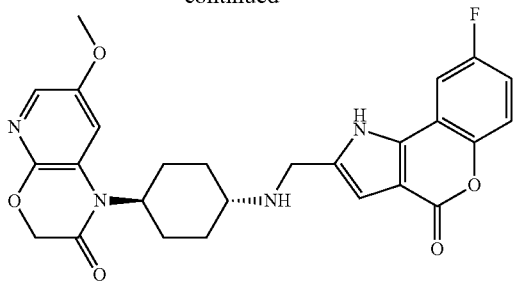

1-[trans-4-aminocyclohexyl]-7-methoxy-1H-pyrido[2,3-b][1,4]oxazin-2(3H)-one HCl (307 mg, 878 µmol) was dissolved in methanol (10 mL) and treated with triethylamine (354 mg, 4 eq), followed by 3 Å molecular sieves (500 mg) and 8-fluoro-4-oxo-1,4-dihydrochromeno[4,3-b]pyrrole-2-carbaldehyde (231 mg, 1 eq). The reaction mixture was stirred at 60° C. for 18 h, cooled to room temperature and treated with NaBH₄ (134 mg, 4 eq). The resulting mixture was stirred for 18 h at room temperature then was cooled, filtered through celite and the combined filtrates evaporated. The resulting material was purified by flash column chromatography eluting with 0 to 100% ethyl acetate/iso-hexane followed by 0 to 100% methanol/ethyl acetate to give 123 mg of crude product. This material was triturated with DMF followed by ether, filtered and dried in vacuum to give the title compound (52 mg, 12.1% yield). LC-MS (M–H⁺)=493. ¹H NMR (400 MHz, DMSO): δ 13.35 (bs, 1H), 9.30 (bs, 1H), 7.88 (dd, J=2.6, 8.5 Hz, 1H), 7.60 (d, J=2.3 Hz, 1H), 7.53 (dd, J=4.5, 9.1 Hz, 1H), 7.44-7.35 (m, 2H), 6.92 (s, 1H), 4.65 (s, 2H), 4.34-4.34 (m, 2H), 4.11 (m, 1H), 3.85 (s, 3H), 3.19 (m, 1H), 2.41 (d, J=11.4 Hz, 2H), 2.23 (m, 2H), 1.87 (d, J=1.3 Hz, 2H), 1.64-1.63 (m, 2H).

Preparation of Compound 303

Compound 303 was prepared as described herein below.

Step 1—Synthesis of Tert-butyl 4-(2-chloroacetamido)piperidine-1-carboxylate

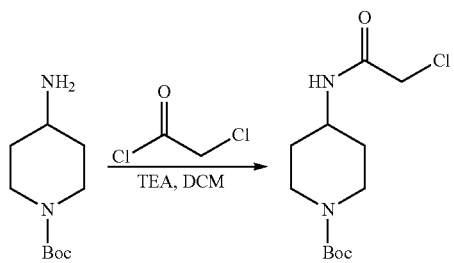

To a solution of tert-butyl 4-aminopiperidine-1-carboxylate (2.5 g, 12.5 mmol) in dichloromethane (30 mL) and triethylamine (2.25 mL, 16.1 mmol) was added at 0° C. chloroacetyl chloride (1.1 mL, 13.8 mmol). The reaction mixture was allowed to warm to room temperature and stirring continued for 1 hour. The reaction was quenched by addition of a saturated NaHCO₃ solution and extracted with ethyl acetate. The combined organic extracts were evaporated and the residue purified by flash column chromatography eluting with ethyl acetate to afford the title compound (3.5 g, 100% yield). ¹H NMR (400 MHz, CDCl3): δ 6.46 (d, J=6.1 Hz, 1H), 4.08-4.05 (m, 1H), 4.04 (s, 2H), 4.00-3.89 (m, 2H), 2.88 (dd, J=12.2, 12.2 Hz, 2H), 1.96-1.89 (m, 2H), 1.46 (s, 9H), 1.44-1.29 (m, 2H).

Step 2—Synthesis of Tert-butyl 4-(7-fluoro-2-oxo-2,3-dihydro-1H-pyrido[2,3-b][1,4]oxazin-1-yl)piperidine-1-carboxylate

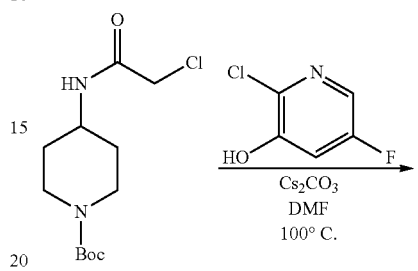

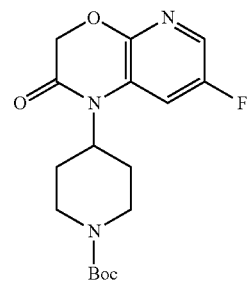

tert-butyl 4-(2-chloroacetamido)piperidine-1-carboxylate (2.02 g, 7.31 mmol) and 2-chloro-5-fluoropyridin-3-ol (1.08 g, 7.32 mmol) were dissolved in DMF (70 mL). Caesium carbonate (4.88 g, 15 mmol) was added and the mixture heated to 100° C. for 18 hours. After cooling to room temperature the mixture was partitioned between ethyl acetate and water and the organic phase washed with water. The organic layer was then evaporated onto silica and purified by flash column chromatography eluting with 20 to 100% ethyl acetate/iso-hexane to give the title compound (2.19 g, 85% yield). ¹H NMR (400 MHz, CDCl₃): δ 7.80 (d, J=2.5 Hz, 1H), 7.23 (dd, J=2.7, 9.0 Hz, 1H), 4.70 (s, 2H), 4.43-4.29 (m, 3H), 2.81 (m, 2H), 2.50-2.37 (m, 2H), 1.74 (dd, J=1.5, 11.6 Hz, 2H), 1.50 (s, 9H).

Step 3—Synthesis of 7-fluoro-1-(piperidin-4-yl)-1H-pyrido[2,3-b][1,4]oxazin-2(3H)-one Hydrogen Chloride

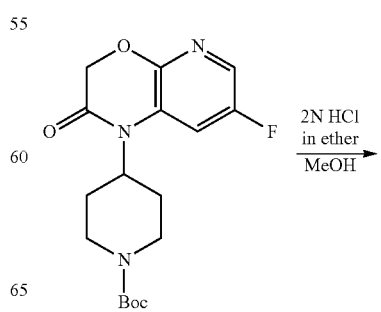

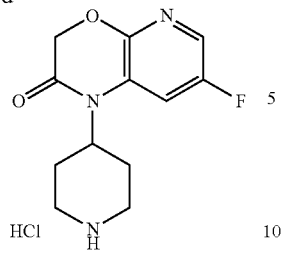

tert-butyl 4-(7-fluoro-2-oxo-2,3-dihydro-1H-pyrido[2,3-b][1,4]oxazin-1-yl)piperidine-1-carboxylate (2.19 g, 6.23 mmol) was dissolved in MeOH (3 mL) and treated with a 2 N solution of HCl in diethyl ether (6 mL) at room temperature for 18 hours. The mixture was evaporated to furnish the title compound (1.6 g) that was used without further purification in the next step. $^1$H NMR (400 MHz, DMSO): δ 9.26-9.20 (m, 1H), 8.69-8.67 (m, 1H), 8.02 (dd, J=2.6, 10.1 Hz, 1H), 7.90 (d, J=2.5 Hz, 1H), 4.76 (s, 2H), 4.43-4.34 (m, 1H), 3.37 (d, J=12.3 Hz, 2H), 3.12-3.00 (m, 2H), 2.79-2.66 (m, 2H), 1.91 (d, J=12.7 Hz, 2H).

Step 4—Synthesis of 1-[1-(3-amino-2-hydroxypropyl)piperidin-4-yl]-7-fluoro-1H-pyrido[2,3-b][1,4]oxazin-2(3H)-one

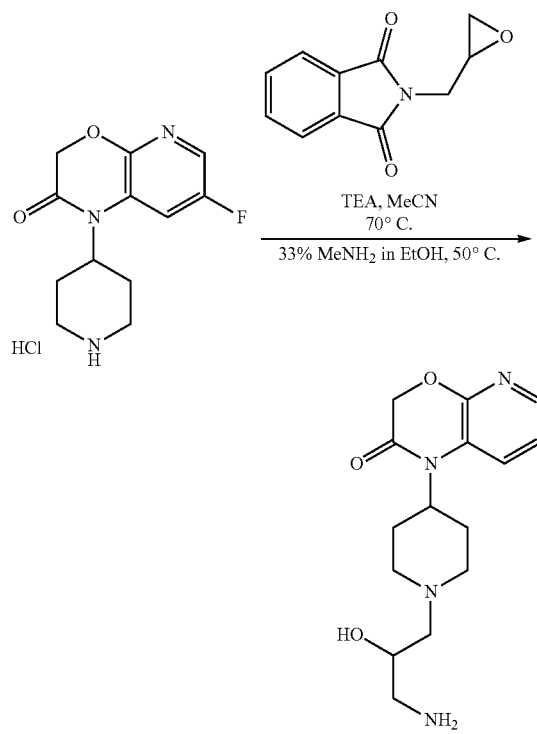

7-Fluoro-1-(piperidin-4-yl)-1H-pyrido[2,3-b][1,4]oxazin-2(3H)-one hydrogen chloride (1.6 g, 6.23 mmol) and 2-(oxiran-2-ylmethyl)isoindoline-1,3-dione (1.28 g, 6.3 mmol) were suspended in acetonitrile (60 mL) and triethylamine (4 mL) was added. The mixture was heated at 70° C. for 20 hours, then cooled to room temperature and evaporated to dryness. The residue (2.8 g, 6.23 mmol) was treated with methylamine (20 mL, 33% in ethanol) in a sealed tube at 50° C. for 3 hours. The mixture was evaporated and purified by reverse phase preparative HPLC to afford the title compound (119 mg). LC-MS (M–H$^+$)=325

Step 5—Synthesis of 6-fluoro-2-oxo-2H-1-benzopyran-4-yl trifluoromethanesulfonate

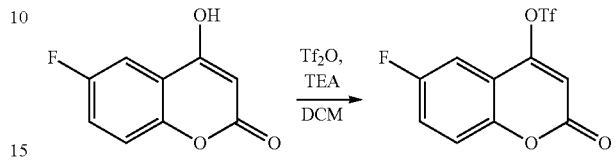

To a solution of 6-fluoro-4-hydroxy-2H-chromen-2-one (720 mg, 4 mmol) and triethylamine (1.4 mL, 10 mmol) in dichloromethane (30 mL), trifluoromethane sulfonic anhydride (0.74 mL, 4.4 mmol) was added dropwise at 0° C. under nitrogen. The reaction was allowed to warm to room temperature and stirred overnight. The mixture was then poured into diethyl ether/iso-hexane (1:1, 600 mL) and filtered through a silica plug. The filtrate was evaporated to give the title compound (647 mg, 52% yield) which was used without further purification in the next step.

Step 6—Synthesis of 7-fluoro-1-(1-{3-[(6-fluoro-2-oxo-2H-1-benzopyran-4-yl)amino]-2-hydroxypropyl}piperidin-4-yl)-1H-pyrido[2,3-b][1,4]oxazin-2(3H)-one (Compound 303)

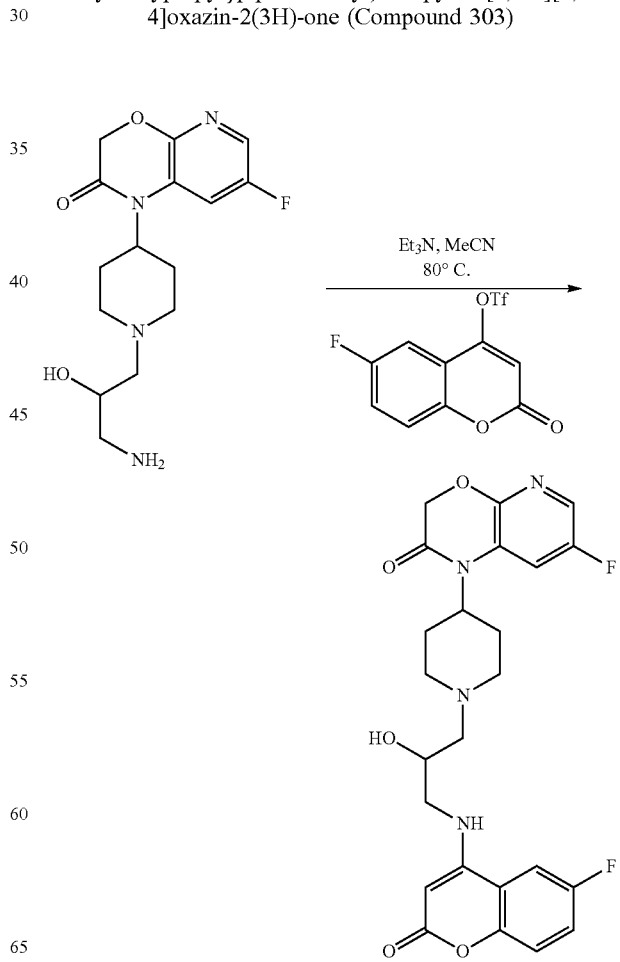

1-(1-(3-Amino-2-hydroxypropyl)piperidin-4-yl)-7-fluoro-1H-pyrido[2,3-b][1,4]oxazin-2(3H)-one (95 mg, 277 µmol) and 6-fluoro-2-oxo-2H-chromen-4-yl trifluoromethane sulfonate (320 mg, 1 mmol) were dissolved in acetonitrile (10 mL) and triethylamine (1 mL) and heated to 80° C. for 2 hours in a sealed tube. The reaction mixture was cooled to room temperature and evaporated to dryness. The crude material was purified by reverse phase preparative HPLC to afford the title compound (25 mg, 18% yield). $^1$H NMR (400 MHz, DMSO): δ 8.07 (dd, J=2.8, 10.1 Hz, 1H), 7.91 (m, 2H), 7.74 (dd, J=5.6, 5.6 Hz, 1H), 7.56-7.50 (m, 1H), 7.43 (dd, J=4.8, 9.1 Hz, 1H), 5.38 (s, 1H), 4.98 (d, J=4.5 Hz, 1H), 4.78 (s, 2H), 4.14-4.06 (m, 1H), 3.98-3.93 (m, 1H), 3.44-3.48 (m, 1H), 3.29-3.20 (m, 1H), 3.04 (dd, J=11.5, 25.1 Hz, 2H), 2.67-2.58 (m, 1H), 2.50-2.38 (m, 2H), 2.25 (dd, J=11.7, 15.5 Hz, 2H), 1.74-1.68 (m, 2H).

Preparation of Compound 314

Compound 314 was prepared as described herein below.

Step 1—Synthesis of 5-(benzyloxy)-2-(hydroxymethyl)pyridin-4(1H)-one

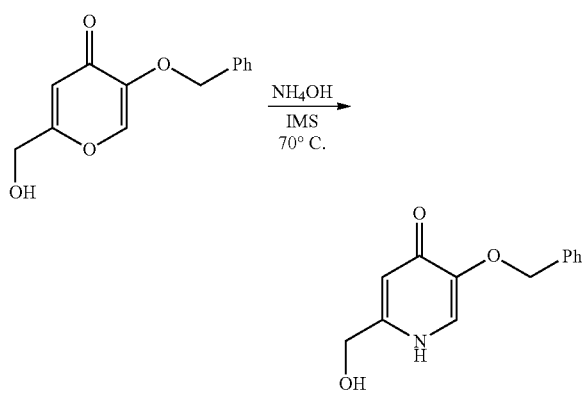

A suspension of 5-(benzyloxy)-2-(hydroxymethyl)-4H-pyran-4-one (53.2 g, 229 mmol) in IMS (75 mL) and aq. NH$_4$OH solution (400 mL) was stirred at 70° C. for 18 h. The cooled solution was diluted with water (400 mL), cooled to 5° C. and the suspension stirred for 30 min. The solid was filtered and dried under vacuum to leave the title compound as a pale brown solid (42.5 g, 80% yield). LC-MS (M–H$^+$)=232. $^1$H NMR (300 MHz, DMSO-d6): δ 11.08 (br s, 1H), 7.51-7.28 (m, 6H), 6.16 (br s, 1H), 5.56 (br s, 1H), 5.01 (s, 2H), 4.34 (s, 2H).

Step 2—Synthesis of 5-(benzyloxy)-3-bromo-2-(hydroxymethyl) pyridin-4(1H)-one

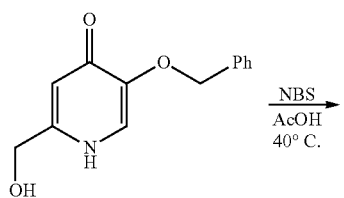

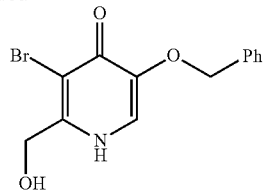

A suspension of 5-(benzyloxy)-2-(hydroxymethyl)pyridine-4(1H)-one (11.6 g, 50.0 mmol) and NBS (10.2 g, 57.5 mmol) in AcOH (75 mL) was stirred at 40° C. for 1 h. The cooled suspension was filtered, the solid washed with AcOH (25 mL) and dried under vacuum to leave the title compound as a pale yellow solid (13.7 g, 89% yield). LC-MS (M–H$^+$)=310-312. $^1$H NMR (300 MHz, DMSO-d6): δ 7.56 (s, 1H), 7.47-7.30 (m, 5H), 5.12 (s, 2H), 4.56 (s, 2H).

Step 3—Synthesis of 5-bromo-6-(hydroxymethyl)pyridine-3,4-diol Hydrochloride

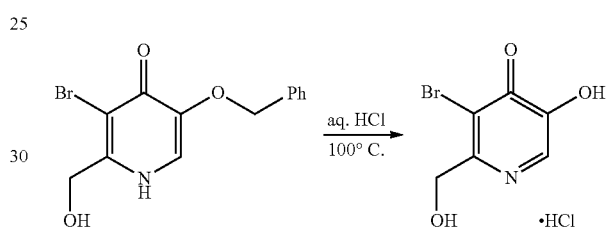

A suspension of 5-(benzyloxy)-3-bromo-2-(hydroxymethyl)pyridin-4(1H)-one (3.07 g, 9.90 mmol) in water (10 mL) and conc. aq. HCl solution (10 mL) was stirred at 100° C. for 2 h. The mixture was cooled to 0° C., then the suspension filtered. The solid was washed with EtOAc (10 mL) then dried under vacuum to leave a brown solid (1.93 g, 76% yield). LC-MS (M–H$^+$)=220-222. $^1$H NMR (300 MHz, DMSO-d6): δ 7.88 (s, 1H), 4.63 (s, 2H), 2.42 (s, 1H).

Step 4—Synthesis of (8-bromo-2,3-dihydro[1,4]dioxino[2,3-c]pyridin-7-yl)methanol

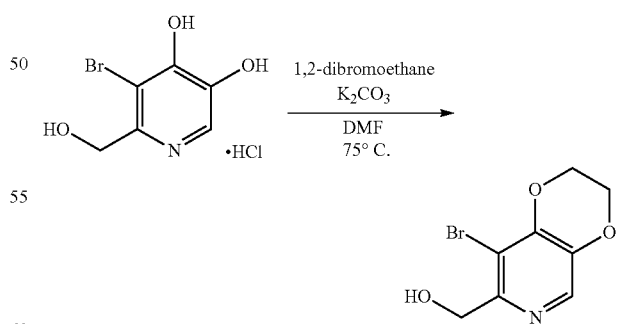

A suspension of 5-bromo-6-(hydroxymethyl)pyridine-3,4-diol hydrochloride (1.93 g, 7.52 mmol), 1,2-dibromoethane (2.12 g, 11.3 mmol) and K$_2$CO$_3$ (1.56 g, 11.3 mmol) in DMF (5 mL) was stirred at 75° C. for 5 h. The cooled suspension was concentrated under vacuum, then suspended in DCM-MeOH (98:2, 25 mL) and filtered through Celite.

The filter cake was washed with DCM-MeOH (98:2, 50 mL) then the combined organics were concentrated under vacuum to leave a pale brown crystalline solid (1.30 g, 70% yield). LC-MS (M–H$^+$)=246-248. $^1$H NMR (300 MHz, DMSO-d6): δ 8.08 (s, 1H), 4.66 (s, 2H), 4.50-4.46 (m, 2H), 4.35-4.30 (m, 2H).

Step 5—Synthesis of 8-bromo-2,3-dihydro[1,4]dioxino[2,3-c]pyridine-7-carbaldehyde

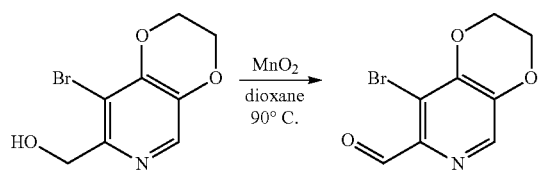

A suspension of (8-bromo-2,3-dihydro-[1,4]dioxino[2,3-c]pyridin-7-yl)methanol (1.25 g, 5.08 mmol) and MnO$_2$ (4.42 g, 51 mmol) in dioxane (25 mL) was stirred at 90° C. for 5 h. The suspension was cooled to RT then was filtered through Celite, and the filter cake washed with warm dioxane (40° C., 25 mL). The combined organics were concentrated under vacuum to leave a pale orange solid (715 mg, 58% yield). $^1$H NMR (300 MHz, CDCl3): δ 10.16 (s, 1H), 8.29 (s, 1H), 4.54-4.49 (m, 2H), 4.43-4.39 (m, 2H).

Step 6—Synthesis of 9-tert-butyl 8-methyl 2,3-dihydro-9H-[1,4]dioxino[2,3-d]pyrrolo[3,2-b]pyridine-8,9-dicarboxylate

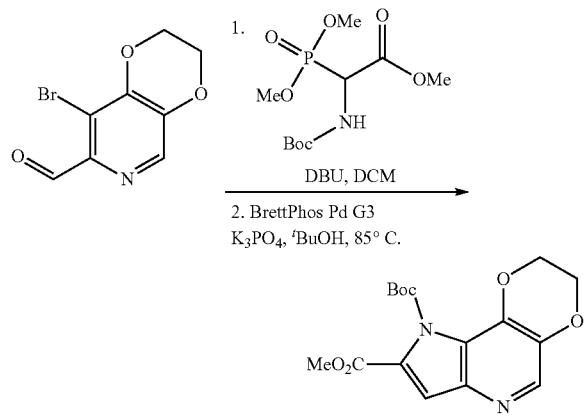

To a solution of 8-bromo-2,3-dihydro-[1,4]dioxino[2,3-c]pyridine-7-carbaldehyde (715 mg, 2.93 mmol) and N-Boc-2-phosphonoglycine trimethyl ester (1.09 g, 3.66 mmol) in DCM (20 mL) at RT was added DBU (558 mg, 3.66 mmol) and the resulting mixture stirred at RT for 30 min. Aq. citric acid solution (10%, 20 mL) was added, then the aq. layer extracted with DCM (20 mL). The combined organics were passed through a hydrophobic frit and concentrated under vacuum to 3 mL volume. FCC (10-35% EtOAc in iso-hexane) gave the intermediate methyl (Z)-3-(8-bromo-2,3-dihydro-[1,4]dioxino[2,3-c]pyridin-7-yl)-2-((tert-butoxycarbonyl)-amino)acrylate as an off-white solid (835 mg, 69% yield, LC-MS (M–H$^+$)=415-417). N$_2$ was bubbled through a suspension of the intermediate, K$_3$PO$_4$ (862 mg, 4.06 mmol) and 3 Å MS (400 mg) in t-BuOH (40 mL) at 50° C. for 30 min. BrettPhos Pd G3 (CAS: 1470372-59-8; 92 mg, 0.10 mmol) was added, then the flask evacuated and purged with N$_2$ thrice. The mixture was stirred at 85° C. for 4.5 h. The cooled suspension was diluted with EtOAc (40 mL) then the mixture filtered through Celite. The filter cake was washed with EtOAc (40 mL), then the combined organics concentrated under vacuum to leave a gum (810 mg). FCC (10-60% EtOAc in iso-hexane) gave a crystalline orange solid (543 mg, 80% yield). LC-MS (M–H$^+$)=335. $^1$H NMR (300 MHz, CDCl$_3$): δ 8.22 (s, 1H), 7.26 (s, 1H), 4.47-4.42 (m, 2H), 4.41-4.36 (m, 2H), 3.93 (s, 3H), 1.64 (s, 9H).

Step 7—Synthesis of Methyl 2,3-dihydro-9H-[1,4]dioxino[2,3-d]pyrrolo[3,2-b]pyridine-8-carboxylate

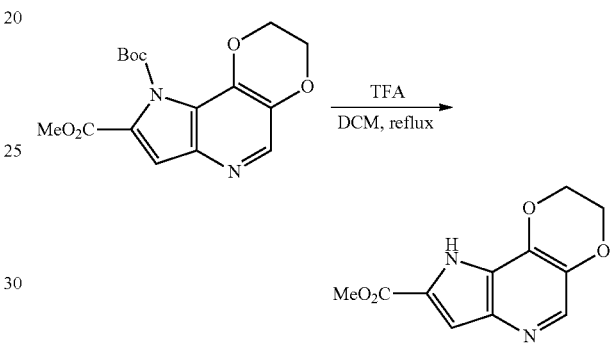

A solution of 9-(tert-butyl) 8-methyl 2,3-dihydro-9H-[1,4]dioxino[2,3-d]pyrrolo[3,2-b]pyridine-8,9-dicarboxylate (543 mg, 1.62 mmol) in TFA (2 mL) and DCM (10 mL) was stirred at reflux for 1 h. The cooled solution was concentrated under vacuum, dissolved in MeOH (3 mL), applied to an SCX-2 cartridge (10 g) and washed with MeOH (40 mL). The product was eluted with a 2 M solution of NH$_3$ in MeOH (40 mL); concentration under vacuum left the title product as a pale yellow solid (346 mg, 91% yield). LC-MS (M–H$^+$)=235. $^1$H NMR (300 MHz, DMSO-d6): δ 12.22 (1H, br s), 8.08 (1H, s), 7.12 (1H, s), 4.50-4.44 (2H, m), 4.41-4.35 (2H, m), 3.85 (3H, s).

Step 8—Synthesis of (2,3-dihydro-9H-[1,4]dioxino[2,3-d]pyrrolo[3,2-b]pyridin-8-yl)methanol

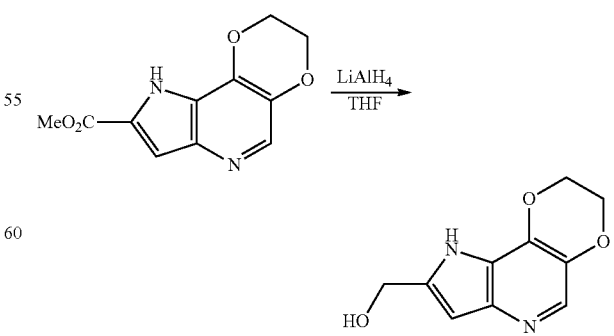

To a suspension of methyl 2,3-dihydro-9H-[1,4]dioxino[2,3-d]pyrrolo[3,2-b]pyridine-8-carboxylate (344 mg, 1.47 mmol) in dry THF (20 mL) was added lithium aluminium hydride (1 M in THF, 2.9 mL, 2.9 mmol) dropwise, at 0° C. under N₂. The suspension was stirred at 0° C. for 5 min and then at RT for 1 h. The suspension was cooled to 0° C., then water (0.12 mL), aq. NaOH solution (15%, 0.12 mmol), water (0.36 mL) and Na₂SO₄ were added sequentially. The suspension was stirred at RT for 30 min, then filtered through Celite. The filter cake was washed with DCM-MeOH (9:1, 50 mL), then the combined organics concentrated under vacuum to leave the title compound as a pale yellow solid (110 mg, 36% yield). LC-MS (M–H⁺)=207. ¹H NMR (300 MHz, DMSO-d6): δ 11.18 (br s, 1H), 7.86 (s, 1H), 6.28 (s, 1H), 5.16 (t, J=4.6 Hz, 1H), 4.55 (d, J=4.6 Hz, 2H), 4.47-4.42 (m, 2H), 4.34-4.29 (m, 2H).

Step 9—Synthesis of 2,3-dihydro-9H-[1,4]dioxino [2,3-d]pyrrolo[3,2-b]pyridine-8-carbaldehyde

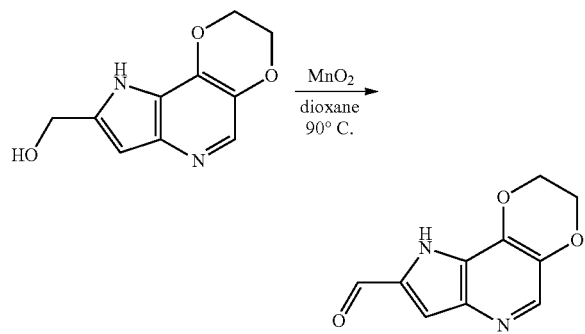

A suspension of (2,3-dihydro-9H-[1,4]dioxino[2,3-d]pyrrolo[3,2-b]pyridin-8-yl)methanol (108 mg, 0.524 mmol) and MnO₂ (228 mg, 2.62 mmol) in dioxane (5 mL) was stirred at 90° C. for 2 h. The suspension was cooled to 50° C., then filtered through Celite. The filter cake was washed with dioxane (10 mL), then the combined organics concentrated under vacuum to leave the title compound as a yellow solid (84 mg, 79% yield). LC-MS (M–H⁺)=205. ¹H NMR (300 MHz, DMSO-d6): δ 12.32 (br s, 1H), 9.83 (s, 1H), 8.13 (s, 1H), 7.38 (s, 1H), 4.51-4.45 (m, 2H), 4.43-4.37 (m, 2H).

Step 10—Synthesis of 1-[trans-4-{[(2,3-dihydro-9H-[1,4]dioxino[2,3-d]pyrrolo[3,2-b]pyridin-8-yl) methyl]amino}cyclohexyl]-7-fluoro-1H-pyrido [2,3-b][1,4]oxazin-2(3H)-one (Compound 314)

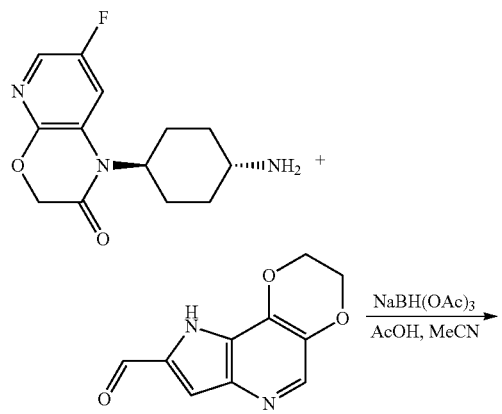

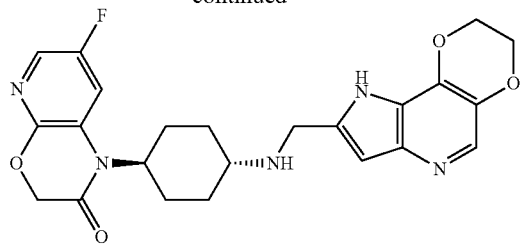

A solution of 1-(trans-4-aminocyclohexyl)-7-fluoro-1H-pyrido[2,3-b][1,4]oxazin-2(3H)-one (106 mg, 0.400 mmol), 2,3-dihydro-9H-[1,4]dioxino[2,3-d]pyrrolo[3,2-b]pyridine-8-carbaldehyde (82 mg, 0.40 mmol), sodium triacetoxyborohydride (340 mg, 1.6 mmol) and AcOH (46 µL, 0.80 mmol) in MeCN (10 mL) was stirred at RT for 7 h. The mixture was concentrated under vacuum, suspended in a mixture of water and sat. aq. NaHCO₃ solution (1:1, 10 mL) and extracted with DCM-MeOH (19:1, 2×10 mL). The combined organics were passed through a hydrophobic frit and concentrated under vacuum to leave an orange-yellow gum. FCC (15 µm silica, 2-6% [2M NH₃ in MeOH] in DCM) followed by trituration with warm MeCN (50° C.) provided the title compound as an off-white solid (89 mg, 49% yield). LC-MS (M–H⁺)=454.3. ¹H NMR (400 MHz, DMSO-d6): δ 11.09 (br s, 1H), 7.86-7.82 (m, 3H), 6.28 (s, 1H), 4.68 (s, 2H), 4.48-4.44 (m, 2H), 4.34-4.31 (m, 2H), 4.01 (tt, J=3.6, 12.1 Hz, 1H), 3.82 (s, 2H), 2.42 (tt, J=3.5, 11.0 Hz, 1H), 2.27 (dq, J=2.9, 12.6 Hz, 2H), 2.14 (br s, 1H), 1.96 (apparent br d, J=11.9 Hz, 2H), 1.69 (apparent br d, J=11.9 Hz, 2H), 1.24 (dq, J=3.4, 12.3 Hz, 2H).

Preparation of Compound 343

Compound 343 was prepared as described herein below.

Step 1—Synthesis of [(2S)-3,8-dioxo-1,2-dihydro-3H,8H-2a,5,8a-triazaacenaphthylen-2-yl]methyl Methanesulfonate

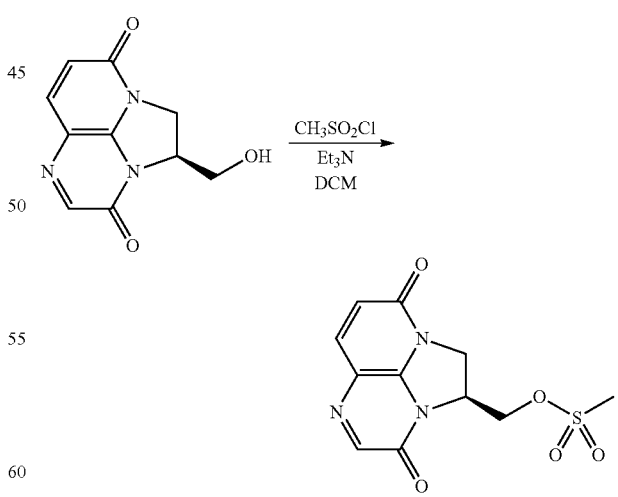

To an ice-cooled suspension of (2S)-2-(hydroxymethyl)-1,2-dihydro-3H,8H-2a,5,8a-triazaacenaphthylene-3,8-dione (prepared as in WO2009/141398, 0.500 g, 2.28 mmol) in DCM (35 mL) was added Et₃N (0.48 mL, 3.4 mmol), then methanesulfonyl chloride (0.21 mL, 2.7 mmol) was added over 3 min. The mixture was stirred at RT for 45 min then purified directly by FCC (2-10% MeOH in DCM) to give the title compound (0.64 g, 94% yield). LC-MS (M−H⁺)=298. ¹H NMR (400 MHz, DMSO-d6): δ 7.88 (d, J=9.6 Hz, 1H), 7.79 (s, 1H), 6.27 (d, J=9.6 Hz, 1H), 5.36-5.30 (m, 1H), 4.86 (dd, J=3.5, 11.2 Hz, 1H), 4.62 (dd, J=2.4, 11.2 Hz, 1H), 4.43 (dd, J=10.1, 12.0 Hz, 1H), 4.25 (dd, J=5.1, 12.1 Hz, 1H), 3.21 (s, 3H).

Step 2—Synthesis of 4-chloro-6-fluoro-2H-1-benzopyran-2-one

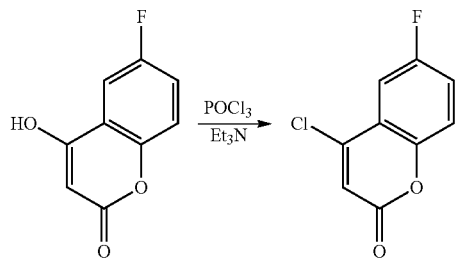

Et₃N (3.5 mL, 25 mmol) was added over 5 min to a suspension of 6-fluoro-4-hydroxy-2H-1-benzopyran-2-one (3.0 g, 16.7 mmol) in POCl₃ (42 mL, 450 mmol). The mixture was stirred at RT for 10 min then heated at reflux for 16 h. The reaction was cooled to RT and then concentrated under reduced pressure. Toluene was added and evaporated. The residue was partitioned between DCM and aq. sodium bicarbonate. The aqueous phase was extracted with DCM, then the combined organic extracts were washed with water, dried over Na₂SO₄ and evaporated. The residue was purified by FCC (2-6% EtOAc in toluene) to give the title compound (3.082 g, 93% yield). LC-MS (M−H⁺)=199. ¹H NMR (400 MHz, CDCl3): δ 7.57 (dd, J=2.4, 8.2 Hz, 1H), 7.39-7.32 (m, 2H), 6.67 (s, 1H).

Step 3—Synthesis of Tert-butyl 4-{2-[(6-fluoro-2-oxo-2H-1-benzopyran-4-yl)amino]-1-hydroxyethyl}piperidine-1-carboxylate

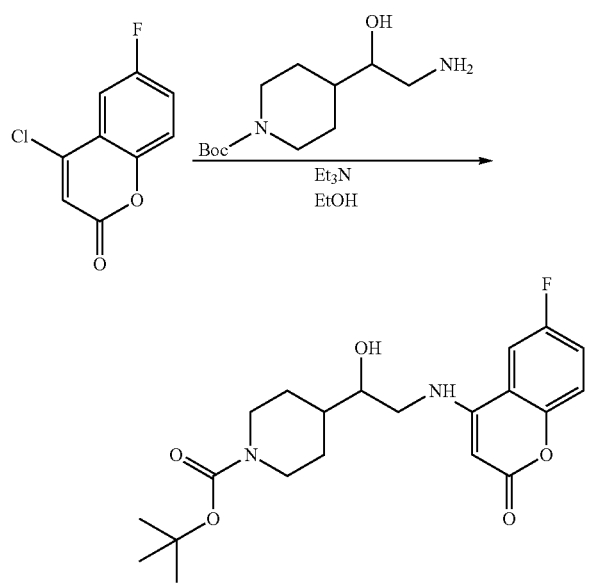

Et₃N (1.0 mL, 7.2 mmol) was added to a solution of tert-butyl 4-(2-amino-1-hydroxyethyl)piperidine-1-carboxylate (0.818 g, 3.34 mmol) in EtOH (25 mL). 4-chloro-6-fluoro-2H-1-benzopyran-2-one (0.65 g, 3.27 mmol) was added and the mixture was stirred at RT for 5 min then heated at 70° C. for 7.5 h. The reaction mixture was allowed to cool and then evaporated. The residue was purified by FCC (2-8% [2M NH₃ in MeOH] in DCM) to give the title compound (0.859 g, 65% yield). LC-MS (M−Na⁺)=429. ¹H NMR (400 MHz, DMSO-d6): δ 8.01 (dd, J=2.9, 10.0 Hz, 1H), 7.55 (br t, J=5.3 Hz, 1H), 7.50-7.45 (m, 1H), 7.37 (dd, J=4.9, 9.1 Hz, 1H), 5.23 (s, 1H), 4.95 (d, J=5.3 Hz, 1H), 4.04-3.91 (m, 2H), 3.62-3.57 (m, 1H), 3.36-3.30 (m, 1H, under water peak), 3.18-3.11 (m, 1H), 2.74-2.53 (m, 2H), 1.77-1.69 (m, 1H), 1.61-1.53 (m, 2H), 1.39 (s, 9H), 1.32-1.13 (m, 2H).

Step 4—Synthesis of 6-fluoro-4-{[2-hydroxy-2-(piperidin-4-yl)ethyl]amino}-2H-1-benzopyran-2-one

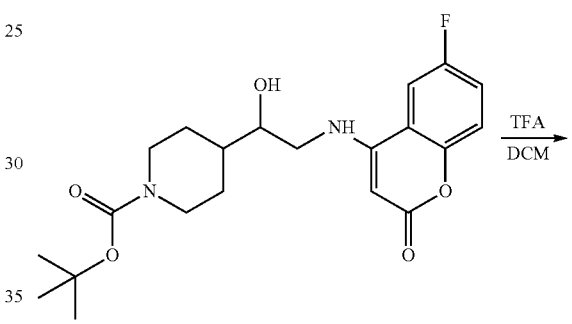

TFA (7.5 mL) was added to an ice-cooled solution of tert-butyl 4-{2-[(6-fluoro-2-oxo-2H-1-benzopyran-4-yl)amino]-1-hydroxyethyl}piperidine-1-carboxylate (0.859 g, 2.11 mmol) in DCM (30 mL). The mixture was stirred at RT for 1 h. Toluene was added and evaporated. The residue was dissolved in MeOH (25 mL), applied to an SCX-2 cartridge and washed with MeOH. The product was eluted with a 2 M solution of NH₃ in MeOH and the evaporation gave the title compound (0.502 g, 78% yield). LC-MS (M−H⁺)=307. ¹H NMR (400 MHz, DMSO-d6): δ 8.03 (dd, J=2.9, 10.1 Hz, 1H), 7.57 (t, J=5.4 Hz, 1H), 7.50-7.45 (m, 1H), 7.37 (dd, J=4.8, 9.1 Hz, 1H), 5.20 (s, 1H), 4.88 (br s, 1H), 3.56-3.51 (m, 1H), 3.18-3.08 (m, 2H), 2.99-2.90 (m, 2H), 2.46-2.37 (m, 2H), 1.70-1.65 (m, 1H), 1.55-1.41 (m, 2H), 1.31-1.13 (m, 2H).

Step 5—Synthesis of (2R)-2-[(4-{2-[(6-fluoro-2-oxo-2H-1-benzopyran-4-yl)amino]-1-hydroxyethyl}piperidin-1-yl)methyl]-1,2-dihydro-3H,8H-2a,5,8a-triazaacenaphthylene-3,8-dione (Compound 343, Diastereomeric Mixture)

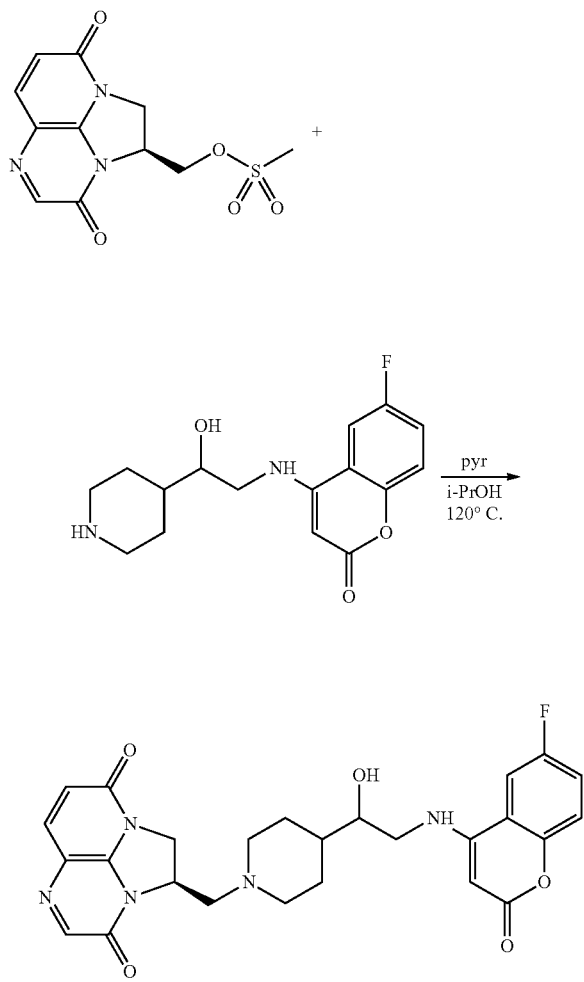

A mixture of (S)-(3,8-dioxo-1,2-dihydro-3H,8H-2a,5,8a-triazaacenaphthylen-2-yl)methyl methane-sulfonate (0.300 g, 1.01 mmol), 6-fluoro-4-{[2-hydroxy-2-(piperidin-4-yl)ethyl]amino}-2H-1-benzopyran-2-one (0.464 g, 1.51 mmol), pyridine (0.33 mL, 4.0 mmol) and i-PrOH (20 mL) was stirred in a sealed vial at 120° C. for 2.5 h. The cooled mixture was evaporated to dryness and purified via FCC (2-14% [2M NH$_3$ in MeOH] in DCM) to give the title compound (0.167 g, 33% yield) as an off-white solid. LC-MS (M–H$^+$)=508.4. $^1$H NMR (400 MHz, DMSO-d6): δ 8.01 (dd, J=2.9, 10.0 Hz, 1H), 7.85 (d, J=9.6 Hz, 1H), 7.73 (s, 1H), 7.52 (t, J=5.0 Hz, 1H), 7.50-7.45 (m, 1H), 7.37 (dd, J=4.9, 9.1 Hz, 1H), 6.25 (d, J=9.5 Hz, 1H), 5.21 (s, 1H), 5.08-5.02 (m, 1H), 4.88 (dd, J=1.0, 5.4 Hz, 1H), 4.33 (dd, J=9.4, 11.8 Hz, 1H), 4.25 (dd, J=5.0, 11.7 Hz, 1H), 3.57-3.51 (m, 1H), 3.32-3.28 (m, 1H), 3.15-3.08 (m, 1H), 3.03-2.95 (m, 2H), 2.78 (dd, J=8.9, 12.6 Hz, 1H), 2.71-2.65 (m, 1H), 2.18-2.00 (m, 2H), 1.75-1.66 (m, 1H), 1.59-1.51 (m, 1H), 1.39-1.18 (m, 3H).

Preparation of Compound 354

Compound 354 was prepared as described herein below.

Step 1—Synthesis of tert-butyl (2-{[trans-4-(7-fluoro-2-oxo-2,3-dihydro-1H-pyrido[2,3-b][1,4]oxazin-1-yl)cyclohexyl]amino}ethyl) Carbamate

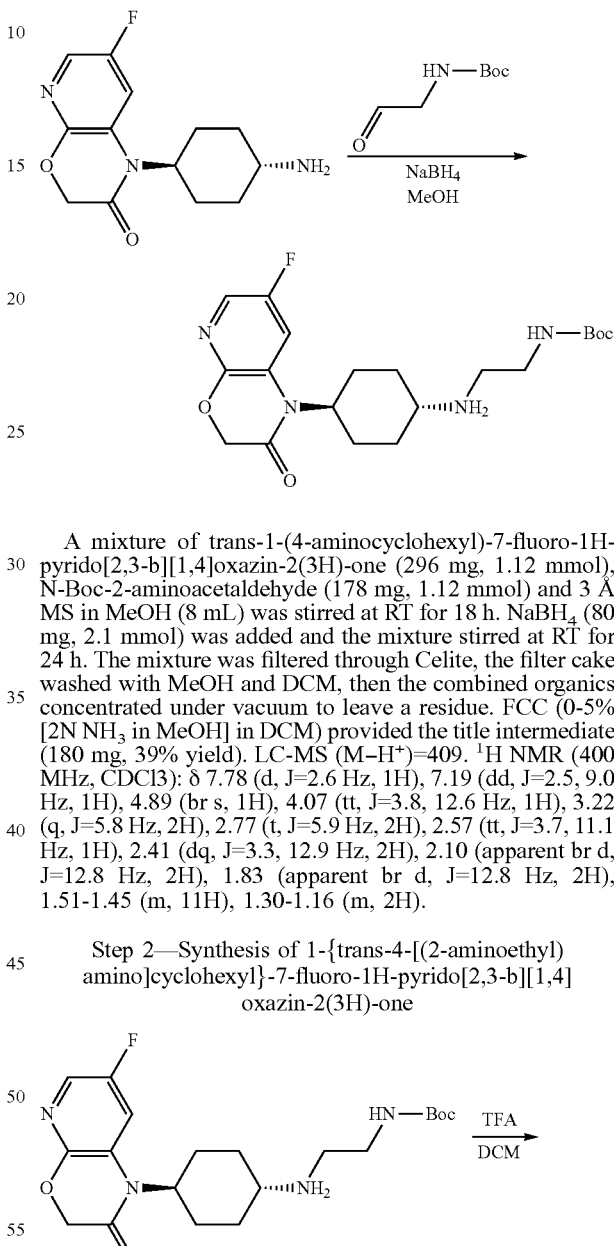

A mixture of trans-1-(4-aminocyclohexyl)-7-fluoro-1H-pyrido[2,3-b][1,4]oxazin-2(3H)-one (296 mg, 1.12 mmol), N-Boc-2-aminoacetaldehyde (178 mg, 1.12 mmol) and 3 Å MS in MeOH (8 mL) was stirred at RT for 18 h. NaBH$_4$ (80 mg, 2.1 mmol) was added and the mixture stirred at RT for 24 h. The mixture was filtered through Celite, the filter cake washed with MeOH and DCM, then the combined organics concentrated under vacuum to leave a residue. FCC (0-5% [2N NH$_3$ in MeOH] in DCM) provided the title intermediate (180 mg, 39% yield). LC-MS (M–H$^+$)=409. $^1$H NMR (400 MHz, CDCl3): δ 7.78 (d, J=2.6 Hz, 1H), 7.19 (dd, J=2.5, 9.0 Hz, 1H), 4.89 (br s, 1H), 4.07 (tt, J=3.8, 12.6 Hz, 1H), 3.22 (q, J=5.8 Hz, 2H), 2.77 (t, J=5.9 Hz, 2H), 2.57 (tt, J=3.7, 11.1 Hz, 1H), 2.41 (dq, J=3.3, 12.9 Hz, 2H), 2.10 (apparent br d, J=12.8 Hz, 2H), 1.83 (apparent br d, J=12.8 Hz, 2H), 1.51-1.45 (m, 11H), 1.30-1.16 (m, 2H).

Step 2—Synthesis of 1-{trans-4-[(2-aminoethyl)amino]cyclohexyl}-7-fluoro-1H-pyrido[2,3-b][1,4]oxazin-2(3H)-one

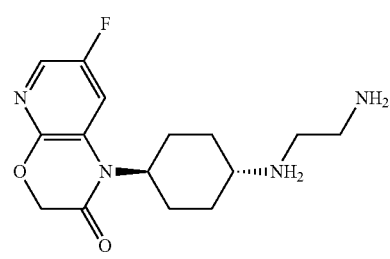

A mixture of tert-butyl (2-trans-4-(7-fluoro-2-oxo-2,3-dihydro-1H-pyrido[2,3-b][1,4]oxazin-1-yl)cyclohexyl)amino)ethyl)carbamate (180 mg, 0.44 mmol) in TFA (0.50 mL) and DCM (2 mL) was stirred at RT for 1.5 h. The mixture was applied to an SCX-2 cartridge, washed with MeOH and then eluted with $NH_3$ in MeOH (2 N); concentration under vacuum left a brown solid (113 mg, 83% yield). LC-MS (M–H$^+$)=309. $^1$H NMR (400 MHz, CDCl3): δ 7.78 (d, J=2.6 Hz, 1H), 7.20 (dd, J=2.6, 9.0 Hz, 1H), 4.67 (s, 2H), 4.06 (tt, J=3.9, 12.3 Hz, 1H), 2.83 (dd, J=5.3, 6.2 Hz, 2H), 2.71 (dd, J=5.2, 6.4 Hz, 2H), 2.58 (tt, J=3.7, 11.1 Hz, 1H), 2.43 (dq, J=3.4, 12.9 Hz, 2H), 2.15-2.09 (m, 2H), 1.87-1.81 (m, 2H), 1.25 (ddt, J=3.6, 12.5, 12.3 Hz, 2H).

Step 3—Synthesis of 7-fluoro-1-[trans-4-({2-[(6-fluoro-2-oxo-2H-1-benzopyran-4-yl)amino]ethyl}amino)cyclohexyl]-1H-pyrido[2,3-b][1,4]oxazin-2(3H)-one (Compound 354)

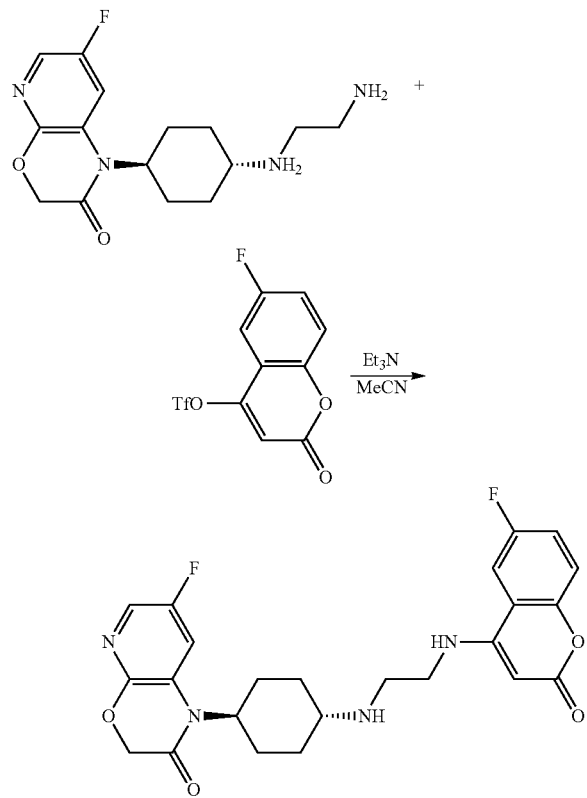

To a solution of 1-{trans-4-[(2-aminoethyl)amino]cyclohexyl}-7-fluoro-1H-pyrido[2,3-b][1,4]oxazin-2(3H)-one (110 mg, 0.36 mmol) and Et$_3$N (43 mg, 0.43 mmol) in MeCN (3 mL), 6-fluoro-2-oxo-2H-chromen-4-yl trifluoromethanesulfonate was added and the mixture stirred at RT for 2 h. The mixture was partitioned between water and EtOAc, then the aq. phase extracted with EtOAc. The combined organics were dried (MgSO$_4$), filtered and concentrated under vacuum to leave the crude product. FCC (15 μm silica, 0-3.5% [2M $NH_3$ in MeOH] in DCM) gave an off-white solid. The solid was triturated with MeCN (1 mL) to leave a wet solid that was dried under vacuum at 60° C. to give the title compound (46 mg, 27% yield). LC-MS (M–H$^+$)=471.3. $^1$H NMR (400 MHz, DMSO-d6): δ 7.98 (dd, J=2.9, 10.0 Hz, 1H), 7.87-7.81 (m, 2H), 7.55 (s, 1H), 7.48 (ddd, J=2.9, 8.0, 9.0 Hz, 1H), 7.37 (dd, J=4.8, 9.1 Hz, 1H), 5.25 (s, 1H), 4.70 (s, 2H), 4.04 (tt, J=3.7, 11.9 Hz, 1H), 3.32 (2H, methylene signal under water peak), 2.82 (t, J=6.5 Hz, 2H), 2.50 (1H, methine signal under solvent peak), 2.35 (dq, J=2.9, 12.7 Hz, 2H), 1.94 (d, J=11.9 Hz, 2H), 1.71 (d, J=11.4 Hz, 2H), 1.28-1.16 (m, 2H).

Biological Assays

Example 1

Inhibition of DNA Gyrase and Topo IV in *E. coli* and *S. aureus*

The above compounds were tested for the inhibition of the enzyme DNA gyrase in a gyrase supercoiling assay and for the inhibition of the enzyme topoisomerase IV in a decatenation assay, in both Gram positive and Gram negative bacteria, according to the following methods.

Both the assays were carried out according to a set-up method modified from the article to Blanche F, et al. "Differential Behaviors of *Staphylococcus aureus* and *Escherichia coli* Type II DNA Topoisomerases", Antimicrob. Agents Chemother., 1996, Vol. 40, No. 12 p. 2714-2720.

The compounds were screened at single concentration (200, 100 or 50 μM), in duplicate.

Ciprofloxacin and novobiocin were used as reference compounds, at single concentration of 200 and 50 μM, respectively.

DNA Gyrase Supercoiling Assay.

Reagents from *S. aureus* and *E. coli* Gyrase Supercoiling Assay kits (Inspiralis, UK) were used. A master mix with a total volume sufficient for the number of reactions to perform was prepared with the following reagents: 5× assay buffer, relaxed pBR322 substrate (0.5 μg/reaction), RNase-DNase free water. Aliquotes of this mix were dispensed in each tube, then 10× compound stock solutions or vehicle control (DMSO), were added to each reaction tube.

Reaction was started with *E. Coli* (2 U/reaction) or *S. aureus* (1 U/reaction) gyrase enzyme addition.

A sample added with an equal volume of dilution buffer was used as negative control (without enzyme).

The reaction tubes were gentle vortexed and incubated 30 minutes at 37° C. Each reaction was stopped by adding 30 μl of Stop Buffer and 30 μl chloroform/isoamyl alcohol (24/1), briefly vortexed for 5-10 seconds and centrifuged at 20000×g for 2 minutes. Samples were loaded onto 1% agarose gel and subjected to electrophoresis for 1 hour at 80V constant voltage in TAE (40 mM Tris-acetate, 2 mM EDTA).

Data acquisition and analysis. Treatment of relaxed pBR322 with DNA gyrase converted the relaxed topoisomers (DNAs of different linking number) to the supercoiled form of the plasmid, which migrates faster on an agarose gel. An upper band might also be visible, which consists of open-circular (nicked) DNA which is present in the relaxed substrate but co-migrates with some of the relaxed topoisomers.

Bands were visualized by ethidium bromide staining (dilution 1:20000) for 30 minutes followed by destaining in distilled water for 10 minutes.

In order to evaluate the compounds activity on the enzyme, the bands of supercoiled DNAs in the gel were photographed by a digital imaging system ImageQuant LAS 4000 (GE Healthcare) according to manufacturer's instructions.

The fluorescent intensity of each band was analyzed by ImageQuant TL software and it was expressed as volume (volume of the uncalibrated quantity of material in the image feature after subtraction of the background intensity by using rolling ball method).

Each band intensity was compared, as percentage, to vehicle sample band intensity, which served as positive control, on the same gel.

Inhibitory activity was expressed as percent of inhibition versus the positive control.

The results are summarized in the following Table 2.

Topoisomerase IV Decatenation Assay

S. aureus and E. coli Topoisomerase IV decatenation kits (Inspiralis, UK) were used. A master mix with a total volume sufficient for the number of reactions to perform was prepared with the following reagents: 5× assay buffer (50 mM HEPES-KOH (pH 7.6), 100 mM potassium glutamate, 10 mM magnesium acetate, 10 mM DTT, 1 mM ATP, 50 µg/ml albumin), kDNA substrate (200 ng/reaction), RNase-DNase free water. Aliquots of this mix were dispensed in each tube, then 10× compound stock solutions or vehicle control (DMSO), were added in each reaction tube.

Reaction was started with Topoisomerase IV enzyme (0.5 U/reaction) addition.

A sample added with an equal volume of dilution buffer was used as negative control (without enzyme).

The reaction tubes were gentle vortexed and incubated 30 minutes at 37° C. Each reaction was stopped by adding 30 µl of Stop Buffer and 30 µl of chloroform/isoamyl alcohol (24/1), briefly vortexed for 5-10 seconds and centrifuged at 20000×g for 2 minutes. Samples taken from the upper phase were loaded into 1% agarose gel and subjected to electrophoresis for 1 hour at 80V constant voltage in TAE (40 mM Tris-acetate, 2 mM EDTA).

Data acquisition and analysis. Due to the high molecular mass, kDNA could not enter an agarose gel under normal electrophoresis conditions, but remained in the wells. In the presence of Topo IV topoisomerase mini-circles (2.5 Kb) were released from kDNA by decatenation and were quickly and easily resolved in the gel at relatively high voltages.

Bands were visualized by ethidium bromide staining (dil 1:20000) for 30 minutes followed by destaining in distilled water for 10 minutes.

For single concentration screening assay, in order to evaluate the compounds activity on the enzymes, the bands of decatenated DNAs in the gel were photographed by a digital imaging system ImageQuant LAS 4000 (GE Healthcare) according to manufacturer's instructions.

The fluorescent intensity of each band was analyzed by ImageQuant TL software and it was expressed as volume (volume of the uncalibrated quantity of material in the image feature after subtraction of the background intensity by using rolling ball method).

Each band intensity was compared, as percentage, to vehicle sample band intensity, which served as positive control, on the same gel.

Inhibitory activity was expressed as percent of inhibition versus the positive control.

The results are summarized in the following Table 2.

TABLE 2

| Compound No. | conc. (µM) | E. coli % inhibition DNA gyrase | E. coli % inhibition Topo IV | S. aureus % inhibition DNA gyrase | S. aureus % inhibition Topo IV |
|---|---|---|---|---|---|
| 157 | 50 | 83 | 100 | 89 | 100 |
| 160 | 50 | 50 | 60 | 65 | n/a |
| 164 | 50 | 100 | 100 | 100 | 100 |
| 165 | 50 | 70 | 90 | 100 | 100 |
| 180 | 50 | 58 | 57 | 90 | 50 |
| 181 | 50 | 53 | 91 | 92 | 50 |
| 182 | 50 | 61 | 52 | 92 | 50a |
| 183 | 50 | 81 | 77 | 84 | 85 |
| 193 | 50 | 77 | 50 | 86 | 74 |
| 194 | 50 | 79 | 50 | 60 | 50 |
| 197 | 50 | 87 | 63 | 90 | 79 |
| 200 | 50 | 90 | 100 | 100 | 100 |
| 201 | 50 | 100 | 100 | 100 | 100 |
| 202 | 50 | 100 | 100 | 100 | 100 |
| 204 | 50 | 100 | 100 | 100 | 100 |
| 205 | 50 | 100 | 100 | 100 | 100 |
| 206 | 50 | 100 | 100 | 100 | 100 |
| 207 | 50 | 100 | 100 | 100 | 100 |
| 208 | 50 | 100 | 100 | 100 | 100 |
| 209 | 50 | 100 | 100 | 100 | 100 |
| 210 | 50 | 92 | 86 | 100 | 84 |
| 211 | 50 | 100 | 100 | 100 | 100 |
| 212 | 50 | 100 | 100 | 100 | 100 |
| 213 | 50 | 98 | 97 | 100 | 84 |
| 214 | 50 | 99 | 100 | 100 | 100 |
| 215 | 50 | 69 | n/a | 96 | n/a |
| 216 | 50 | 100 | 100 | 100 | 100 |
| 217 | 50 | 82 | 50 | 100 | 100 |
| 219 | 50 | 100 | 100 | 100 | 100 |
| 220 | 50 | 100 | 50 | 100 | 100 |
| 221 | 50 | 81 | 50 | 100 | 100 | n/a = not active

The above results showed that the exemplified compounds effectively inhibited both DNA gyrase and Topo IV of E. coli, which is a Gram positive bacterium, and/or S. aureus, which is a Gram negative bacterium.

Example 2

Determination of $IC_{50}$

The compounds that in the above example 1 showed an inhibitory activity were further assayed in concentration-response curve (eight half-log concentrations ranging from 0.1 to 300 µM) in order to determine the $IC_{50}$.

The supercoiled or decatenated DNA bands obtained as described in Example 1 were analysed as follows.

Bands were analyzed by gel documentation equipment (Syngene, Cambridge, UK) and quantitated using Syngene Gene Tools software. Raw gel data (fluorescent band volumes) collected from Syngene, GeneTools gel analysis software were converted to a percentage of the 100% control (the fully supercoiled or decatenated DNA band). These data were analyzed using SigmaPlot Version 12.3 (2013). The IC50 data were calculated by using the global curve fit non-linear regression tool by selecting the Single, 2 Parameter fit function from the Exponential Decay equation category.

The results are reported in the following table 3.

TABLE 3

| Compound No. | E. coli | | S. aureus | |
|---|---|---|---|---|
| | IC$_{50}$ DNA gyrase | IC$_{50}$ Topo IV | IC$_{50}$ DNA gyrase | IC$_{50}$ Topo IV |
| 157 | 2.34 | 0.64 | 2.48 | 1.02 |
| 160 | n/a | 21.5 | 20.8 | n/a |
| 164 | 3.77 | 1.78 | 1.46 | 0.7 |
| 165 | 5.25 | 1.24 | 3.60 | 1.12 |
| 180 | 0.48 | 3.78 | 1.70 | 0.11 |
| 181 | 0.44 | 3.67 | 0.73 | 0.36 |
| 182 | 0.74 | 3.21 | 0.64 | 0.74 |
| 183 | 0.77 | 2.48 | 0.74 | 0.19 |
| 193 | 0.25 | 1.38 | 0.28 | 2.25 |
| 194 | 0.25 | 6.06 | 0.49 | 0.69 |
| 200 | 0.04 | <0.1 | <0.1 | <0.1 |
| 201 | <0.1 | <0.1 | 0.19 | <0.1 |
| 204 | 0.05 | <0.1 | 0.64 | <0.1 |
| 205 | 0.1 | 0.31 | 0.17 | 0.1 |
| 206 | 0.05 | <0.1 | 0.13 | <0.1 |
| 207 | <0.1 | <0.1 | <0.1 | <0.1 |
| 208 | 0.08 | 0.27 | 0.11 | 0.13 |
| 209 | 0.13 | 1.00 | 0.3 | 0.22 |
| 210 | 0.44 | 13.77 | 1.3 | 1.31 |
| 211 | <0.1 | <0.1 | <0.1 | <0.1 |
| 212 | 0.1 | 0.17 | 0.14 | 0.07 |
| 213 | 0.11 | 1.00 | 0.28 | 0.58 |
| 214 | 0.12 | 1.03 | 0.16 | 0.57 |
| 216 | 0.13 | 0.25 | 0.31 | 0.29 |
| 217 | 1.45 | 0.69 | 2.15 | 2.72 |
| 219 | 0.22 | 0.22 | 0.22 | 0.65 |
| 220 | 0.68 | 0.74 | 1.97 | 2.91 |
| 221 | 0.92 | 0.67 | 2.76 | 2.63 |

Example 3

Determination of IC$_{50}$

Compounds 301-303, 314, 343 and 354 were assayed in concentration-response curve (eight half-log concentrations ranging from 0.1 to 300 µM) in order to determine the IC$_{50}$, following the procedure described in example 2.

The results are reported in the following table 4.

TABLE 4

| Compound No. | E. coli | | S. aureus | |
|---|---|---|---|---|
| | IC$_{50}$ DNA gyrase | IC$_{50}$ Topo IV | IC$_{50}$ DNA gyrase | IC$_{50}$ Topo IV |
| 301 | 0.46 | 0.43 | 0.72 | 70.3 |
| 302 | 0.59 | 0.12 | 0.58 | 3.26 |
| 303 | 2.67 | 0.62 | 9.92 | >100 |
| 314 | 0.85 | 1.14 | 7.1 | >100 |
| 343 | 0.91 | 1.27 | 1.98 | 8.73 |
| 354 | 0.47 | 0.18 | 0.35 | 0.92 |

The data of Table 3 are comparable to the data of Table 2, and confirmed the activity of Compounds 301-303, 314, 343 and 354 to effectively inhibit both DNA gyrase and Topo IV of E. coli and/or S. aureus.

The invention claimed is:

1. A compound of formula (1):

A-L$_1$-Y-L$_2$-R—B  (1)

wherein
A is a cyclic group having the following formulae (I):

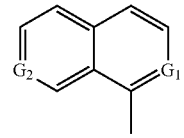

(I)

wherein
G$_1$ is CH or N;
G$_2$ is CR$_1$ or N;
R$_1$ is hydrogen atom, halogen atom, cyano or (C$_{1-3}$) alkoxy group;
L$_1$ is σ bond, or (C$_{1-3}$)alkylenyl group, optionally substituted with hydroxy group;
Y is a ring selected from the group consisting of piperidinyl, piperazinyl, pyrrolidinyl, 1-3 cyclobutyl, 1-3 cyclopentyl, 1-2 cyclopropyl, azetidinyl, azabicyclooctyl, morpholinyl and cyclohexyl ring, said ring being optionally substituted by one or more substituent selected from the group consisting of hydroxy group, (C$_{1-3}$)alkylenyl-OH group, (C$_{1-3}$)alkylenyl-O—(C$_{1-3}$) alkyl group, (C$_{1-3}$)alkylenyl-CONR'R" group, and CONR'R" group, wherein R' and R" are hydrogen atom or (C$_{1-3}$)alkyl;
L$_2$ is σ bond, —(C$_{1-3}$)alkylenyl- group, NR''' group, NR'''—(C$_{1-3}$)alkylenyl group, (C$_{1-3}$)alkylenyl-NR''' group, NR'''—(C$_{1-3}$)alkylenyl-NR''' group, or (C$_{1-3}$) alkylenyl-NR''' —(C$_{1-3}$)alkylenyl group, said group being optionally substituted with a hydroxy group, wherein R''' is hydrogen, (C$_{1-3}$)alkyl, (C$_{1-3}$)alkylenyl-OH, (C$_{1-3}$)alkylenyl-O—(C$_{1-3}$)alkyl, or (C$_{1-3}$)alkylenyl-CONR'R", wherein R' and R" are hydrogen atom or (C$_{1-3}$)alkyl;
R is σ bond or heterocyclic ring, aliphatic or aromatic, having 5 members containing one or more nitrogen atoms, optionally substituted with CH$_2$OH, CH$_2$CN, CN or CONR'R", wherein R' and R" are hydrogen atom or (C$_{1-3}$)alkyl; and
B is cyclic group having the following formulae (V):

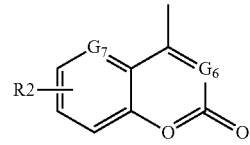

(V)

wherein
G$_6$ is CH or N;
G$_7$ is CH or N; and
R$_2$ is hydrogen atom or halogen atom,
with the proviso that when Y is piperidinyl ring or piperazinyl ring, if A is represented by formula (I) and B is represented by formula (V), then G$_2$ is only N,
or an addition salt with a pharmaceutically acceptable organic or inorganic acid or base, an enantiomer, an N-oxide, or a quaternary ammonium salt of said compound of formula (1).

2. The compound according to claim 1, wherein R$_1$ is a halogen atom, a cyano group, or an alkoxy group having from 1 to 2 carbon atoms.

3. The compound according to claim 2, wherein $R_1$ is selected from the group consisting of a fluorine atom, a chlorine atom, a cyano group and a methoxy group.

4. The compound according to claim 1, wherein $L_1$ is a σ bond or a methylene group (—$CH_2$).

5. The compound according to claim 1, wherein $L_2$ is a σ bond, a ($C_{1-3}$)alkylenyl group, NR''' group, —NR'''—($C_{1-3}$)alkylenyl group, ($C_{1-3}$)alkylenyl-NR'''— group, —NR'''—($C_{1-3}$)alkylenyl-NR'''— group, or ($C_{1-3}$)alkylenyl-NR'''—($C_{1-3}$)alkylenyl group, said group being optionally substituted with one or more hydroxy group.

6. The compound according to claim 5, wherein $L_2$ is a σ bond, a ($C_{1-2}$)alkylenyl group, NR''' group, —NR'''—($C_{1-2}$)alkylenyl group, ($C_{1-2}$)alkylenyl-NR'''— group, —NR'''—($C_{1-2}$)alkylenyl-NR'''— group, or ($C_{1-2}$)alkylenyl-NR'''—($C_{1-2}$)alkylenyl group, said group being optionally substituted with one hydroxy group.

7. The compound according to claim 1, wherein R is a σ bond or an aromatic heterocyclic ring having 5 members containing one or more nitrogen atoms, optionally substituted with $CH_2CN$ or CN.

8. The compound according to claim 7, wherein R is a σ bond, a 1H-imidazol-4-yl group, or a 1H-pyrrol-2-yl group, optionally substituted with $CH_2CN$ or CN.

9. The compound according to claim 1, wherein A is a cyclic group having one of the following formulae:

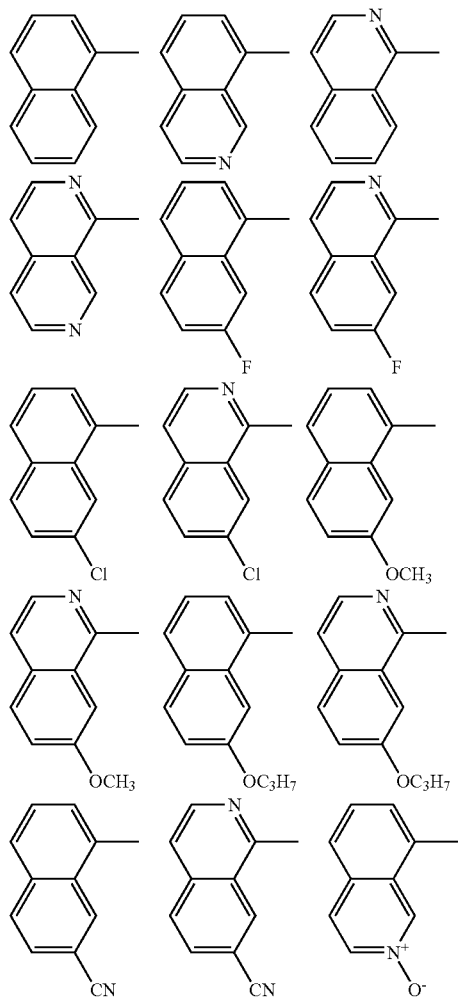

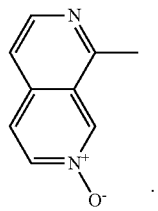

10. The compound according to claim 1, wherein Y is a ring having one of the following formulae:

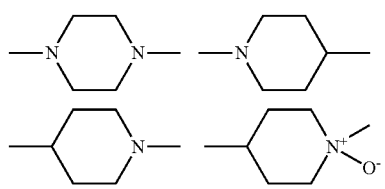

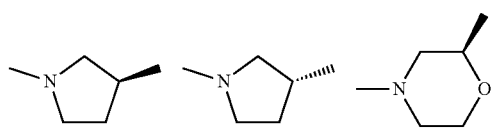

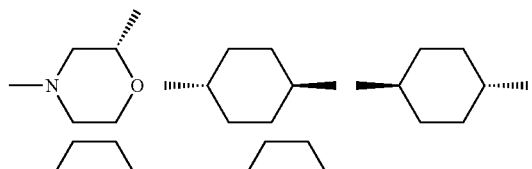

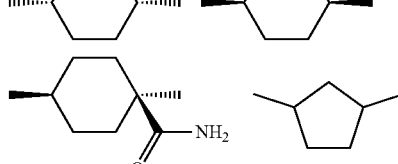

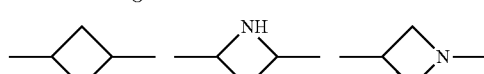

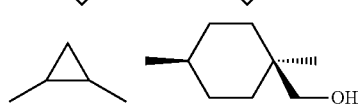

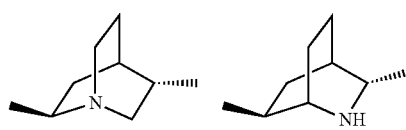

11. The compound according to claim 1, wherein B is a cyclic group having one of the following formulae:

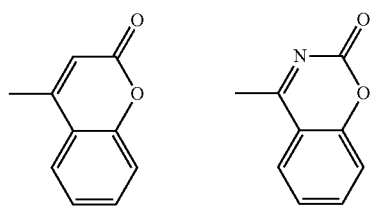

-continued

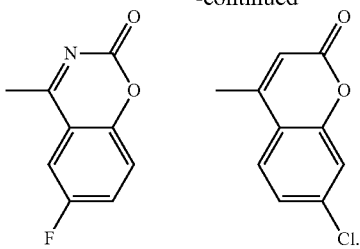

12. A pharmaceutical composition, comprising at least one compound, salt thereof with a pharmaceutically acceptable organic or inorganic acid or with a pharmaceutically acceptable organic or inorganic base, enantiomer, quaternary ammonium salt, or N-oxide according to claim 1, and at least one inert pharmaceutically acceptable excipient.

13. A method for treating a bacterial infection, comprising administering an effective amount of a compound, salt with a pharmaceutically acceptable organic or inorganic acid or with a pharmaceutically acceptable organic or inorganic base, enantiomer, quaternary ammonium salt, or N-oxide according to claim 1 to a patient in need thereof.

14. The method according to claim 13, wherein said bacterial infection is selected from the group consisting of a skin infection, a mucosal infection, a gynecological infection, a respiratory tract infection (RTI), a CNS infections, a gastro-intestinal infection, a bone infection, a cardiovascular infection, a sexually transmitted infection, and a urinary tract infection.

15. The compound according to claim 1, wherein Y is a ring having one of the following formulae:

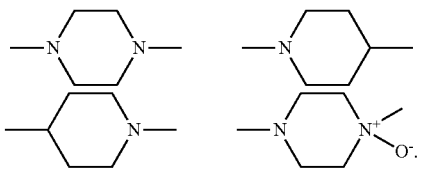

16. The method of according to claim 13, wherein said bacterial infection is an *E. coli* infection or an *S. aureus* infection.

17. The method of according to claim 13, wherein said bacterial infection is an *E. coli* infection.

18. The method of according to claim 13, wherein said bacterial infection is an *S. aureus* infection.

* * * * *